(12) United States Patent
Yi et al.

(10) Patent No.: US 11,612,358 B2
(45) Date of Patent: Mar. 28, 2023

(54) FEEDBACK DEVICE AND METHOD FOR PROVIDING THERMAL FEEDBACK USING THE SAME

(71) Applicant: TEGWAY CO., LTD., Daejeon (KR)

(72) Inventors: Kyoungsoo Yi, Daejeon (KR); Ockkyun Oh, Daejeon (KR); Jong Ok Ko, Incheon (KR)

(73) Assignee: TEGWAY CO., LTD., Daejeon (KR)

( * ) Notice: Subject to any disclaimer, the term of this patent is extended or adjusted under 35 U.S.C. 154(b) by 0 days.

(21) Appl. No.: 17/394,816

(22) Filed: Aug. 5, 2021

(65) Prior Publication Data

US 2021/0369210 A1  Dec. 2, 2021

Related U.S. Application Data

(63) Continuation of application No. 16/736,678, filed on Jan. 7, 2020, now Pat. No. 11,191,491, which is a
(Continued)

(30) Foreign Application Priority Data

Nov. 25, 2016 (KR) ........................ 10-2016-0158762
Nov. 25, 2016 (KR) ........................ 10-2016-0158764
(Continued)

(51) Int. Cl.
*H04B 3/36* (2006.01)
*A61B 5/00* (2006.01)
(Continued)

(52) U.S. Cl.
CPC .............. *A61B 5/7271* (2013.01); *A61B 5/01* (2013.01); *A61B 5/015* (2013.01);
(Continued)

(58) Field of Classification Search
CPC ......... A61B 5/7271; A61B 5/01; A61B 5/015; A61B 18/1477; F25B 21/02;
(Continued)

(56) References Cited

U.S. PATENT DOCUMENTS

| 5,709,219 A | 6/1998 | Chen et al. |
| 5,803,810 A | 9/1998 | Norton et al. |

(Continued)

FOREIGN PATENT DOCUMENTS

| EP | 2 128 907 A1 | 12/2009 |
| EP | 2 511 793 A2 | 10/2012 |

(Continued)

OTHER PUBLICATIONS

International Search Report issued in corresponding application No. PCT/KR2017/010430, dated May 29, 2018.
(Continued)

*Primary Examiner* — Anh V La
(74) *Attorney, Agent, or Firm* — Maschoff Brennan

(57) ABSTRACT

A method for providing a thermal feedback, includes executing a virtual reality application providing a virtual space that includes a virtual area to which an area temperature attribute is assigned, and a virtual object to which an object temperature attributed is assigned. An area event that reflects that a player character enters the virtual area is detected. A feedback device is controlled to output thermal feedback associated to the area temperature attribute when the area event is detected, the feedback device outputting the thermal feedback using a thermoelectric element performing a thermoelectric operation. An object event reflecting the player character is influenced by the virtual object is detected. The feedback device is controlled to override the thermal feedback associated to the area temperature attribute and output thermal feedback associated to the object temperature when
(Continued)

the object is detected while the player character is in the virtual area.

15 Claims, 69 Drawing Sheets

Related U.S. Application Data continuation of application No. 15/633,341, filed on Jun. 26, 2017, now Pat. No. 10,561,374.

(60) Provisional application No. 62/415,437, filed on Oct. 31, 2016.

(30) Foreign Application Priority Data

| Nov. 25, 2016 | (KR) | ........................ 10-2016-0158765 |
| Nov. 25, 2016 | (KR) | ........................ 10-2016-0158767 |
| Nov. 25, 2016 | (KR) | ........................ 10-2016-0158770 |
| Nov. 25, 2016 | (KR) | ........................ 10-2016-0158774 |
| Nov. 25, 2016 | (KR) | ........................ 10-2016-0158777 |
| Nov. 25, 2016 | (KR) | ........................ 10-2016-0158781 |
| Nov. 25, 2016 | (KR) | ........................ 10-2016-0158783 |
| Nov. 25, 2016 | (KR) | ........................ 10-2016-0158785 |

(51) Int. Cl.
*G06F 3/01* (2006.01)
*H05B 1/02* (2006.01)
*A61B 5/01* (2006.01)
*A61B 18/14* (2006.01)
*F25B 21/02* (2006.01)
*G05D 23/19* (2006.01)
*G05D 23/20* (2006.01)

(52) U.S. Cl.
CPC .......... *A61B 18/1477* (2013.01); *F25B 21/02* (2013.01); *G05D 23/192* (2013.01); *G05D 23/20* (2013.01); *G06F 3/011* (2013.01); *H05B 1/0227* (2013.01); *F25B 2321/0212* (2013.01); *Y02B 30/70* (2013.01)

(58) Field of Classification Search
CPC .......... F25B 2321/0212; G05D 23/192; G05D 23/20; G06F 3/011; H05B 1/0227; Y02B 30/70; H01L 35/02; H04N 5/222; H04N 21/816
USPC ....... 165/259; 340/407.1, 407.2; 463/30, 36, 463/37, 38, 47
See application file for complete search history.

(56) References Cited

U.S. PATENT DOCUMENTS

| 5,952,728 | A | 9/1999 | Imanishi et al. |
| 6,353,623 | B1 | 3/2002 | Munks et al. |
| 6,362,740 | B1 | 3/2002 | Jung |
| 6,496,200 | B1 | 12/2002 | Snibbe et al. |
| 8,016,673 | B2 | 9/2011 | Takatsuka |
| 8,550,905 | B2 | 10/2013 | Mikhailov |
| 8,902,159 | B1 | 12/2014 | Matthews et al. |
| 9,672,702 | B2 | 6/2017 | Coish et al. |
| 9,983,697 | B1* | 5/2018 | Gribetz ................. G06T 19/006 |
| 10,101,810 | B2 | 10/2018 | Li et al. |
| 2005/0091989 | A1 | 5/2005 | Leija et al. |
| 2008/0238937 | A1 | 10/2008 | Muraki |
| 2009/0131165 | A1 | 5/2009 | Buchner |
| 2009/0149928 | A1 | 6/2009 | Relin |
| 2009/0233710 | A1 | 9/2009 | Roberts |
| 2010/0154856 | A1 | 6/2010 | Hiroyama et al. |
| 2012/0198616 | A1 | 8/2012 | Makansi et al. |
| 2012/0258800 | A1 | 10/2012 | Mikhailov |
| 2013/0021234 | A1 | 1/2013 | Umminger |
| 2014/0022162 | A1 | 1/2014 | Yu |
| 2014/0165607 | A1 | 6/2014 | Alexander |
| 2014/0192247 | A1 | 7/2014 | Cheong |
| 2014/0194726 | A1 | 7/2014 | Mishelevich et al. |
| 2014/0338713 | A1 | 11/2014 | Nakanuma |
| 2014/0364212 | A1 | 12/2014 | Osman et al. |
| 2016/0056360 | A1 | 2/2016 | Cho et al. |
| 2016/0093107 | A1* | 3/2016 | Yamamoto ............... A63F 13/25 345/633 |
| 2016/0098095 | A1 | 4/2016 | Gonzalez-Banos |
| 2016/0133151 | A1 | 5/2016 | O'Dowd et al. |
| 2016/0153508 | A1 | 6/2016 | Battlogg |
| 2016/0238040 | A1 | 8/2016 | Gallo et al. |
| 2016/0246370 | A1 | 8/2016 | Osman |
| 2016/0274662 | A1* | 9/2016 | Rimon ...................... G06F 3/16 |
| 2016/0312505 | A1 | 10/2016 | Wuerth et al. |
| 2017/0038830 | A1* | 2/2017 | Clement ............. G06F 3/04847 |
| 2017/0084140 | A1 | 3/2017 | Bhatia |
| 2017/0354190 | A1 | 12/2017 | Cauchy |
| 2017/0365764 | A1 | 12/2017 | Shingai et al. |
| 2018/0095534 | A1 | 4/2018 | Omote |
| 2019/0063797 | A1 | 2/2019 | Yi et al. |
| 2019/0381314 | A1 | 12/2019 | Howard |
| 2020/0046936 | A1 | 2/2020 | Nofzinger et al. |
| 2020/0060905 | A1 | 2/2020 | Bogie et al. |

FOREIGN PATENT DOCUMENTS

| JP | 2003-308009 | | 10/2003 |
| JP | 2005-077066 | A | 3/2005 |
| JP | 2005-234881 | | 9/2005 |
| JP | 2008-227178 | A1 | 9/2008 |
| JP | 2012-217861 | A | 11/2012 |
| JP | 2013-175627 | A | 9/2013 |
| KR | 10-2007-0066931 | A | 6/2007 |
| KR | 10-2010-0051386 | A | 5/2010 |
| KR | 10-1056950 | B1 | 8/2011 |
| KR | 10-2013-0137417 | A | 12/2013 |
| KR | 10-2014-0105045 | A | 9/2014 |
| KR | 10-2015-0028748 | A | 3/2015 |
| KR | 10-2015-0035634 | A | 4/2015 |
| KR | 10-2015-0154087 | A | 11/2015 |
| KR | 10-2016-0033585 | A | 3/2016 |
| KR | 10-2016-0036383 | A | 4/2016 |
| KR | 10-2016-0117944 | A | 10/2016 |
| KR | 10-2016-0124388 | A | 10/2016 |
| KR | 10-1493792 | B1 | 2/2017 |
| KR | 10-1493797 | B1 | 2/2017 |
| KR | 10-2017-0089441 | A | 8/2017 |

OTHER PUBLICATIONS

U.S. Notice of Allowance issued in corresponding U.S. Appl. No. 15/858,351, dated Jun. 25, 2019.
U.S. Office Action issued in corresponding U.S. Appl. No. 15/633,501, dated Jun. 27, 2019.
ISR of PCT Patent Application No. PCT/KR2017/011865 with translation, Feb. 13, 2018.
ISR Written Opinion of PCT Patent Application No. PCT/KR2017/011865 with translation, Feb. 13, 2018.
ISR of PCT Patent Application No. PCT/KR2017/011866 with translation, Mar. 7, 2018.
ISR Written Opinion of PCT Patent Application No. PCT/KR2017/011866 with translation, Mar. 7, 2018.
ISR of PCT Patent Application No. PCT/KR2017/011867 with translation, Mar. 19, 2018.
ISR Written Opinion of PCT Patent Application No. PCT/KR2017/011867 with translation, Mar. 19, 2018.
Office Action of U.S. Appl. No. 15/633,341, dated Jun. 13, 2019.
Notice of Allowance of U.S. Appl. No. 15/633,341, dated Oct. 8, 2019.
Final Office Action of U.S. Appl. No. 15/633,501, dated Dec. 31, 2019.
Notice of Allowance of U.S. Appl. No. 15/633,501, dated Apr. 2, 2020.

(56) References Cited

OTHER PUBLICATIONS

Office Action of U.S. Appl. No. 16/310,430, dated Jun. 26, 2020.
Notice of Allowance of U.S. Appl. No. 16/310,430, dated Jan. 8, 2021.
Office Action of KR Patent Application No. 10-2017-0062594 with translation, dated Jan. 27, 2021.
Notice of Allowance of U.S. Appl. No. 16/736,678, dated Apr. 2, 2021.
Notice of Allowance of U.S. Appl. No. 16/310,430, dated May 17, 2021.
Office Action of Korean Patent Application No. 10-2017-0062589 with translation, dated May 31, 2021.
EP Search Report in Application No. 17863485.3 dated Oct. 6, 2020.
U.S. Office Action in U.S. Appl. No. 16/221,509 dated Nov. 25, 2020.
U.S. Office Action in U.S. Appl. No. 16/221,509 dated Jul. 31, 2020.
U.S. Notice of Allowance in U.S. Appl. No. 15/633,501 dated Apr. 2, 2020.
U.S. Notice of Allowance in U.S. Appl. No. 16/310,432 dated Apr. 21, 2020.

\* cited by examiner 1400-1

1400a

1640

| level | forward voltage | sat. temp. of a hot feedback | reverse voltage | sat. temp. of a cold feedback |
|---|---|---|---|---|
| 1 | V1+ | ΔT1+ | V1− | ΔT1−=−ΔT1+ |
| 2 | V2+ | ΔT2+=2ΔT1+ | V2− | ΔT2−=−2ΔT1+ |
| 3 | V3+ | ΔT3+=3ΔT1+ | V3− | ΔT3−=−3ΔT1+ |
| 4 | V4+ | ΔT4+=4ΔT1+ | V4− | ΔT4−=−4ΔT1+ |
| 5 | V5+ | ΔT5+=5ΔT1+ | V5− | ΔT5−=−5ΔT1+ |

| neutral ratio | operating voltage for a first group | operating voltage for a second group |
|---|---|---|
| 2 | V1+, V2+ | V2−, V4− |
| 2.5 | V2+ | V5− |
| 3 | V1+ | V3− |
| 4 | V1+ | V4− |
| 5 | V1+ | V5− |

*Fig. 43*

```
<HEADER>
CALIBRATION_TIME_HOT = (0.0, 0.1, 0.2, 0.3, 0.4)
CALIBRATION_TIME_COLD = (0.0, 0.15, 0.3, 0.45, 0.6)
<BODY>
00:00:05.15, 00:00:10.15 : (BOTH, HOT_1)
00:00:18.01, 00:00:19.55 : (RIGHT, HOT_2), (LEFT, HOT_3)
00:01:04.25, 00:01:05.25 : (BOTH, COLD_4)
00:01:06.22, 00:01:08.10 : (RIGHT, COLD_3)
    .   .   .   .
01:25:16.32, 01:25:17.44 : (BOTH, HOT_3)
1:25:31.44, 01:25:33.00 : (BOTH, HOT_2)
<END>
```

*Fig. 46*

| SKILL ID | ELEMENTAL ATTRIBUTE | FEEDBACK TYPE | SKILL TIER | SKILL LV | FEEDBACK GRADE | FEEDBACK DURATION |
|---|---|---|---|---|---|---|
| FIREBOLT | FIRE | HOT | LOW | 1 | HOT_1 | 0.3 SEC |
| | | | | 2 | HOT_1 | 0.4 SEC |
| | | | | 3 | HOT_2 | 0.4 SEC |
| | | | | 4 | HOT_3 | 0.5 SEC |
| FIREBALL | FIRE | HOT | MID | 1 | HOT_2 | 0.4 SEC |
| | | | | 2 | HOT_2 | 0.5 SEC |
| | | | | 3 | HOT_3 | 0.5 SEC |
| | | | | 4 | HOT_4 | 0.6 SEC |
| FIRESTORM | FIRE | HOT | HIGH | 1 | HOT_2 | 1.5 SEC |
| | | | | 2 | HOT_3 | 1.6 SEC |
| | | | | 3 | HOT_4 | 1.7 SEC |
| | | | | 4 | HOT_5 | 1.8 SEC |
| ICEBOLT | ICE | COLD | LOW | 1 | COLD-1 | 0.3 SEC |
| | | | | 2 | COLD-1 | 0.4 SEC |
| | | | | 3 | COLD-2 | 0.4 SEC |
| | | | | 4 | COLD-3 | 0.5 SEC |
| LIGHTNING CHAIN | ELECTRIC | PAIN | MID | 1 | PAIN_1 | 0.4 SEC |
| | | | | 2 | PAIN_2 | 0.4 SEC |
| | | | | 3 | PAIN_3 | 0.4 SEC |
| | | | | 4 | PAIN_4 | 0.4 SEC |

*Fig. 50*

FEEDBACK DEVICE AND METHOD FOR PROVIDING THERMAL FEEDBACK USING THE SAME

CROSS-REFERENCE TO RELATED APPLICATION

This application is continuation of U.S. patent application Ser. No. 16/736,678 filed Jan. 7, 2020, which is a continuation of U.S. patent application Ser. No. 15/633,341 filed Jun. 26, 2017, which claims the benefit of U.S. provisional patent application 62/415,437 filed Oct. 31, 2016, which are herein incorporated by reference in their entirety This application also claims foreign priority benefits of the filing date of Korean Application Serial No. 10-2016-0158762, 10-2016-0158764, 10-2016-0158765, 10-2016-0158767, 10-2016-0158770, 10-2016-0158774, 10-2016-0158777, 10-2016-0158781, 10-2016-0158783, and 10-2016-0158785, filed on Nov. 25, 2016, and which are incorporated hereby by reference in their entirety.

TECHNICAL FIELD

The present disclosure relates generally to a feedback device and a method for providing a thermal feedback using the feedback device. In particular, the present disclosure relates to a feedback device for outputting a thermal feedback according to a reproduction of a multimedia content, a content reproduction device for reproducing the multimedia content, a system and a method for providing a thermal feedback using the devices.

BACKGROUND

At the Consumer Electronics Show (CES) in 2016, virtual reality was introduced as one of the most promising future technologies. The development of technologies such as virtual reality (VR) or augmented reality (AR) have increased the demand for devices and methods that enhance user experience (UX). For example, there is interest in methods that enhance user's immersion in the content by stimulating multiple human senses. VR and AR are normally confined mainly to visual and auditory senses. However, efforts are under way to include various human senses such as olfactory and tactile sense.

Thermoelectric elements (TEs) are electrical devices that generate or absorb heat using the Peltier effect. TEs may be used to provide a thermal feedback to a user. However, the incorporation of the thermoelectric elements in VR or AR applications has been limited because it is difficult to fabricate conventional thermoelectric elements using flat substrates. Thus, it is challenging to have TEs that make tight contact with a body part of a user.

In recent years, however, the Assignee of the present Application has successfully developed flexible thermoelectric elements (FTEs) e.g., as disclosed in Korean Application Serial No. 10-2015-0154087 filed on Nov. 3, 2015. It is expected that the thermal feedback can be effectively delivered to users by overcoming the problems of the conventional thermoelectric elements.

SUMMARY

The following sets forth a simplified summary of selected aspects, embodiments, and examples of the present disclosure for providing a basic understanding of the disclosure. However, the summary does not constitute an extensive overview of all the aspects, embodiments, and examples of the disclosure. Neither is the summary intended to identify critical aspects or delineate the scope of the disclosure. The sole purpose of the summary is to present selected aspects, embodiments, and examples of the disclosure in a concise form as an introduction to the more detailed description of the aspects, embodiments, and examples of the disclosure that follow the summary.

One aspect of the present disclosure is directed to a method for providing a thermal feedback. The method may include executing a virtual reality application providing a virtual space, the virtual space including a virtual area to which an area temperature attribute is assigned, and a virtual object to which an object temperature attribute is assigned; detecting an area event, the area event reflecting that a player character enters the virtual area; controlling a feedback device to output a thermal feedback corresponding to the area temperature attribute when it is determined that the area event occurs, the feedback device outputting the thermal feedback using a thermoelectric element performing a thermoelectric operation; detecting an object event, the object event reflecting that the player character is influenced by the virtual object; and controlling the feedback device to override the thermal feedback corresponding to the area temperature attribute and output a thermal feedback corresponding to the object temperature attribute when it is determined that the object event occurs while the player character is in the virtual area.

Another aspect of the present disclosure is directed to a content reproduction device that reproduces a multimedia content. The content reproduction device may include: a non-transitory computer readable medium storing data; a communication module communicating with a feedback device; and a controller configured to execute instructions in the non-transitory computer readable medium to: execute a virtual reality application providing a virtual space. The virtual space may include a virtual area to which an area temperature attribute is assigned, and a virtual object to which an object temperature attribute is assigned, detect an area event, the area event reflecting that a player character enters the virtual area; control, via the communication module, the feedback device to output a thermal feedback associated to the area temperature attribute when it is determined that the area event occurs, the feedback device outputs the thermal feedback using a thermoelectric element performing a thermoelectric operation, detect an object event, the object event reflecting that the player character is influenced by the virtual object; and control, via the communication module, the feedback device to override the thermal feedback associated to the area temperature attribute and output a thermal feedback associated to the object temperature attribute when it is determined that the object event occurs while the player character is in the virtual area.

Yet another aspect of the present disclosure is directed to a method for providing a thermal feedback. The method may include executing a virtual reality application providing a virtual space. The virtual space may include a global area and a local area included in the global area, the global area being assigned a global temperature attribute and the local area being assigned a local temperature attribute; controlling a feedback device to output a thermal feedback corresponding to the global temperature attribute when it is determined that a player character enters the global area, the feedback device outputting the thermal feedback using a thermoelectric element performing a thermoelectric operation; and controlling the feedback device to override the thermal feedback corresponding to the global temperature attribute and output a thermal feedback corresponding to the local temperature attribute when it is determined that the player character enters the local area.

Another aspect of the present disclosure is directed to content reproduction device that reproduces multimedia content. The content reproduction device may include a non-transitory computer readable medium storing a data; a communication module communicating with the feedback device; a controller configured to execute instructions in the non-transitory computer readable medium to: execute a virtual reality application providing a virtual space. The virtual space may include a global area and a local area included in the global area, the global area being assigned a global temperature attribute and the local area being assigned a local temperature attribute; control, via the communication module, a feedback device to output a thermal feedback corresponding to the global temperature attribute when it is determined that a player character enters the global area, the feedback device outputting the thermal feedback using a thermoelectric element performing a thermoelectric operation, and control, via the communication module, the feedback device to override the thermal feedback corresponding to the global temperature attribute and output the thermal feedback corresponding to the local temperature attribute when it is determined that the player character enters the local area.

One aspect of the present disclosure is directed to a thermal feedback providing system and a thermal feedback providing method that provide a thermal feedback by outputting thermal feedback when reproducing multimedia content to a user.

In particular, the present disclosure aims to improve the user's content immersion by interlocking the audiovisual output of the multimedia content with the thermal feedback.

One aspect of the present disclosure is directed to a method for providing a thermal feedback, including: reproducing a multimedia content, wherein the multimedia content includes a video data related to a video content and a feedback data related to a thermal feedback corresponding to a specific scene of the video content; obtaining a start time of the thermoelectric operation, wherein the start time is set to be prior to a display time of the specific scene considering a delay duration from when the thermoelectric operation for the thermal feedback is started to when a user senses the thermal feedback, outputting, via a display, the specific scene when the play time of the multimedia content reaches the display time; and sending, to a feedback device for outputting the thermal feedback using a thermoelectric element, a start message related to the thermal feedback when a play time of the multimedia content reaches the start time to provide, to the user, the thermal feedback and the specific scene together at the display time.

Another aspect of the present disclosure is directed to a content reproduction device for providing a thermal feedback, including: a memory storing a data; a communication module communicating with an external device; and a controller configured to: obtain, from the memory, a multimedia content and reproduce the multimedia content, wherein a multimedia content includes a video data related to a video content and a feedback data related to a thermal feedback corresponding to a specific scene of the video content, wherein the controller obtains a start time of the thermoelectric operation, wherein the start time is set to be prior to a display time of the specific scene considering a delay duration from when the thermoelectric operation for the thermal feedback is started to when a user senses the thermal feedback, outputs, via a display, the specific scene when the play time of the multimedia content reaches the display time and sends, via the communication module, a start message related to the thermal feedback to a feedback device for outputting the thermal feedback using a thermoelectric element when a play time of the multimedia content reaches the start time to provide, to the user, the thermal feedback and the specific scene together at the display time.

Another aspect of the present disclosure is directed to a system for providing a thermal feedback, including: a content reproduction device including: a memory storing a data, a first communication module communicating with an external device, and an application controller configured to obtain, from the memory, a multimedia content and reproduce the multimedia content, wherein a multimedia content includes a video data related to a video content and a feedback data related to a thermal feedback corresponding to a specific scene of the video content; and a feedback device including: a second communication module communicating with an external device, a thermoelectric element performing a thermoelectric operation for outputting the thermal feedback, a feedback controller applying a power to the thermoelectric element, and a contact surface which is configured to contact with a body of a user and transmits a heat generated due to the thermoelectric operation, wherein the application controller obtains a start time of the thermoelectric operation, wherein the start time is set to be prior to a display time of the specific scene considering a delay duration from when the thermoelectric operation for the thermal feedback is started to when a user senses the thermal feedback, sends, via the first communication module, a start message related to the thermal feedback to the feedback device when a play time of the multimedia content reaches the start time, and outputs, via a display, the specific scene when the play time of the multimedia content reaches the display time, and wherein the feedback controller receives, via the second communication module, the start message, applies the power to the thermoelectric element upon the receipt of the start message to provide, to the user, the thermal feedback and the specific scene together at the display time.

Another aspect of the present disclosure is directed to a feedback device for providing a thermal feedback related to a multimedia content, wherein the multimedia content includes a video data related to a video content and a feedback data related to a thermal feedback corresponding to a specific scene of the video content, the device including: a thermoelectric element performing a thermoelectric operation for outputting the thermal feedback; a feedback controller applying, to the thermoelectric element, a power for the thermoelectric operation, wherein the feedback controller applies the power to the thermoelectric element at a start time which is set to be prior to a display time of the specific scene considering a delay duration from when the thermoelectric operation for the thermal feedback is started to when a user senses the thermal feedback so that the thermal feedback and the specific scene together is provided to the user at the display time; and a contact surface being configured to contact with a body of a user, wherein a heat generated due to the thermoelectric operation is transmitted to the user through the contact surface.

Another aspect of the present disclosure is directed to a method for generating a multimedia content providing a thermal feedback, wherein the thermal feedback is implemented by using a feedback device, and wherein the feedback device provides a thermal feedback due to a thermoelectric operation of a thermoelectric element via a contact surface contacting with a body of a user during a reproduction of a video, including: obtaining a display time of a specific scene from a play period of the video, wherein the specific scene is a scene to correspond to the thermal feedback; obtaining a start time of the thermoelectric operation, wherein the start time is set to be prior to the display time considering a delay duration from when the thermoelectric operation for the thermal feedback is started to when a user senses the thermal feedback to provide, to the user, the thermal feedback and the specific scene together at the display time; and generating a feedback data related to the thermal feedback, the data including the start time of the thermoelectric operation.

Another aspect of the present disclosure is directed to an electronic device for generating a multimedia content providing a thermal feedback, wherein the thermal feedback is implemented by using a feedback device, and wherein the feedback device provides a thermal feedback due to a thermoelectric operation of a thermoelectric element via a contact surface contacting with a body of a user during a reproduction of a video, including: a memory storing a data; and a controller configured to: obtain a display time of a specific scene from a play period of the video, wherein the specific scene is a scene to correspond to the thermal feedback, obtain a start time of the thermoelectric operation, wherein the start time is set to be prior to the display time considering a delay duration from when the thermoelectric operation for the thermal feedback is started to when a user senses the thermal feedback to provide, to the user, the thermal feedback and the specific scene together at the display time, and generate a feedback data related to the thermal feedback, the data including the start time of the thermoelectric operation.

Another aspect of the present disclosure is directed to a method for providing a thermal feedback related to an electronic game, performed by a content reproduction device which executes the electronic game and cooperates with a feedback device outputting a thermal feedback using a thermoelectric element, the method including: executing the game including a player and an enemy character which attacks the player by performing an attack action having an elemental attribute, wherein the elemental attribute includes a fire element, a cold element and an electricity element; when the a get-hit event, reflecting that the player gets hit by the attack action, occurs in the game, determining a type of the thermal feedback based on the elemental attribute of the attack action, wherein the type of the thermal feedback is determined as a hot feedback when the elemental attribute of the attack action related to the get-hit event is the fire element, the type of the thermal feedback is determined as a cold feedback when the elemental attribute of the attack action related to the get-hit event is the cold element, and the type of the thermal feedback is determined as a thermal grill feedback when the elemental attribute of the attack action related to the get-hit event is the electricity element; and controlling the feedback device to output the thermal feedback related to the get-hit event together with displaying a get-hit graphic so that the thermoelectric element performs a heat generating operation when the type of the thermal feedback is the hot feedback, performs a heat absorbing operation when the type of the thermal feedback is the cold feedback, and performs a thermal grill operation when the type of the thermal feedback is the thermal grill feedback, the thermal grill operation in which the heat generating operation and a heat absorbing operation is combined.

Another aspect of the present disclosure is directed to a content reproduction device cooperating with a feedback device outputting a thermal feedback using a thermoelectric element, including: a memory storing a data; a communication module communicating with an external device; and a controller configured to: execute an electronic game including a player and an enemy character which attacks the player by performing an attack action having an elemental attribute, wherein the elemental attribute includes a fire element, a cold element and an electricity element, when the a get-hit event, reflecting that the player gets hit by the attack action, occurs in the game, determines a type of the thermal feedback based on the elemental attribute of the attack action, and controls, via the communication module, the feedback device to output the thermal feedback related to the get-hit event together with displaying a get-hit graphic, wherein the controller determines the type of the thermal feedback as a hot feedback when the elemental attribute of the attack action related to the get-hit event is the fire element, determines the type of the thermal feedback as a cold feedback when the elemental attribute of the attack action related to the get-hit event is the cold element, and determines the type of the thermal feedback as a thermal grill feedback when the elemental attribute of the attack action related to the get-hit event is the electricity element, and wherein the controller controls the thermoelectric element to perform a heat generating operation when the type of the thermal feedback is the hot feedback, to perform a heat absorbing operation when the type of the thermal feedback is the cold feedback, and to perform a thermal grill operation when the type of the thermal feedback is the thermal grill feedback, the thermal grill operation in which the heat generating operation and a heat absorbing operation is combined.

Another aspect of the present disclosure is directed to a method for providing a thermal feedback, performed by a feedback device, wherein the feedback device may include a thermoelectric element which performs a thermoelectric operation including a heat generating operation, a heat absorbing operation and a thermal grill operation in which the heat generating operation and the heat absorbing operation is combined, and a contact surface which is configured to contact with a body of a user, and outputs a thermal feedback by transmitting, via the contact surface, a heat generated due to the thermoelectric operation to the user, the method including: connecting with a content reproduction device executing the game including a player and an enemy character which attacks the player by performing an attack action having an elemental attribute, wherein the elemental attribute includes a fire element, a cold element and an electricity element; when the player gets hit in the game by the attack action of which the elemental attribute is the fire element, outputting a hot feedback by applying a forward power to the thermoelectric element to perform the heat generating operation, when the player gets hit in the game by the attack action of which the elemental attribute is the cold element, outputting a cold feedback by applying a reverse power to the thermoelectric element to perform the heat absorbing operation, and when the player gets hit in the game by the attack action of which the elemental attribute is the electricity element, outputting a thermal grill feedback by applying, simultaneously or alternatively, the forward power and the reverse power to the thermoelectric element to perform the thermal grill operation.

Another aspect of the present disclosure is directed to a feedback device for outputting a thermal feedback corresponding to an elemental attribute in an electronic game, wherein the feedback device cooperates with a content reproduction executing the game including a player and an enemy character which attacks the player by performing an attack action having the elemental attribute, the device including: a heat outputting module including a thermoelectric element which performs a thermoelectric operation including a heat generating operation, a heat absorbing operation and a thermal grill operation in which the heat generating operation and the heat absorbing operation is combined, a power terminal supplying a power to the thermoelectric element, and a contact surface which is configured to contact with a body of a user, wherein the heat outputting module outputs the thermal feedback by transmitting, via the contact surface, a heat generated due to the thermoelectric operation to the user; and a feedback controller configured to: output a hot feedback by applying a forward power to the thermoelectric element to perform the heat generating operation when the player gets hit in the game by the attack action of which the elemental attribute is a fire element, output a cold feedback by applying a reverse power to the thermoelectric element to perform the heat absorbing operation when the player gets hit in the game by the attack action of which the elemental attribute is a cold element, and output a thermal grill feedback by applying, simultaneously or alternatively, the forward power and the reverse power to the thermoelectric element to perform the thermal grill operation when the player gets hit in the game by the attack action of which the elemental attribute is an electricity element.

Another aspect of the present disclosure is directed to a system for providing a thermal feedback, including: a content reproduction device executing an electronic game; a display displaying an image related to the game; and a feedback device connecting with the content reproduction device and outputting a thermal feedback using a thermoelectric element, wherein the content reproduction device may include: a first communication module communicating with the feedback device, and a controller configured to: execute the game including a player and an enemy character which attacks the player by performing an attack action having an elemental attribute, wherein the elemental attribute includes a fire element, a cold element and an electricity element, and when the a get-hit event, reflecting that the player gets hit by the attack action, occurs in the game, display, via the display, a get-hit graphic related to the get-hit event, determine a type of the thermal feedback based on the elemental attribute of the attack action, and control, via the first communication module, the feedback device to output the thermal feedback related to the get-hit event together with displaying the get-hit graphic, wherein the controller determines the type of the thermal feedback as a hot feedback when the elemental attribute of the attack action related to the get-hit event is the fire element, determines the type of the thermal feedback as a cold feedback when the elemental attribute of the attack action related to the get-hit event is the cold element, and determines the type of the thermal feedback as a thermal grill feedback when the elemental attribute of the attack action related to the get-hit event is the electricity element, wherein the feedback device may include: a second communication module communicating with the content reproduction device, a heat outputting module including a thermoelectric element which performs a thermoelectric operation including a heat generating operation, a heat absorbing operation and a thermal grill operation in which the heat generating operation and the heat absorbing operation is combined, a power terminal supplying a power to the thermoelectric element, and a contact surface which is configured to contact with a body of a user, wherein the heat outputting module outputs the thermal feedback by transmitting, via the contact surface, a heat generated due to the thermoelectric operation to the user, and a feedback controller configured to: receives, via the second communication module, the type of the thermal feedback, and apply the power to the thermoelectric element to output the thermal feedback of the received type, and wherein the feedback controller applies, upon the receipt of the type indicating the hot feedback, a forward power to the thermoelectric element to perform the heat generating operation, applies upon the receipt of the type indicating the cold feedback, a reverse power to the thermoelectric element to perform the heat absorbing operation, and applies, upon the receipt of the type indicating the thermal grill feedback, the forward power and the reverser power, simultaneously or alternatively, to the thermoelectric element to perform the thermal grill operation.

Another aspect of the present disclosure is directed to a method for providing a thermal feedback related to an electronic game, performed by a content reproduction device which executes the electronic game and cooperates with a feedback device outputting a thermal feedback using a thermoelectric element, the method including: executing the game including a player performing a specific action having an elemental attribute, wherein the elemental attribute includes a fire element, a cold element and an electricity element; causing the player to perform the specific action according to a user command; displaying a graphic related to the specific action; determining a type of the thermal feedback based on the element attribute, wherein the type is determined as a hot feedback when the elemental attribute of the specific action is the fire element, the type is determined as a cold feedback when the elemental attribute of the specific action is the cold element, and the type is determined as a thermal grill feedback when the elemental attribute of the specific action is the electricity element, and controlling the feedback device to output the thermal feedback together with displaying the graphic related to the specific action so that the thermoelectric element performs a heat generating operation when the type is the hot feedback, performs a heat absorbing operation when the type is the cold feedback, and performs a thermal grill operation when the type is the thermal grill feedback, the thermal grill operation in which the heat generating operation and a heat absorbing operation is combined.

Another aspect of the present disclosure is directed to a content reproduction device cooperating with a feedback device outputting a thermal feedback using a thermoelectric element, including: a memory storing a data; a communication module communicating with an external device; and a controller configured to: execute the game including a player performing a specific action having an elemental attribute, wherein the elemental attribute includes a fire element, a cold element and an electricity element, cause the player to perform the specific action according to a user command, display a graphic related to the specific action, determine a type of the thermal feedback based on the element attribute of the specific action, and control, via the communication module, the feedback device to output the thermal feedback together with displaying of the graphic related to the specific action, wherein the controller determines the type as a hot feedback when the elemental attribute of the specific action is the fire element, determines the type as a cold feedback when the elemental attribute of the specific action is the cold element, and determines the type as a thermal grill feedback when the elemental attribute of the specific action is the electricity element, and wherein the controller controls the thermoelectric element to perform a heat generating operation when the type is the hot feedback, controls the thermoelectric element to perform a heat absorbing operation when the type is the cold feedback, and controls the thermoelectric element to perform a thermal grill operation when the type is the thermal grill feedback, the thermal grill operation in which the heat generating operation and the heat absorbing operation is combined.

Another aspect of the present disclosure is directed to a method for providing a thermal feedback, performed by a feedback device, wherein the feedback device may include a thermoelectric element performing a thermoelectric operation including at least one of a heat generating operation, a heat absorbing operation and a thermal grill feedback in which the heat generating operation and the heat absorbing operation is combined, and a contact surface which is configured to contact with a body of a user and transmits a heat generated by the thermoelectric operation, the method including: connecting with a content reproduction device executing an electronic game, wherein the game includes a player performing an attack action having an elemental attribute, wherein the elemental attribute includes a fire element, a cold element and an electricity element; when the player performs the attack action of the fire element, outputting a hot feedback by applying a forward power to the thermoelectric element to perform the heat generating operation; when the player performs the attack action of the cold element, outputting a cold feedback by applying a reverse power to the thermoelectric element to perform the heat absorbing operation; and when the player performs the attack action of the electricity element, outputting a thermal grill feedback by applying, simultaneously or alternatively, the forward power and the reverse power to the thermoelectric element to perform the thermal grill operation.

Another aspect of the present disclosure is directed to a feedback device for outputting a thermal feedback correspond to an elemental attribute of an attack action, wherein the feedback device cooperates with a content reproduction device executing an electronic game which includes a player performing the attack action having the elemental attribute, the elemental attribute including a fire element, a cold element and an electricity element, the device including: an input module acquiring a user input; a heat outputting module including a thermoelectric element performing a thermoelectric operation including a heat generating operation, a heat absorbing operation and a thermal grill operation in which the heat generating operation and the heat absorbing operation is combined, a power terminal supplying a power to the thermoelectric element, and a contact surface which is provided on one side of the thermoelectric element and is configured to contact with a body part of a user, wherein the heat outputting module outputs the thermal feedback by transmitting, via the contact surface, a heat generated due to the thermoelectric operation to the user; and a feedback controller configured to: output, via the heat outputting module, a hot feedback by applying a forward power to the thermoelectric element to perform the heat generating operation when the controller receives, via the input module, the user input instructing the attack action having the fire element, output, via the heat outputting module, a hot feedback by applying a reverse power to the thermoelectric element to perform the heat absorbing operation when the controller receives, via the input module, the user input instructing the attack action having the cold element, wherein a current direction of the reverse power is opposite to a current direction of the forward power, and output, via the heat outputting module, a hot feedback by applying, simultaneously or alternatively, the forward power and reverse power to the thermoelectric element to perform the thermal grill generating operation when the controller receives, via the input module, the user input instructing the attack action having the electricity element.

Another aspect of the present disclosure is directed to a method for providing a thermal feedback related to a multimedia content, performed by a content reproduction device which executes the multimedia content including an electronic game and a feedback application and cooperates with a feedback device outputting a thermal feedback using a thermoelectric element, the method including: executing the multimedia content, wherein the multimedia content includes a player and a virtual object, implements a get-hit event in which the player gets hit by the virtual object, and assigns, to the player, a thermal resistance related to the get-hit event; generating the get-hit event in the game; setting an intensity of the thermal feedback based on the get-hit event; adjusting the intensity of the thermal feedback based on the thermal resistance; and controlling the feedback device to output the thermal feedback having the adjusted intensity.

Another aspect of the present disclosure is directed to a content reproduction device, wherein the content reproduction device cooperates with a feedback device outputting a thermal feedback using a thermoelectric element, including: a memory storing a data; a communication module communicating with an external device; and a controller configured to: execute a multimedia content including an electronic game and a feedback application, wherein the multimedia content includes a player and a virtual object, implements a get-hit event in which the player gets hit by the virtual object, and assigns, to the player, a thermal resistance related to the get-hit event, set, upon an occurrence of the get-hit event, an intensity of the thermal feedback based on the get-hit event, adjust the intensity of the thermal feedback based on the thermal resistance, and control, via the communication module, the feedback device to output the thermal feedback having the adjusted intensity.

Another aspect of the present disclosure is directed to a feedback device, wherein the feedback device cooperates with a content reproduction device executing a multimedia content provided as an electronic game or a feedback application, and wherein the multimedia content includes a player and a virtual object, implements a get-hit event in which the player gets hit by the virtual object, and assigns, to the player, a thermal resistance related to the get-hit event, including: a casing having a grip portion gripped by a user and forming an exterior of the feedback device; an input module receiving the user input according to a manipulation of the user; a communication module communicating with the content reproduction device; a heat outputting module including a thermoelectric element performing a thermoelectric operation, a power terminal applying a power to the thermoelectric element, and a contact surface which is disposed on the grip portion and configured to contact with the user, wherein the heat outputting module outputs the thermal feedback by transmitting, via the contact surface, a heat generated by the thermoelectric operation to the user; and a controller configured to: receive, via the input module, the user input, send, via the communication module, the user input to the content reproduction device to cause the player to act according to the manipulation of the user, receive, via the communication module, an intensity of the thermal feedback from the content reproduction device, select an operating voltage among a plurality of pre-set voltage values based on the intensity of the thermal feedback, generate an operating power having the operating voltage, and apply the operating power to the power terminal so that the heat outputting module outputs the thermal feedback, and wherein the controller applies a first operating voltage when the get-hit event occurs, in the game, to the player who has a first thermal resistance, and applies a second operating voltage greater than the first operating voltage when the get-hit event occurs, in the game, to the player who has a second thermal resistance greater than the first thermal resistance.

Another aspect of the present disclosure is directed to a method for providing a thermal feedback related to a multimedia content, performed by a content reproduction device, wherein the content reproduction device executes the multimedia content including an electronic game and a feedback application and cooperates with a feedback device outputting a thermal feedback using a thermoelectric element, including: executing the multimedia content, wherein the multimedia content includes a thermal event causing the thermal feedback, a player and an equipment to which a thermal resistance is assigned; when the thermal event occurs, determining whether or not the player equips the equipment; when the player does not equip the equipment, setting an intensity of the thermal feedback to a first intensity level; when the player equips the equipment, setting the intensity of the thermal feedback to a second intensity level which is different from the first intensity level; and controlling the feedback device to output the thermal feedback according to the determined intensity.

Another aspect of the present disclosure is directed to a method for providing a thermal feedback related to a multimedia content, performed by a content reproduction device, wherein the content reproduction device executes the multimedia content including an electronic game and a feedback application and cooperates with a feedback device outputting a thermal feedback using a thermoelectric element, including: executing the multimedia content, wherein the multimedia content includes a thermal event causing the thermal feedback, a player and an equipment to which a thermal resistance is assigned; when the thermal event occurs, determining whether or not the player equips the equipment; determining whether or not to output the thermal feedback related to the thermal feedback based on whether or not the player equips the equipment; and controlling the feedback device to output the thermal feedback only when the player does not equip the equipment.

Another aspect of the present disclosure is directed to a content reproduction device, wherein the content reproduction device cooperates with a feedback device outputting a thermal feedback using a thermoelectric element, including: a memory storing a data; a communication module communicating with an external device; and a controller configured to: execute the multimedia content, wherein the multimedia content is provided as an electronic game or a feedback application and includes a thermal event causing the thermal feedback, a player and an equipment to which a thermal resistance is assigned, determine, upon an occurrence of the thermal event, whether or not the player equips the equipment, set an intensity of the thermal feedback to a first intensity level when the player does not equip the equipment, set the intensity of the thermal feedback to a second intensity level which is different from the first intensity level when the player equips the equipment, and control, via the communication module, the feedback device to output the thermal feedback according to the determined intensity.

Another aspect of the present disclosure is directed to a content reproduction device, wherein the content reproduction device cooperates with a feedback device outputting a thermal feedback using a thermoelectric element, including: a memory storing a data; a communication module communicating with an external device; and a controller configured to: execute the multimedia content, wherein the multimedia content includes a thermal event causing the thermal feedback, a player and an equipment to which a thermal resistance is assigned, determine, upon an occurrence of the thermal event, whether or not the player equips the equipment, determine whether or not to output the thermal feedback related to the thermal feedback based on whether or not the player equips the equipment, and control, via the communication module, the feedback device to output the thermal feedback only when the player does not equip the equipment.

Another aspect of the present disclosure is directed to a feedback device for outputting a thermal feedback, wherein the feedback device cooperates with a content reproduction device executing a multimedia content provided as an electronic game or a feedback application, and wherein the multimedia content includes a thermal event causing the thermal feedback, a player and an equipment to which a thermal resistance is assigned, including: a casing having a grip portion gripped by a user and forming an exterior of the feedback device; an input module receiving the user input according to a manipulation of the user; a communication module communicating with the content reproduction device; and a heat outputting module including a thermoelectric element performing a thermoelectric operation, a power terminal supplying a power to the thermoelectric element, and a contact surface which is disposed on the grip portion and configured to contact with the user, wherein the heat outputting module outputs the thermal feedback by transmitting, via the contact surface, a heat generated by the thermoelectric operation to the user; and a controller configured to: obtain, via the input module, the user input, send, via the communication module, the user input to the content reproduction device to cause the user to act according to the manipulation of the user, receive, via the communication module, a message requesting outputting the thermal feedback from the content reproduction device, and apply, upon the receipt of the message, the power to the power terminal so that the heat outputting module outputs the thermal feedback, wherein when the controller outputs, via the heat outputting module, the thermal feedback upon an occurrence of the thermal event during the reproduction of the multimedia content, the controller performs a first operation in which whether or not to output the thermal feedback is determined based on whether or not the player equips the equipment or a second operation in which an intensity of the thermal feedback is adjusted based on whether or not the player equips the equipment, wherein the controller performs the first operation by applying an operating power to the thermoelectric element when the player does not equip the equipment and by not applying the operating power to the thermoelectric element when the player equips the equipment, and wherein the controller performs the second operation by applying a first operating power to the thermoelectric element when the player does not equip the equipment and by applying a second operating power of which a voltage magnitude is smaller than that of the first operating power.

Another aspect of the present disclosure is directed to a method for providing a thermal feedback, performed by a content reproduction device cooperating with a feedback device outputting the thermal feedback using a thermoelectric element, including: executing an electronic game including a player acting according to a manipulation of a user, wherein the player has health points and dies in the game when all of the health points is exhausted; obtaining at least one of an intensity of the thermal feedback and a type of the thermal feedback according to a change of the health points during a reproduction of the game; and controlling the feedback device to output the thermal feedback according to the determined at least one of the intensity and the type, wherein the obtaining includes at least one of: obtaining the intensity of the thermal feedback based on a change amount of the health points, obtaining the intensity of the thermal feedback based on a ratio of the change amount to a total amount of the health points, and obtaining the type of the thermal feedback based on whether the health points is increased or decreased.

Another aspect of the present disclosure is directed to a method for providing a thermal feedback, performed by a content reproduction device cooperating with a feedback device outputting the thermal feedback using a thermoelectric element, including: executing an electronic game including a player acting according to a manipulation of a user, wherein the player has health points and dies in the game when all of the health points is exhausted; determining at least one of whether or not to output the thermal feedback, an intensity of the thermal feedback and a type of the thermal feedback based on at least one of a remaining amount of the health points and a ratio of the remaining amount to a total amount of the health point, during a reproduction of the game; and controlling the feedback device to output the thermal feedback according to the determined at least one of the whether or not to output the thermal feedback, the intensity and the type.

Another aspect of the present disclosure is directed to a content reproduction device, wherein the content reproduction device cooperates with a feedback device outputting the thermal feedback using a thermoelectric element, including: a memory storing a data; a communication module communicating with an external device; and a controller configured to: execute an electronic game including a player acting according to a manipulation of a user, wherein the player has health points and dies in the game when all of the health points is exhausted, obtain at least one of an intensity of the thermal feedback and a type of the thermal feedback according to a change of the health points during a reproduction of the game; and control, via the communication module, the feedback device to output the thermal feedback according to the determined at least one of the intensity and the type, wherein the controller determines the intensity of the thermal feedback based on at least one of a change amount of the health points, and determines the type of the thermal feedback based on whether the health points is increased or decreased.

Another aspect of the present disclosure is directed to a content reproduction device, wherein the content reproduction device cooperates with a feedback device outputting the thermal feedback using a thermoelectric element, including: a memory storing a data; a communication module communicating with an external device; and a controller configured to: execute an electronic game including a player acting according to a manipulation of a user, wherein the player has health points and dies in the game when all of the health points is exhausted, determine at least one of whether or not to output the thermal feedback, an intensity of the thermal feedback and a type of the thermal feedback based on at least one of a remaining amount of the health points and a ratio of the remaining amount to a total amount of the health point, during a reproduction of the game, and control, via the communication module, the feedback device to output the thermal feedback according to the determined at least one of the whether or not to output the thermal feedback, the intensity and the type.

Another aspect of the present disclosure is directed to a feedback device for outputting a thermal feedback, wherein the feedback device cooperates with a content reproduction device executing an electronic game including a player acting according to a manipulation of a user, and wherein the player has health points and dies in the game when all of the health points is exhausted, including: a casing having a grip portion gripped by a user and forming an exterior of the gaming controller; an input module receiving the user input according to a manipulation of the user; a communication module communicating with the content reproduction device; a heat outputting module including a thermoelectric element performing a thermoelectric operation, a power terminal applying a power to the thermoelectric element, and a contact surface which is disposed on the grip portion and configured to contact with the user, wherein the heat outputting module outputs the thermal feedback by transmitting, via the contact surface, a heat generated by the thermoelectric operation to the user; and a controller configured to receive, via the communication module, the user input, send, via the communication module, the received user input to the content reproduction device to cause the player acts corresponding to the manipulation of the user, and apply an operating power according to a change of the health points to the power terminal so that the heat outputting module outputs the thermal feedback corresponding to the change of the health points, wherein the controller performs at least one of a first operation, a second operation and a third operation, wherein the controller performs the first operation by applying a first operating power when a change amount of the health points or a ratio of the change amount to a total amount of the health points is a first value and applying a second operating power of which the voltage magnitude is greater than that of the first operating power when the change amount or the ratio is a second value greater than the first value, wherein the controller performs the second operation by applying one of a forward power for the hot feedback and a reverser power for the cold feedback when the health points is increased and applying another of the forward power and the reverser power when the health points is decreased, and wherein the controller performs the third operation by applying a third operating power when a remaining amount of the health points or a ratio of the remaining amount to the total amount is a third value and applying a fourth operating power of which the voltage magnitude is greater than that of the third operating power when the remaining amount or the ratio of the remaining amount is a fourth value smaller than the third value.

Another aspect of the present disclosure is directed to a method for providing a thermal feedback, performed by a content reproduction device cooperating with a feedback device outputting the thermal feedback using a thermoelectric element, including: executing a multimedia content provided as an electronic game or a feedback application, wherein the multimedia content includes a virtual heat source to which a heat transferring attribute including a conduction type and a radiation type is assigned; determining, based on the heat transferring attribute of the virtual heat source, a virtual heat transferring amount transferred from the virtual heat source to a player of the multimedia content, obtaining an intensity of the thermal feedback based on the determined virtual heat transferring amount; and controlling the feedback device to output the thermal feedback having the determined intensity. wherein the determining the virtual heat transferring amount includes calculating the virtual heat transferring amount based on a temperature value of the virtual heat source when the heat transferring attribute of the virtual heat source is the conduction type, and calculating the virtual heat transferring amount based on the temperature value and a distance between the player and the virtual heat source when the heat transferring attribute of the virtual heat source is the radiation type.

Another aspect of the present disclosure is directed to a content reproduction device, wherein the content reproduction device cooperates with a feedback device outputting the thermal feedback using a thermoelectric element, including: a memory storing a data; a communication module communicating with an external device; and a controller configured to: execute a multimedia content provided as an electronic game or a feedback application, wherein the multimedia content includes a virtual heat source to which a heat transferring attribute including a conduction type and a radiation type is assigned, determine, based on the heat transferring attribute of the virtual heat source, a virtual heat transferring amount transferred from the virtual heat source to a player of the multimedia content, obtain an intensity of the thermal feedback based on the determined virtual heat transferring amount, and control, via the communication module, the feedback device to output the thermal feedback having the determined intensity. wherein the controller calculates the virtual heat transferring amount the virtual heat transferring amount based on a temperature value of the virtual heat source when the heat transferring attribute of the virtual heat source is the conduction type, and calculates the virtual heat transferring amount based on the temperature value and a distance between the player and the virtual heat source when the heat transferring attribute of the virtual heat source is the radiation type.

Another aspect of the present disclosure is directed to a feedback device for outputting the thermal feedback, wherein the feedback device cooperates with a content reproduction device executing an electronic game or a feedback application which includes a virtual heat source, and outputs the thermal feedback corresponding to a virtual heat transferring amount transferred from the virtual heat source to a player of the game or the application, including: a heat outputting module including a thermoelectric element which performs a thermoelectric operation including a heat generating operation, a heat absorbing operation and a thermal grill operation in which the heat generating operation and the heat absorbing operation, a power terminal applying a power to the thermoelectric element, and a contact surface which is disposed on the grip portion and configured to contact with the user, wherein the heat outputting module outputs the thermal feedback by transmitting, via the contact surface, a heat generated by the thermoelectric operation to the user; and a controller configured to: control the thermoelectric element to output the thermal feedback reflecting the virtual heat transferring amount transferred by a conduction from a first virtual heat source to the player, by applying a first power to the power terminal when the player is contacted with the first virtual heat source and by stopping the application of the first power when the player is apart from the first virtual heat source, and control the thermoelectric element to output the thermal feedback reflecting the virtual heat transferring amount transferred by a radiation from a second virtual heat source of a different type than a first virtual heat source, by applying a second power to the power terminal when the player is spaced a first distance from the second virtual heat source and by applying a third power greater than the second power to the power terminal when the player is spaced a second distance smaller than the first distance the from the second virtual heat source.

Another aspect of the present disclosure is directed to a method for providing a thermal feedback, performed by a content reproduction device which executes a multimedia content provided as an electronic game or a feedback application and cooperates with a feedback device outputting a thermal feedback using a thermoelectric element, the method including: executing the multimedia content, wherein the multimedia content includes a virtual object and a player, and implements an interaction between the player and the virtual object such as a touch or a grab, the virtual object having a thermal attribute including a temperature information and a texture information; changing an intensity of the thermal feedback according to at least one of a lasting duration of the interaction, the temperature information and the texture information; and controlling the feedback device to output the thermal feedback having the intensity.

Another aspect of the present disclosure is directed to a content reproduction device, wherein the content reproduction device executes a multimedia content provided as an electronic game or a feedback application, and cooperates with a feedback device outputting the thermal feedback using a thermoelectric element, including: a heat outputting module including a thermoelectric element which performs a heat generating operation and a heat absorbing operation a power terminal applying a power to the thermoelectric element, and a contact surface which is disposed on the grip portion and configured to contact with the user, wherein the heat outputting module outputs the thermal feedback by transmitting, via the contact surface, a heat generated from the thermoelectric element to the user; a memory storing a data; a communication module communicating with an external device; and a controller configured to: execute the multimedia content, wherein the multimedia content includes a virtual object and a player, and implements an interaction between the player and the virtual object such as a touch or a grab, the virtual object having a thermal attribute including a temperature information and a texture information, change an intensity of the thermal feedback according to at least one of a lasting duration of the interaction, the temperature information and the texture information, control the feedback device to output the thermal feedback having the intensity.

Another aspect of the present disclosure is directed to a feedback device for outputting a thermal feedback, wherein the feedback device cooperates with a content reproduction device executing a multimedia content provided as an electronic game or a feedback application, and wherein the multimedia content includes a virtual object and a player, and implements an interaction between the player and the virtual object such as a touch or a grab, the virtual object having a thermal attribute including a temperature information and a texture information, the feedback device including: a casing having a grip portion gripped by a user and forming an exterior of the feedback device; an input module receiving the user input according to a manipulation of the user; a communication module communicating with the content reproduction device; a heat outputting module including a thermoelectric element performing a thermoelectric operation, a power terminal applying a power to the thermoelectric element, and a contact surface which is disposed on the grip portion and configured to contact with the user, wherein the heat outputting module outputs the thermal feedback by transmitting, via the contact surface, a heat generated by the thermoelectric operation to the user;

and a feedback controller configured to increase a voltage magnitude or a current magnitude of the power applied to the thermoelectric element as a lasting duration of the interaction increases when the interaction between the player and the virtual object is started according to the user's operation.

Another aspect of the present disclosure is directed to a method for providing a thermal feedback, including: executing an electronic game using a physic engine supporting a collision processing function related to a collision between virtual objects, wherein the collision processing function includes a collision type in which a behavior of the virtual objects is calculated considering at least a momentum of the virtual objects and a trigger type in which one virtual object passes through another virtual object; determining the collision processing function related to a get-hit event which occurs when a player character gets hit by the virtual object is the collision type or the trigger type; deciding an intensity of the thermal feedback based on a result of the determination; and controlling, based on the intensity of the thermal feedback, an intensity of an thermoelectric operation performed by a feedback device, wherein the feedback device outputs the thermal feedback using a thermoelectric element performing the thermoelectric operation.

Another aspect of the present disclosure is directed to a content reproduction device, cooperating with a feedback device outputting a thermal feedback using a thermoelectric element, including: a memory storing a data; a communication module communicating with the feedback device; and a controller configured to: execute an electronic game using a physic engine supporting a collision processing function related to a collision between virtual objects, wherein the collision processing function includes a collision type in which a behavior of the virtual objects is calculated considering at least a momentum of the virtual objects and a trigger type in which one virtual object passes through another virtual object, determine the collision processing function related to a get-hit event which occurs when a player character gets hit by the virtual object is the collision type or the trigger type, decide an intensity of the thermal feedback based on a result of the determination, and control, via the communication module, an intensity of an thermoelectric operation performed by the thermoelectric element based on the intensity of the thermal feedback.

Another aspect of the present disclosure is directed to a method for providing a thermal feedback, performed by a content reproduction device executing a multimedia content and cooperating with a plurality of feedback devices outputting a thermal feedback using a thermoelectric element, including: executing a virtual reality application providing a virtual space; obtaining a FOV (Field-Of-View) of the virtual space according to a direction of a user's sight detected from a HMD (Head-Mounted-Display); when a thermal event occurs in the virtual space, determining at least one target device among the plurality of the feedback devices based on an orientation of the thermal event with respect to the FOV; and transmitting a signal instructing outputting the thermal feedback to the target feedback device.

Another aspect of the present disclosure is directed to a content reproduction device, wherein the content reproduction device reproduces a multimedia content and cooperates with a plurality of feedback devices outputting a thermal feedback using a thermoelectric element, including: a memory storing a data; a communication module communicating with the feedback devices; a controller configured to execute a virtual reality application providing a virtual space, obtain a FOV (Field-Of-View) of the virtual space according to a direction of a user's sight detected from a HMD (Head-Mounted-Display), when a thermal event occurs in the virtual space, determine at least one target device among the plurality of the feedback devices based on an orientation of the thermal event with respect to the FOV, and transmit a signal instructing outputting the thermal feedback to the target feedback device.

Another aspect of the present disclosure is directed to a method for providing a thermal feedback, including: executing a virtual reality application providing a virtual space, wherein the virtual space includes a virtual area to which a temperature attribute is assigned and a virtual object to which the temperature attribute is assigned; when an area event reflecting that a player character enters the virtual area occurs, control a feedback device to output the thermal feedback related to the area event, wherein the feedback device outputs the thermal feedback using a thermoelectric element performing a thermoelectric operation; detecting an occurrence of an object event reflecting that a player is influenced by the virtual object when the area event is lasting; and when the occurrence of the object event is detected during the area event, controlling the feedback device to override the thermal feedback related to the area event by the thermal feedback related to the object event.

Another aspect of the present disclosure is directed to a content reproduction device, wherein the content reproduction device reproduces a multimedia content and cooperates with at least one feedback device outputting a thermal feedback using a thermoelectric element, including: a memory storing a data; a communication module communicating with the feedback device; a controller configured to: execute a virtual reality application providing a virtual space, wherein the virtual space includes a virtual area to which a temperature attribute is assigned and a virtual object to which the temperature attribute is assigned, when an area event reflecting that a player character enters the virtual area occurs, control, via the communication module, the feedback device to output the thermal feedback related to the area event, wherein the feedback device outputs the thermal feedback using a thermoelectric element performing a thermoelectric operation, detect an occurrence of an object event reflecting that a player is influenced by the virtual object when the area event is lasting, and when the occurrence of the object event is detected during the area event, control, via the communication module, the feedback device to override the thermal feedback related to the area event by the thermal feedback related to the object event.

Another aspect of the present disclosure is directed to a method for providing a thermal feedback, including: executing a virtual reality application providing a virtual space, wherein the virtual space includes a virtual area to which a temperature attribute is assigned, the virtual area having a global area and a local area included in the global area; when a player character enters the global area, controlling a feedback device to output the thermal feedback corresponding to the temperature attribute of the global area, wherein the feedback device outputs the thermal feedback using a thermoelectric element performing a thermoelectric operation; and when the player character enters the local area, controlling the feedback device to override the thermal feedback corresponding to the temperature attribute of the global area with the thermal feedback corresponding to the temperature attribute of the local area.

Another aspect of the present disclosure is directed to a content reproduction device, wherein the content reproduction device reproduces a multimedia content and cooperates with at least one feedback device outputting a thermal feedback using a thermoelectric element, including: a memory storing a data; a communication module communicating with the feedback device; a controller configured to: execute a virtual reality application providing a virtual space, wherein the virtual space includes a virtual area to which a temperature attribute is assigned, the virtual area having a global area and a local area included in the global area, when a player character enters the global area, control, via the communication module, a feedback device to output the thermal feedback corresponding to the temperature attribute of the global area, wherein the feedback device outputs the thermal feedback using a thermoelectric element performing a thermoelectric operation, and when the player character enters the local area, control, via the communication module, the feedback device to override the thermal feedback corresponding to the temperature attribute of the global area with the thermal feedback corresponding to the temperature attribute of the local area.

Another aspect of the disclosure is directed to a non-transitory computer-readable medium storing instructions which, when executed, cause one or more processors to perform the methods disclosed herein. The computer-readable medium may include volatile or non-volatile, magnetic, semiconductor, tape, optical, removable, non-removable, or other types of computer-readable medium or computer-readable storage devices. For example, the computer-readable medium may be implemented as a storage unit or memory module having the computer instructions stored thereon. In some embodiments, the computer-readable medium may be implemented as a disc or a flash drive having the computer instructions stored thereon.

BRIEF DESCRIPTION OF THE DRAWINGS

FIG. 43 is a table of voltages for providing the neutral thermal grill feedback in a voltage control manner according to an embodiment of the present disclosure.

FIG. 46 is a diagram illustrating an example of thermal feedback data used in the first implementation of the thermal feedback providing method according to an embodiment of the present disclosure.

FIG. 50 is a diagram of a skill-thermal feedback table used in the third implementation of the thermal feedback providing method according to an embodiment of the present disclosure.

DETAILED DESCRIPTION

Figure 1:
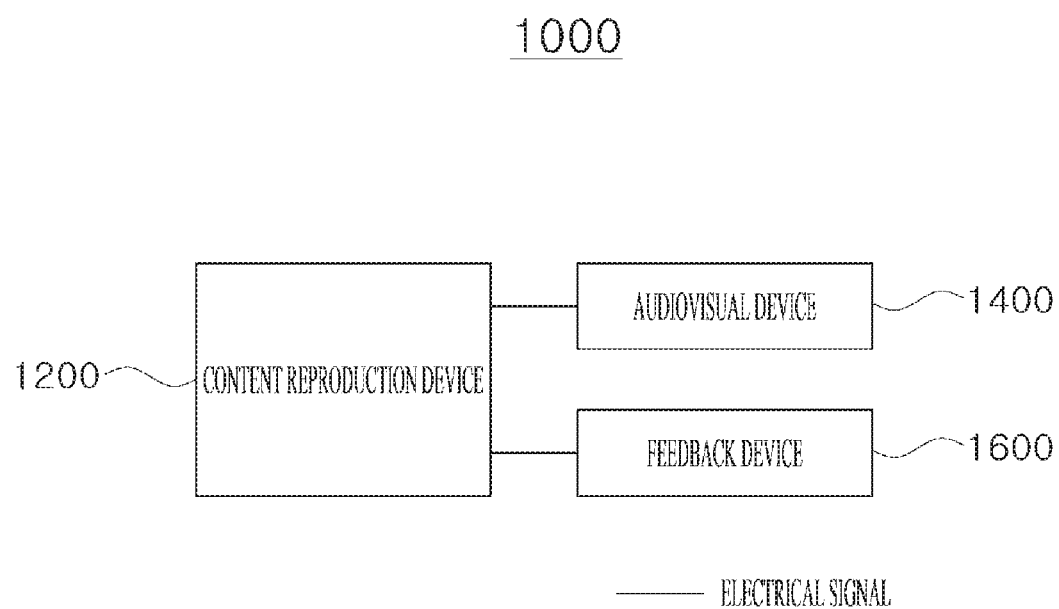
FIG. 1 is a block diagram of a configuration of a thermal feedback providing system according to an embodiment of the present disclosure.

One aspect of the present disclosure is directed to a method for providing a thermal feedback, including: reproducing a multimedia content, wherein the multimedia content includes a video data related to a video content and a feedback data related to a thermal feedback corresponding to a specific scene of the video content; obtaining a start time of the thermoelectric operation, wherein the start time is set to be prior to a display time of the specific scene considering a delay duration from when the thermoelectric operation for the thermal feedback is started to when a user senses the thermal feedback, outputting, via a display, the specific scene when the play time of the multimedia content reaches the display time; and sending, to a feedback device for outputting the thermal feedback using a thermoelectric element, a start message related to the thermal feedback when a play time of the multimedia content reaches the start time to provide, to the user, the thermal feedback and the specific scene together at the display time.

The start time may be prior to the display time by the delay duration.

The feedback data may include an identification information indicating the specific scene corresponding to the thermal feedback. And the obtaining may include: obtaining the identification information from the feedback information, obtaining the display time from the video data based on the identification information and calculating the start time based on the display time and the delay duration.

The calculating may be performed by subtracting the delay duration from the display time.

The feedback data may include a output time of the thermal feedback, the output time being set to be same with the display time. And the obtaining may include: obtaining the output time from the feedback information, and calculating the start time based on the output time and the delay duration.

The calculating may be performed by subtracting the delay duration from the output time.

The thermoelectric operation may include at least one of a heat generating operation and a heat absorbing operation which are performed by the thermoelectric element when the power is applied thereto.

The feedback data may include a feedback type information including a hot feedback and cold feedback. And the method may further include: determining a type of the thermal feedback based on the feedback data, and obtaining the delay duration based on the type of the thermal feedback.

The feedback data may include a feedback intensity information, and the method may further include: determining an intensity of the thermal feedback based on the feedback data, and obtaining the delay duration considering the intensity of the thermal feedback.

The intensity of the thermal feedback may include a first intensity and a second intensity stronger than the first intensity, and a first duration which is the delay duration related to the first intensity may be smaller than a second duration which is the delay duration related to the second intensity.

The intensity of the thermal feedback may include a first intensity and a second intensity stronger than the first intensity, and a first duration which is the delay duration related to the first intensity may be greater than a second duration which is the delay duration related to the second intensity.

The method may further include: obtaining, from the feedback device, a device information identifying the feedback device; and obtaining the delay duration based on the device information.

The method may further include receiving, from the feedback device, the delay duration.

The video data and the feedback data may be included in a single file.

The video data and the feedback data may be included in different files.

The outputting may be performed by transmitting a video signal to an external device having the display.

Another aspect of the present disclosure is directed to a content reproduction device for providing a thermal feedback, including: a memory storing a data; a communication module communicating with an external device; and a controller configured to: obtain, from the memory, a multimedia content and reproduce the multimedia content, wherein a multimedia content includes a video data related to a video content and a feedback data related to a thermal feedback corresponding to a specific scene of the video content, wherein the controller obtains a start time of the thermoelectric operation, wherein the start time is set to be prior to a display time of the specific scene considering a delay duration from when the thermoelectric operation for the thermal feedback is started to when a user senses the thermal feedback, outputs, via a display, the specific scene when the play time of the multimedia content reaches the display time and sends, via the communication module, a start message related to the thermal feedback to a feedback device for outputting the thermal feedback using a thermoelectric element when a play time of the multimedia content reaches the start time to provide, to the user, the thermal feedback and the specific scene together at the display time.

The start time may be prior to the display time by the delay duration.

The feedback data may include an identification information indicating the specific scene corresponding to the thermal feedback, and the controller may obtain the identification information from the feedback information, obtain the display time from the video data based on the identification information and calculate the start time based on the display time and the delay duration.

The controller may calculate the start time by subtracting the delay duration from the display time.

The feedback data may include an output time of the thermal feedback, the output time being set to be same with the display time, and the controller may obtain the output time from the feedback information, and calculate the start time based on the output time and the delay duration.

The controller may calculate the start time by subtracting the delay duration from the output time.

The thermoelectric operation may include at least one of a heat generating operation and a heat absorbing operation which are performed by the thermoelectric element when the power is applied thereto The feedback data may include a feedback type information including a hot feedback and cold feedback, and the controller may determine a type of the thermal feedback based on the feedback data, and obtains the delay duration based on the type of the thermal feedback.

The feedback data may include a feedback intensity information, and the controller may determine an intensity of the thermal feedback based on the feedback data, and obtains the delay duration considering the intensity of the thermal feedback.

The intensity of the thermal feedback may include a first intensity and a second intensity stronger than the first intensity, and a first duration which is the delay duration related to the first intensity may be smaller than a second duration which is the delay duration related to the second intensity.

The intensity of the thermal feedback may include a first intensity and a second intensity stronger than the first intensity, and a first duration which is the delay duration related to the first intensity may be greater than a second duration which is the delay duration related to the second intensity.

The controller may receive, via the communication module, a device information identifying the feedback device from the feedback device, and obtain the delay duration based on the device information.

The controller may receive, via the communication module, the delay duration from the feedback device.

The memory may store a single file including the video data and the feedback data together.

The memory may store one file including the video data and another file including the feedback data.

The controller may receive, via the communication module, the multimedia content and store the received multimedia content in the memory.

The controller may transmit, via the communication module, a video signal to an external device having the display so that the display displays the specific scene.

Another aspect of the present disclosure is directed to a system for providing a thermal feedback, including: a content reproduction device including: a memory storing a data, a first communication module communicating with an external device, and an application controller configured to obtain, from the memory, a multimedia content and reproduce the multimedia content, wherein a multimedia content includes a video data related to a video content and a feedback data related to a thermal feedback corresponding to a specific scene of the video content; and a feedback device including: a second communication module communicating with an external device, a thermoelectric element performing a thermoelectric operation for outputting the thermal feedback, a feedback controller applying a power to the thermoelectric element, and a contact surface which is configured to contact with a body of a user and transmits a heat generated due to the thermoelectric operation, wherein the application controller obtains a start time of the thermoelectric operation, wherein the start time is set to be prior to a display time of the specific scene considering a delay duration from when the thermoelectric operation for the thermal feedback is started to when a user senses the thermal feedback, sends, via the first communication module, a start message related to the thermal feedback to the feedback device when a play time of the multimedia content reaches the start time, and outputs, via a display, the specific scene when the play time of the multimedia content reaches the display time, and wherein the feedback controller receives, via the second communication module, the start message, applies the power to the thermoelectric element upon the receipt of the start message to provide, to the user, the thermal feedback and the specific scene together at the display time.

Another aspect of the present disclosure is directed to a feedback device for providing a thermal feedback related to a multimedia content, wherein the multimedia content includes a video data related to a video content and a feedback data related to a thermal feedback corresponding to a specific scene of the video content, the device including: a thermoelectric element performing a thermoelectric operation for outputting the thermal feedback; a feedback controller applying, to the thermoelectric element, a power for the thermoelectric operation, wherein the feedback controller applies the power to the thermoelectric element at a start time which is set to be prior to a display time of the specific scene considering a delay duration from when the thermoelectric operation for the thermal feedback is started to when a user senses the thermal feedback so that the thermal feedback and the specific scene together is provided to the user at the display time; and a contact surface being configured to contact with a body of a user, wherein a heat generated due to the thermoelectric operation is transmitted to the user through the contact surface.

Another aspect of the present disclosure is directed to a method for generating a multimedia content providing a thermal feedback, wherein the thermal feedback is implemented by using a feedback device, and wherein the feedback device provides a thermal feedback due to a thermoelectric operation of a thermoelectric element via a contact surface contacting with a body of a user during a reproduction of a video, including: obtaining a display time of a specific scene from a play period of the video, wherein the specific scene is a scene to correspond to the thermal feedback; obtaining a start time of the thermoelectric operation, wherein the start time is set to be prior to the display time considering a delay duration from when the thermoelectric operation for the thermal feedback is started to when a user senses the thermal feedback to provide, to the user, the thermal feedback and the specific scene together at the display time; and generating a feedback data related to the thermal feedback, the data including the start time of the thermoelectric operation.

The start time may be prior to the display time by the delay duration.

In a step of the obtaining the start time, the start time may be calculated by subtracting the delay duration from the display time.

The thermoelectric operation may include at least one of a heat generating operation and a heat absorbing operation.

The method may further include: obtaining information on a type of the thermal feedback including a hot feedback and a cold feedback; and obtaining the delay duration considering the type of the thermal feedback.

The method may further include: obtaining information on an intensity of the thermal feedback; and obtaining the delay duration considering the intensity of the thermal feedback.

The intensity of the thermal feedback may include a first intensity and a second intensity stronger than the first intensity. And a first duration which is the delay duration related to the first intensity may be smaller than a second duration which is the delay duration related to the second intensity.

The intensity of the thermal feedback may include a first intensity and a second intensity stronger than the first intensity. And a first duration which is the delay duration related to the first intensity may be greater than a second duration which is the delay duration related to the second intensity.

The method may further include: obtaining an identification information on the feedback device; and obtaining the delay duration considering the identification information.

The method may further include: generating the multimedia content in form of a single file including the feedback data and a video data related to the video.

The method may further include: generating the multimedia content in form of multi files, a first file of the multi files including the feedback data and a second file of the multi files including a video data related to the video. And the first file and the second file may be linked to each other.

Another aspect of the present disclosure is directed to an electronic device for generating a multimedia content providing a thermal feedback, wherein the thermal feedback is implemented by using a feedback device, and wherein the feedback device provides a thermal feedback due to a thermoelectric operation of a thermoelectric element via a contact surface contacting with a body of a user during a reproduction of a video, including: a memory storing a data; and a controller configured to: obtain a display time of a specific scene from a play period of the video, wherein the specific scene is a scene to correspond to the thermal feedback, obtain a start time of the thermoelectric operation, wherein the start time is set to be prior to the display time considering a delay duration from when the thermoelectric operation for the thermal feedback is started to when a user senses the thermal feedback to provide, to the user, the thermal feedback and the specific scene together at the display time, and generate a feedback data related to the thermal feedback, the data including the start time of the thermoelectric operation.

The start time may be prior to the display time by the delay duration.

The controller may calculate the start time by subtracting the delay duration from the display time.

The thermoelectric operation may include at least one of a heat generating operation and a heat absorbing operation.

The device may further include: an input module receiving an user input, and the controller may receive, via the input module, the user input including information on a type of the thermal feedback including a hot feedback and a cold feedback, and determine the delay duration considering the type of the thermal feedback.

The memory may store a matching table of the intensity and the delay duration, and the controller may obtain the delay duration corresponding to the intensity using the matching table. And the matching table may include a first intensity, a second intensity stronger than the first intensity, a first duration related to the first intensity and a second duration related to the second intensity greater than the first duration.

The controller may obtain an identification information on the feedback device and obtain the delay duration considering the identification information.

The controller may generate the multimedia content in form of a single file including the feedback data and a video data related to the video.

The controller may generate the multimedia content in form of multi files, a first file of the multi files including the feedback data and a second file of the multi files including a video data related to the video. And the first file and the second file may be linked to each other Another aspect of the present disclosure is directed to a method for providing a thermal feedback related to an electronic game, performed by a content reproduction device which executes the electronic game and cooperates with a feedback device outputting a thermal feedback using a thermoelectric element, the method may include: executing the game including a player and an enemy character which attacks the player by performing an attack action having an elemental attribute, wherein the elemental attribute includes a fire element, a cold element and an electricity element; when the a get-hit event, reflecting that the player gets hit by the attack action, occurs in the game, determining a type of the thermal feedback based on the elemental attribute of the attack action, wherein the type of the thermal feedback is determined as a hot feedback when the elemental attribute of the attack action related to the get-hit event is the fire element, the type of the thermal feedback is determined as a cold feedback when the elemental attribute of the attack action related to the get-hit event is the cold element, and the type of the thermal feedback is determined as a thermal grill feedback when the elemental attribute of the attack action related to the get-hit event is the electricity element; and controlling the feedback device to output the thermal feedback related to the get-hit event together with displaying a get-hit graphic so that the thermoelectric element performs a heat generating operation when the type of the thermal feedback is the hot feedback, performs a heat absorbing operation when the type of the thermal feedback is the cold feedback, and performs a thermal grill operation when the type of the thermal feedback is the thermal grill feedback, the thermal grill operation in which the heat generating operation and a heat absorbing operation is combined.

The method further include: determining an intensity of the thermal feedback based on at least one of an attack power of the attack action, a damage amount of the player due to the get-hit event, a ratio of the damage amount to a total health point of the player, and a remaining health point of the player, and the controlling may include controlling the feedback device to output the thermal feedback with the determined intensity.

When the attack action is performed by using a specific skill in the game, the elemental attribute of the attack action may be determined based on the elemental attribute assigned to the specific skill.

The method may further include: determining an intensity of the thermal feedback based on at least one of a level of the specific skill, a damage amount of the specific skill, and a tier of the specific skill, wherein the tier reflects a position of the specific skill in a skill tree having the specific skill and other skills of which the elemental attribute is same with the specific skill, and the controlling may include controlling the feedback device to output the thermal feedback with the determined intensity.

When the attack action is performed by using a melee weapon, the elemental attribute of the attack action may be determined based on the elemental attribute assigned to the melee weapon.

The method may further include: determining an intensity of the thermal feedback based on at least one of a grade of the melee weapon and an attack power of the melee weapon, and the controlling may include controlling the feedback device to output the thermal feedback with the determined intensity.

When the attack action is performed by using a ranged weapon, the elemental attribute of the attack action may be determined based on the elemental attribute assigned to the ranged weapon or the elemental attribute assigned to a projectile of the ranged weapon.

The elemental attribute of the attack action may be determined by the elemental attribute assigned to the projectile when the projectile has the elemental attribute or the elemental attribute of the attack action may be determined by the elemental attribute assigned to the ranged weapon when the projectile does not have a the elemental attribute.

The method may further include: determining an intensity of the thermal feedback based on at least one of a grade of the ranged weapon, an attack power of the ranged weapon, a grade of the projectile, and an attack power of the projectile, and the controlling may include controlling the feedback device to output the thermal feedback with the determined intensity.

The method may further include: causing a debuff effect related to the get-hit event to the player, and the controlling may include controlling the feedback device to output the thermal feedback for a debuff duration of the debuff effect.

The controlling may include controlling the feedback device to decrease the intensity of the thermal feedback as the debuff duration passes.

The electronic game may include a two dimensional type, a virtual reality type and an augmented reality type.

Another aspect of the present disclosure is directed to a content reproduction device cooperating with a feedback device outputting a thermal feedback using a thermoelectric element, including: a memory storing a data; a communication module communicating with an external device; and a controller configured to: execute an electronic game including a player and an enemy character which attacks the player by performing an attack action having an elemental attribute, wherein the elemental attribute includes a fire element, a cold element and an electricity element, when the a get-hit event, reflecting that the player gets hit by the attack action, occurs in the game, determines a type of the thermal feedback based on the elemental attribute of the attack action, and controls, via the communication module, the feedback device to output the thermal feedback related to the get-hit event together with displaying a get-hit graphic, wherein the controller determines the type of the thermal feedback as a hot feedback when the elemental attribute of the attack action related to the get-hit event is the fire element, determines the type of the thermal feedback as a cold feedback when the elemental attribute of the attack action related to the get-hit event is the cold element, and determines the type of the thermal feedback as a thermal grill feedback when the elemental attribute of the attack action related to the get-hit event is the electricity element, and wherein the controller controls the thermoelectric element to perform a heat generating operation when the type of the thermal feedback is the hot feedback, to perform a heat absorbing operation when the type of the thermal feedback is the cold feedback, and to perform a thermal grill operation when the type of the thermal feedback is the thermal grill feedback, the thermal grill operation in which the heat generating operation and a heat absorbing operation is combined.

The controller may execute the game by loading the game from the memory in which the game is installed.

The controller may execute the game by loading, via the communication, the game from a game server storing the game.

The device may further include: a recording medium drive reading a recording medium; and the controller may execute the game by loading, via the recording medium drive, the game from the recording medium storing the game.

The device may further include: a display displaying an image; and the controller may display, via the display, a game graphic including the get-hit graphic.

The controller may control an external display to display a game graphic including the get-hit graphic.

The controller may determine an intensity of the thermal feedback based on at least one of an attack power of the attack action, a damage amount of the player due to the get-hit event, a ratio of the damage amount to a total health point of the player, and a remaining health point of the player, and control the feedback device to output the thermal feedback with the determined intensity.

When the attack action is performed by using a specific skill in the game, the controller may determine the elemental attribute of the attack action based on the elemental attribute assigned to the specific skill.

The controller may determine an intensity of the thermal feedback based on at least one of a level of the specific skill, a damage amount of the specific skill, and a tier of the specific skill, wherein the tier reflects a position of the specific skill in a skill tree having the specific skill and other skills of which the elemental attribute is same with the specific skill, and control the feedback device to output the thermal feedback with the determined intensity.

The controller may cause a debuff effect related to the get-hit event to the player, and control the feedback device to output the thermal feedback for a debuff duration of the debuff effect.

The controller may control, via the communication module, the feedback device to decrease the intensity of the thermal feedback as the debuff duration passes.

The electronic game may include a two dimensional type, a virtual reality type and an augmented reality type.

Another aspect of the present disclosure is directed to a method for providing a thermal feedback, performed by a feedback device, wherein the feedback device may include a thermoelectric element which performs a thermoelectric operation including a heat generating operation, a heat absorbing operation and a thermal grill operation in which the heat generating operation and the heat absorbing operation is combined, and a contact surface which is configured to contact with a body of a user, and outputs a thermal feedback by transmitting, via the contact surface, a heat generated due to the thermoelectric operation to the user, the method may include: connecting with a content reproduction device executing the game including a player and an enemy character which attacks the player by performing an attack action having an elemental attribute, wherein the elemental attribute includes a fire element, a cold element and an electricity element; when the player gets hit in the game by the attack action of which the elemental attribute is the fire element, outputting a hot feedback by applying a forward power to the thermoelectric element to perform the heat generating operation, when the player gets hit in the game by the attack action of which the elemental attribute is the cold element, outputting a cold feedback by applying a reverse power to the thermoelectric element to perform the heat absorbing operation, and when the player gets hit in the game by the attack action of which the elemental attribute is the electricity element, outputting a thermal grill feedback by applying, simultaneously or alternatively, the forward power and the reverse power to the thermoelectric element to perform the thermal grill operation.

Another aspect of the present disclosure is directed to a feedback device for outputting a thermal feedback corresponding to an elemental attribute in an electronic game, wherein the feedback device cooperates with a content reproduction executing the game including a player and an enemy character which attacks the player by performing an attack action having the elemental attribute, the device may include: a heat outputting module including a thermoelectric element which performs a thermoelectric operation including a heat generating operation, a heat absorbing operation and a thermal grill operation in which the heat generating operation and the heat absorbing operation is combined, a power terminal supplying a power to the thermoelectric element, and a contact surface which is configured to contact with a body of a user, wherein the heat outputting module outputs the thermal feedback by transmitting, via the contact surface, a heat generated due to the thermoelectric operation to the user; and a feedback controller configured to: output a hot feedback by applying a forward power to the thermoelectric element to perform the heat generating operation when the player gets hit in the game by the attack action of which the elemental attribute is a fire element, output a cold feedback by applying a reverse power to the thermoelectric element to perform the heat absorbing operation when the player gets hit in the game by the attack action of which the elemental attribute is a cold element, and output a thermal grill feedback by applying, simultaneously or alternatively, the forward power and the reverse power to the thermoelectric element to perform the thermal grill operation when the player gets hit in the game by the attack action of which the elemental attribute is an electricity element.

The thermoelectric element may be provided as a thermoelectric couple array having a plurality of thermoelectric couple groups which is able to be controlled individually. And when the feedback controller may apply the forward power to a first group including one portion of the thermoelectric groups and apply the reverse power to a second group including another portion of the thermoelectric groups when the player in the game gets hit by the attack action of which the elemental attribute is the electricity element.

Another aspect of the present disclosure is directed to a system for providing a thermal feedback, including: a content reproduction device executing an electronic game; a display displaying an image related to the game; and a feedback device connecting with the content reproduction device and outputting a thermal feedback using a thermoelectric element, wherein the content reproduction device may include: a first communication module communicating with the feedback device, and a controller configured to: execute the game including a player and an enemy character which attacks the player by performing an attack action having an elemental attribute, wherein the elemental attribute includes a fire element, a cold element and an electricity element, and when the a get-hit event, reflecting that the player gets hit by the attack action, occurs in the game, display, via the display, a get-hit graphic related to the get-hit event, determine a type of the thermal feedback based on the elemental attribute of the attack action, and control, via the first communication module, the feedback device to output the thermal feedback related to the get-hit event together with displaying the get-hit graphic, wherein the controller determines the type of the thermal feedback as a hot feedback when the elemental attribute of the attack action related to the get-hit event is the fire element, determines the type of the thermal feedback as a cold feedback when the elemental attribute of the attack action related to the get-hit event is the cold element, and determines the type of the thermal feedback as a thermal grill feedback when the elemental attribute of the attack action related to the get-hit event is the electricity element, wherein the feedback device may include: a second communication module communicating with the content reproduction device, a heat outputting module including a thermoelectric element which performs a thermoelectric operation including a heat generating operation, a heat absorbing operation and a thermal grill operation in which the heat generating operation and the heat absorbing operation is combined, a power terminal supplying a power to the thermoelectric element, and a contact surface which is configured to contact with a body of a user, wherein the heat outputting module outputs the thermal feedback by transmitting, via the contact surface, a heat generated due to the thermoelectric operation to the user, and a feedback controller configured to: receives, via the second communication module, the type of the thermal feedback, and apply the power to the thermoelectric element to output the thermal feedback of the received type, and wherein the feedback controller applies, upon the receipt of the type indicating the hot feedback, a forward power to the thermoelectric element to perform the heat generating operation, applies upon the receipt of the type indicating the cold feedback, a reverse power to the thermoelectric element to perform the heat absorbing operation, and applies, upon the receipt of the type indicating the thermal grill feedback, the forward power and the reverser power, simultaneously or alternatively, to the thermoelectric element to perform the thermal grill operation.

Another aspect of the present disclosure is directed to a method for providing a thermal feedback related to an electronic game, performed by a content reproduction device which executes the electronic game and cooperates with a feedback device outputting a thermal feedback using a thermoelectric element, the method may include: executing the game including a player performing a specific action having an elemental attribute, wherein the elemental attribute includes a fire element, a cold element and an electricity element; causing the player to perform the specific action according to a user command; displaying a graphic related to the specific action; determining a type of the thermal feedback based on the element attribute, wherein the type is determined as a hot feedback when the elemental attribute of the specific action is the fire element, the type is determined as a cold feedback when the elemental attribute of the specific action is the cold element, and the type is determined as a thermal grill feedback when the elemental attribute of the specific action is the electricity element, and controlling the feedback device to output the thermal feedback together with displaying the graphic related to the specific action so that the thermoelectric element performs a heat generating operation when the type is the hot feedback, performs a heat absorbing operation when the type is the cold feedback, and performs a thermal grill operation when the type is the thermal grill feedback, the thermal grill operation in which the heat generating operation and a heat absorbing operation is combined.

The specific action may include at least one of an attack action attacking an enemy character in the game and a buffing action helping a player in the game.

The specific action may be an attack action attacking an enemy character in the game. The method may further include: determining an intensity of the thermal feedback based on at least one of an attack power of the attack action, a skill property related to the attack action and a weapon property related to the attack action. The controlling may include controlling the feedback device to output the thermal feedback with the determined intensity. And the skill property may include at least one of a skill level, a skill damage and a skill tier in a skill tree including a plurality of skills of a same elemental attribute, and the weapon property may include at least one of a weapon grade, a weapon attack power, a projectile grade and a projectile attack power.

The controlling may include controlling the feedback device to output the thermal feedback for a casting duration of the specific action.

The method may further include: controlling the feedback device to increase the intensity of the thermal feedback as the casting duration passes.

The controlling may include when a result of the specific action remains for a remaining duration, controlling the feedback device to maintain outputting the thermal feedback for the remaining duration.

The method may further include: controlling the feedback device to decrease the intensity of the thermal feedback as the remaining duration passes.

The electronic game may include a two dimensional type, a virtual reality type and an augmented reality type.

Another aspect of the present disclosure is directed to a content reproduction device cooperating with a feedback device outputting a thermal feedback using a thermoelectric element, including: a memory storing a data; a communication module communicating with an external device; and a controller configured to: execute the game including a player performing a specific action having an elemental attribute, wherein the elemental attribute includes a fire element, a cold element and an electricity element, cause the player to perform the specific action according to a user command, display a graphic related to the specific action, determine a type of the thermal feedback based on the element attribute of the specific action, and control, via the communication module, the feedback device to output the thermal feedback together with displaying of the graphic related to the specific action, wherein the controller determines the type as a hot feedback when the elemental attribute of the specific action is the fire element, determines the type as a cold feedback when the elemental attribute of the specific action is the cold element, and determines the type as a thermal grill feedback when the elemental attribute of the specific action is the electricity element, and wherein the controller controls the thermoelectric element to perform a heat generating operation when the type is the hot feedback, controls the thermoelectric element to perform a heat absorbing operation when the type is the cold feedback, and controls the thermoelectric element to perform a thermal grill operation when the type is the thermal grill feedback, the thermal grill operation in which the heat generating operation and the heat absorbing operation is combined.

The specific action may include at least one of an attack action attacking an enemy character in the game and a buffing action helping a player in the game.

The specific action may be an attack action attacking an enemy character in the game. The controller may determine an intensity of the thermal feedback based on at least one of an attack power of the attack action, a skill property related to the attack action and a weapon property related to the attack action and controls, via the communication module, the feedback device to output the thermal feedback with the determined intensity. And the skill property may include at least one of a skill level, a skill damage and a skill tier in a skill tree including a plurality of skills of a same elemental attribute, and the weapon property may include at least one of a weapon grade, a weapon attack power, a projectile grade and a projectile attack power.

The controller may control the feedback device to output the thermal feedback for a casting duration of the specific action.

The controller may control the feedback device to increase the intensity of the thermal feedback as the casting duration passes.

When a result of the specific action remains for a remaining duration, the controller may control the feedback device to maintain outputting the thermal feedback for the remaining duration.

The controller may control the feedback device to decrease the intensity of the thermal feedback as the remaining duration passes.

Another aspect of the present disclosure is directed to a method for providing a thermal feedback, performed by a feedback device, wherein the feedback device may include a thermoelectric element performing a thermoelectric operation including at least one of a heat generating operation, a heat absorbing operation and a thermal grill feedback in which the heat generating operation and the heat absorbing operation is combined, and a contact surface which is configured to contact with a body of a user and transmits a heat generated by the thermoelectric operation, the method may include: connecting with a content reproduction device executing an electronic game, wherein the game includes a player performing an attack action having an elemental attribute, wherein the elemental attribute includes a fire element, a cold element and an electricity element; when the player performs the attack action of the fire element, outputting a hot feedback by applying a forward power to the thermoelectric element to perform the heat generating operation; when the player performs the attack action of the cold element, outputting a cold feedback by applying a reverse power to the thermoelectric element to perform the heat absorbing operation; and when the player performs the attack action of the electricity element, outputting a thermal grill feedback by applying, simultaneously or alternatively, the forward power and the reverse power to the thermoelectric element to perform the thermal grill operation.

Another aspect of the present disclosure is directed to a feedback device for outputting a thermal feedback correspond to an elemental attribute of an attack action, wherein the feedback device cooperates with a content reproduction device executing an electronic game which includes a player performing the attack action having the elemental attribute, the elemental attribute including a fire element, a cold element and an electricity element, the device may include: an input module acquiring a user input; a heat outputting module including a thermoelectric element performing a thermoelectric operation including a heat generating operation, a heat absorbing operation and a thermal grill operation in which the heat generating operation and the heat absorbing operation is combined, a power terminal supplying a power to the thermoelectric element, and a contact surface which is provided on one side of the thermoelectric element and is configured to contact with a body part of a user, wherein the heat outputting module outputs the thermal feedback by transmitting, via the contact surface, a heat generated due to the thermoelectric operation to the user; and a feedback controller configured to: output, via the heat outputting module, a hot feedback by applying a forward power to the thermoelectric element to perform the heat generating operation when the controller receives, via the input module, the user input instructing the attack action having the fire element, output, via the heat outputting module, a hot feedback by applying a reverse power to the thermoelectric element to perform the heat absorbing operation when the controller receives, via the input module, the user input instructing the attack action having the cold element, wherein a current direction of the reverse power is opposite to a current direction of the forward power, and output, via the heat outputting module, a hot feedback by applying, simultaneously or alternatively, the forward power and reverse power to the thermoelectric element to perform the thermal grill generating operation when the controller receives, via the input module, the user input instructing the attack action having the electricity element.

The thermoelectric element may be provided as a thermoelectric couple array having a plurality of thermoelectric couple groups which are able to be controlled individually. And the feedback controller may apply, upon the receipt of the user input instructing the attack action having the electricity element, the forward power to a first group being one portion of the thermoelectric couple groups and the reverse power to a second group being another portion of the thermoelectric couple groups.

Another aspect of the present disclosure is directed to a method for providing a thermal feedback related to a multimedia content, performed by a content reproduction device which executes the multimedia content including an electronic game and a feedback application and cooperates with a feedback device outputting a thermal feedback using a thermoelectric element, the method may include: executing the multimedia content, wherein the multimedia content includes a player and a virtual object, implements a get-hit event in which the player gets hit by the virtual object, and assigns, to the player, a thermal resistance related to the get-hit event; generating the get-hit event in the game; setting an intensity of the thermal feedback based on the get-hit event; adjusting the intensity of the thermal feedback based on the thermal resistance; and controlling the feedback device to output the thermal feedback having the adjusted intensity.

The get-hit event may include at least one of a hot-hit event and a cold-hit event, and the thermal feedback may include at least of a hot feedback and a cold feedback. The method may further include: determining a type of the thermal feedback based on a type of the get-hit event. And the controlling may include controlling the feedback device to output the thermal feedback of the determined type of the thermal feedback.

The thermal resistance may include at least one of a hot resistance corresponding to the hot-hit event and a cold resistance corresponding to the cold-hit event. And the adjusting may include adjusting the intensity of the thermal feedback based on the thermal resistance corresponding to the type of the generated get-hit event.

The method may further include: calculating the thermal resistance based on a thermal resistance assigned to the player and a thermal resistance assigned to an equipment equipped by the player.

The adjusting may include reducing the intensity of the thermal feedback.

The intensity of the thermal feedback may include a plurality of intensity levels. The setting may include obtaining, from the plurality of intensity levels, a first intensity level as the intensity of the thermal feedback related to the get-hit event. And the adjusting may include obtaining, from the plurality of the intensity levels, a second intensity level lower than the first intensity level.

The adjusting may include determining the second intensity based on the first intensity and the thermal resistance.

The obtaining the second intensity level may be performed when the first intensity level is not a lowest intensity level among the plurality of the intensity levels. And the adjusting may further include maintaining the first intensity level as the intensity of the thermal feedback related to the get-hit event when the first intensity level is the lowest intensity level among the plurality of the intensity levels.

Another aspect of the present disclosure is directed to a content reproduction device, wherein the content reproduction device cooperates with a feedback device outputting a thermal feedback using a thermoelectric element, including: a memory storing a data; a communication module communicating with an external device; and a controller configured to: execute a multimedia content including an electronic game and a feedback application, wherein the multimedia content includes a player and a virtual object, implements a get-hit event in which the player gets hit by the virtual object, and assigns, to the player, a thermal resistance related to the get-hit event, set, upon an occurrence of the get-hit event, an intensity of the thermal feedback based on the get-hit event, adjust the intensity of the thermal feedback based on the thermal resistance, and control, via the communication module, the feedback device to output the thermal feedback having the adjusted intensity.

The get-hit event may include at least one of a hot-hit event and a cold-hit event, and the thermal feedback may include at least of a hot feedback and a cold feedback. And the controller may determine a type of the thermal feedback based on a type of the get-hit event, and control the feedback device to output the thermal feedback of the determined type of the thermal feedback.

The thermal resistance may include at least one of a hot resistance corresponding to the hot-hit event and a cold resistance corresponding to the cold-hit event. And the controller may adjust the intensity of the thermal feedback based on the thermal resistance corresponding to the type of the generated get-hit event.

The controller may calculate the thermal resistance based on a thermal resistance assigned to the player and a thermal resistance assigned to an equipment equipped by the player.

The controller may adjust the intensity of the thermal feedback by reducing the intensity of the thermal feedback considering the thermal resistance.

The intensity of the thermal feedback may include a plurality of intensity levels. The controller may set the intensity of the thermal feedback related to the get-hit event to a first intensity among the plurality of the intensity levels, and adjust the intensity of the thermal feedback related to the get-hit event to a second intensity level, which is lower than the first intensity level, among the plurality of the intensity levels.

The controller may determine the second intensity based on the first intensity and the thermal resistance.

The controller may adjust the intensity of the thermal feedback related to the get-hit event to the second intensity level when the first intensity level is not a lowest intensity level among the plurality of the intensity levels, and maintain the first intensity level as the intensity of the thermal feedback related to the get-hit event when the first intensity level is the lowest intensity level among the plurality of the intensity levels.

Another aspect of the present disclosure is directed to a feedback device, wherein the feedback device cooperates with a content reproduction device executing a multimedia content provided as an electronic game or a feedback application, and wherein the multimedia content includes a player and a virtual object, implements a get-hit event in which the player gets hit by the virtual object, and assigns, to the player, a thermal resistance related to the get-hit event, including: a casing having a grip portion gripped by a user and forming an exterior of the feedback device; an input module receiving the user input according to a manipulation of the user; a communication module communicating with the content reproduction device; a heat outputting module including a thermoelectric element performing a thermoelectric operation, a power terminal applying a power to the thermoelectric element, and a contact surface which is disposed on the grip portion and configured to contact with the user, wherein the heat outputting module outputs the thermal feedback by transmitting, via the contact surface, a heat generated by the thermoelectric operation to the user; and a controller configured to: receive, via the input module, the user input, send, via the communication module, the user input to the content reproduction device to cause the player to act according to the manipulation of the user, receive, via the communication module, an intensity of the thermal feedback from the content reproduction device, select an operating voltage among a plurality of pre-set voltage values based on the intensity of the thermal feedback, generate an operating power having the operating voltage, and apply the operating power to the power terminal so that the heat outputting module outputs the thermal feedback, and wherein the controller applies a first operating voltage when the get-hit event occurs, in the game, to the player who has a first thermal resistance, and applies a second operating voltage greater than the first operating voltage when the get-hit event occurs, in the game, to the player who has a second thermal resistance greater than the first thermal resistance.

Another aspect of the present disclosure is directed to a method for providing a thermal feedback related to a multimedia content, performed by a content reproduction device, wherein the content reproduction device executes the multimedia content including an electronic game and a feedback application and cooperates with a feedback device outputting a thermal feedback using a thermoelectric element, including: executing the multimedia content, wherein the multimedia content includes a thermal event causing the thermal feedback, a player and an equipment to which a thermal resistance is assigned; when the thermal event occurs, determining whether or not the player equips the equipment; when the player does not equip the equipment, setting an intensity of the thermal feedback to a first intensity level; when the player equips the equipment, setting the intensity of the thermal feedback to a second intensity level which is different from the first intensity level; and controlling the feedback device to output the thermal feedback according to the determined intensity.

The second intensity level may be smaller than the first intensity level.

The second intensity level may be calculated based on the first intensity level and the thermal resistance of the equipment.

Another aspect of the present disclosure is directed to a method for providing a thermal feedback related to a multimedia content, performed by a content reproduction device, wherein the content reproduction device executes the multimedia content including an electronic game and a feedback application and cooperates with a feedback device outputting a thermal feedback using a thermoelectric element, including: executing the multimedia content, wherein the multimedia content includes a thermal event causing the thermal feedback, a player and an equipment to which a thermal resistance is assigned; when the thermal event occurs, determining whether or not the player equips the equipment; determining whether or not to output the thermal feedback related to the thermal feedback based on whether or not the player equips the equipment; and controlling the feedback device to output the thermal feedback only when the player does not equip the equipment.

Another aspect of the present disclosure is directed to a content reproduction device, wherein the content reproduction device cooperates with a feedback device outputting a thermal feedback using a thermoelectric element, including: a memory storing a data; a communication module communicating with an external device; and a controller configured to: execute the multimedia content, wherein the multimedia content is provided as an electronic game or a feedback application and includes a thermal event causing the thermal feedback, a player and an equipment to which a thermal resistance is assigned, determine, upon an occurrence of the thermal event, whether or not the player equips the equipment, set an intensity of the thermal feedback to a first intensity level when the player does not equip the equipment, set the intensity of the thermal feedback to a second intensity level which is different from the first intensity level when the player equips the equipment, and control, via the communication module, the feedback device to output the thermal feedback according to the determined intensity.

The second intensity level may be smaller than the first intensity level.

The controller may calculate the second intensity level based on the first intensity level and the thermal resistance assigned to the equipment.

Another aspect of the present disclosure is directed to a content reproduction device, wherein the content reproduction device cooperates with a feedback device outputting a thermal feedback using a thermoelectric element, including: a memory storing a data; a communication module communicating with an external device; and a controller configured to: execute the multimedia content, wherein the multimedia content includes a thermal event causing the thermal feedback, a player and an equipment to which a thermal resistance is assigned, determine, upon an occurrence of the thermal event, whether or not the player equips the equipment, determine whether or not to output the thermal feedback related to the thermal feedback based on whether or not the player equips the equipment, and control, via the communication module, the feedback device to output the thermal feedback only when the player does not equip the equipment.

Another aspect of the present disclosure is directed to a feedback device for outputting a thermal feedback, wherein the feedback device cooperates with a content reproduction device executing a multimedia content provided as an electronic game or a feedback application, and wherein the multimedia content includes a thermal event causing the thermal feedback, a player and an equipment to which a thermal resistance is assigned, including: a casing having a grip portion gripped by a user and forming an exterior of the feedback device; an input module receiving the user input according to a manipulation of the user; a communication module communicating with the content reproduction device; and a heat outputting module including a thermoelectric element performing a thermoelectric operation, a power terminal supplying a power to the thermoelectric element, and a contact surface which is disposed on the grip portion and configured to contact with the user, wherein the heat outputting module outputs the thermal feedback by transmitting, via the contact surface, a heat generated by the thermoelectric operation to the user; and a controller configured to: obtain, via the input module, the user input, send, via the communication module, the user input to the content reproduction device to cause the user to act according to the manipulation of the user, receive, via the communication module, a message requesting outputting the thermal feedback from the content reproduction device, and apply, upon the receipt of the message, the power to the power terminal so that the heat outputting module outputs the thermal feedback, wherein when the controller outputs, via the heat outputting module, the thermal feedback upon an occurrence of the thermal event during the reproduction of the multimedia content, the controller performs a first operation in which whether or not to output the thermal feedback is determined based on whether or not the player equips the equipment or a second operation in which an intensity of the thermal feedback is adjusted based on whether or not the player equips the equipment, wherein the controller performs the first operation by applying an operating power to the thermoelectric element when the player does not equip the equipment and by not applying the operating power to the thermoelectric element when the player equips the equipment, and wherein the controller performs the second operation by applying a first operating power to the thermoelectric element when the player does not equip the equipment and by applying a second operating power of which a voltage magnitude is smaller than that of the first operating power.

Another aspect of the present disclosure is directed to a method for providing a thermal feedback, performed by a content reproduction device cooperating with a feedback device outputting the thermal feedback using a thermoelectric element, including: executing an electronic game including a player acting according to a manipulation of a user, wherein the player has health points and dies in the game when all of the health points is exhausted; obtaining at least one of an intensity of the thermal feedback and a type of the thermal feedback according to a change of the health points during a reproduction of the game; and controlling the feedback device to output the thermal feedback according to the determined at least one of the intensity and the type, wherein the obtaining includes at least one of: obtaining the intensity of the thermal feedback based on a change amount of the health points, obtaining the intensity of the thermal feedback based on a ratio of the change amount to a total amount of the health points, and obtaining the type of the thermal feedback based on whether the health points is increased or decreased.

In a step of the obtaining the intensity of the thermal feedback based on the change amount of the health points, a first intensity may be obtained when the change amount is a first value and a second intensity greater than the first intensity may be obtained when the change amount is a second value greater than the first value.

In a step of the obtaining the intensity of the thermal feedback based on the ratio of the change amount to the total amount of the health points, a first intensity may be obtained when the ratio is a first value and a second intensity greater than the first intensity may be obtained when the ratio is a second value greater than the first value.

In a step of the obtaining the intensity of the thermal feedback based on whether the health points is increased or decreased, one of a hot feedback and a cold feedback may be obtained as the type of the thermal feedback when the health points is increased and another of the hot feedback and the cold feedback may be obtained as the type of the thermal feedback when the health points is decreased.

Another aspect of the present disclosure is directed to a method for providing a thermal feedback, performed by a content reproduction device cooperating with a feedback device outputting the thermal feedback using a thermoelectric element, including: executing an electronic game including a player acting according to a manipulation of a user, wherein the player has health points and dies in the game when all of the health points is exhausted; determining at least one of whether or not to output the thermal feedback, an intensity of the thermal feedback and a type of the thermal feedback based on at least one of a remaining amount of the health points and a ratio of the remaining amount to a total amount of the health point, during a reproduction of the game; and controlling the feedback device to output the thermal feedback according to the determined at least one of the whether or not to output the thermal feedback, the intensity and the type.

Another aspect of the present disclosure is directed to a content reproduction device, wherein the content reproduction device cooperates with a feedback device outputting the thermal feedback using a thermoelectric element, including: a memory storing a data; a communication module communicating with an external device; and a controller configured to: execute an electronic game including a player acting according to a manipulation of a user, wherein the player has health points and dies in the game when all of the health points is exhausted, obtain at least one of an intensity of the thermal feedback and a type of the thermal feedback according to a change of the health points during a reproduction of the game; and control, via the communication module, the feedback device to output the thermal feedback according to the determined at least one of the intensity and the type, wherein the controller determines the intensity of the thermal feedback based on at least one of a change amount of the health points, and determines the type of the thermal feedback based on whether the health points is increased or decreased.

The controller may obtain a first intensity as the intensity of the thermal feedback when the change amount is a first value, and obtain a second intensity greater than the first intensity as the intensity of the thermal feedback when the change amount is a second value greater than the first value.

The controller may obtain a first intensity as the intensity of the thermal feedback when the ratio is a first value, and obtain a second intensity greater than the first intensity as the intensity of the thermal feedback when the ratio is a second value greater than the first value.

The controller may obtain one of a hot feedback and a cold feedback as the type of the thermal feedback when the health points is increased, and obtain another of the hot feedback and the cold feedback as the type of the thermal feedback when the health points is decreased.

Another aspect of the present disclosure is directed to a content reproduction device, wherein the content reproduction device cooperates with a feedback device outputting the thermal feedback using a thermoelectric element, including: a memory storing a data; a communication module communicating with an external device; and a controller configured to: execute an electronic game including a player acting according to a manipulation of a user, wherein the player has health points and dies in the game when all of the health points is exhausted, determine at least one of whether or not to output the thermal feedback, an intensity of the thermal feedback and a type of the thermal feedback based on at least one of a remaining amount of the health points and a ratio of the remaining amount to a total amount of the health point, during a reproduction of the game, and control, via the communication module, the feedback device to output the thermal feedback according to the determined at least one of the whether or not to output the thermal feedback, the intensity and the type.

Another aspect of the present disclosure is directed to a feedback device for outputting a thermal feedback, wherein the feedback device cooperates with a content reproduction device executing an electronic game including a player acting according to a manipulation of a user, and wherein the player has health points and dies in the game when all of the health points is exhausted, including: a casing having a grip portion gripped by a user and forming an exterior of the gaming controller; an input module receiving the user input according to a manipulation of the user; a communication module communicating with the content reproduction device; a heat outputting module including a thermoelectric element performing a thermoelectric operation, a power terminal applying a power to the thermoelectric element, and a contact surface which is disposed on the grip portion and configured to contact with the user, wherein the heat outputting module outputs the thermal feedback by transmitting, via the contact surface, a heat generated by the thermoelectric operation to the user; and a controller configured to receive, via the communication module, the user input, send, via the communication module, the received user input to the content reproduction device to cause the player acts corresponding to the manipulation of the user, and apply an operating power according to a change of the health points to the power terminal so that the heat outputting module outputs the thermal feedback corresponding to the change of the health points, wherein the controller performs at least one of a first operation, a second operation and a third operation, wherein the controller performs the first operation by applying a first operating power when a change amount of the health points or a ratio of the change amount to a total amount of the health points is a first value and applying a second operating power of which the voltage magnitude is greater than that of the first operating power when the change amount or the ratio is a second value greater than the first value, wherein the controller performs the second operation by applying one of a forward power for the hot feedback and a reverser power for the cold feedback when the health points is increased and applying another of the forward power and the reverser power when the health points is decreased, and wherein the controller performs the third operation by applying a third operating power when a remaining amount of the health points or a ratio of the remaining amount to the total amount is a third value and applying a fourth operating power of which the voltage magnitude is greater than that of the third operating power when the remaining amount or the ratio of the remaining amount is a fourth value smaller than the third value.

Another aspect of the present disclosure is directed to a method for providing a thermal feedback, performed by a content reproduction device cooperating with a feedback device outputting the thermal feedback using a thermoelectric element, including: executing a multimedia content provided as an electronic game or a feedback application, wherein the multimedia content includes a virtual heat source to which a heat transferring attribute including a conduction type and a radiation type is assigned; determining, based on the heat transferring attribute of the virtual heat source, a virtual heat transferring amount transferred from the virtual heat source to a player of the multimedia content, obtaining an intensity of the thermal feedback based on the determined virtual heat transferring amount; and controlling the feedback device to output the thermal feedback having the determined intensity. wherein the determining the virtual heat transferring amount includes calculating the virtual heat transferring amount based on a temperature value of the virtual heat source when the heat transferring attribute of the virtual heat source is the conduction type, and calculating the virtual heat transferring amount based on the temperature value and a distance between the player and the virtual heat source when the heat transferring attribute of the virtual heat source is the radiation type.

The determining may include when the player is separated from the heat source of the conduction type, determining that the virtual heat source of the conduction type transfers no virtual heat to the player or that the virtual heat transferring amount is zero (0).

In a step of the calculating the virtual heat transferring amount related to the virtual heat source of the radiation type, the virtual heat transferring amount may get greater as the distance gets smaller.

In a step of the calculating the virtual heat transferring amount related to the virtual heat source of the radiation type, a first heat amount may be obtained as the virtual heat transferring amount when the distance is a first distance, and a second heat amount greater than the first heat amount may be obtained as the virtual heat transferring amount when the distance is a second distance smaller than the first distance.

The heat transferring attribute may further include a directional type. The determining may further include calculating the virtual heat transferring amount based on the temperature value of the virtual heat source when the heat transferring attribute of the virtual heat source is the directional type, the virtual heat transferring amount related to the virtual heat source of the directional type being constant even when the distance between the player and the virtual heat source varies.

The heat transferring attribute may further include an area type. The determining may further include calculating the virtual heat transferring amount based on the temperature value of the virtual heat source when the heat transferring attribute of the virtual heat source is the area type. And a virtual heat may transfer only when the distance between the player and the virtual heat source of the area type is smaller than a predetermined distance.

The method may further include: determining whether a type of the thermal feedback is a hot feedback or a cold feedback based on whether the virtual heat transferring amount is positive or negative. And the controlling may include controlling the feedback device to outputs the thermal feedback having the determined type of the thermal feedback.

Another aspect of the present disclosure is directed to a content reproduction device, wherein the content reproduction device cooperates with a feedback device outputting the thermal feedback using a thermoelectric element, including: a memory storing a data; a communication module communicating with an external device; and a controller configured to: execute a multimedia content provided as an electronic game or a feedback application, wherein the multimedia content includes a virtual heat source to which a heat transferring attribute including a conduction type and a radiation type is assigned, determine, based on the heat transferring attribute of the virtual heat source, a virtual heat transferring amount transferred from the virtual heat source to a player of the multimedia content, obtain an intensity of the thermal feedback based on the determined virtual heat transferring amount, and control, via the communication module, the feedback device to output the thermal feedback having the determined intensity. wherein the controller calculates the virtual heat transferring amount the virtual heat transferring amount based on a temperature value of the virtual heat source when the heat transferring attribute of the virtual heat source is the conduction type, and calculates the virtual heat transferring amount based on the temperature value and a distance between the player and the virtual heat source when the heat transferring attribute of the virtual heat source is the radiation type.

The controller may determine that the virtual heat source of the conduction type transfers no virtual heat to the player or that the virtual heat transferring amount is 0 when the player is separated from the heat source of the conduction type.

The controller may determine that the virtual heat transferring amount related to the virtual heat source of the radiation type gets greater as the distance gets smaller The controller may determine that the virtual heat transferring amount is a first heat amount when the distance is a first distance, and determine that the virtual heat transferring amount a second heat amount greater than the first heat amount when the distance is a second distance smaller than the first distance.

The heat transferring attribute may further include a directional type. And the controller may calculate the virtual heat transferring amount related to the virtual heat source of the directional type based on the temperature value of the virtual heat source, and may determine the virtual heat transferring amount related to the virtual heat source of the directional type being constant even when the distance between the player and the virtual heat source varies.

The heat transferring attribute may further include an area type. And the controller may calculate the virtual heat transferring amount related to the virtual heat source of the area type based on the temperature value of the virtual heat source, and determine that a virtual heat transfers only when the distance between the player and the virtual heat source of the area type is smaller than a predetermined distance.

The controller determine whether a type of the thermal feedback is a hot feedback or a cold feedback based on whether the virtual heat transferring amount is positive or negative, and control the feedback device to outputs the thermal feedback having the determined type of the thermal feedback.

Another aspect of the present disclosure is directed to a feedback device for outputting the thermal feedback, wherein the feedback device cooperates with a content reproduction device executing an electronic game or a feedback application which includes a virtual heat source, and outputs the thermal feedback corresponding to a virtual heat transferring amount transferred from the virtual heat source to a player of the game or the application, including: a heat outputting module including a thermoelectric element which performs a thermoelectric operation including a heat generating operation, a heat absorbing operation and a thermal grill operation in which the heat generating operation and the heat absorbing operation, a power terminal applying a power to the thermoelectric element, and a contact surface which is disposed on the grip portion and configured to contact with the user, wherein the heat outputting module outputs the thermal feedback by transmitting, via the contact surface, a heat generated by the thermoelectric operation to the user; and a controller configured to: control the thermoelectric element to output the thermal feedback reflecting the virtual heat transferring amount transferred by a conduction from a first virtual heat source to the player, by applying a first power to the power terminal when the player is contacted with the first virtual heat source and by stopping the application of the first power when the player is apart from the first virtual heat source, and control the thermoelectric element to output the thermal feedback reflecting the virtual heat transferring amount transferred by a radiation from a second virtual heat source of a different type than a first virtual heat source, by applying a second power to the power terminal when the player is spaced a first distance from the second virtual heat source and by applying a third power greater than the second power to the power terminal when the player is spaced a second distance smaller than the first distance the from the second virtual heat source.

Another aspect of the present disclosure is directed to a method for providing a thermal feedback, performed by a content reproduction device which executes a multimedia content provided as an electronic game or a feedback application and cooperates with a feedback device outputting a thermal feedback using a thermoelectric element, the method may include: executing the multimedia content, wherein the multimedia content includes a virtual object and a player, and implements an interaction between the player and the virtual object such as a touch or a grab, the virtual object having a thermal attribute including a temperature information and a texture information; changing an intensity of the thermal feedback according to at least one of a lasting duration of the interaction, the temperature information and the texture information; and controlling the feedback device to output the thermal feedback having the intensity.

The method may further include: setting a maximum intensity of the thermal feedback based on the temperature information, increasing the intensity as the lasting duration increases, and stopping changing the intensity of the thermal feedback when the intensity reaches the maximum intensity.

The changing may include adjusting an intensity change rate per time based on the texture information.

Another aspect of the present disclosure is directed to a content reproduction device, wherein the content reproduction device executes a multimedia content provided as an electronic game or a feedback application, and cooperates with a feedback device outputting the thermal feedback using a thermoelectric element, including: a heat outputting module including a thermoelectric element which performs a heat generating operation and a heat absorbing operation a power terminal applying a power to the thermoelectric element, and a contact surface which is disposed on the grip portion and configured to contact with the user, wherein the heat outputting module outputs the thermal feedback by transmitting, via the contact surface, a heat generated from the thermoelectric element to the user; a memory storing a data; a communication module communicating with an external device; and a controller configured to: execute the multimedia content, wherein the multimedia content includes a virtual object and a player, and implements an interaction between the player and the virtual object such as a touch or a grab, the virtual object having a thermal attribute including a temperature information and a texture information, change an intensity of the thermal feedback according to at least one of a lasting duration of the interaction, the temperature information and the texture information, control the feedback device to output the thermal feedback having the intensity.

The controller may set a maximum intensity of the thermal feedback based on the temperature information, increase the intensity as the lasting duration increases, and stop changing the intensity of the thermal feedback when the intensity reaches the maximum intensity.

The controller may adjust an intensity change rate per time based on the texture information.

Another aspect of the present disclosure is directed to a feedback device for outputting a thermal feedback, wherein the feedback device cooperates with a content reproduction device executing a multimedia content provided as an electronic game or a feedback application, and wherein the multimedia content includes a virtual object and a player, and implements an interaction between the player and the virtual object such as a touch or a grab, the virtual object having a thermal attribute including a temperature information and a texture information, the feedback device may include: a casing having a grip portion gripped by a user and forming an exterior of the feedback device; an input module receiving the user input according to a manipulation of the user; a communication module communicating with the content reproduction device; a heat outputting module including a thermoelectric element performing a thermoelectric operation, a power terminal applying a power to the thermoelectric element, and a contact surface which is disposed on the grip portion and configured to contact with the user, wherein the heat outputting module outputs the thermal feedback by transmitting, via the contact surface, a heat generated by the thermoelectric operation to the user; and a feedback controller configured to increase a voltage magnitude or a current magnitude of the power applied to the thermoelectric element as a lasting duration of the interaction increases when the interaction between the player and the virtual object is started according to the user's operation.

The feedback controller may increase the voltage magnitude or the current magnitude of the power with a first rate when the texture information of the virtual object indicates a tree, and increase the voltage magnitude or the current magnitude of the power with a second rate greater than the first rate when the texture information of the virtual object indicates a metal.

The feedback controller may set the maximum voltage or the maximum current to be different when the temperature information of the virtual object is different.

The feedback controller may set a change rate of the voltage magnitude or the current magnitude differently when the texture information of the virtual object is different.

Another aspect of the present disclosure is directed to a method for providing a thermal feedback, including: executing an electronic game using a physic engine supporting a collision processing function related to a collision between virtual objects, wherein the collision processing function includes a collision type in which a behavior of the virtual objects is calculated considering at least a momentum of the virtual objects and a trigger type in which one virtual object passes through another virtual object; determining the collision processing function related to a get-hit event which occurs when a player character gets hit by the virtual object is the collision type or the trigger type; deciding an intensity of the thermal feedback based on a result of the determination; and controlling, based on the intensity of the thermal feedback, an intensity of an thermoelectric operation performed by a feedback device, wherein the feedback device outputs the thermal feedback using a thermoelectric element performing the thermoelectric operation.

The deciding may include deciding the intensity of the thermal feedback based on the momentum calculated using the collision processing function of the collision type when the get-hit event relates to the collision type.

The intensity of the thermal feedback may get greater as the calculated momentum gets greater.

The deciding may include deciding the intensity of the thermal feedback to be a predetermined value when the get-hit event relates to the trigger type.

The deciding may include deciding the intensity of the thermal feedback based on at least one of an identification information of a first object which is the virtual object hitting the player character and an identification information of a second object which is the virtual object launching the first object when the get-hit event relates to the trigger type.

Another aspect of the present disclosure is directed to a content reproduction device, cooperating with a feedback device outputting a thermal feedback using a thermoelectric element, including: a memory storing a data; a communication module communicating with the feedback device; and a controller configured to: execute an electronic game using a physic engine supporting a collision processing function related to a collision between virtual objects, wherein the collision processing function includes a collision type in which a behavior of the virtual objects is calculated considering at least a momentum of the virtual objects and a trigger type in which one virtual object passes through another virtual object, determine the collision processing function related to a get-hit event which occurs when a player character gets hit by the virtual object is the collision type or the trigger type, decide an intensity of the thermal feedback based on a result of the determination, and control, via the communication module, an intensity of an thermoelectric operation performed by the thermoelectric element based on the intensity of the thermal feedback.

The controller may decide the intensity of the thermal feedback based on the momentum calculated using the collision processing function of the collision type when the get-hit event relates to the collision type.

The intensity of the thermal feedback may get greater as the calculated momentum gets greater.

The controller may decide the intensity of the thermal feedback to be a predetermined value when the get-hit event relates to the trigger type.

The controller may decide the intensity of the thermal feedback based on at least one of an identification information of a first object which is the virtual object hitting the player character and an identification information of a second object which is the virtual object launching the first object when the get-hit event relates to the trigger type.

Another aspect of the present disclosure is directed to a method for providing a thermal feedback, performed by a content reproduction device executing a multimedia content and cooperating with a plurality of feedback devices outputting a thermal feedback using a thermoelectric element, including: executing a virtual reality application providing a virtual space; obtaining a FOV (Field-Of-View) of the virtual space according to a direction of a user's sight detected from a HMD (Head-Mounted-Display); when a thermal event occurs in the virtual space, determining at least one target device among the plurality of the feedback devices based on an orientation of the thermal event with respect to the FOV; and transmitting a signal instructing outputting the thermal feedback to the target feedback device.

The determining may include determining that the at least one target device includes a first device grabbed by a right hand of the user and a second device grabbed by a left hand of the user when the thermal event is located in a central region of the FOV.

The method may further include: control the first device and the second device to output the thermal feedback with a same intensity.

The determining may include determining that the at least one target device includes a first device grabbed by a right hand of the user when the thermal event is located in a right region of the FOV and determining that the at least one target device includes a second device grabbed by a left hand of the user when the thermal event is located in a left region of the FOV.

The determining may include determining that the at least one target device includes a first device grabbed by a right hand of the user and a second device grabbed by a left hand of the user when the thermal event is located in a right region or a left region of the FOV. And the method may further include: adjusting an intensity of the thermal feedback of the first device and the second device differently.

The intensity of the thermal feedback of one of the first device and the second device may be greater than the intensity of the thermal feedback of another of the first device and the second device.

Another aspect of the present disclosure is directed to a content reproduction device, wherein the content reproduction device reproduces a multimedia content and cooperates with a plurality of feedback devices outputting a thermal feedback using a thermoelectric element, including: a memory storing a data; a communication module communicating with the feedback devices; a controller configured to execute a virtual reality application providing a virtual space, obtain a FOV (Field-Of-View) of the virtual space according to a direction of a user's sight detected from a HMD (Head-Mounted-Display), when a thermal event occurs in the virtual space, determine at least one target device among the plurality of the feedback devices based on an orientation of the thermal event with respect to the FOV, and transmit a signal instructing outputting the thermal feedback to the target feedback device.

The controller may determine that the at least one target device includes a first device grabbed by a right hand of the user and a second device grabbed by a left hand of the user when the thermal event is located in a central region of the FOV.

The controller may control the first device and the second device to output the thermal feedback with a same intensity.

The controller may determine that the at least one target device includes a first device grabbed by a right hand of the user when the thermal event is located in a right region of the FOV and determines that the at least one target device includes a second device grabbed by a left hand of the user when the thermal event is located in a left region of the FOV.

The controller may determine that the at least one target device includes a first device grabbed by a right hand of the user and a second device grabbed by a left hand of the user when the thermal event is located in a right region or a left region of the FOV, and adjusts an intensity of the thermal feedback of the first device and the second device differently.

The controller may determine that the intensity of the thermal feedback of one of the first device and the second device is greater than the intensity of the thermal feedback of another of the first device and the second device.

Another aspect of the present disclosure is directed to a method for providing a thermal feedback, including: executing a virtual reality application providing a virtual space, wherein the virtual space includes a virtual area to which a temperature attribute is assigned and a virtual object to which the temperature attribute is assigned; when an area event reflecting that a player character enters the virtual area occurs, control a feedback device to output the thermal feedback related to the area event, wherein the feedback device outputs the thermal feedback using a thermoelectric element performing a thermoelectric operation; detecting an occurrence of an object event reflecting that a player is influenced by the virtual object when the area event is lasting; and when the occurrence of the object event is detected during the area event, controlling the feedback device to override the thermal feedback related to the area event by the thermal feedback related to the object event.

The method may further include: detecting an occurrence of a new area event when the object event is lasting; and when the occurrence of the new area event is detected during the object event, controlling the feedback device to override the thermal feedback related to the object event by the thermal feedback related to the new area event.

The method may further include: when the object event or outputting the thermal feedback related to the object event is finished, controlling the feedback device to restart outputting the thermal feedback related to the area event.

Another aspect of the present disclosure is directed to a content reproduction device, wherein the content reproduction device reproduces a multimedia content and cooperates with at least one feedback device outputting a thermal feedback using a thermoelectric element, including: a memory storing a data; a communication module communicating with the feedback device; a controller configured to: execute a virtual reality application providing a virtual space, wherein the virtual space includes a virtual area to which a temperature attribute is assigned and a virtual object to which the temperature attribute is assigned, when an area event reflecting that a player character enters the virtual area occurs, control, via the communication module, the feedback device to output the thermal feedback related to the area event, wherein the feedback device outputs the thermal feedback using a thermoelectric element performing a thermoelectric operation, detect an occurrence of an object event reflecting that a player is influenced by the virtual object when the area event is lasting, and when the occurrence of the object event is detected during the area event, control, via the communication module, the feedback device to override the thermal feedback related to the area event by the thermal feedback related to the object event.

The controller may detect an occurrence of a new area event when the object event is lasting; and when the occurrence of the new area event is detected during the object event, control, via the communication module, the feedback device to override the thermal feedback related to the object event by the thermal feedback related to the new area event.

When the object event or outputting the thermal feedback related to the object event is finished, the controller may control, via the communication module, the feedback device to restart outputting the thermal feedback related to the area event.

Another aspect of the present disclosure is directed to a method for providing a thermal feedback, including: executing a virtual reality application providing a virtual space, wherein the virtual space includes a virtual area to which a temperature attribute is assigned, the virtual area having a global area and a local area included in the global area; when a player character enters the global area, controlling a feedback device to output the thermal feedback corresponding to the temperature attribute of the global area, wherein the feedback device outputs the thermal feedback using a thermoelectric element performing a thermoelectric operation; and when the player character enters the local area, controlling the feedback device to override the thermal feedback corresponding to the temperature attribute of the global area with the thermal feedback corresponding to the temperature attribute of the local area.

The method may further include: when the player character departs the local area, controlling the feedback device to restart outputting the thermal feedback corresponding to the temperature attribute of the local area.

Another aspect of the present disclosure is directed to a content reproduction device, wherein the content reproduction device reproduces a multimedia content and cooperates with at least one feedback device outputting a thermal feedback using a thermoelectric element, including: a memory storing a data; a communication module communicating with the feedback device; a controller configured to: execute a virtual reality application providing a virtual space, wherein the virtual space includes a virtual area to which a temperature attribute is assigned, the virtual area having a global area and a local area included in the global area, when a player character enters the global area, control, via the communication module, a feedback device to output the thermal feedback corresponding to the temperature attribute of the global area, wherein the feedback device outputs the thermal feedback using a thermoelectric element performing a thermoelectric operation, and when the player character enters the local area, control, via the communication module, the feedback device to override the thermal feedback corresponding to the temperature attribute of the global area with the thermal feedback corresponding to the temperature attribute of the local area.

When the player character departs the local area, the controller may control, via the communication module, the feedback device to restart outputting the thermal feedback corresponding to the temperature attribute of the local area.

1. Thermal Feedback Providing System

Hereinafter, a thermal feedback providing system 1000 according to an embodiment of the present disclosure will be described.

1.1. Overview of Thermal Feedback System

The thermal feedback providing system 1000 according to an embodiment of the present disclosure is a system that allows a user to experience Thermal Experiences (TX). Specifically, the thermal feedback providing system 1000 may allow the user to experience a thermal experience by outputting thermal feedback as part of representing multimedia content.

The thermal feedback is a kind of thermal stimulation that makes the user feel a thermal sensation by stimulating the thermal sensory organs of the user, which are distributed throughout the body of the user. In the present specification, thermal feedback refers to all the thermal stimuli that may stimulate the user's thermal sensory system.

Representative examples of the thermal feedback include a hot feedback and a cold feedback. The hot feedback means the thermal feedback making the user feel a hot sensation by applying a "hot heat" or a positive heat to a hot spot on the user's skin. The cold feedback means the thermal feedback making the user feel a cold sensation by applying a "cold heat" or a negative heat to a cold spot on the user's skin.

Since the heat is a physical quantity represented by a scalar form, the expression, "apply cold heat," "or "apply negative heat," may not be an exact expression from a physical point of view. For the convenience of the present description, however, "absorbing heat" may be referred to "applying cold heat" or "transferring cold heat." The term of "negative heat" may be also used instead of "cold heat."

The thermal feedback in the present specification may further include a thermal grill feedback in addition to the hot feedback and the cold feedback. When the hot heat and the cold heat are given at the same time, the user perceives a pain sensation instead of recognizing the hot sensation and the cold sensation individually. This pain sensation is referred to as a so-called thermal grill illusion (TGI). That is, the thermal grill feedback means a thermal feedback which applies a combination of the hot heat and the cold heat, and can be provided by outputting the hot feedback and the cold feedback simultaneously. A more detailed explanation of the thermal grill feedback will be provided below.

The multimedia content may include various kinds of content including a moving picture, a game, a virtual reality application, an augmented reality application, and the like.

In general, the multimedia content are provided to the user mainly in accordance with representing audiovisual information. In embodiments of the present disclosure, however, the thermal experience based on the above-mentioned thermal feedback can be included as part of the multimedia content.

Furthermore, the "playback" or "reproduction" of multimedia content should be interpreted to include all operations of executing multimedia content and representing it to users. Therefore, the term "playback" in the present specification should be construed to include not only an operation of reproducing a moving picture through a media player but also an operation of executing a game program, a training program, a virtual reality application, an augmented reality application, etc.

1.2. Configuration of a Thermal Feedback System

FIG. 1 is a block diagram of a configuration of a thermal feedback providing system 1000 according to an embodiment of the present disclosure.

Referring to FIG. 1, a thermal feedback providing system 1000 may include a content reproduction device 1200, an audiovisual device 1400, and a feedback device 1600.

The content reproduction device 1200 reproduces the multimedia content, and the audiovisual device 1400 outputs an image and/or an audio according to the reproduction of the content, and the feedback device 1600 may output thermal feedback in accordance with the multimedia content.

For example, the content reproduction device 1200 may decode multimedia content including video data, audio data and thermal feedback data to generate a video signal, audio signal and a signal relating to thermal feedback (thermal feedback signal). The video signal and audio signal may be transmitted to the audiovisual device 1400 and the thermal feedback signal may be transmitted to the feedback device 1600. The audiovisual device 1400 receives the video signal and the audio signal and outputs the video and audio, and the feedback device 1600 receives the thermal feedback signal and outputs the thermal feedback.

In some embodiments, the thermal feedback signal may include a thermal feedback message. For example, content reproduction device 1200 may code a thermal feedback message in the form of one or multiple feedback message signals. For example, using Pulse Digital Modulation (PDM), Phase-Shift Keying (PSK), and/or Quadrature Amplitude Modulation (QAM), content reproduction device may include a message for audiovisual device 1400 or feedback device 1600 associated with a thermal feedback operation.

Hereinafter, each component of the thermal feedback providing system 1000 will be described in more detail.

1.2.1. The Content Reproduction Device

The content reproduction device 1200 reproduces the multimedia content.

Figure 2:
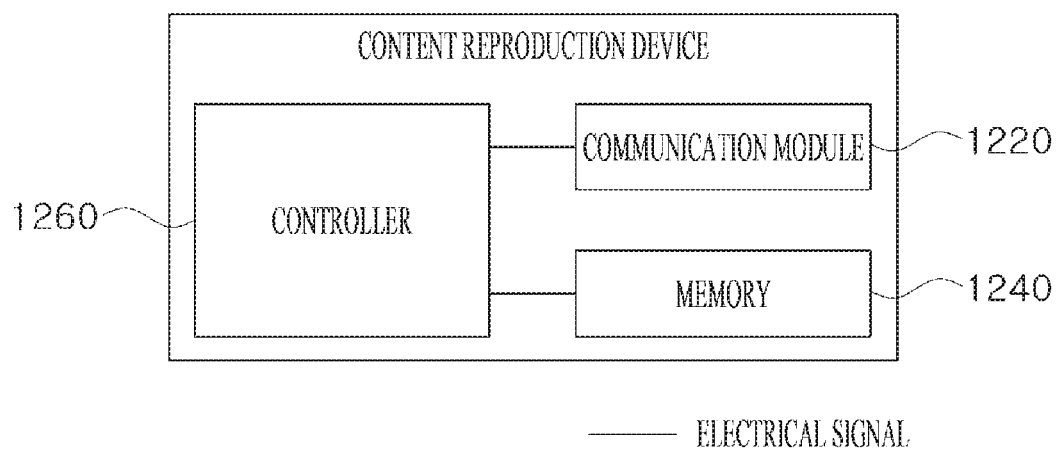
FIG. 2 is a block diagram of a configuration of a content reproduction device according to an embodiment of the present disclosure.

FIG. 2 is a block diagram of a configuration of a content reproduction device 1200 according to an embodiment of the present disclosure.

Referring to FIG. 2, the content reproduction device 1200 may include a communication module 1220, a memory 1240, and a controller 1260.

The communication module 1220 may communicate with an external device. The content reproduction device 1200 may transmit and receive data to and from the audiovisual device 1400 and the feedback device 1600 through the communication module 1220. For example, the content reproduction device 1200 may transmit an A/V signal to the audiovisual device 1400 via the communication module 1220 or a thermal feedback signal to the feedback device 1600. In addition, the content reproduction device 1200 may access the Internet through the communication module 1220 to download the multimedia content.

The communication module 1220 may include a wired-type communication module and a wireless-type communication module. Since the wired-type and the wireless-type each have advantages and disadvantages, the content reproduction device 1200 may be provided with both a wired-type communication module and a wireless-type communication module.

In some embodiments, communication module 1220 may be one or more devices for establishing communication between controller 1260 and other devices of feedback providing system 1000 via a network. For example, communication module 1220 may include circuitry and one or more antennas for communicating wirelessly with memory 1240 using a short range/near-field wireless communication protocol such as Bluetooth™, Bluetooth™ LE, WiFi, WiFi Direct, and Zigbee. Further, communication module 1220 may communicate with feedback device 1600 using any known network protocol including any form of wired or wireless access. LAN (Local Area Network) and USB (Universal Serial Bus) communication are typical examples of the wire-type communication method, and other methods may be used. In the case of the wireless-type communication method, a wireless personal area network (WPAN) based communication method such as Bluetooth or Zigbee may be used. The wireless communication protocol is not limited thereto. For example, a WLAN (Wireless Local Area Network) based communication method such as Wi-Fi or other known communication methods may be used. Proprietary protocols developed for game machines or consoles may also be used as a wire/wireless communication protocol.

The memory 1240 may store various kinds of information. The memory 1240 may store data temporarily or semi-permanently. Examples of the memory 1240 include a hard disk drive (HDD), a solid state drive (SSD), a flash memory, a ROM (Read-Only Memory), and a RAM (Random Access Memory). The memory 1240 may be provided in a form embedded in the content reproduction device 1200 or in a detachable form.

The memory 1240 stores various data for the operation of the content reproduction device 1200 including an operating system (OS) for operating the content reproduction device 1200 or a content to be reproduced by the content reproduction device 1200.

The controller 1260 may control the overall operation of the content reproduction device 1200. For example, the controller 1260 may load the multimedia content from the memory 1240 and reproduce it, or may generate the video signal, the audio signal, or the thermal feedback signal in accordance with the content.

The controller 1260 may be implemented as a CPU (Central Processing Unit) or the like in accordance with hardware, software, or a combination thereof. It may be provided in the form of an electronic circuit that performs a control function by processing an electrical signal in hardware, and may be provided in a form of a program or a code for driving a hardware circuit in software.

1.2.2. Audiovisual Device

The audiovisual device 1400 can output video and audio to reproduce the multimedia content.

Figure 3:
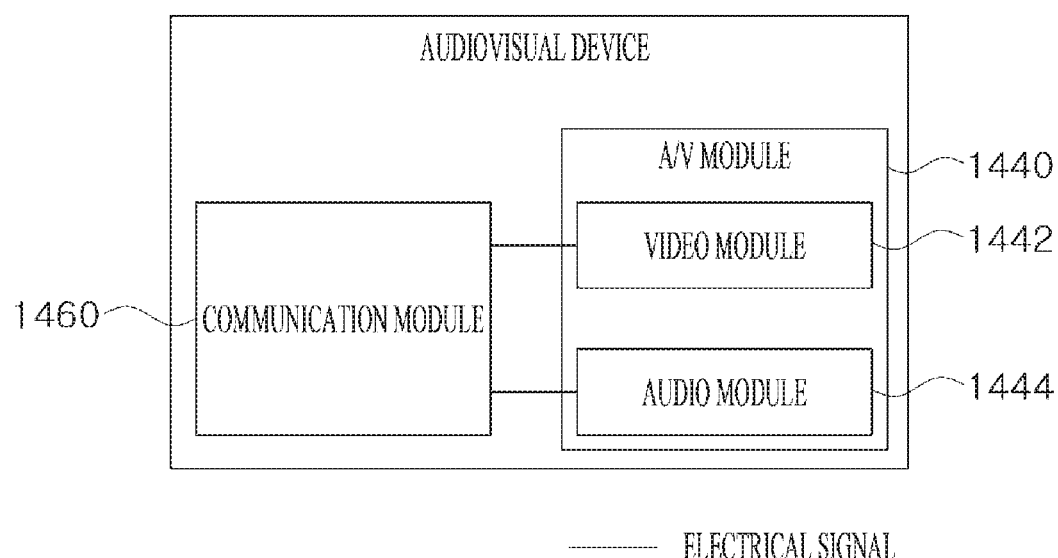
FIG. 3 is a block diagram of a configuration of an audiovisual device according to an embodiment of the present disclosure.

FIG. 3 is a block diagram of a configuration of an audiovisual device 1400 according to an embodiment of the present disclosure.

Referring to FIG. 3, the audiovisual device 1400 may include a communication module 1420 and an A/V module 1440.

The communication module 1420 may communicate with an external device. The audiovisual device 1400 may transmit and receive data to and from the content reproduction device 1200 via the communication module 1420. For example, the audiovisual device 1400 may receive the audio signal and/or video signal from the content reproduction device 1200 via the communication module 1420.

The communication module 1420 of the audiovisual device 1400 may be configured similar to the communication module 1220 of the content reproduction device 1200, and a detailed description thereof will be omitted.

The A/V module 1440 may provide video and/or audio content to the user. For this, the A/V module 1440 may include a video module 1442 and an audio module 1444.

The image module 1442 is generally implemented using a display that can output a video according to the video signal received from the content reproduction device 1200. The audio module 1444 is generally implemented using a speaker that can output audio according to the audio signal received from the content reproduction device 1200.

1.2.3. Feedback Device

The feedback device 1600 may output thermal feedback in response to the reproduction of the multimedia content.

Figure 4:
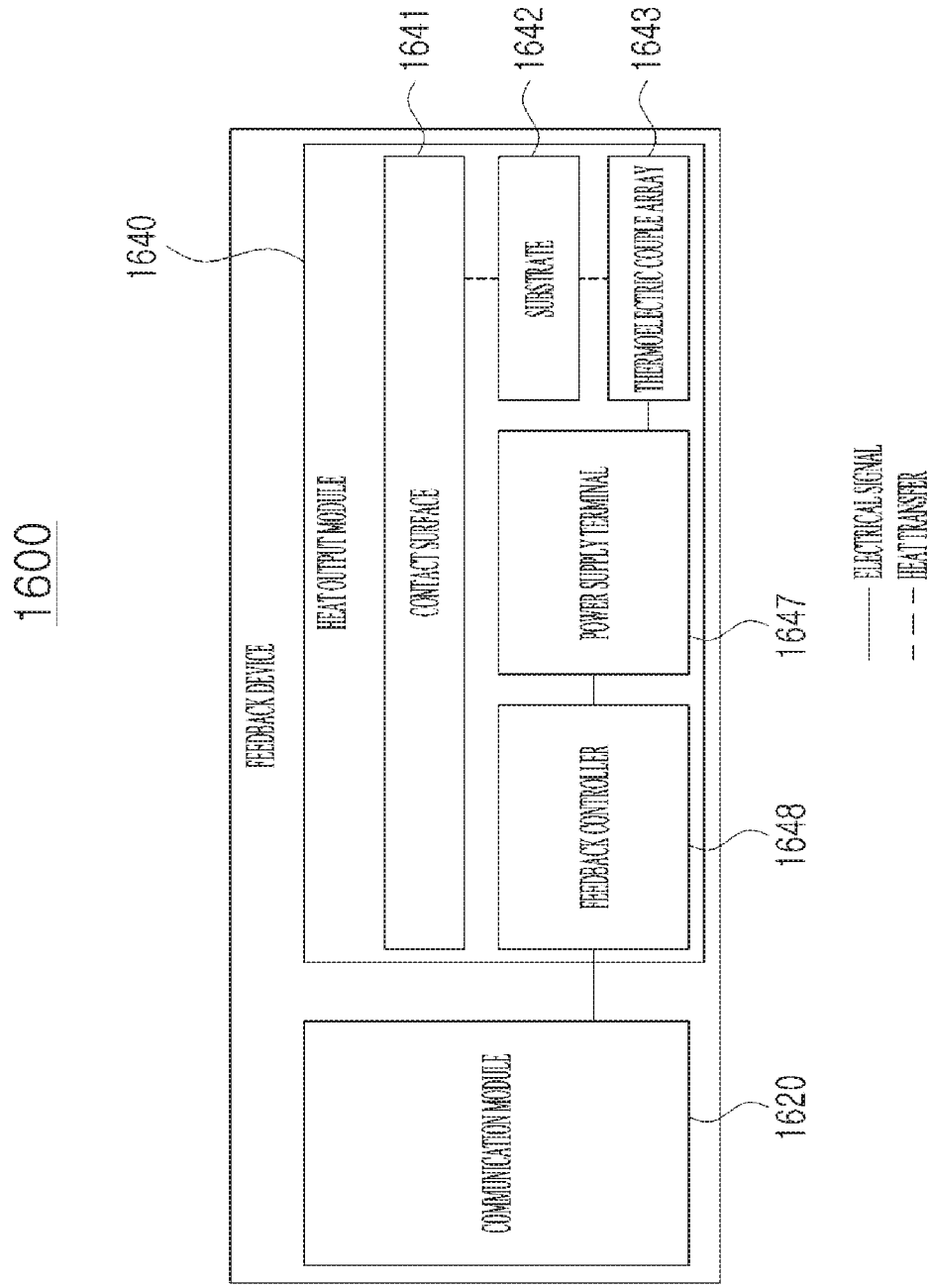
FIG. 4 is a block diagram of a feedback device according to an embodiment of the present disclosure.

FIG. 4 is a block diagram of a feedback device 1600 according to an embodiment of the present disclosure.

FIG. 4, the feedback device 1600 may include a communication module 1620 and a heat output module 1640.

The communication module 1620 may communicate with an external device. The feedback device 1600 may transmit and receive data to and from the content reproduction device 1200 via the communication module 1620. For example, the feedback device 1600 may receive a thermal feedback signal from the content reproduction device 1200 via the communication module 1620.

The heat output module 1640 may output thermal feedback. Thermal feedback may be provided by applying hot heat (positive heat) or cold heat (negative heat) to a user's body. The hot heat (positive heat) and/or the cold heat (negative heat) can be generated by a power output module 1640 and the power output module 1640 may include a contact surface 1641 contacting the user's body and a thermoelectric element connected to the contact surface. The thermal feedback can be provided to the user's body via the contact surface 1641.

The heat output module 1640 may perform a heat generating operation, a heat absorbing operation and/or a thermal grill operation along with a thermal feedback signal received from the content reproduction device 1200 via the communication module 1620 to output thermal feedback, then a user can experience the output thermal feedback.

A more detailed description of the specific configuration and operation of the heat output module 1640 will be described later.

1.3. Implementations of a Thermal Feedback System

The thermal feedback providing system 1000 having the above-described configuration may be implemented in various forms. Hereinafter, some implementations of the thermal feedback providing system 1000 will be described.

1.3.1. First Implementation

The first implementation of the thermal feedback providing system 1000-1 is related to a system for reproducing an augmented reality application or a virtual reality application.

Figure 5:
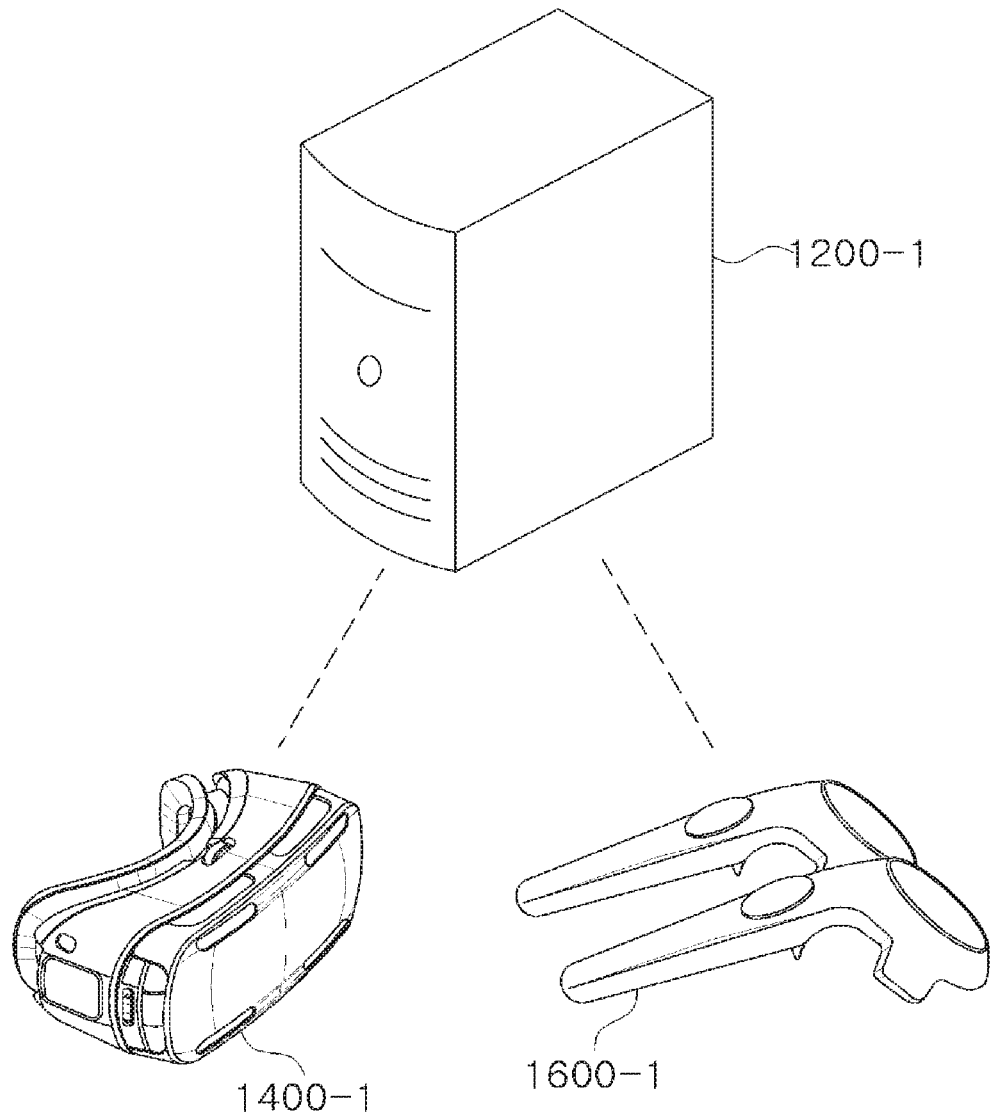
FIG. 5 is a schematic diagram of a first implementation of a thermal feedback providing system according to an embodiment of the present disclosure.
Figure 6:
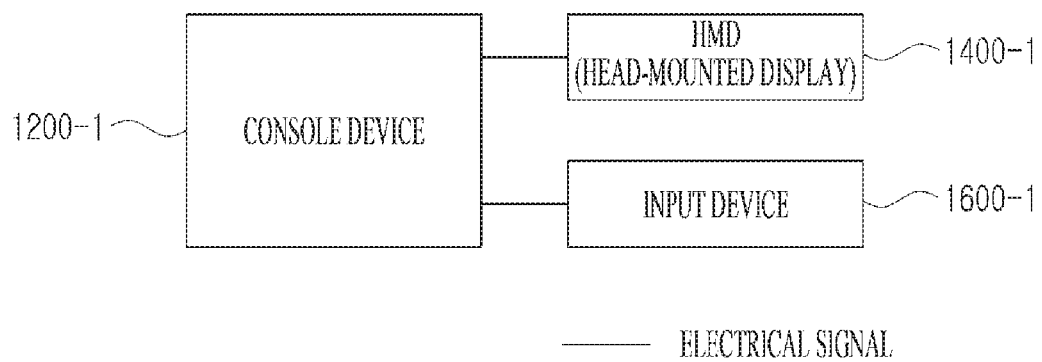
FIG. 6 is a block diagram of a first implementation of a thermal feedback providing system according to an embodiment of the present disclosure

FIG. 5 is a schematic diagram of a first implementation of a thermal feedback providing system 1000-1 according to an embodiment of the present disclosure, and FIG. 6 is a schematic diagram of a first implementation of a thermal feedback providing system 1000-1 according to an embodiment of the present disclosure Referring to FIGS. 5 and 6, the thermal feedback providing system 1000-1 according to the present embodiment includes a console device 1200-1, a head-mounted display (HMD) 1400-1, and input device 1600-1. The console device 1200-1 may correspond to the content reproduction device 1200, the HMD 1400-1 may correspond to the audiovisual device 1400, and the input device 1600-1 may correspond to the feedback device 1600.

Hereinafter, each component of the thermal feedback providing system 1000-1 according to this embodiment will be described.

The console device 1200-1 corresponding to the content reproduction device 1200 may be provided as an electronic device for reproducing an augmented reality application or a virtual reality application. For example, the console device 1200-1 may include a game console for executing a VR application such as a Sony Playstation VR™, or a PC capable of executing an AR/VR application.

The console device 1200-1 may include a communication module 1220, a memory 1240 and a controller 1260, similar to the above-described content reproduction device 1200.

Figure 7:
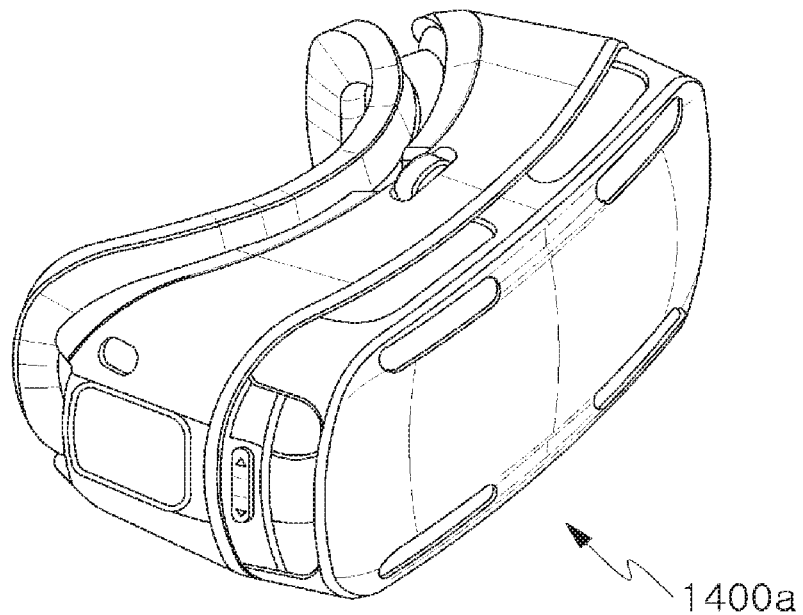
FIG. 7 is a schematic diagrams showing an exemplary form of a HMD of the first implementation of the thermal feedback providing system according to an embodiment of the present disclosure.
Figure 8:
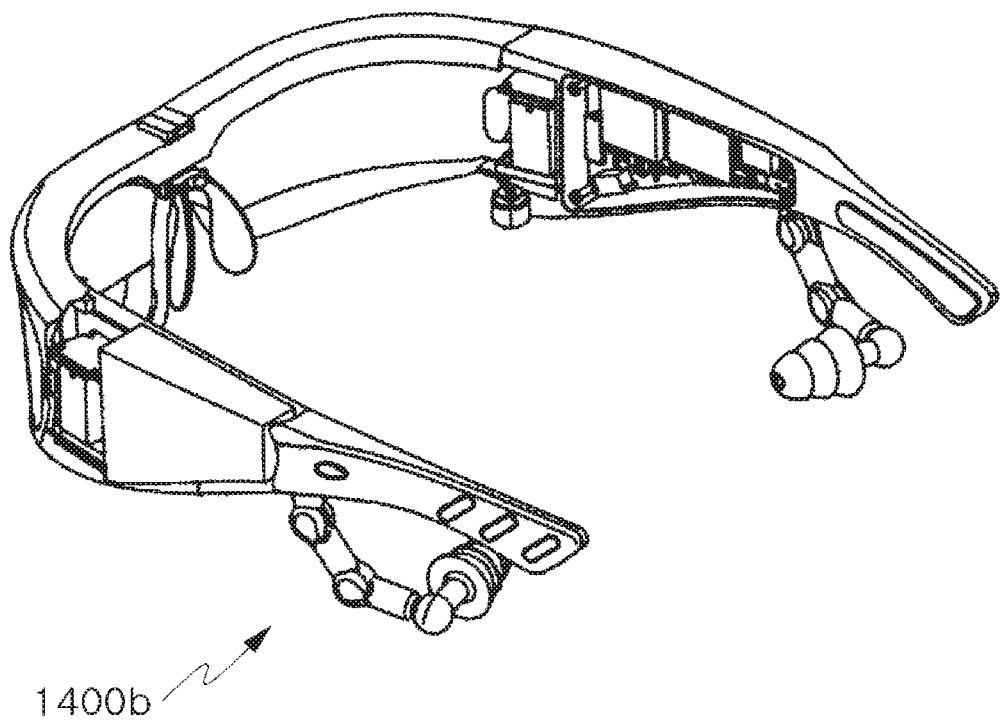
FIG. 8 is a schematic diagrams showing an exemplary form of a HMD of the first implementation of the thermal feedback providing system according to an embodiment of the present disclosure.

FIGS. 7 and 8 are schematic diagrams showing an exemplary form of the HMD 1400-1 of the first implementation of the thermal feedback providing system 1000-1 according to an embodiment of the present disclosure.

The HMD 1400-1 corresponding to the audiovisual device 1400 may be mounted on the head of the user to provide a video and/or an audio to the user. The audio may be provided to the user through an earphone or the like.

For example, as shown in FIG. 7, HMD 1400-1 may be provided as an HMD-type electronic device 1400a such as the Oculus Rift™ or HTC Vive™ and the HMD 1400-1 may be coupled to a PC or game console and may output video through an opaque display.

In another example, the audiovisual device 1400, as shown in FIG. 8, may be implemented as a glasses-type wearable device 1400b such as Google Glass™. The glasses-type wearable device 1400b may display a virtual video (virtual image) through a transparent display. The user can be provided, via the transparent display, with the virtual video which can augment a user's visual experience of the real world. Although the glasses-type wearable device 1400b is conceptually different from the HMD-type electronic device 1400a using the conventional opaque display, the HMD 1400-1 according to the present application should be understood as a comprehensive concept to include the glasses-type wearable device 1400b.

Figure 9:
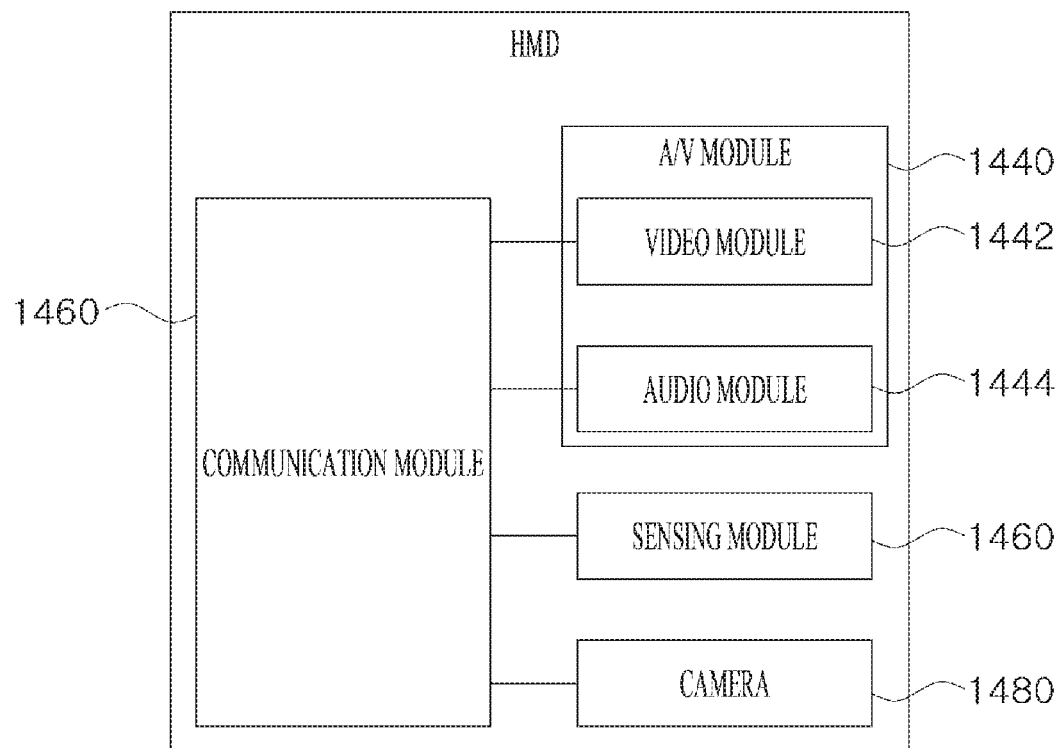
FIG. 9 is a block diagram relating to a configuration of a HMD of the first implementation of the thermal feedback providing system according to an embodiment of the present disclosure.

FIG. 9 is a block diagram relating to a configuration of the HMD 1400-1 of the first implementation of the thermal feedback providing system 1000-1 according to an embodiment of the present disclosure.

Referring to FIG. 9, HMD 1400-1 may include a communication module 1420 and an A/V module 1440, similarly to audiovisual device 1400 described above.

However, in the present embodiment, the communication module 1420 may transmit information sensed by the sensing module 1460 to the console device 1200-1 in addition to receiving the A/V signal from the console device 1200-1. Also, the communication module 1420 may be provided as a wireless-type so that the HMD 1400-1 mounted on the head of the user does not disturb the user's movement.

In addition, the image module 1442 in the A/V module 1440 may include two displays. One display is for the user's left eye and the other display is for the user's right eye, so that the two displays can output a stereoscopic 3D virtual reality or augmented reality image. The image module 1442 may be provided in the form of a transparent display or a projector for projecting a virtual image on a transparent glass so that a virtual image and a real image may be viewed by the user together.

Referring back to FIG. 9, the HMD 1400-1 may further include a sensing module 1460 and a camera 1480.

The sensing module 1460 may sense various information for realizing an augmented reality or a virtual reality. In particular, the video output may be controlled in accordance with the movement of the head of the user, so as to provide a realistic augmented reality or virtual reality image. Therefore, the sensing module 1460 may include a posture sensor for sensing the user's posture and/or a motion sensor for sensing of the user's motion.

The camera 1480 may capture an image and/or a video. To realize the augmented reality, the image photographed by the camera 1480 may be used, so that the user may recognize the actual space. Also, the captured image and/or video may be used to generate an augmented image synthesized with a virtual image.

Figure 10:
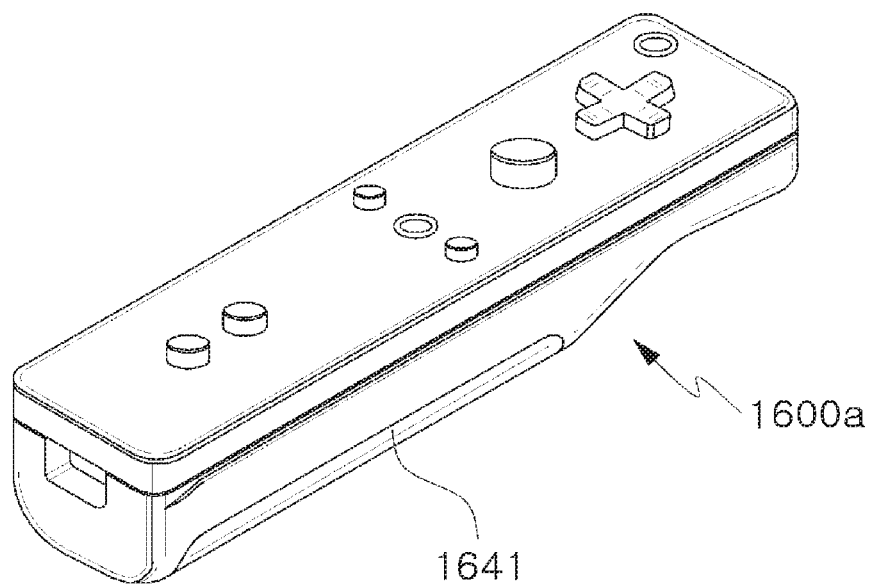
FIG. 10 is a schematic diagrams showing an exemplary form of an input device of the first implementation of the thermal feedback providing system according to an embodiment of the present disclosure.
Figure 11:
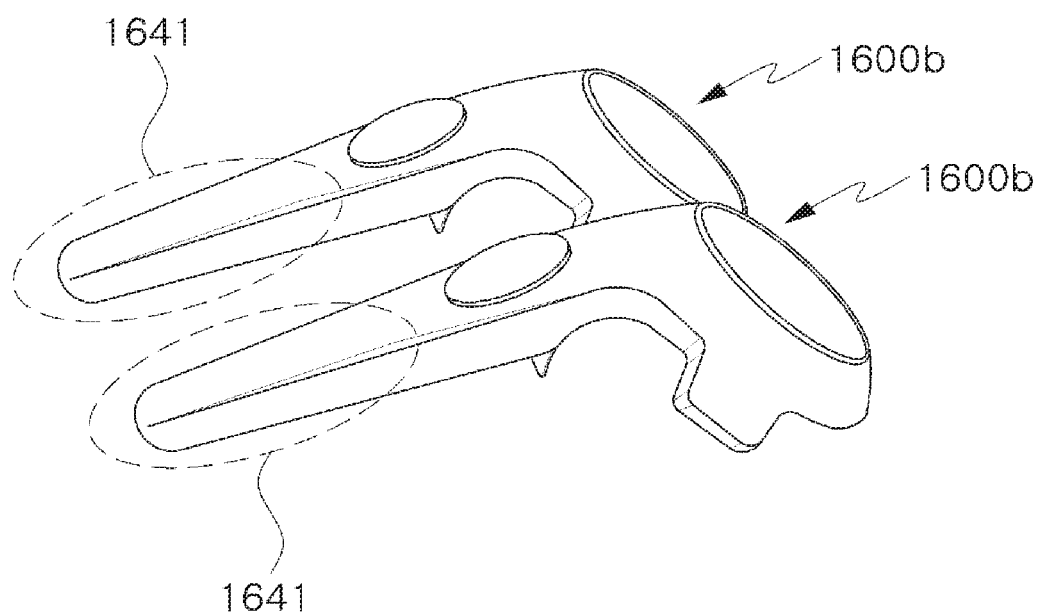
FIG. 11 is schematic diagrams showing an exemplary form of an input device of the first implementation of the thermal feedback providing system according to an embodiment of the present disclosure.

FIGS. 10 and 11 are schematic diagrams showing an exemplary form of the input device 1600-1 of the first implementation of the thermal feedback providing system 1000-1 according to an embodiment of the present disclosure.

The input device 1600-1 corresponding to the feedback device 1600 may receive user input and may output thermal feedback.

For example, as shown in FIG. 10, the input device 1600-1 may be provided as a bar-type input device 1600a gripped by the user's hand such as the gaming controller for the Sony Move Motion™ or Vive™. The bar-type input device 1600b may also be implemented in pairs, as shown in FIG. 11, one bar held in each hand of the user.

Figure 12:
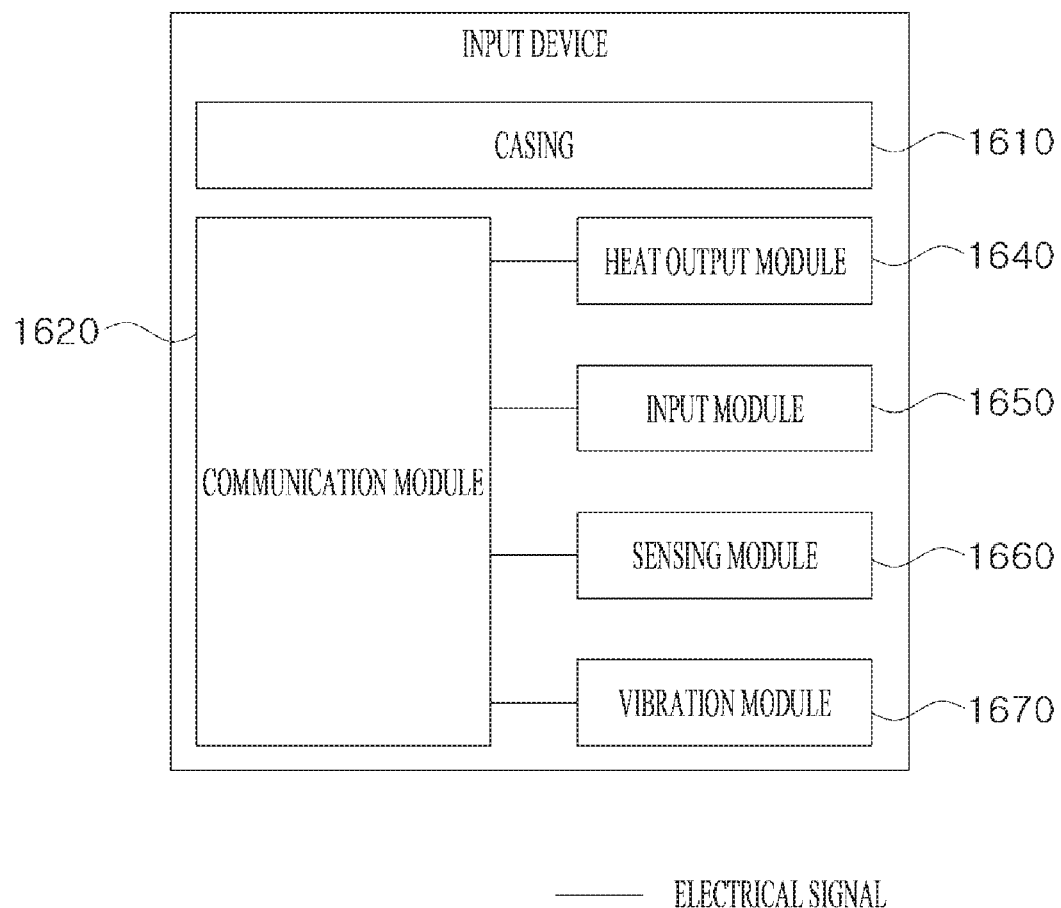
FIG. 12 is a block diagram relating to a configuration of an input device of the first implementation of the thermal feedback providing system according to an embodiment of the present disclosure

FIG. 12 is a block diagram relating to a configuration of the input device 1600-1 of the first implementation of the thermal feedback providing system 1000-1 according to an embodiment of the present disclosure.

Referring to FIG. 12, the input device 1600-1 may include a communication module 1620 and a heat output module 1640, similarly to the feedback device 1600 described above.

However, in the present embodiment, the communication module 1620 may receive the thermal feedback signal from the console device 1200-1. Also, the communication module 1620 may transmit information related to the user operation inputted through the input module 1650 and/or information sensed by the sensing module 1660 to the console device 1200-1. The communication module 1620 may be implemented as a wireless-type so that the user can easily maneuver the input module 1650.

Referring to FIG. 12, the input device 1600-1 may further include a casing 1610, an input module 1650, a sensing module 1660, and a vibration module 1670.

The casing 1610 forms the appearance of the input device 1600-1 and may house other components of the input device 1600-1 therein. Accordingly, the housed components can be protected from an external impact or the like by the casing.

A grip portion 1612 for gripping the input device 1600-1 by the user may be provided on the input device 1600-1. The grip portion 1612 is a portion where the input device 1600-1 contacts the user's body. The touch surface 1641 of the heat output module 1640 may be provided on the grip portion 1612. Further, the grip portion 1612 may be made of a material having a high frictional force (e.g., rubber or urethane) and may have a non-slip shape (e.g., irregular shape, etc.). The grip portion may also be made of a material which absorbs perspiration.

Input module 1650 may obtain user input from a user. The input module 1650 may be implemented in a button-type and/or a joystick-type, so that the user can input the user input by pressing a button and/or manipulating the joystick in a specific direction. Implementation of the input module 1650 is not limited to the above-described exemplary forms, however, and any other suitable type of input device (e.g., a wheel, a touch screen, etc.) may be used.

The sensing module 1660 may sense various information related to the input device 1600-1. Examples of the typical sensing module 1660 include a posture sensor for sensing the posture of the input device 1600-1, a motion sensor for sensing the motion of the input device 1600-1, and a biosensor for sensing a user's biological signal. A gyro sensor and/or an acceleration sensor may be used as the posture sensor and/or the motion sensor. The biosensor may include, e.g., a temperature sensor for sensing a user's body temperature and/or an electrocardiogram sensor for sensing an electrocardiogram.

The vibration module 1670 may output vibration feedback. Vibration feedback can serve to further enhance user experience with the game along with thermal feedback.

The above-described input device 1600-1 may be provided in various forms other than the bar-type.

FIGS. 13-17 are schematic diagrams illustrating other exemplary forms of input device 1600-1 in accordance with embodiments of the present disclosure.

Figure 13:
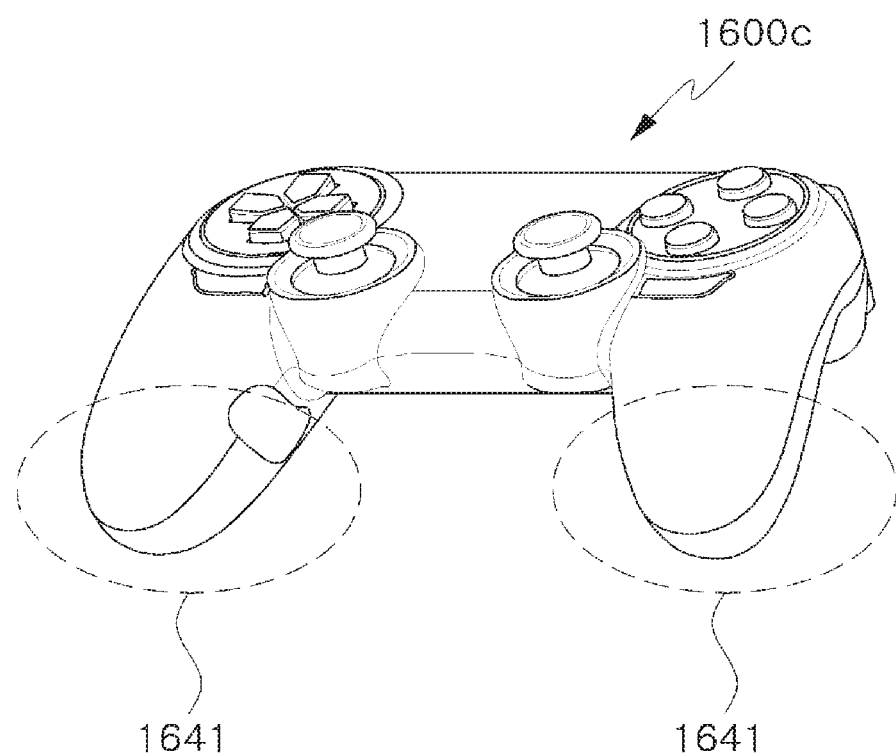
FIG. 13 is a schematic diagram illustrating an exemplary form of input device of a first implementation of a thermal feedback providing system in accordance with an embodiment of the present disclosure.

Referring to FIG. 13, the input device 1600-1 may be provided as in a two-handheld gaming controller-type device such as a gaming controller for Sony's PlayStation™ Dual Shock™ or Microsoft's Xbox™.

In case that the input device 1600-1 is implemented as the gaming controller-type device, two grip portions 1612 may be provided at two spaced apart portions of the casing 1610 so as to be gripped by both hands. The contact surface 1641 may be provided on each of the grip portions 1612.

Figure 14:
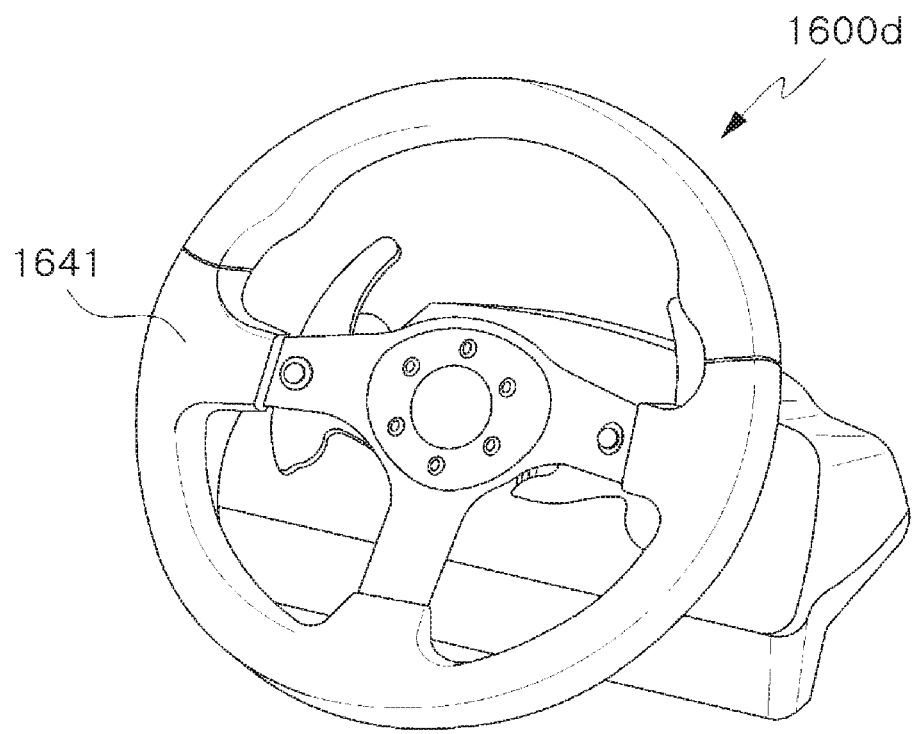
FIG. 14 is a schematic diagram illustrating an exemplary form of input device of a first implementation of a thermal feedback providing system in accordance with an embodiment of the present disclosure.
Figure 15:
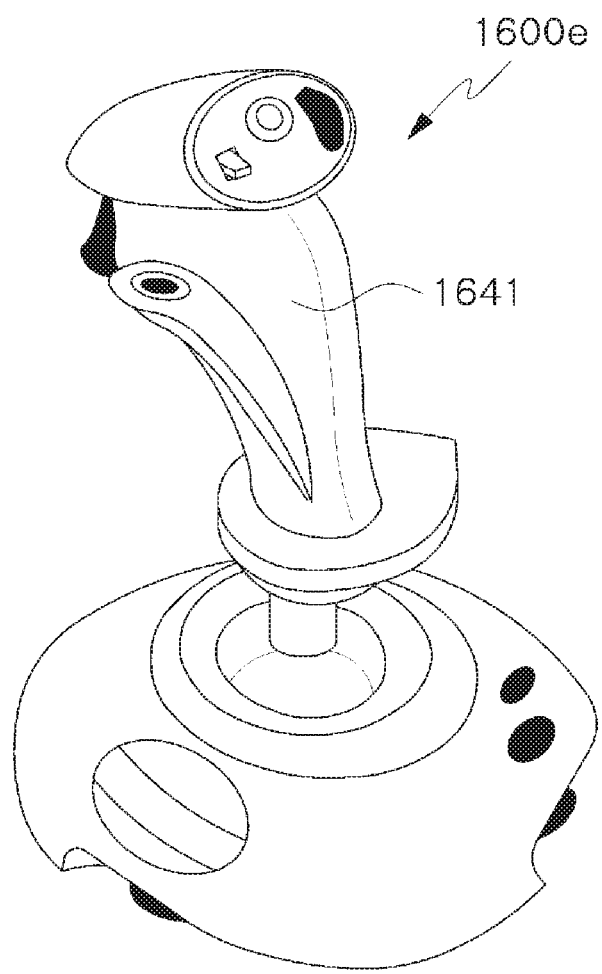
FIG. 15 is a schematic diagram illustrating an exemplary form of input device of a first implementation of a thermal feedback providing system in accordance with an embodiment of the present disclosure.
Figure 16:
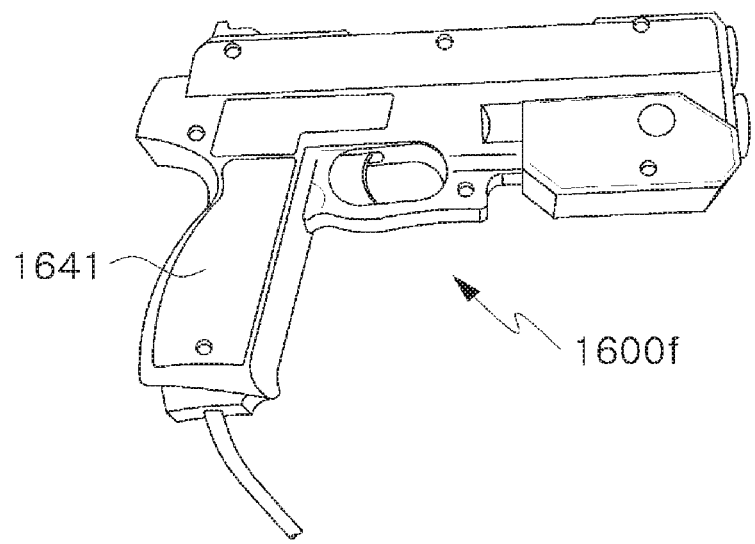
FIG. 16 is a schematic diagram illustrating an exemplary form of input device of a first implementation of a thermal feedback providing system in accordance with an embodiment of the present disclosure.
Figure 17:
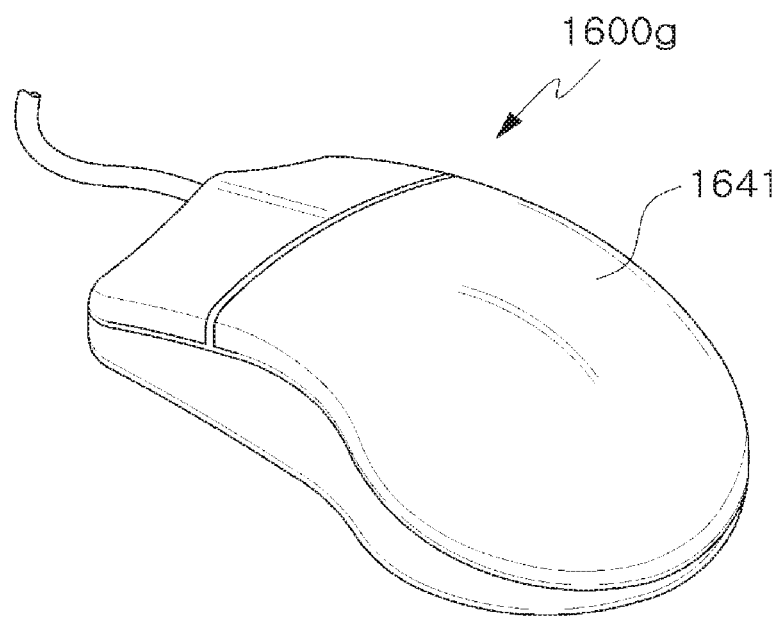
FIG. 17 is schematic diagram illustrating an exemplary form of input device of a first implementation of a thermal feedback providing system in accordance with an embodiment of the present disclosure.

In addition, the input device 1600-1 may include a wheel-type device 1600d (used in a racing game) as shown in FIG. 14, a joystick-type device 1600e (used in a flight simulator game) as shown in FIG. 15, a gun-type device 1600f (used in a First Person Shooter (FPS) game) as shown in FIG. 16 and/or a mouse-type device 1600g (commonly used in computer gaming environments) as shown in FIG. 17.

Further, in the present embodiment, the thermal feedback providing system 1000-1 may further include a wearable device 1600-1', or the input device 1600-1 may be replaced with the wearable device 1600-1'. In this case, the wearable device 1600-1' may correspond to the feedback device 1600.

Figure 18:
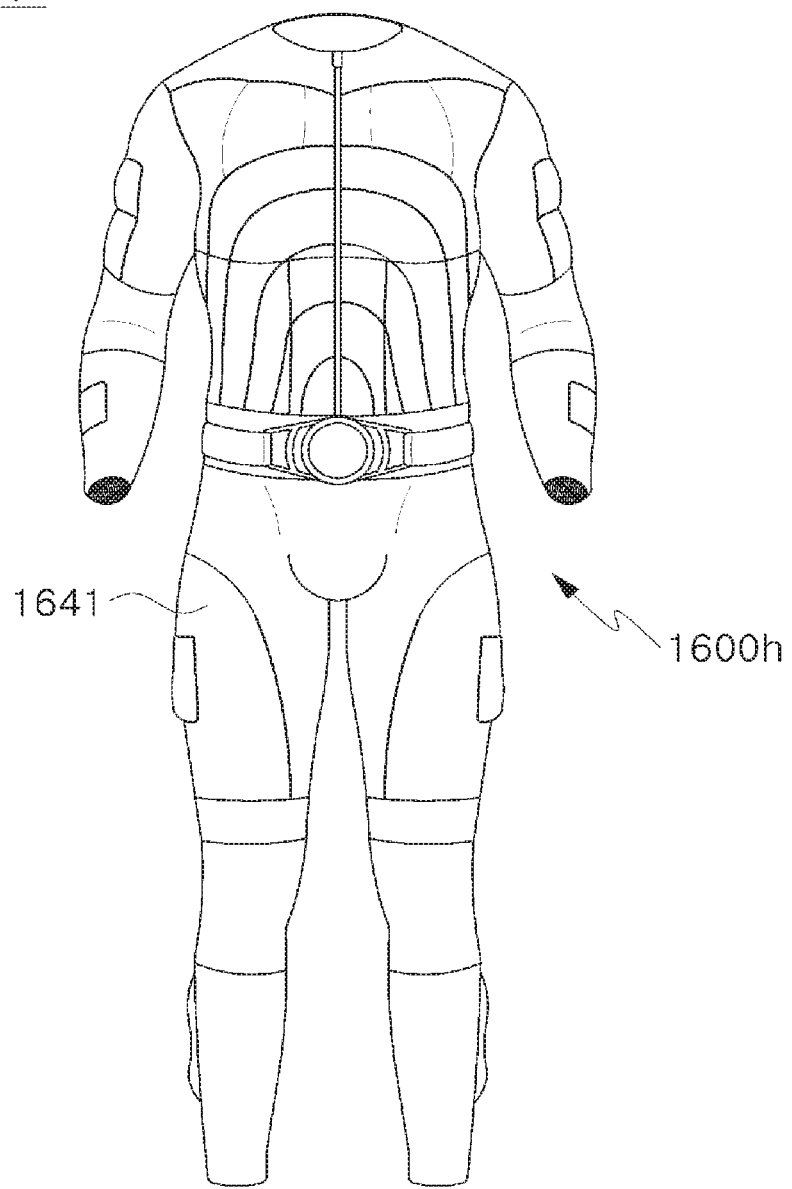
FIG. 18 is a schematic view showing an exemplary form of a wearable device in the first implementation of the thermal feedback providing system according to an embodiment of the present disclosure.
Figure 22:
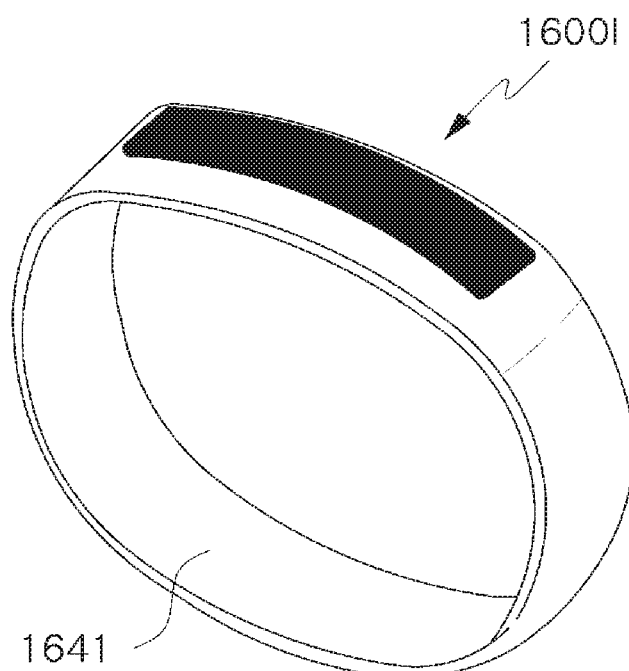
FIG. 22 is a schematic view showing an exemplary form of a wearable device "in the first implementation of the thermal feedback providing system according to an embodiment of the present disclosure.

FIGS. 18 and 22 are schematic views showing exemplary forms of the wearable device 1600-1' according to embodiments of the present disclosure.

The wearable device 1600-1' corresponding to the feedback device 1600 may be worn on the user's body to serve as a human-machine interface (HMI) and output thermal feedback.

Figure 19:
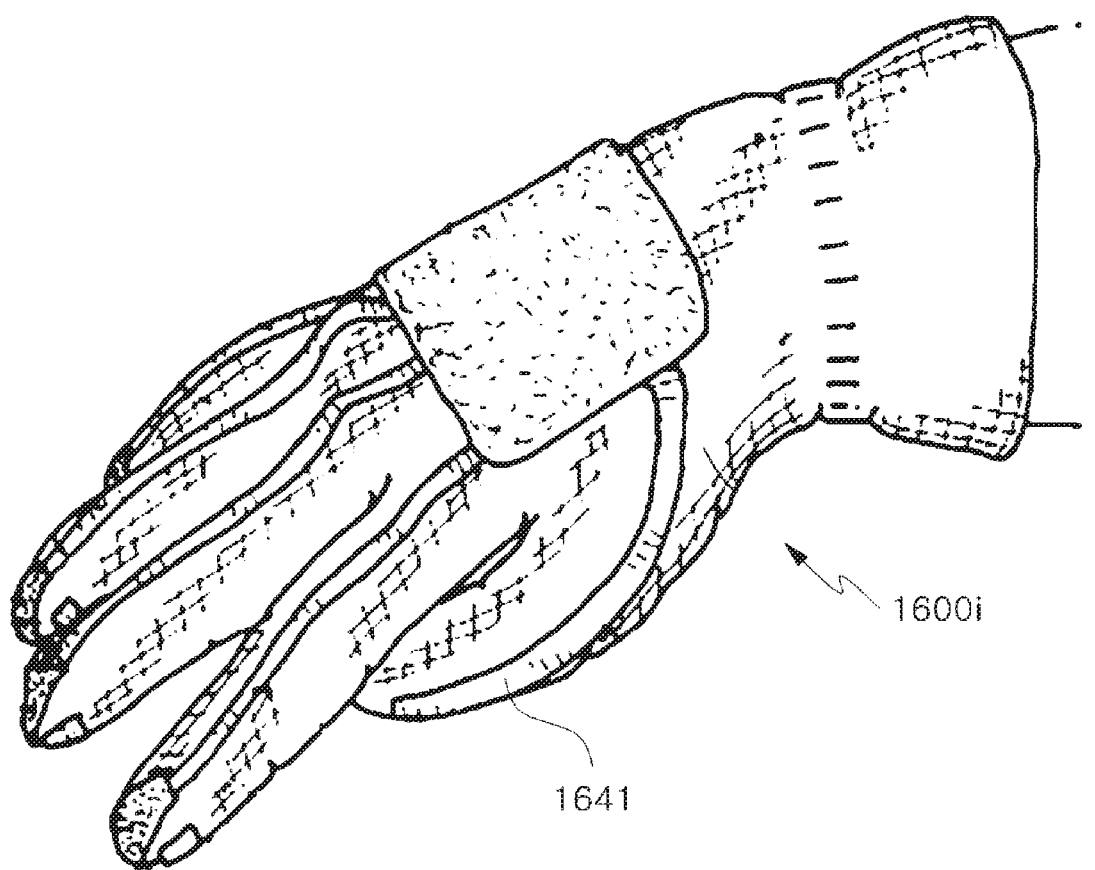
FIG. 19 is a schematic view showing an exemplary form of a wearable device in the first implementation of the thermal feedback providing system according to an embodiment of the present disclosure.
Figure 20:
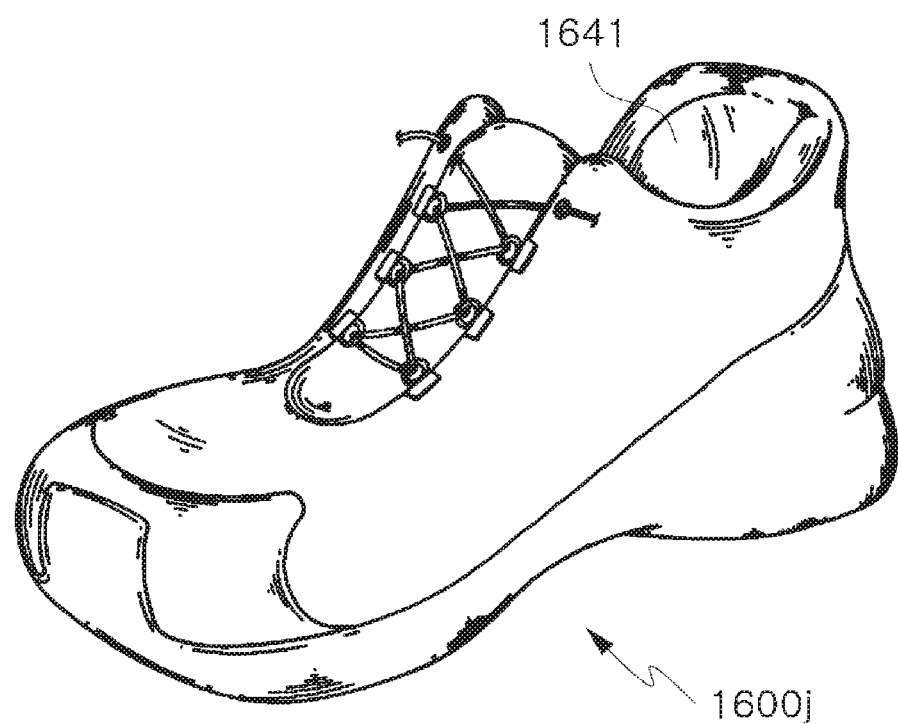
FIG. 20 is a schematic view showing an exemplary form of a wearable device "in the first implementation of the thermal feedback providing system according to an embodiment of the present disclosure.
Figure 21:
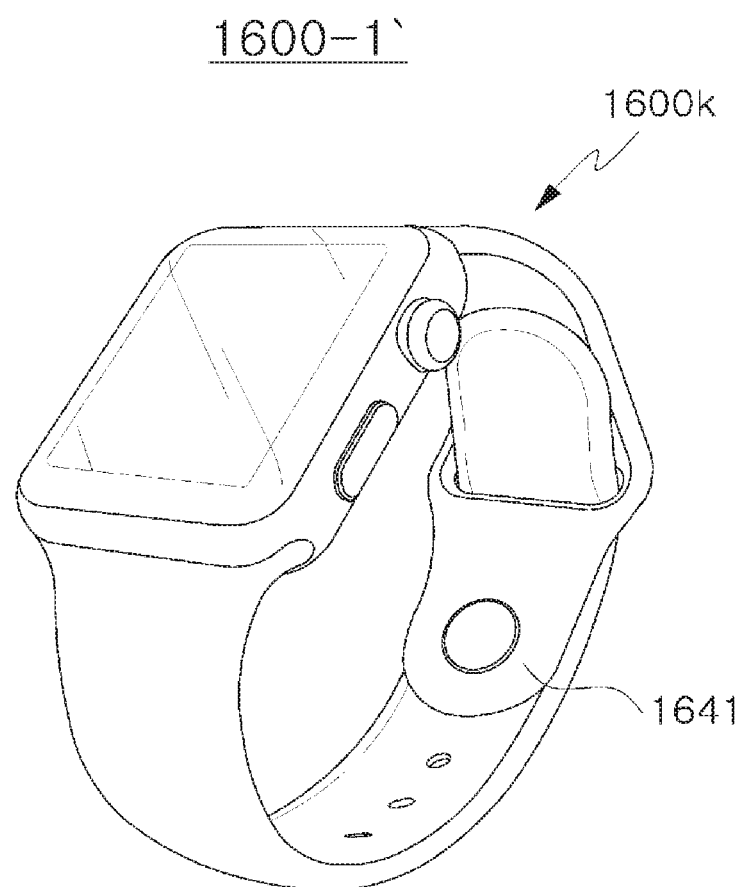
FIG. 21 is a schematic view showing an exemplary form of a wearable device "in the first implementation of the thermal feedback providing system according to an embodiment of the present disclosure.

The wearable device 1600-1' may be provided in various forms. For example, the wearable device 1600-1' may include a glasses or HMD-type device as described above, a suit-type device 1600h as shown in FIG. 18, a glove-type device 1600i as shown in FIG. 19, a shoe-type device 1600j as shown in FIG. 20, a watch-type device 1600k as shown in FIG. 21, or a band-type device 16001 as shown in FIG. 22.

The wearable device 1600-1' may include a communication module 1620 and a heat output module 1640, as described above with respect to the input device 1600-1.

The wearable device 1600-1' may include a body which forms the appearance of the wearable device 1600-1' and a sensing module 1660 that can sense the user's action, posture, and/or biological information. The contact surface 1641 of the heat output module 1640 may be formed on the body of the wearable device.

The wearable device 1600-1' may also include additional components. For example, a band-type or a watch-type wearable device 1600-1' may have a display for displaying various information.

1.3.2. Second Implementation

The second implementation of the thermal feedback providing system 1000-2 is related to a system for reproducing an augmented reality application or a virtual reality application.

Figure 23:
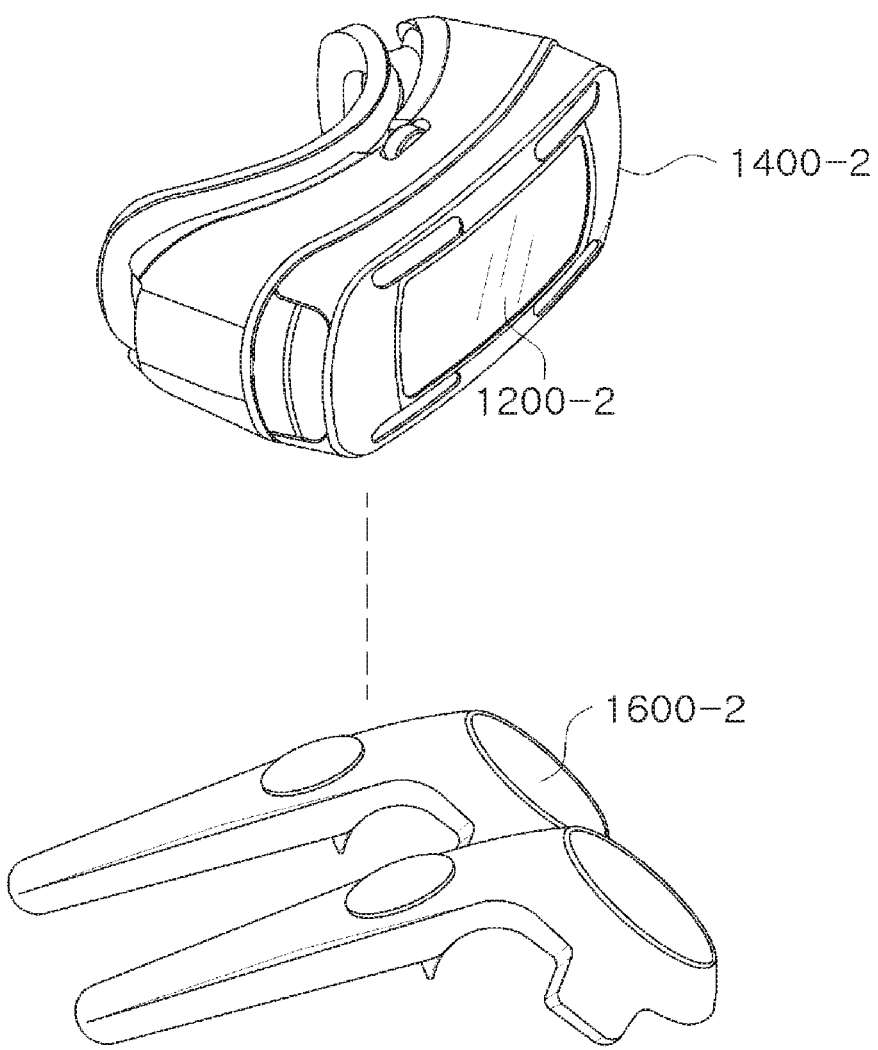
FIG. 23 is a schematic diagram of the second implementation of a thermal feedback providing system according to an embodiment of the present disclosure.
Figure 24:
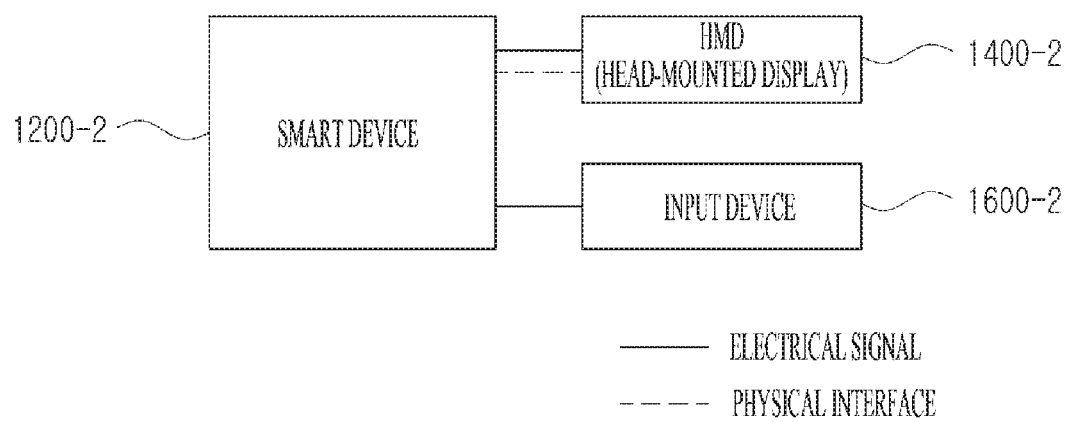
FIG. 24 is a block diagram of the second implementation of a thermal feedback providing system according to an embodiment of the present disclosure.

FIG. 23 is a schematic diagram of the second implementation of a thermal feedback providing system 1000-2 according to an embodiment of the present disclosure. FIG. 24 is a block diagram of the second implementation of a thermal feedback providing system 1000-2 according to an embodiment of the present disclosure.

The second implementation of the thermal feedback providing system 1000-2 is for processing an augmented reality application or a virtual reality application and may be provided similarly to the first implementation of the thermal feedback providing system 1000-1. However, referring to FIG. 23, the console device 1200-1 may be replaced with the smart device 1200-2 in the present implementation. The smart device 1200-2 may correspond to both the content reproduction device 1200 and the audiovisual device 1400.

For example, the smart device 1200-2 may be provided in a smartphone-type device such as a Galaxy S8™ of Samsung Electronics. The smart device 1200-2 generally includes a display, an audio output terminal, a camera, a posture sensor, and the like, and may be mounted on the HMD 1400-2 to realize a virtual reality or augmented reality.

Figure 25:
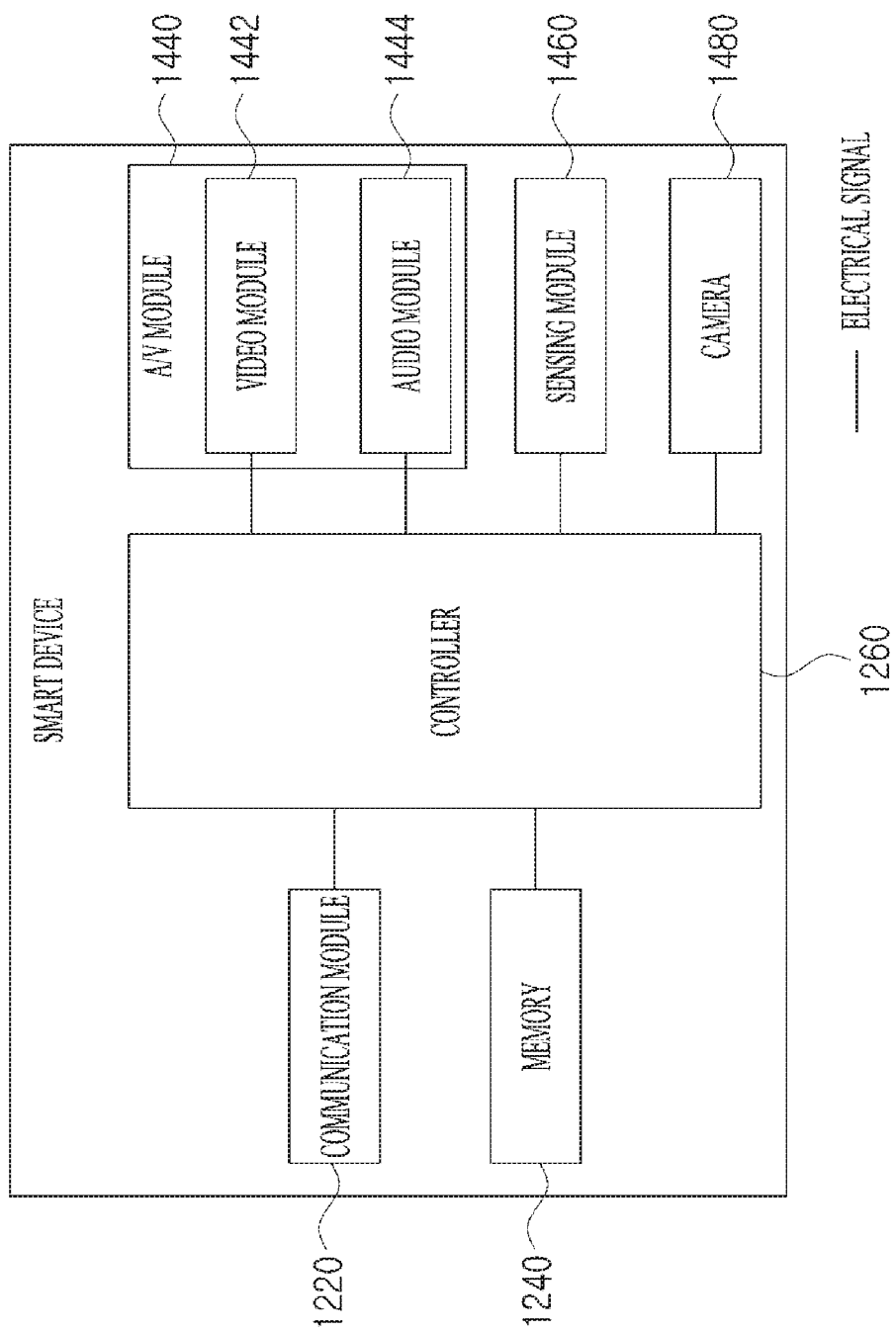
FIG. 25 is a block diagram relating to a configuration of the smart device of the second implementation of the thermal feedback providing system according to the present application.

FIG. 25 is a block diagram relating to a configuration of the smart device 1200-2 of the second implementation of the thermal feedback providing system 1000-2 according to the present application.

According to the second implementation, the smart device 1200-2 may include an NV module 1440, a sensing module 1460 and a camera 1480. In the second implementation, the A/V module 1440, the sensing module 1460 and the camera 1480 may be provided in the smart device instead of the HMD 1400-2.

1.3.3. Third Implementation

The third implementation of the thermal feedback providing system 1000-3 is related to a system for reproducing an augmented reality application or a virtual reality application.

Figure 26:
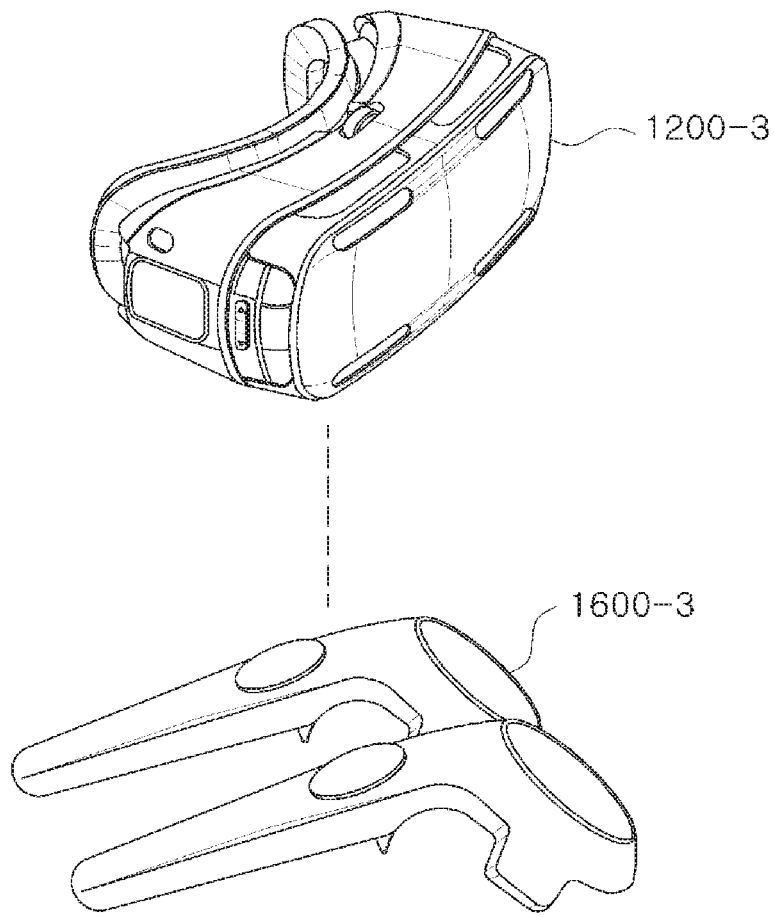
FIG. 26 is a schematic diagram of the third implementation of a thermal feedback providing system according to an embodiment of the present
Figure 27:
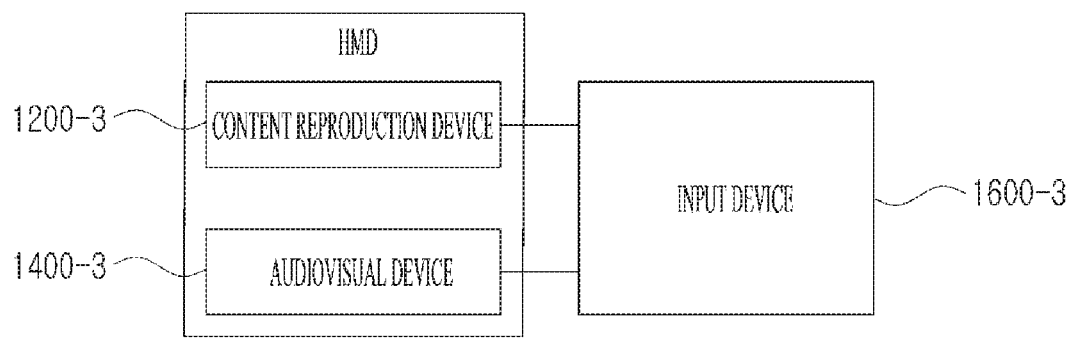
FIG. 27 is a schematic diagram of the third implementation of a thermal feedback providing system according to an embodiment of the present disclosure.

FIG. 26 is a schematic diagram of the third implementation of a thermal feedback providing system 1000-3 according to an embodiment of the present disclosure. FIG. 27 is a schematic diagram of the third implementation of a thermal feedback providing system 1000-3 according to an embodiment of the present disclosure.

The third implementation of the thermal feedback providing system 1000-3 is for processing an augmented reality application or a virtual reality application and may be provided similarly to the first implementation of the thermal feedback providing system 1000-1. However, referring to FIG. 27, the console device 1200-1 of the first implementation may be incorporated in the HMD 1200-3 in the third implementation. Therefore, the HMD 1200-3 may correspond to both the content reproduction device 1200 and the audiovisual device 1400.

For example, the HMD 1200-3 may be provided in the form of an HMD having a built-in CPU such as Microsoft's Hololens™. Accordingly, the HMD 1200-3 can independently execute the virtual reality or the augmented reality application without connecting with the console device 1200-1. Accordingly, in the present implementation, the console device 1200-1 may be omitted in the thermal feedback providing system 1000-3, and the HMD 1200-3 may include the memory 1240 and the controller 1260.

1.3.4. Fourth Implementation

The fourth embodiment of the thermal feedback providing system 1000-4 is related to a system for reproducing multimedia content such as a video content or a game content through a conventional 2D screen.

Figure 28:
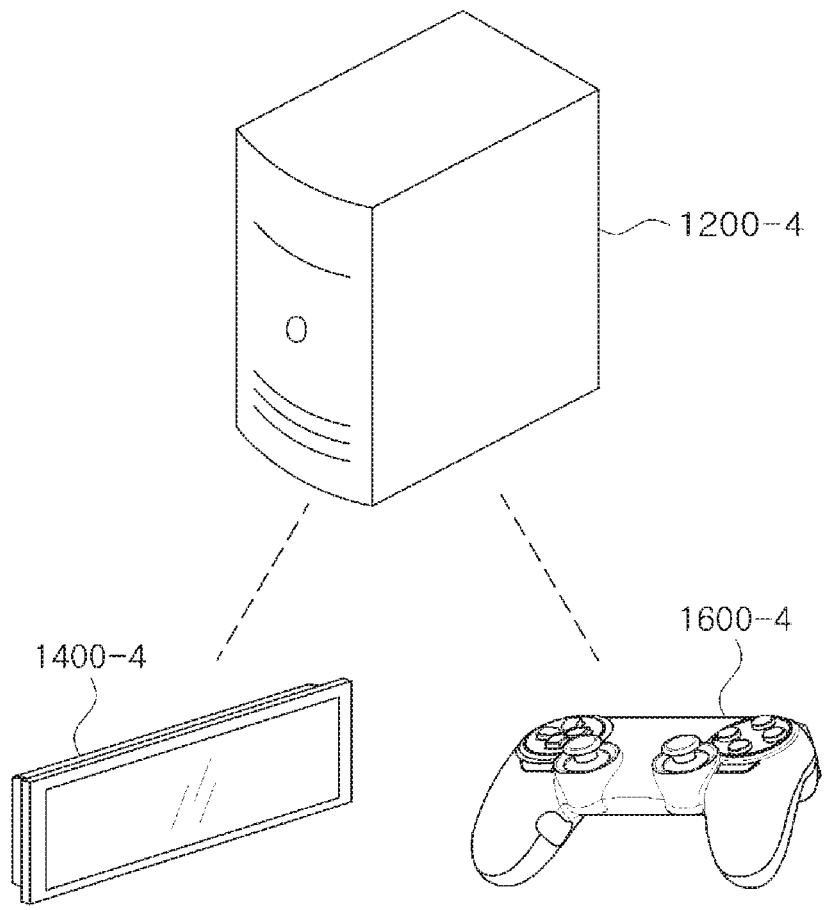
FIG. 28 is a schematic diagram of a fourth implementation of a thermal feedback providing system according to an embodiment of the present disclosure.

FIG. 28 is a schematic diagram of a fourth implementation of a thermal feedback providing system 1000-4 according to an embodiment of the present disclosure.

The fourth implementation of the thermal feedback providing system 1000-4 is for processing multimedia content on a conventional 2D screen and may be provided similarly to the first implementation of the thermal feedback providing system 1000-1. Referring to FIG. 28, in the present implementation, the HMD 1400-1 of the first implementation may be replaced with a display device 1400-4 that provides a 2D screen. The console device 1200-4 may correspond to the content reproduction device 1200, and the display device 1400-4 may correspond to the audiovisual device 1400. Also, the input device 1600-4 may correspond to the feedback device 1600.

The display device 1400-4 may include the communication module 1420 and A/V module 1440 of the first implementation described above. For example, the display device 1400-4 may be provided in the form of a TV, a monitor, a projector, or the like. Also, the display device 1400-4 may provide a 3D image to the user in a stereoscopic manner.

1.3.5. Fifth Implementation

The fifth implementation of the thermal feedback providing system 1000-5 is related to a system for reproducing multimedia content such as a video content or a game content through a conventional 2D screen.

Figure 29:
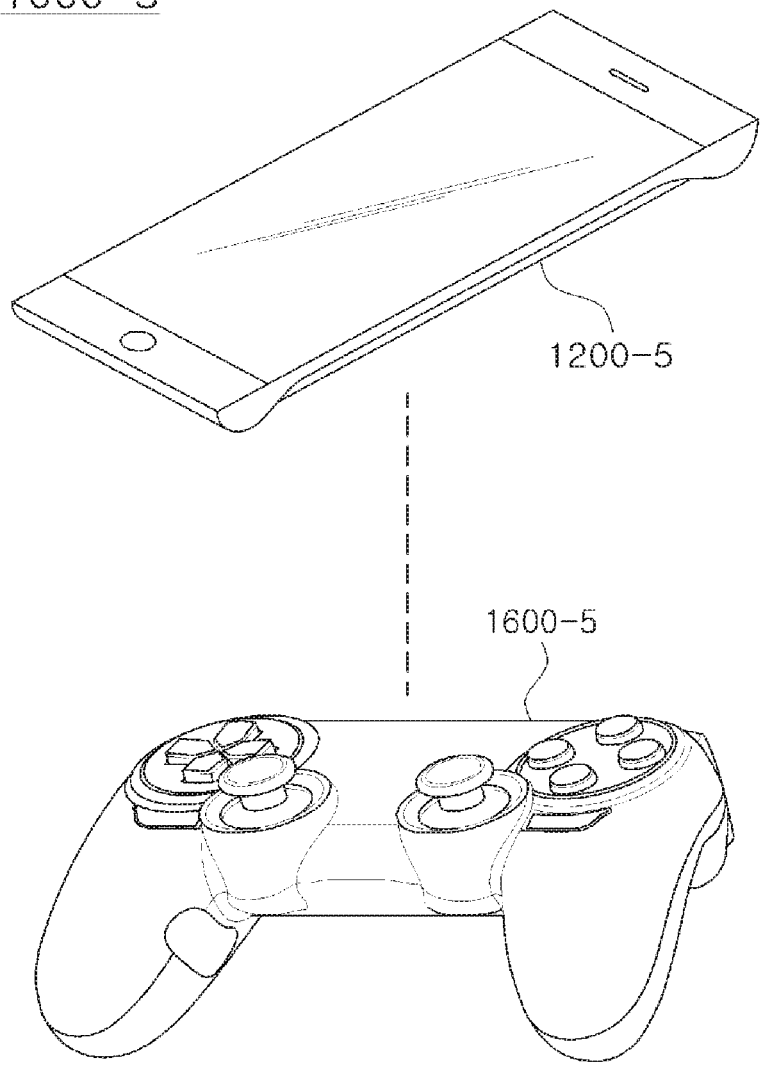
FIG. 29 is a schematic diagram of a fifth implementation of a thermal feedback providing system according to an embodiment of the present disclosure.

FIG. 29 is a schematic diagram of a fifth implementation of a thermal feedback providing system 1000-5 according to an embodiment of the present disclosure.

The fifth embodiment of the thermal feedback providing system 1000-5 may be provided for processing an augmented reality application or a virtual reality application similarly to the fourth implementation of the thermal feedback providing system 1000-4. Referring to FIG. 29, in the present implementation, the console device 1200-4 and the display device 1400-4 which are described in the fourth implementation may be replaced with a smart device 1200-5. In the present fifth implementation, the console device 1200-4 and the display device 1400-4 may be integrated in the smart device 1200-5. The smart device 1200-5 may correspond to both the content reproduction device 1200 and the audiovisual device 1400.

For example, the smart device 1200-5 may be provided in the form of a smart phone, a notebook, a tablet, or the like. Accordingly, in the present implementation, the smart device 1200-5 may further include an A/V module 1440.

1.3.6. Sixth Implementation

In the sixth implementation of the thermal feedback providing system 1000-6, the thermal feedback providing system 1000-6 may include a portable smart device 1200-6 and a peripheral device 1600-6 connected to the portable smart device 1200-6. This implementation may be useful to a user when the user is carrying the smart device 1200-6.

Figure 30:
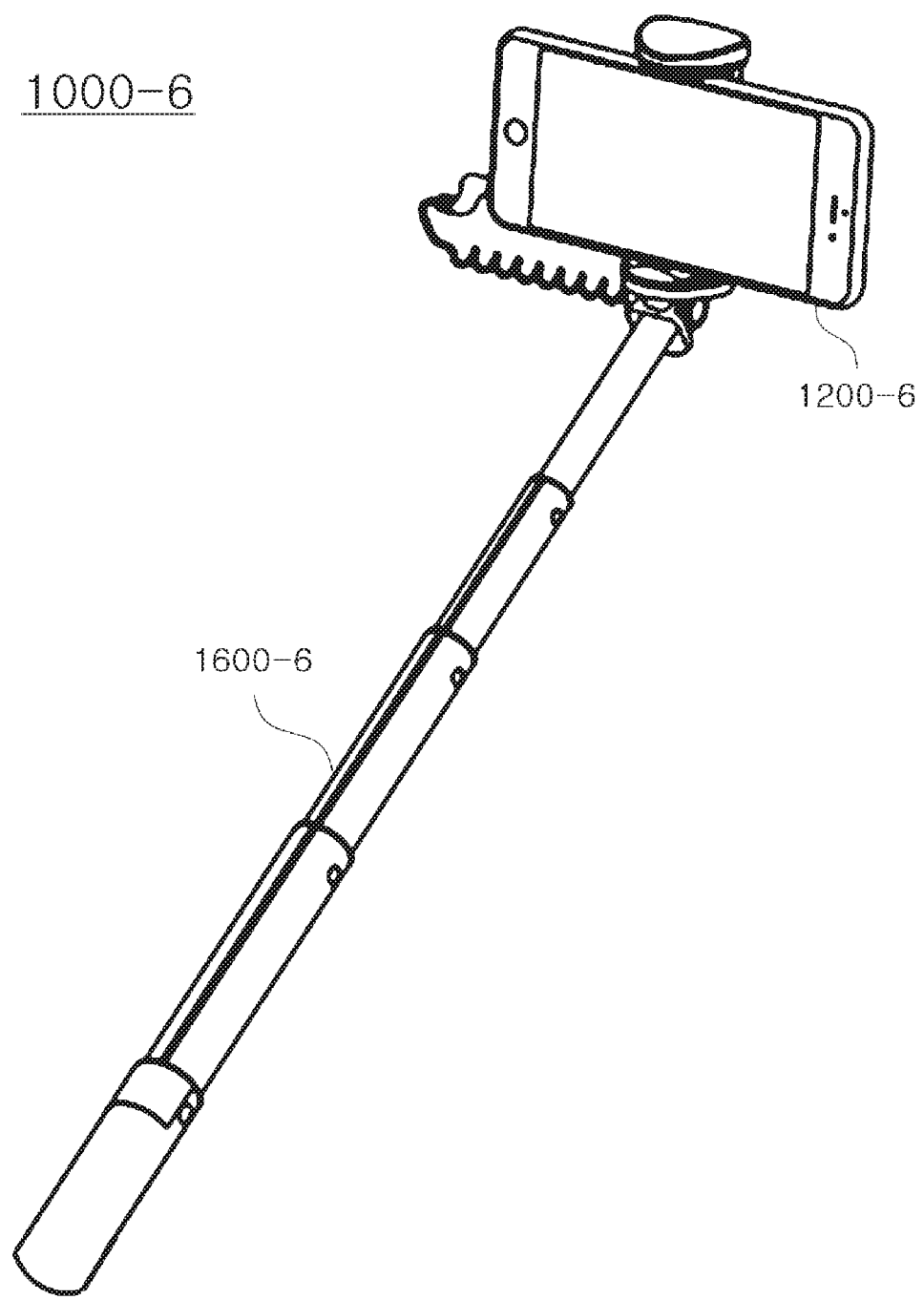
FIG. 30 is a schematic diagram of a sixth embodiment of a thermal feedback providing system according to an embodiment of the present disclosure.

FIG. 30 is a schematic diagram of a sixth embodiment of a thermal feedback providing system 1000-6 according to an embodiment of the present disclosure.

In the present implementation, the smart device 1200-6 may be provided similarly to the smart device 1000-5 of the fifth implementation.

The peripheral device 1600-6 also includes a basic configuration of the feedback device 1600 and may additionally include a mount to which the portable smart device 1200-6 can be mounted and a battery for outputting thermal feedback. For example, the peripheral device 1600-6 may be provided as a selfie-stick or a smart phone case as shown in FIG. 30. The peripheral device 1600-6 may output thermal feedback in conjunction with the portable smart device 1200-6.

2. Heat Output Module

Hereinafter, a heat output module 1640 according to an embodiment of the present disclosure will be described.

2.1. Overview of the Heat Output Module

The heat output module 1640 may perform a heat generating operation, a heat absorption operation, and/or a thermal grill operation to output thermal feedback to the user by applying hot heat and cold heat. In the thermal feedback providing system 1000, the heat output module 1640 mounted on the feedback device 1600 outputs thermal feedback to a user of the thermal feedback providing system 1000 when the feedback device 1600 receives the thermal feedback signal. Accordingly, the user can be provided with a thermal feedback.

The heat output module 1640 may use a thermoelectric element such as a Peltier element to perform the heat generating operation, the heat absorbing operation, or the thermal grill operation.

The Peltier effect is a thermoelectric phenomenon discovered by Jean Peltier in 1834. According to the Peltier effect, when an electric current is made to flow through a junction between two conductors a heat generation occurs at the one side of the junction and a heat absorption occurs at the other side of the junction. Peltier elements are elements that produce such a Peltier effect. Peltier elements were initially made of a junction of different metals such as Bismuth and Antimony, but in recent years they have been manufactured by arranging N-P semiconductors between substrates for a higher thermal efficiency.

A Peltier element is capable of generating and absorbing heat on both sides of the element in substantially instantaneous response with application of an electric power, switching between the heat generation and the heat absorption by changing the current direction of the applied power, and adjusting an intensity of the heat generation or absorption precisely by controlling the magnitude of the voltage or the current value of the applied power. A Peltier element is suitable to be used for the heat generating operation or heat absorbing operation for the thermal feedback. In particular, with Assignee's development of the flexible thermoelectric element been developed, it is now possible to manufacture the thermoelectric element in a form that can be easily placed in contact with the user's body, and the possibility of commercial use as the feedback device 100 is increasing.

The heat outputting module 1640 can perform the heat generating operation or the heat absorbing operation as electricity is applied to the thermoelectric element. Although the heat generation and the absorption occur at the same time in the thermoelectric elements that are physically supplied with electric power, in the present specification the heat generating operation and the heat absorbing operation of the heat outputting module 1640 is defined with reference to the contact surface 1641. More specifically, the heat generating operation is an operation that causes heat generation at the contact surface 1641 in contact with the user's body and the heat absorbing operation is an operation that causes heat absorption at the contact surface 1641. For example, the thermoelectric element may be manufactured by disposing an N-P semiconductor on a substrate such that, when an electric power is applied to the thermoelectric element, heat is generated at one side of the thermoelectric element and heat is absorbed at the other side of the thermoelectric element. We may arbitrarily define one side of the thermoelectric element facing the body of the user as the front side, and the opposite side as the rear side. Then an operation that causes the heat generation at the front side and the heat absorption at the rear side is defined as the heat generating operation, and an operation that causes the heat absorption at the front side is defined as the heat absorbing operation.

Since the thermoelectric effect is induced by the electric charge flowing in the thermoelectric element, it is possible to describe the electric energy inducing the heat generating operation or the heat absorbing operation of the heat outputting module 1640 in terms of the electric current. However, in the present description we will describe the electric energy applied to the thermoelectric element mainly in terms of the electric voltage. This is merely for the sake of the convenience of explanation and a person skilled in the arts would understand the operation of the disclosed embodiments in terms of the electric current, based on the voltage-based description. The present disclosure is therefore not limited to expression in terms of the voltage.

2.2. Configuration of the Heat Output Module

Figure 31:
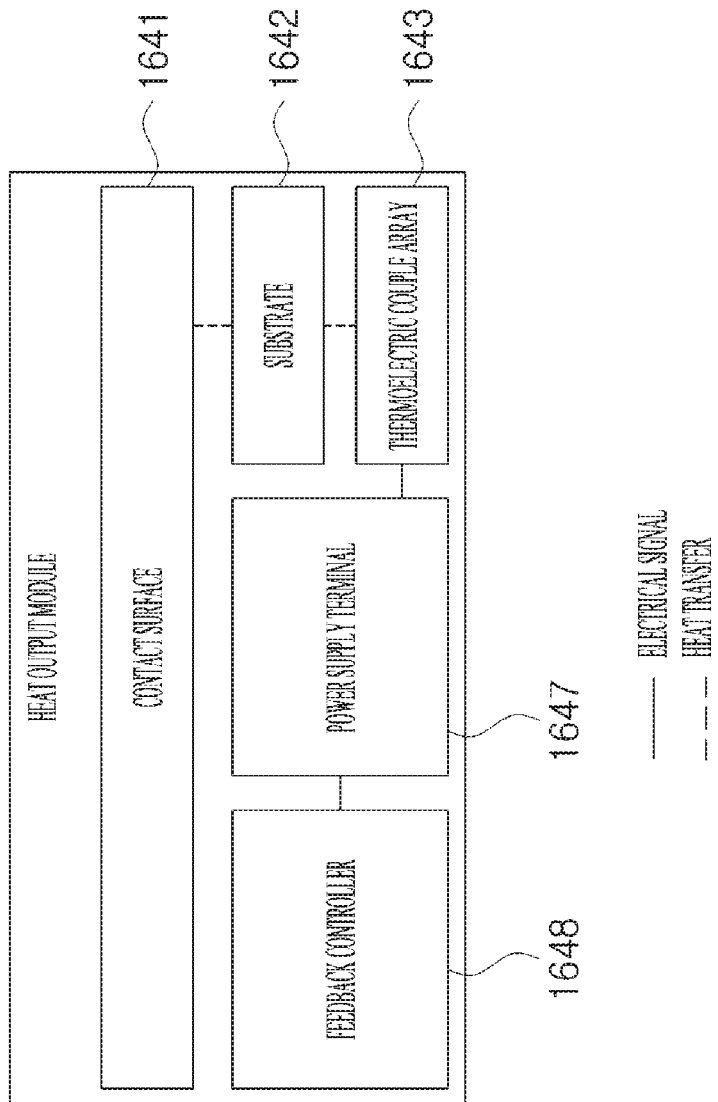
FIG. 31 is a block diagram of a configuration of a heat output module 1640 according to an embodiment of the present disclosure

FIG. 31 is a block diagram of a configuration of a heat output module 1640 according to an embodiment of the present disclosure.

Referring to FIG. 31, the heat output module 1640 includes a contact surface 1641, a substrate 1642, a thermoelectric couple array 1643 disposed on the substrate 1642, a power supply terminal 1640 for applying power to the heat output module 1640 and a feedback controller 1645.

The contact surface 1641 is configured to directly contact the user's body to transmit hot heat or cold heat generated by the heat output module 1640 to the user's skin. The portion of the external surface of the feedback device 1600 that directly contacts the user's body may be the contact surface 1641. For example, the contact surface 1641 may be formed on a grip portion of a casing of the feedback device 1600 gripped by the user.

The contact surface 1641 may be configured as a layer directly or indirectly attached to an outer surface (in the direction toward the user's body) of the thermoelectric couple array 1643 that performs the heat generating operation or the heat absorbing operation in the heat output module 1640. This type of contact surface 1641 is disposed between the thermoelectric couple array 1643 and the skin of the user to perform heat transfer. The contact surface 1641 may be made of a material having a high thermal conductivity so that heat transfer from the thermoelectric couple array 1643 to the user's body is performed efficiently. The layer-type contact surface 1641 can prevent direct exposure of the thermoelectric couple array 1643 to the outside, thereby protecting the thermoelectric couple array 1643 from external impacts.

In the above description, the contact surface 1641 is disposed on the outer surface of the thermoelectric couple array 1643. However, the outer surface of the thermoelectric couple array 1643 itself may serve as the contact surface 1641. A part or all of a front surface of the thermoelectric couple array 1643 can be the contact surface 1641.

The substrate 1642 may be configured to support a thermoelectric couple unit 1645 and may be provided as an insulating material. For example, ceramics may be selected as the material of the substrate 1642. The substrate 1642 may be of a flat plate shape. Alternatively, the substrate may have another shape, e.g., to fit the form of the body part intended to receive the thermal feedback.

The substrate 1642 may be provided with a flexible material so it may be formed into various shapes and universally used for the various types of feedback devices 1600. In the feedback controller 1600 of a gaming controller-type device, for example, the grip portion where a user grasps a gaming controller with the palm of a hand may have a curved surface. To use the heat output module 1640 with such a curved portion of the body, the substrate 1642 may be made flexible. Examples of the flexible material used for the substrate 1642 include glass fiber and flexible plastic.

Thermoelectric couple array 1643 may include a plurality of thermoelectric couple units 1645 disposed on a substrate 1642. Semiconductor pairs of N-type and P-type may be used as the thermoelectric couple unit 1241. Alternatively, the thermoelectric couple unit 1241 may be implemented using different pairs of metals (for example, Bismuth and Antimony).

In the thermoelectric couple unit 1645, the semiconductor pairs are electrically connected to each other at one end and electrically connected to semiconductor of the adjacent thermoelectric couple unit 1645 at the other end. Electrical connection between the semiconductor pair 1645a and 1645b or adjacent semiconductor pairs is achieved by a conductor member 1646 disposed on the substrate 1642. The conductor member 1646 may be a lead or an electrode such as copper or silver.

The thermoelectric couple unit 1645 may be electrically connected in series. The plurality of the thermoelectric couple units 1645 connected in series may form a thermoelectric couple group 1644. At least one of the thermoelectric couple group 1644 may form a thermoelectric couple array 1643.

The power supply terminal 1647 may apply power to the heat output module 1640. The thermoelectric couple array 1643 can generate heat or absorb heat according to the power applied to the power supply terminal 1647. According to a voltage value and/or a current direction of the power, it is determined whether the thermoelectric couple array generates heat or absorbs heat. A pair of the power supply terminals 1644 may be connected to one thermoelectric couple group 1644. When the heat output module 1640 (the thermoelectric couple array 1643) is configured with a plurality of thermoelectric couple groups 1644, plural pairs of the power terminals 1644 may be arranged. Accordingly, the voltage value and the current direction are individually controlled for each thermoelectric couple group 1643, so as to control whether the heat generating operation or the heat absorbing operation is performed for each individual thermoelectric couple array 1643. Furthermore, a degree of heat generation or heat absorption also can be controlled for each individual thermoelectric couple array 1643 in the heat output module 1640.

As will be described later, the power supply terminal 1647 receives the electrical signal output by the feedback controller 1645. The feedback controller 1645 may adjust the current direction and/or voltage value of the electrical signal. Accordingly, the heat generating operation and the heat absorbing operation of the heat output module 1640 can be controlled. When a plurality of the thermoelectric couple groups 1644 are provided in the heat output module 1640, the electric signals applied to the power supply terminals 1644 may be separately controlled for each thermoelectric couple group 1644.

The feedback controller 1645 may apply an electrical signal to the thermoelectric couple array 1643 via the power supply terminal 1647. Specifically, the feedback controller 1645 may receive information related to thermal feedback from the controller 1260 of the content reproduction device 1200 via the communication module 1620, and then the feedback controller 1645 may analyze the received information to determine a type and degree of the thermoelectric operation. Then, the feedback controller 1645 may generate an electric signal according to the determination result. The generated electric signal may be applied to the power supply terminal 1647 so that the thermoelectric couple array 1643 can output thermal feedback.

The feedback controller 1645 may perform calculations and processing of various information and control an operation of the heat output module 1640 by outputting an electric signal to the heat output module according to the result of the calculations and processing. Thus, the feedback controller 1645 may be implemented in a computer or similar device as a hardware, software or combination thereof. The feedback controller 1645 may be provided in the form of an electronic circuit that performs a control function by processing an electrical signal. The feedback controller 1645 may alternatively be provided in a form of a program or a code for driving a microprocessor or other hardware circuit.

The feedback device 1600 may also be provided with a plurality of the above-described thermal output modules 1640. For example, if the feedback device 1600 has a plurality of the grip portions 1621 as shown in FIG. 13, a thermal output module 1640 may be mounted for each grip portion 1621 of the feedback device 1600.

If a feedback device 1600 is provided with a plurality of thermal output modules 1640, the feedback device 1600 may be provided with a feedback controller 1660 for each heat output module 1640. Alternatively, a single feedback controller 1660 may be provided to integrally manage all of the heat output modules 1640 in the feedback device 1600. Also, as shown in FIG. 11, when a plurality of feedback devices 1600 are provided in the thermal feedback system 1000, one or a plurality of heat output modules 1640 may be disposed in each feedback device 1600.

2.3. Type of Heat Output Module

Some embodiments of the heat output module 1640 will be described based on the description of the configuration of the heat output module 1640.

Figure 32:
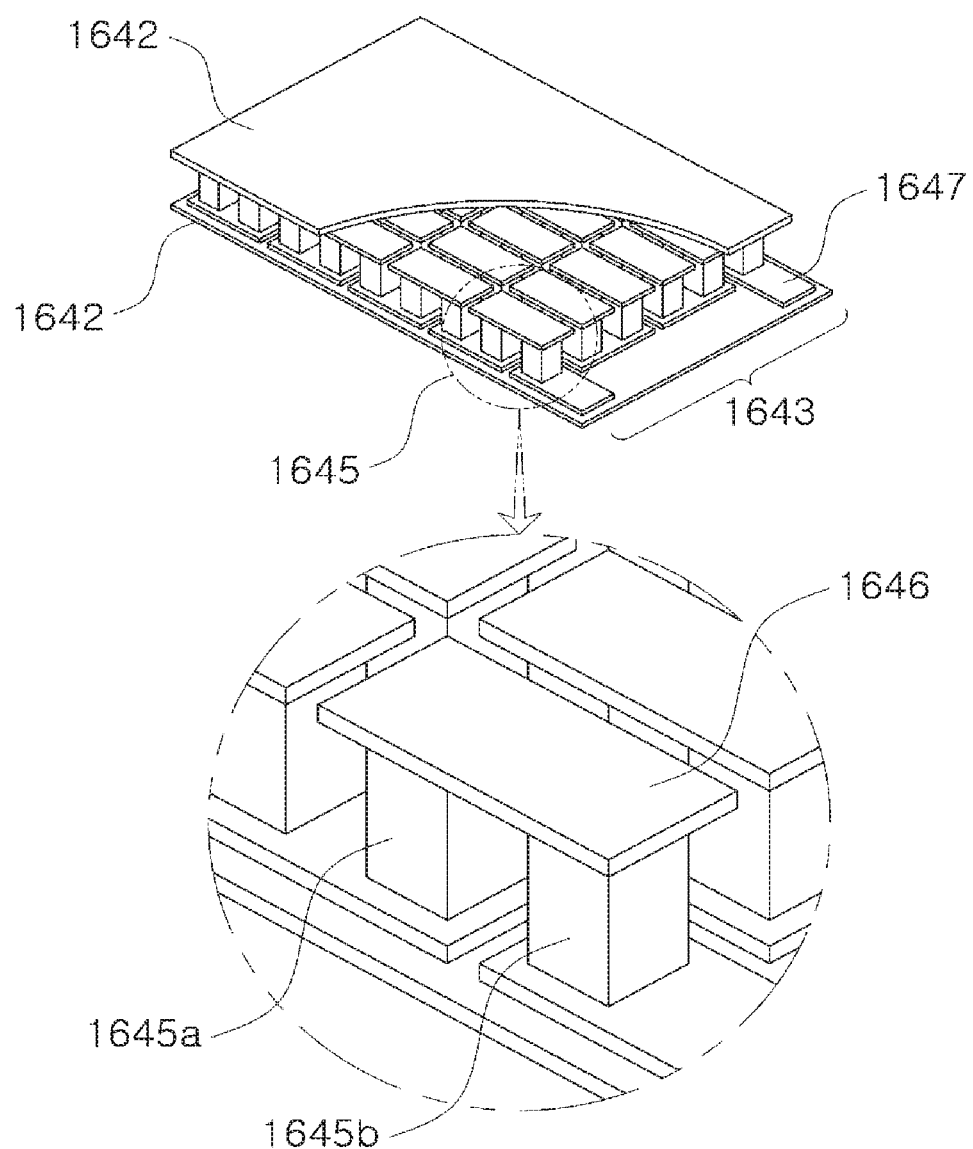
FIG. 32 is a diagram of one embodiment of a heat output module 1640 according to an embodiment of the present disclosure.

FIG. 32 is a diagram of one embodiment of a heat output module 1640 according to an embodiment of the present disclosure.

Referring to FIG. 32, a pair of substrates 1642 are provided so as to face each other in one embodiment of the heat output module 1640. A contact surface 1641 is located on an outer surface of one of the two substrates 1642 to transmit heat generated by the heat output module 1640 to the user's body.

A plurality of thermoelectric couple units 1645 may be disposed between the substrates 1642. Each thermoelectric couple unit 1645 is composed of a semiconductor pair of an N-type semiconductor and a P-type semiconductor. In one embodiment of the thermoelectric couple units 1645, the N-type semiconductor and the P-type semiconductor are electrically connected to each other by a conductor member 1646 at one end. The other ends of the N-type semiconductor and the P-type semiconductor of the thermoelectric couple unit 1645 are respectively connected to a P-type semiconductor of one adjacent thermoelectric couple unit and a N-type semiconductor of the other adjacent thermoelectric couple unit 1645. The electrical connection between the thermoelectric couple units is achieved by the substrate 1642. Accordingly, the thermoelectric couple units are connected in series to form one thermoelectric couple group 1644. In this embodiment, since the thermoelectric couple array 1643 is composed of one thermoelectric couple group 1644 and all the thermoelectric couple units 1645 are connected in series between the power supply terminals 1644, the thermal output module 1640 can perform the same thermoelectric operation over the entire contact surface (front surface). That is, when power is applied to the power supply terminals 1644 in one direction, the heat outputting module 1640 performs the heat generating operation, and when the power is applied in the opposite direction, the heat outputting module 1640 performs the heat absorbing operation.

Figure 33:
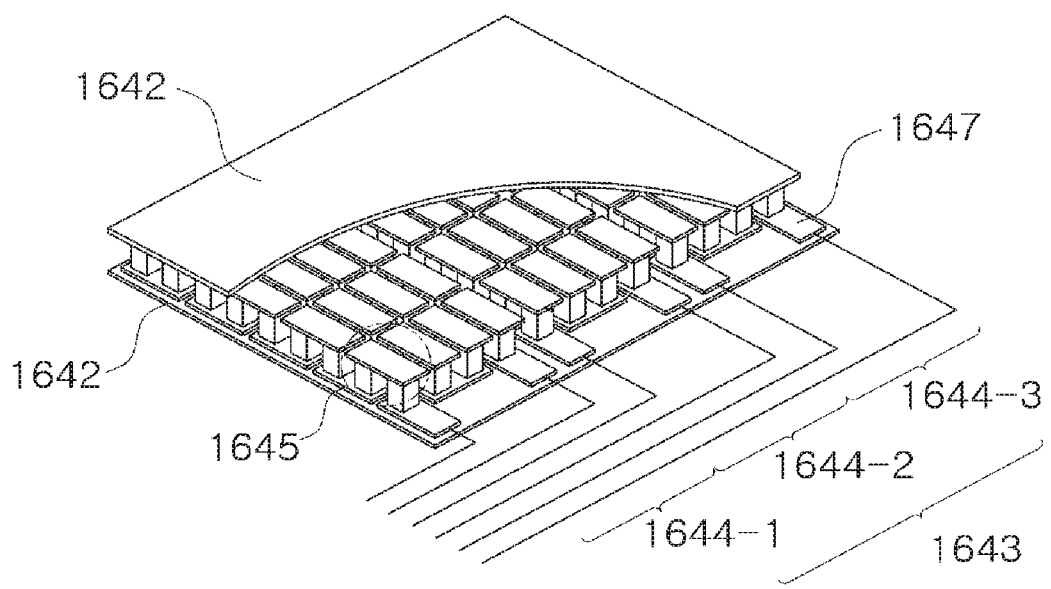
FIG. 33 is a diagram of an embodiment of a heat output module according to an embodiment of the present disclosure.

FIG. 33 is a diagram of another embodiment of a heat output module 1640 according to an embodiment of the present disclosure.

Referring to FIG. 33, the thermal output module 1640 of another embodiment is similar to the one embodiment described above. In this embodiment, however, the thermoelectric couple array 1643 has a plurality of thermoelectric couple groups 1644 and each thermoelectric couple group 1644 is connected to the respective power supply terminals 1644. For example, a direction of a first current applied to a first thermoelectric couple group 1644-1 can be different from a direction of a second current applied to a second thermoelectric couple group 1644-2 so that if the first thermoelectric couple group 1644-1 performs the heat generating operation, the second thermoelectric couple group 1644-2 may perform the heat absorbing operation. In addition, a first voltage value applied to the first thermoelectric couple group 1644-1 can be different from a second voltage value applied to the second thermoelectric couple group 1644-2 so that a degree of a first thermoelectric operation performed by the first thermoelectric group 1644-1 can be different from a degree of a second thermoelectric operation performed by the second thermoelectric couple group 1644-2.

Figure 34:
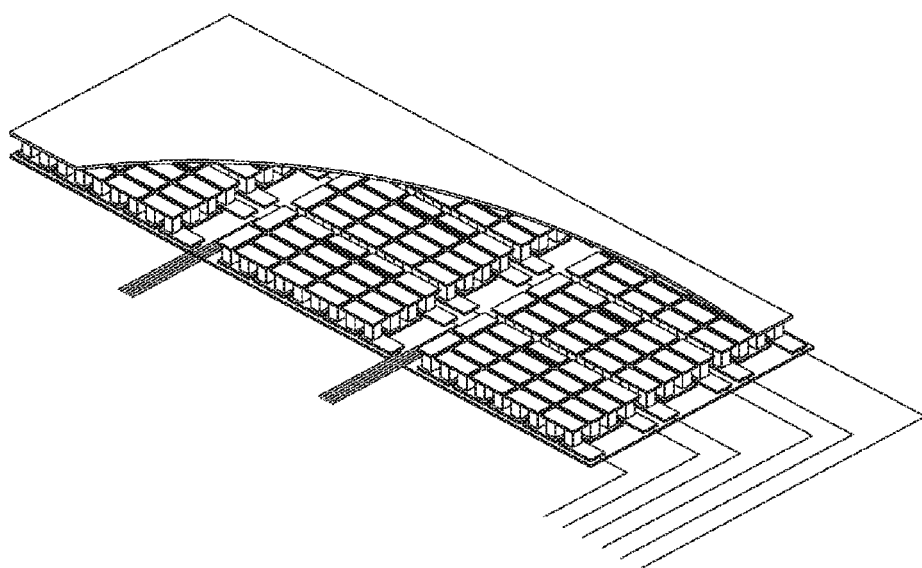
FIG. 34 is a diagram of an embodiment of a heat output module 1640 according to an embodiment of the present disclosure.

As illustrated in FIG. 33, the thermoelectric couple groups 1644 may be arranged in a one-dimensional array in the thermoelectric couple array 1643. Alternatively, thermoelectric couple groups 1644 may alternatively be arranged in a two-dimensional array in the thermoelectric couple array 1643. FIG. 34 is a diagram of another embodiment of a heat output module 1640 according to an embodiment of the present disclosure. As shown in FIG. 34, according to one embodiment of the present application, the thermoelectric couple group 1644 may be arranged in a two-dimensional array in the thermoelectric array 1643. Due to the two-dimensional array, the thermoelectric operation of the thermoelectric couple array 1643 may be controlled in two-dimensional way.

Figure 35:
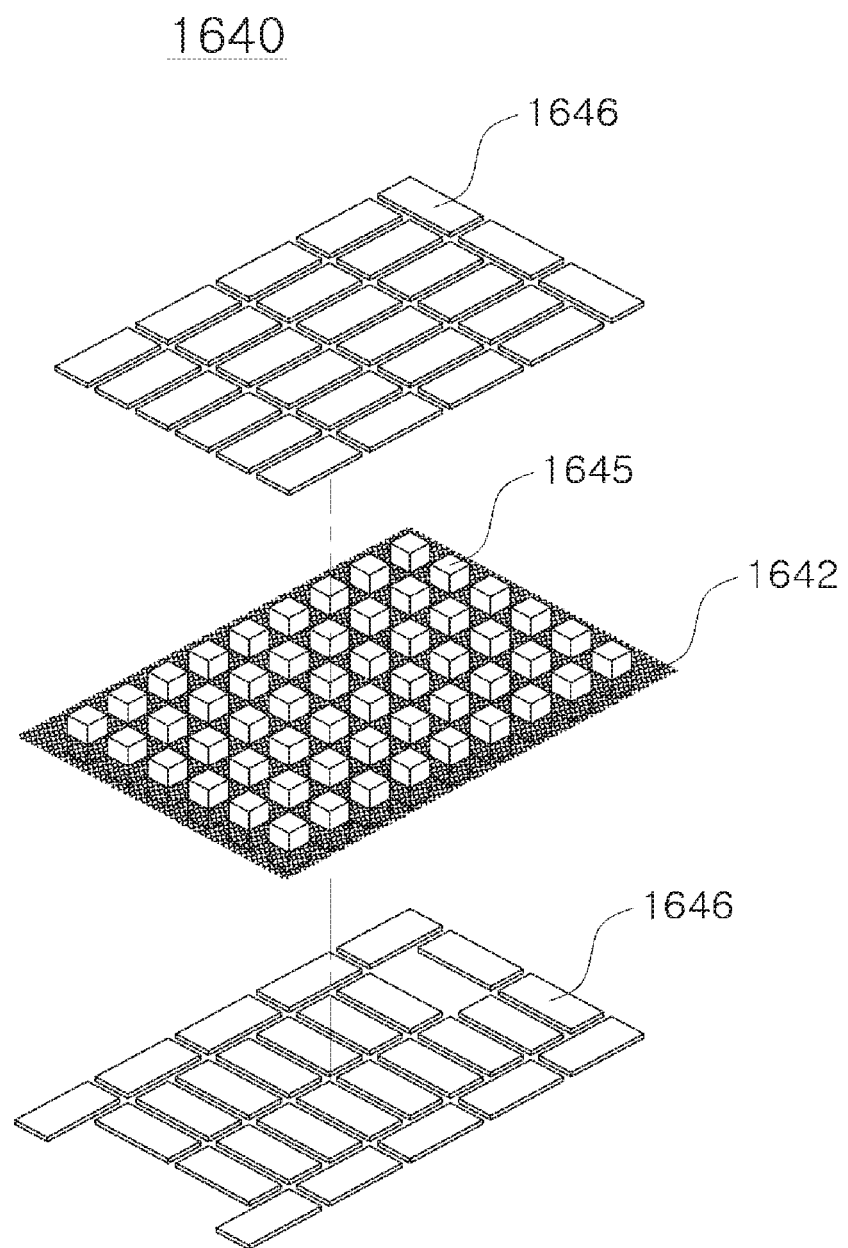
FIG. 35 is an diagram of an embodiment of a heat output module 1640 according to an embodiment of the present application.

Although the above-described embodiments of the heat output module 1640 are described as using a pair of opposed substrates 1642, a single substrate 1642 may also be used. FIG. 35 is another diagram of another embodiment of a heat output module 1640 according to an embodiment of the present application. Referring to FIG. 35, a thermoelectric couple unit 1645 may be embedded in a single substrate 1642. In this embodiment, glass fiber or the like can be used as a material of the substrate 1642 and the thermoelectric couple unit 1645 can be supported at a middle portion thereof by the single substrate 1642. The use of a single substrate 1642 of the present embodiment can provide greater flexibility to the heat output module 1640.

Various embodiments of the heat output module 1640 described above can be combined to each other or modified within the scope of the present application. For example, although the contact surface 1641 is formed on the front surface of the heat output module 1640 as a separate layer from the heat output module 1640 in the above embodiments, one surface of the heat output module 1640 can alternatively serve as the contact surface 1641 without the separate layer. That is, the outer surface of one substrate 1642 described in the above embodiments can be the contact surface 1641.

2.4. Thermal Feedback Output

Hereinafter, the thermal feedback output operation performed by the feedback device 1600 will be described.

The feedback device 1600 may output thermal feedback as the heat output module 1640 performs a heat generating operation or a heat absorbing operation. The thermal feedback includes a hot feedback, a cold feedback, and a thermal grill feedback.

The hot feedback can be output by performing the heat generating operation, and the cold feedback can be output by performing the heat absorbing operation. Also, the thermal grill feedback can be output through a thermal grill operation in which the heat generating operation and the heat absorbing operation are simultaneously performed.

Alternatively, the feedback device 1600 can output the above thermal feedback at various intensities. The intensity of the thermal feedback can be adjusted in such a manner that the feedback controller 1645 of the heat output module 1640 adjusts a magnitude of the voltage applied to the thermoelectric couple array 1643 via the power supply terminal 1647. Here, a method of controlling the magnitude of the voltage includes applying a power to the thermoelectric couple array 1643 after smoothing a duty signal. That is, a way of adjusting the voltage level by adjusting the duty rate of the duty signal may be used for adjusting the magnitude of the voltage (voltage level).

Hereinafter, the heat generating operation, the heat absorbing operation and the thermal grill operation will be described in more detail.

2.4.1. Heat Generating/Absorbing Operation

The feedback device 1600 may perform a heat generating operation by using the heat output module 1640 to provide the hot feedback to the user. Similarly, the heat output module 1640 may perform an heat absorbing operation to provide cold feedback to the user.

Figure 36:
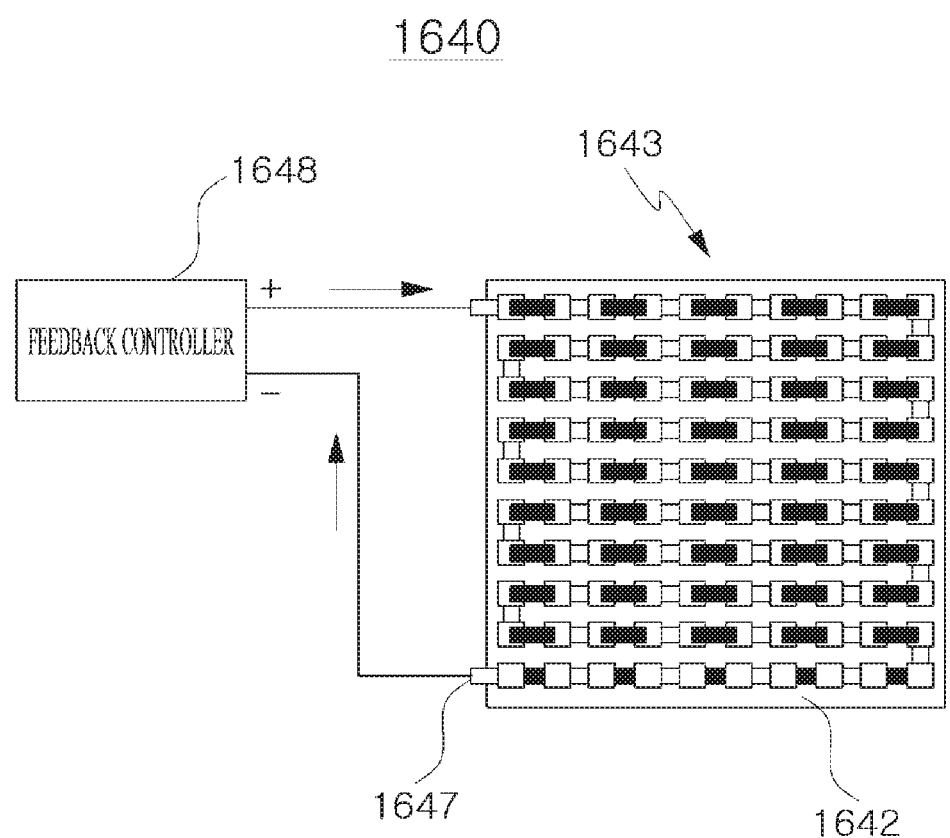
FIG. 36 is a diagram illustrating a heat generating operation for providing hot feedback according to an embodiment of the present disclosure.
Figure 37:
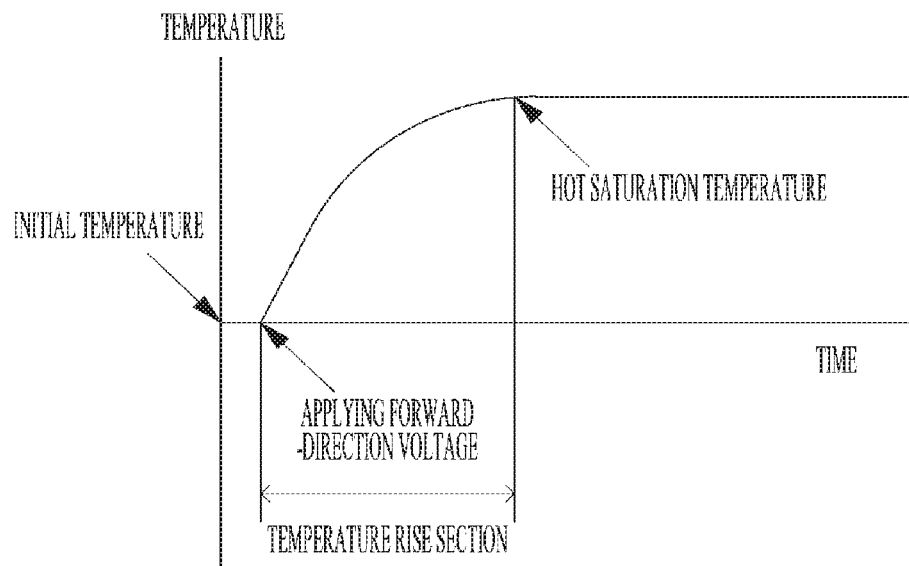
FIG. 37 is a graph relating to temperature during the hot feedback in accordance with an embodiment of the present disclosure.

FIG. 36 is a diagram illustrating a heat generating operation for providing hot feedback according to an embodiment of the present disclosure, and FIG. 37 is a graph relating to temperature during the hot feedback in accordance with an embodiment of the present disclosure.

Referring to FIG. 36, the heat generating operation may be performed by inducing a heat generating reaction on the contact surface 1641 as the feedback controller 1645 applies a forward-direction current to the thermoelectric couple array 1643. Here, when the feedback controller 1645 applies the forward-direction voltage (hereinafter, the voltage which is applied to induce the heat generating reaction on the contact surface 1641 may be referred to as a "forward-direction voltage" or "forward voltage") to the thermoelectric couple array 1643, the thermoelectric couple array 1643 starts the heat generating operation. In accordance with the heat generating operation, the temperature of the contact surface 1641 may rise to a saturation temperature with time as shown in FIG. 37. Therefore, at the beginning of the heat generating operation, the user can feel no hot feedback or a weak hot feedback, then the user can start to feel the hot feedback until the temperature reaches the saturation temperature (hereinafter, referred as "hot saturation temperature"), and the user may feel consistently a hot feedback corresponding to the saturation temperature (hot saturation temperature), after a saturation time (hereinafter, referred to as "hot temperature saturation time" or "hot saturation time").

Figure 38:
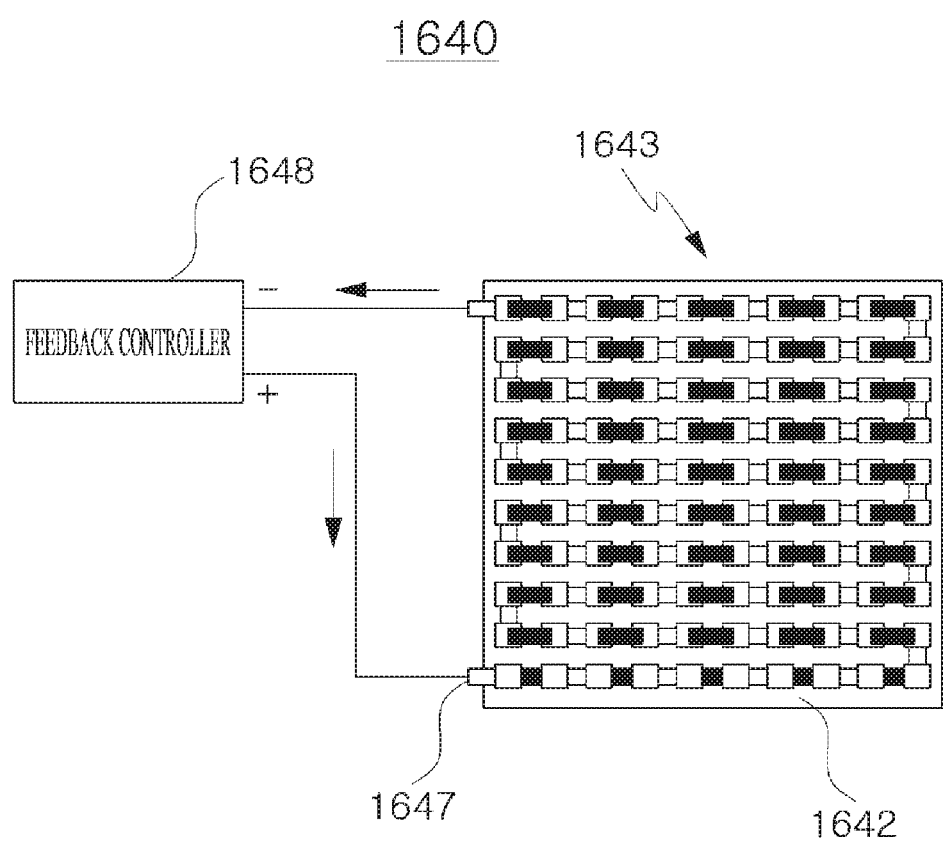
FIG. 38 is a diagram illustrating a heat absorbing operation for providing a cold feedback according to an embodiment of the present disclosure.
Figure 39:
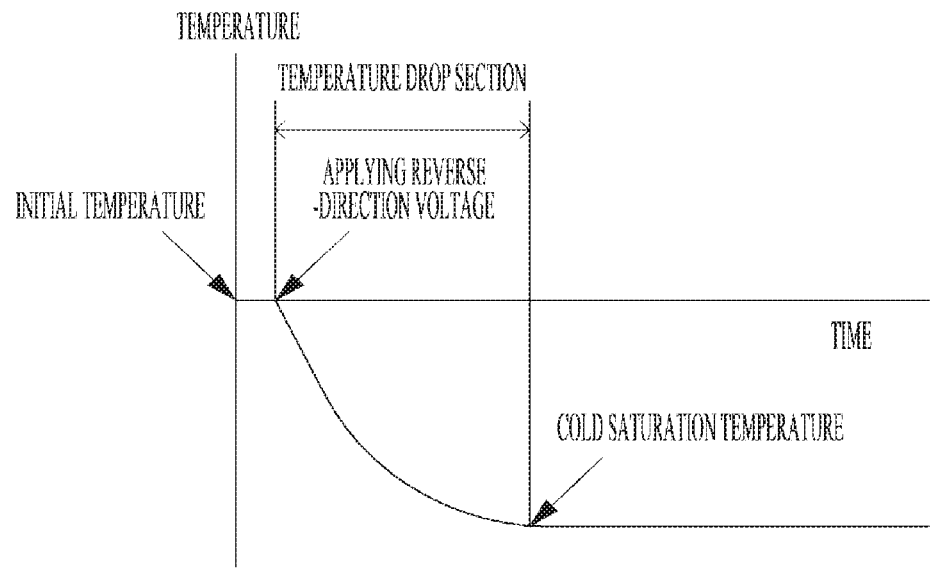
FIG. 39 is a graph relating to temperature during the cold feedback in accordance with an embodiment of the present disclosure.

FIG. 38 is a diagram illustrating a heat absorbing operation for providing a cold feedback according to an embodiment of the present disclosure, and FIG. 39 is a graph relating to temperature during the cold feedback in accordance with an embodiment of the present disclosure.

Referring to FIG. 38, the heat absorbing operation may be performed by inducing a heat absorbing reaction in the contact surface 1641 as the feedback controller 1645 applies a reverse-direction current to the thermoelectric couple array 1643. Here, when the feedback controller 1645 applies the reverse-direction voltage (hereinafter, the voltage which is applied to induce the heat absorbing reaction on the contact surface 1641 may be referred to as a "reverse-direction voltage" or "reverse voltage") to the thermoelectric couple array 1643, the thermoelectric couple array 1643 starts the heat absorbing operation. In accordance with the heat absorbing operation, the temperature of the contact surface 1641 rises to a saturation temperature with time as shown in FIG. 39. Therefore, at the beginning of the heat absorbing operation, the user may feel no cold feedback or feel only a weak cold feedback. Then the user can start to feel the cold feedback until the temperature reaches the saturation temperature (hereinafter, referred to as "cold saturation temperature"), and the user may feel consistently a cold feedback corresponding to the saturation temperature (cold saturation temperature) after a saturation time (hereinafter, referred to as "cold temperature saturation time" of "cold saturation time").

Alternatively, when a power is applied to a thermoelectric element, in addition to a heat generating reaction and a heat absorbing reaction occurring on both sides of the thermoelectric element, electric energy may be converted into thermal energy. That is, a Joule's heat can be generated.

Therefore, when a voltage of the same magnitude is applied to the thermoelectric couple array 1643 by changing only the direction of the current, the temperature change amount due to the heat generating operation may be larger than the temperature change amount due to the heat absorbing operation. The temperature change amount means the temperature difference between the saturation temperature and an initial temperature in a state where the heat output module 1640 is not operated.

Hereinafter, the heat generating operation and the heat absorbing operation performed by the thermoelectric element using electric energy will be collectively referred to as a "thermoelectric operation". In addition, a thermal grill operation which will be described below can also be interpreted as a kind of the "thermoelectric operation" since the thermal grill operation can be realized by combining the heat generating operation and the heat absorbing operation.

2.4.2. Degree of Intensity Control of Heat Generating Operation/Heat Absorbing Operation As described above, when the heat output module 1640 performs the heat generating operation or the heat absorbing operation, the feedback controller 1645 may control the heat generation degree or the heat absorption degree of the heat output module 1640 by adjusting a magnitude of the applied voltage. Specifically, the feedback controller 1645 may adjust a direction of the current to select the type of thermoelectric operation among the heat generating operation and the heat absorbing operation, and may adjust the magnitude of the voltage to adjust a degree of the intensity of the hot feedback (which is provided when the heat output module 1640 performs the heat generating operation) or the cold feedback (which is provided when the heat output module 1640 performs the heat absorbing operation).

Figure 40:
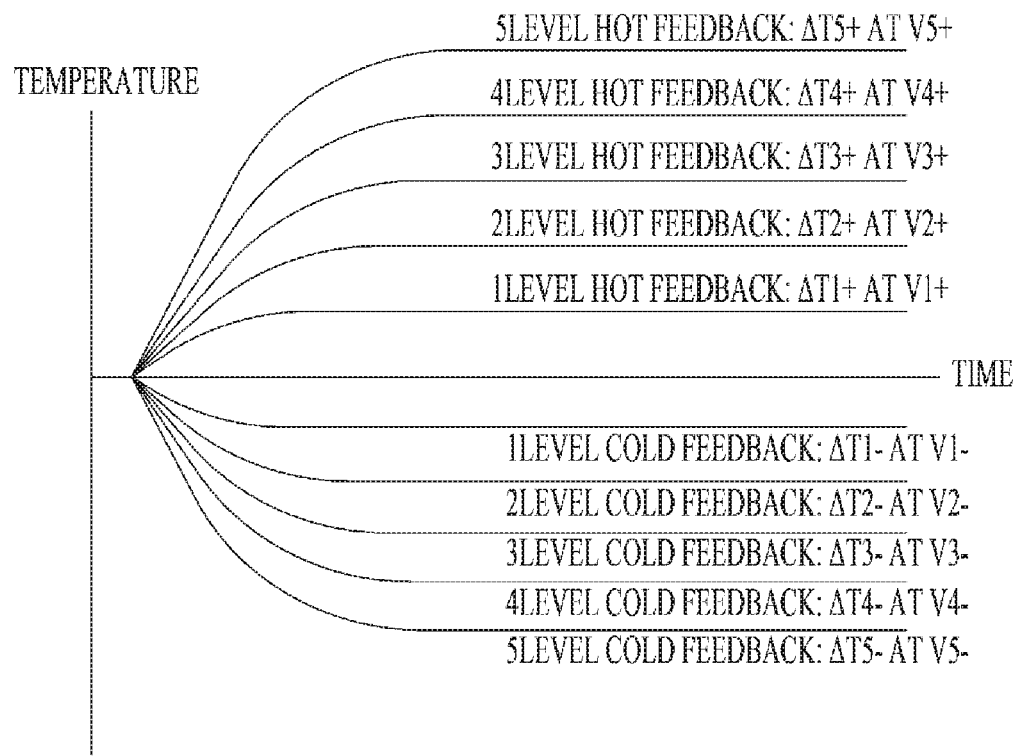
FIG. 40 is a graph illustrating the degree of the intensity of the hot/cold feedback based on an adjustment of a magnitude of voltage according to an embodiment of the present disclosure.

FIG. 40 is a graph illustrating the degree of the intensity of the hot/cold feedback based on an adjustment of a magnitude of voltage according to an embodiment of the present disclosure.

For example, referring to FIG. 40, the feedback controller 1645 may apply a voltage with five levels in a forward direction or a backward direction so that the feedback device 1600 can provide the user with a ten distinguishable thermal feedbacks. However, the number of levels provided for the hot and cold feedback need not be the same. Moreover, while FIG. 40 shows the hot feedback and the cold feedback having the same degree (level) of feedback intensity are implemented by changing the current direction using the same magnitude voltage, the magnitude of the voltage value applied for the same intensity degree (level) of the hot feedback and the cold feedback need not be equal to each other.

Figure 41:
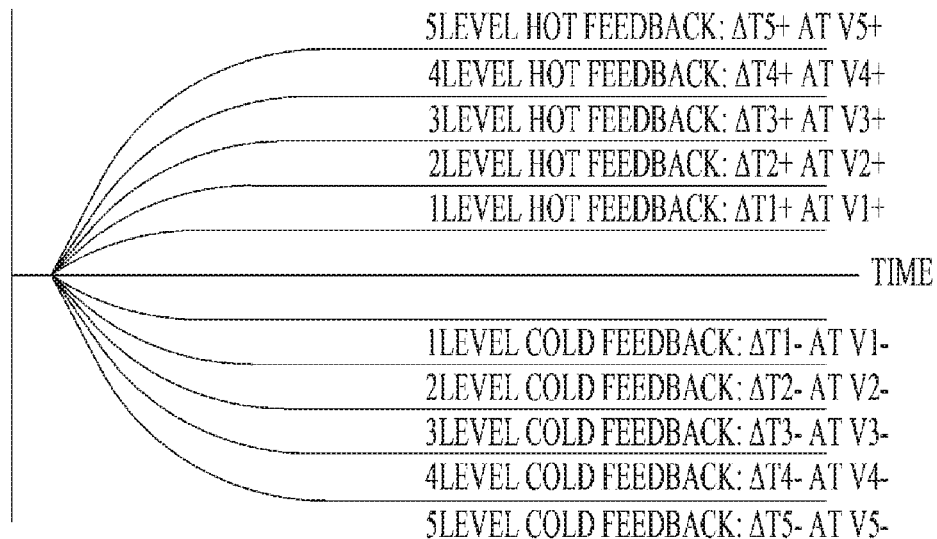
FIG. 41 is a graph relating to hot/cold feedback with the same temperature change amount according to an embodiment of the present disclosure.

FIG. 41 is a graph relating to hot/cold feedback with the same temperature change amount according to an embodiment of the present disclosure.

In general, when the same magnitude of voltage is applied to perform the heat generating operation and the heat absorbing operation, the temperature change amount of the heat generating operation is larger than the temperature change amount of the heat absorbing operation. Accordingly, for the same level (degree of intensity) of the hot feedback and the cold feedback, a magnitude of the voltage for the cold feedback may be larger than a magnitude of the voltage for the hot feedback as shown in FIG. 41.

As described above, by adjusting the intensity of the thermal feedback, the thermal feedback may be provided with various levels of intensity, such as strong hot sensation, weak hot sensation, weak cold sensation, strong cold sensation, etc. Such multi-level thermal feedback can provide a greater immersion for the user in a game environment or a virtual/augmented reality environment, and also makes it possible to inspect a patient's senses more precisely when applied to a medical device.

2.4.3. Thermal Grill Operation 2.4.3.1. Types of Thermal Grill Feedback

The thermal grill feedback may include a neutral thermal grill feedback, a hot thermal grill feedback, and a cold grill feedback.

The neutral thermal grill feedback, the hot thermal grill feedback, and the cold thermal grill feedback provide the user a neutral thermal grill illusion, a hot thermal grill illusion, and a cold thermal grill illusion, respectively. The neutral thermal grill illusion means a thermal grill illusion without feelings of hot and cold. The hot thermal grill illusion means an illusion that makes a user to feel heat in addition to the thermal grill illusion. The cold thermal grill illusion means an illusion that makes a user feel cold in addition to the thermal grill illusion.

The neutral thermal grill illusion can be realized when the hot thermal feedback and the cold thermal feedback are provided simultaneously and provided within a predetermined ratio range. A ratio for the neutral thermal grill illusion (hereinafter referred to as "neutral ratio") can be different for each part of the body that is provided with the thermal grill feedback, and even if it is the same body part, it may be slightly different for each individual user. In general, a user is inclined to feel the thermal grill illusion when the body area excited by the hot heat (hot thermal feedback) is larger than the body area excited by the cold heat (cold thermal feedback) or when an amount of hot heat provided to the user is larger than an amount of cold heat provided to the user.

A degree of the intensity of the thermal feedback may be represented as an amount of heat that the feedback device 1600 provides to the body part contacting the contact surface 1641, or an amount of heat absorbed from the body part. When the thermal feedback is provided to a specific body part for a specific time period, a degree of the intensity of the thermal feedback can be expressed using a difference between the temperature (for example, difference between a temperature at initial points and a temperature at equilibrium points for the thermal feedback) of the target body part to which the thermal feedback is applied.

Alternatively, human body temperature is usually between 36.5 and 36.9° C., and skin temperature is different from each other person, but it is known to be about 30~32° C. on average. Specially, a temperature of the palm is about 33° C. which is slightly higher than the average skin temperature. The above-mentioned temperature values may be slightly different depending on the individual, and even the same person may vary to some extent according to the current conditions.

According to one experimental example, it was confirmed that the neutral thermal grill illusion was felt when a hot thermal feedback of about 40° C. and a cold thermal feedback of about 20° C. were given to the palm of 33° C. In the above experimental example, the hot thermal feedback of +7° C. and the cold thermal feedback of −13° C. are given to the palm of 33° C. From the above experimental case, the neutral ratio for a human palm can be represented as 1.86 (=|−13|/|7|) in view of temperature difference.

As can be understood from this, in most people, when the hot heat and cold heat are continuously applied to the same body part, the neutral ratio, which can be represented as a ratio of a hot temperature difference (temperature difference between an initial point and at a hot equilibrium point for the hot heat) and a cold temperature difference (temperature difference between an initial point and at a cold equilibrium point for the cold heat), and according to the present application, the neutral ratio may be in a range of 1.5-5.

In addition, the hot thermal grill illusion can be sensed by a user when the hot heat is applied over the neutral ratio, and the cold thermal grill illusion can be sensed by the user when the cold heat is applied over the neutral ratio.

2.4.3.2. Thermal Grill Operation by an Adjustment of Voltage

The feedback device 1600 may perform a thermal grill operation in a voltage control manner. The thermal grill operation in the voltage control manner can be implemented by the feedback device 1600 in which the thermoelectric couple array 1643 includes a plurality of thermoelectric couple groups 1644. For realizing the thermal grill operation, the feedback device 1600 has a heat output module 1640 including two or more thermoelectric couple groups 1644 that can be individually controlled.

Specifically, the thermal grill operation in the voltage control manner may be performed by 1) applying a positive voltage to a part of the thermoelectric couple group 1644 to perform a heat generating operation and 2) applying a reverse voltage to another part of the thermoelectric couple group 1644 to perform a heat absorbing operation, so that the heat output module 1640 provides a user with the hot thermal feedback and the cold thermal feedback at the same time.

Figure 42:
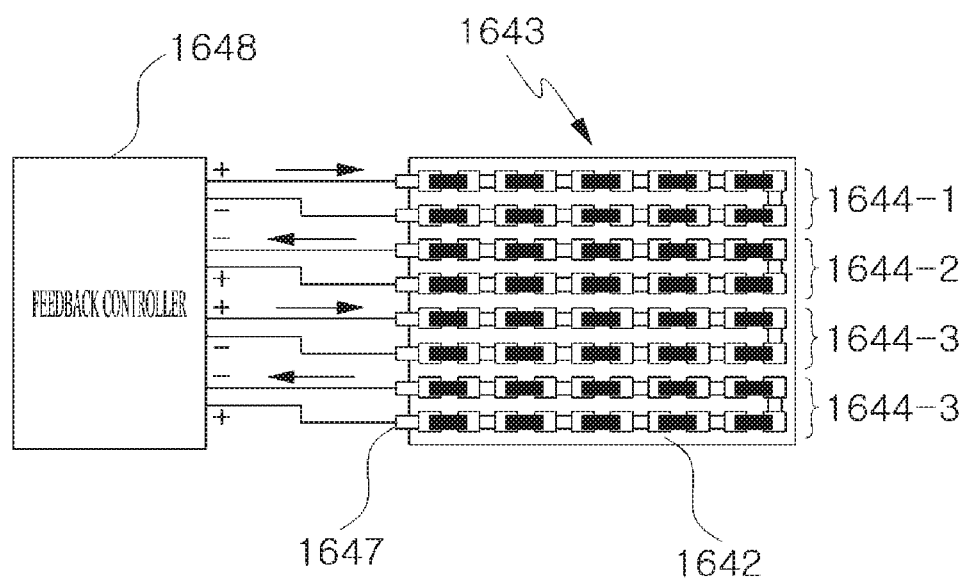
FIG. 42 is a diagram related to a thermal grill operation according to an embodiment of the present disclosure.

FIG. 42 is a diagram related to a thermal grill operation according to an embodiment of the present disclosure.

Referring to FIG. 42, a thermoelectric couple array 1643 includes a plurality of thermoelectric couple groups 1644 in a line arrangement. The feedback controller 1645 allows the first thermoelectric couple groups 1644-1 and 1644-3 (e.g., the thermoelectric couple groups forming the odd-numbered lines) to perform the heat generating operation and allows the second thermocouple groups 1644-2 and 1644-4 (e.g., the thermoelectric couple groups forming the even-numbered lines) to perform the heat absorbing operation. If the thermoelectric couple groups 1644 alternately perform the heat generating operation and the heat absorbing operation according to the line arrangement, the user can be provided with the hot thermal feedback and the cold thermal feedback at the same time. As a result, the thermal grill feedback can be provided to the user. The division of the thermoelectric couple array 1644 into the odd-numbered lines and the even-numbered lines should be understood as an exemplary case and the scope of the present disclosure should not be limited to above embodiment.

The feedback device 1600 may control the saturation temperature of the first thermoelectric couple groups 1644-1 and 1644-3 and the saturation temperature of the second thermoelectric couple groups 1644-2 and 1644-4 to conform to the neutral ratio for the neutral thermal grill feedback.

FIG. 43 is a table of voltages for providing the neutral thermal grill feedback in a voltage control manner according to an embodiment of the present disclosure.

For example, referring to FIG. 43, the feedback controller 1645 may apply five positive voltages and five negative voltages to the heat output module 1640, respectively. The heat output module 1640 may generate five heat generating operations and five heat absorbing operations according to the five positive voltages and the five negative voltages. A temperature change amount according to a heat generating operation having a certain level may be same to a temperature change amount according to a heat absorbing operation having a same level to the heat generating operation. However, the relationship between temperature change amounts of the same-level heat generating/absorbing operations is not limited to the above. Assuming that a temperature change amount between each adjacent heat generating/absorbing operations is constant, when the neutral ratio is set to 3, the feedback controller 1645 may apply a first-level positive voltage (e.g., minimum-level positive voltage) to a first thermoelectric couple group 1644 and a third-level negative voltage to a second thermoelectric couple group 1644 such that the heat output module 1640 can provide the neutral thermal grill feedback. When the neutral ratios is set to 2.5, the feedback controller 1645 may apply a second-level positive voltage to the first thermoelectric couple group 1644 and a fifth-level negative voltage to the second thermoelectric couple group 1644. When the neutral ratio is set to 2, the feedback controller 1645 may apply a first-level positive voltage and a second-level negative voltage of a second-level positive voltage and a fourth-level negative voltage to the thermoelectric couple array 1643. A user may feel the thermal grill feedback which is induced by the combination of the first-level positive voltage and the second-level negative voltage as more painful than the thermal grill feedback which is provided by the combination of the second-level positive voltage and the fourth-level negative voltage. This means that a magnitude of intensity of the latter thermal grill feedback is larger than one of the former thermal grill feedback. The magnitude of intensity of the thermal grill feedback can be adjusted by controlling the applied voltages. The above description for a method of providing the thermal grill feedback should be understood as an exemplary embodiment, thus the present disclosure should not be limited to the above exemplary embodiment. For example, a number of grades (levels) for the heat generating/absorbing operations is not limited to 5, and a number of grades for the heat generating operation need not to be same a number of grades for the heat absorbing operation.

The feedback controller 1645 may also provide a hot thermal grill feedback by adjusting the positive voltage and negative voltage to be below the neutral ratio, or provide a cold thermal grill feedback by adjusting the positive voltage and the negative voltage to be over the neutral ratio.

Figure 45:
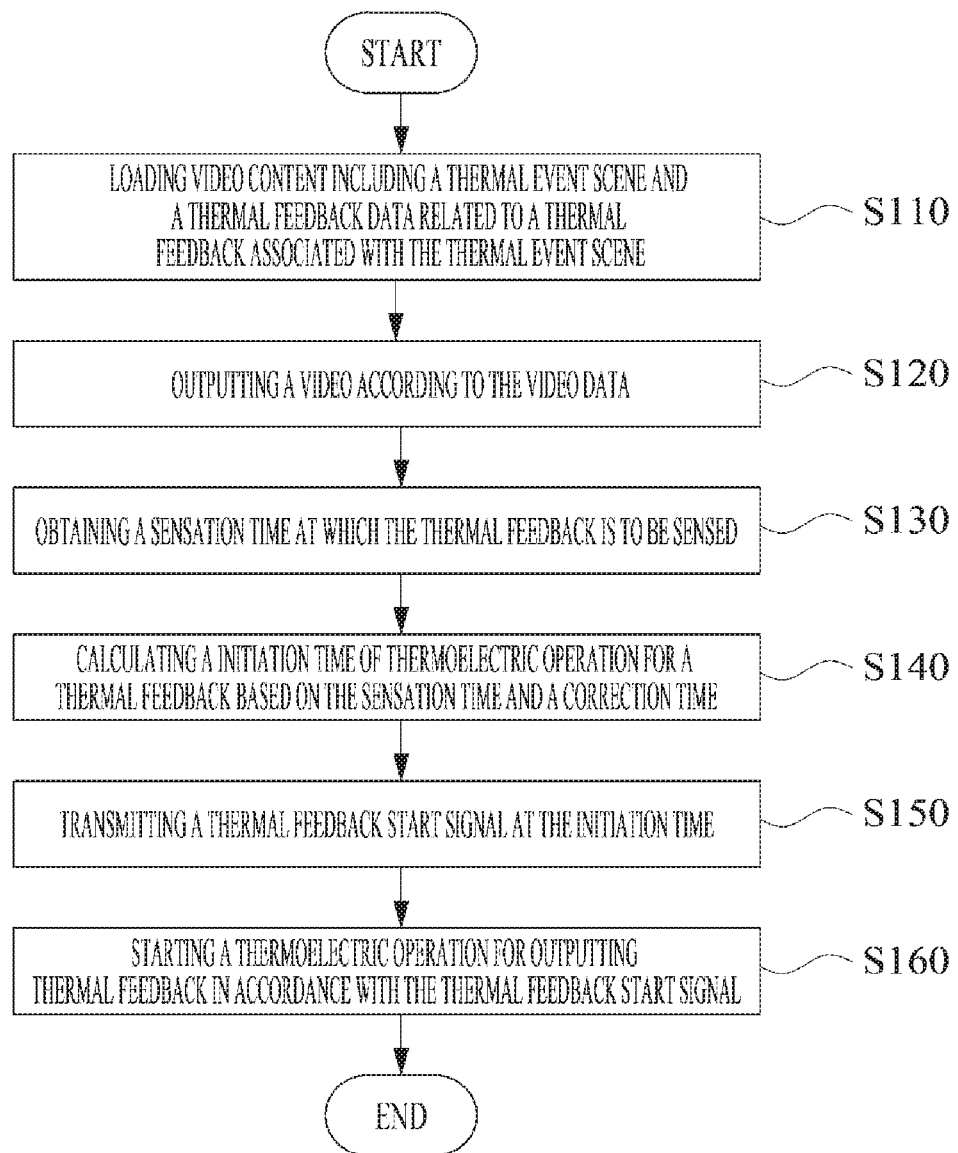
FIG. 45 is a flowchart of a first implementation of a thermal feedback providing method according to an embodiment of the present disclosure.

For example, referring to FIG. 45, when the feedback controller 1645 applies a first-level positive voltage to the first thermoelectric couple group 1644 and a second-level negative voltage to the second thermoelectric couple group 1644 (assuming that the neutral ratio is set to 3), the user can experience a hot thermal feedback and a thermal grill feedback at the same time or a warmer thermal grill feedback than the neutral thermal grill feedback. In addition, when the feedback controller 1645 applies a first-level positive voltage and a fourth/fifth negative voltage to the heat output module 1640, the user can be provided with a cooler thermal grill feedback than the neutral thermal grill feedback.

However, in case of providing the hot thermal grill feedback or the cold thermal grill feedback, when the constant voltage and the reverse voltage are applied at a ratio largely deviated from the neutral ratio, there is a problem that the user does not experience the thermal grill illusion. Therefore, the ratio of the positive voltage and the negative voltage are made adjustable to fall within a proper range.

3. Method of Providing a Thermal Feedback

Hereinafter, a method of providing a thermal feedback according to an embodiment of the present disclosure will be described. The following description will be made with reference to the thermoelectric operation provided by the heat output module 1640 and with reference to the thermal feedback providing system 1000 according to embodiments of the present disclosure. However, this is merely for convenience of explanation, and therefore, the method of providing the thermal feedback according to an embodiment of the present disclosure is not limited thereto.

3.1. Outline of the Method of Providing the Thermal Feedback

Figure 44:
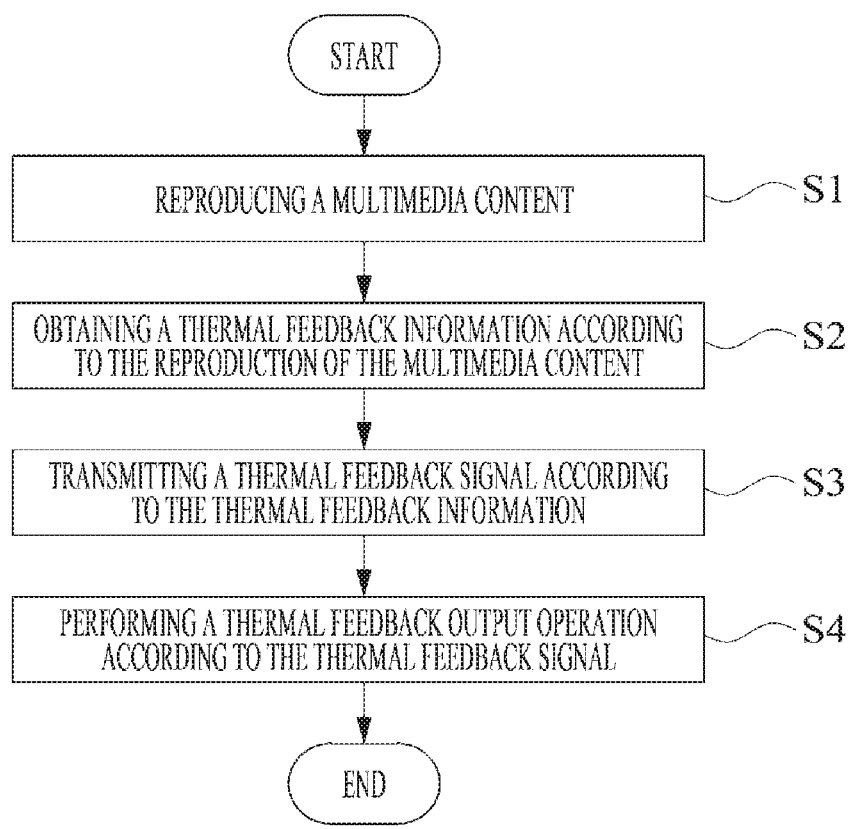
FIG. 44 is a basic flowchart of a thermal feedback providing method according to an embodiment of the present disclosure.

FIG. 44 is a basic flowchart of a thermal feedback providing method according to an embodiment of the present disclosure.

Referring to FIG. 44, a method of providing a thermal feedback according to an embodiment of the present disclosure includes reproducing a multimedia content by a content reproduction device 1200 (S1), obtaining, by the content reproduction device 1200, a thermal feedback information according to the reproduction of the multimedia content (S2), transmitting, by the content reproduction device 1200, a thermal feedback signal to a feedback device 1600 according to the thermal feedback information (S3), and performing, by the feedback device, a thermal feedback output operation (S4). Hereinafter, the above-described steps will be described specifically.

First, the content reproduction device 1200 may reproduce the multimedia content (S1).

The multimedia content may be a video, a game, a virtual reality application, an augmented reality application, a feedback application, and the like. The controller 1260 of the content reproduction device 1200 may load the multimedia content stored in the memory 1240 from the memory 1240. The content reproduction device 1200 may receive the multimedia content through the communication module 1220 and reproduce the multimedia content.

For example, the controller 1260 of the content reproduction device 1200 can reproduce multimedia content such as a game or a movie file stored in the memory 1240. For another example, the content reproduction device 1200 may receive and reproduce the multimedia content by downloading or streaming it from the Internet through the communication module 1220.

The content reproduction device 1200 may obtain a thermal feedback information according to the reproduction of the multimedia content (S2).

The multimedia content may include thermal feedback data or algorithms for processing thermal feedback. The controller 1260 of the content reproduction device 1200 may decode the thermal feedback data in accordance with the reproduction of the multimedia content, or may perform the thermal feedback processing algorithm to obtain the thermal feedback information.

The thermal feedback information may include at least one of a thermal feedback target, a thermal feedback type, a magnitude of intensity for thermal feedback, and time information for thermal feedback.

The thermal feedback target may refer a target which is controlled for providing the thermal feedback to a user. For example, if a plurality of feedback devices 1600 are used in the thermal feedback providing system 1000 (see FIG. 11), or if the feedback device 1600 has a plurality of heat output modules 1640, or if heat output module 1640 is regionally controlled (see FIG. 33), the thermal feedback target may indicate a target to perform the thermal feedback.

A thermal feedback type may refer a kind of thermal feedback. For example, thermal feedback type may include a hot feedback, a cold feedback, and a thermal grill feedback. The thermal grill feedback may also include a neutral thermal grill feedback, a hot thermal grill feedback, and a cold thermal grill feedback.

The thermal feedback intensity may refer an intensity of the thermal feedback. In some cases, the thermal feedback intensity may include a thermal feedback type. For example, the thermal feedback intensity may be classified as grades 1 to 10, with grades 1 to 5 being assigned to the cold thermal feedback and grades 6 to 10 being assigned to the hot thermal feedback. Alternatively, the thermal feedback intensity may be classified as grades −5 to +5, with negative grades being assigned to the cold thermal feedback and positive grades being assigned to the hot thermal feedback.

The thermal feedback providing time may refer a time information related to output of the thermal feedback. The thermal feedback providing time may include a start time, an end time and a running time (time duration) of the thermal feedback output.

The content reproduction device 1200 may transmit the thermal feedback signal to the feedback device 1600 according to the thermal feedback information (S3), and the feedback device 1600 may receive the thermal feedback signal and perform a thermal feedback output operation in accordance with the received signal (S4).

Specifically, the controller 1260 may generate the thermal feedback signal based on the thermal feedback information and transmit the thermal feedback signal to the feedback device 1600 via the communication module 1220. In a thermal feedback providing system 1000 having a plurality of feedback devices 1600, the controller 1260 may select a feedback device 1600 to transmit a thermal feedback signal based on the thermal feedback object information as the thermal feedback target. The feedback controller 1645 may receive the thermal feedback signal through the communication module 1620 and perform the thermal feedback output operation according to the thermal feedback signal.

The thermal feedback signal is a signal for controlling the output of the thermal feedback. In some embodiments, the thermal feedback signal may include a thermal feedback start signal indicating an initiation of the thermal feedback output and a thermal feedback end signal indicating a termination of the thermal feedback output. Additionally or alternatively, the feedback signal may be modulated to transmit a thermal feedback message. For example, controller 1260 may perform an amplitude modulation of the signal to transmit a message feedback device 1600, which may be then decoded to perform a feedback operation. Other modulation methods, such as frequency modulation or pulse width modulation, may also be used to transmit a message via the thermal feedback signal.

The controller 1260 of the content reproduction device 1200 may transmit the start signal (thermal feedback start signal) via the communication module 1220, and then the feedback controller 1645 of the feedback device 1600 may receive the start signal via the communication module 1620. When the feedback device 1600 receives the start signal, the feedback controller 1645 may apply power to the thermoelectric couple array 1643 in response to the start signal to cause the thermoelectric couple array 1643 to perform the thermal feedback output operation.

The controller 1260 of the content reproduction device 1200 may transmit the end signal (thermal feedback end signal) via the communication module 1220, and then the feedback controller 1645 of the feedback device 1600 may receive the end signal via the communication module 1620. When the feedback device 1600 receives the end signal, the feedback controller 1645 may stop applying the power to the thermocouple array 1643 according to the end signal, so that the thermoelectric couple array 1643 can stop the thermal feedback output operation.

The thermal feedback end signal may be used as an optional signal.

For example, if the start signal includes the thermal feedback providing time (especially, end time and/or running time), the feedback controller 1645 determines a timing of the thermal feedback output operation according to the thermal feedback providing time. For example, the feedback controller 1645 may initiate the thermal feedback output operation according to the start time. For another example, the feedback controller 1645 may terminate the thermal feedback output operation according to the end time. For another example, the feedback controller 1645 may maintain the thermal feedback output operating according to the running time (time duration).

In another example, the running time for the thermal feedback output operation may set by to be a predetermined time, and the feedback controller 1645 may maintain the thermal feedback output operation for the predetermined running time. In this case, the end signal may be omitted.

The feedback controller 1645 of the feedback device 1600 may transmit the thermal feedback report signal to the content reproduction device 1200 via the communication module 1620 to report the operating status of the heat output module 1640. The feedback device 1600 may transmit the report signal (thermal feedback report signal) periodically or in response to receipt of the thermal feedback signal to the content reproduction device 1200. The thermal feedback report signal may include information such as whether to output thermal feedback, the type or intensity of the thermal feedback being currently output, the temperature of the contact surface 1641, the user's bio information sensed by the sensing module, an error information and/or a battery level information.

The thermal feedback output operation of the feedback device 1600 in accordance with the thermal feedback signal may be accomplished in a variety of ways.

First, the initiation and termination of the thermal feedback output operation of the feedback device 1600 may be accomplished as follows.

In one embodiment, the feedback device 1600 may perform the thermal feedback output operation only while the thermal feedback signal is received, and may stop the thermal feedback output operation when the thermal feedback signal is not received any more. In this case, the thermal feedback signal may be transmitted continuously.

In another embodiment, upon receipt of the start signal, the feedback device 1600 may output the thermal feedback during a predetermined time (such as a default running time) or a running time included in the start signal. After the predetermined time or the running time included in the start signal is elapsed, the feedback device 1600 may stop the thermal feedback operation.

In another embodiment, the feedback device 1600 may start the thermal feedback output operation at the time of reception of the start signal, and stop the thermal feedback output operation at the time of reception of the end signal.

In some embodiments, the thermal feedback signal may be provided as an ON/OFF signal. According to the present application, the thermal feedback signal, however, may be provided in a form including all or at least a part of the thermal feedback information described above. When the feedback controller 1645 receives the thermal feedback signal, it may extract the information contained therein and control the thermal feedback output operation according to the information. For example, the feedback controller 1645 may determine which heat output module 1640 will perform the thermal feedback output operation based on the thermal feedback target information. As another example, the feedback controller 1645 may determine whether to perform a heat generating operation, a heat absorbing operation, or a thermal grill operation based on the thermal feedback type information. For another example, the feedback controller 1645 may determine the voltage value to be applied to the thermoelectric couple array 1643 based on the thermal feedback intensity information. For another example, the feedback controller 1645 may determine an initiation time and/or a termination time of the thermal feedback output operation based on the thermal feedback providing time information. In some embodiments, at least one of the type/intensity/time of the thermal feedback described above may be set to the thermal feedback device 1600 by default.

3.2. Application of Thermal Feedbacks Providing Method

Traditionally, content such as games and movies have been experienced in the form of audiovisual forms presented by video or audio. To improve the user's immersion into the content, a tactile experience which is represented by vibration feedback and an olfactory experience using smell may be used to support and enhance the existing audiovisual experience. In addition, recently, there have been developed solutions such as virtual reality or augmented reality for providing more realistic enhanced user experiences.

The thermal feedback providing system 1000 realizes a thermal reality (TR) by outputting thermal feedback in cooperation with various situations provided by the conventional methods described above. In this way, the thermal feedback providing system 1000 enhances the user experience.

In this regard, with the thermal feedback providing method described above, the feedback device 1600 outputs thermal feedback through the thermal feedback signal generated according to the reproduction of the multimedia content by the content reproduction device 1200.

Accordingly, the thermal feedback providing method may be applied to various technical fields in which a user experience is requested. Hereinafter, a thermal feedback providing system 1000 and some representative technical fields in which a thermal feedback providing method can be utilized will be schematically described.

3.2.1. Virtual Reality (VR)

Virtual reality is a representative example of the representative technical field in which the thermal feedback providing system 1000 can be used.

Virtual reality means creating a virtual environment or situation so that the user feels as if they are actually in a virtual space. Generally, virtual reality is implemented based on a three-dimensional image (presented using an HMD) that dynamically changes according to a user's field of view.

With the development of smart devices and the release of Samsung's Gear VR™, VR related market is expected to become bigger in the future.

The thermal feedback providing system 1000 of the present disclosure may cooperate with such a virtual reality application and add a thermal sensation to an existing visual/auditory/tactile sense.

For example, the thermal feedback providing system 1000 may assign a temperature to a specific virtual object placed in a virtual space, and when a user's avatar in a virtual reality touches the object, the thermal feedback providing system 1000 may provide a hot (or cold) feedback to the user.

Likewise, the thermal feedback providing system 1000 may assign an appropriate temperature to a virtual space such as a desert or polar regions, and when a user's avatar in a virtual reality is in the virtual space, the thermal feedback providing system 1000 may output a hot feedback or a cold feedback to the user according to the appropriate temperature assigned to the virtual space.

3.2.2. Augmented Reality (AR)

Augmented reality is also a representative example of the field in which the thermal feedback providing system 1000 may be applied.

Augmented reality is a mixed reality in that it combines virtual environments with the real world by presenting virtual objects over a representation of the real world.

Compared to virtual reality, which immerses a user entirely into a virtual space, augmented reality basically enhances the real world by providing virtual objects or additional virtual information. Therefore, an HMD which is used for the augmented reality may be a glass-type transparent display such that a virtual image displayed on the transparent display can be visually sensed by the user. Accordingly, the user can visually experience the real world augmented with the virtual image. Otherwise, when an HMD which is not adopt the transparent display is used for the augmented reality, the HMD may display a synthesized image which is generated by combining the virtual image with an real image captured by a camera 1480 in real time.

Apple's iPhone™ and other smart devices have limited augmented reality capabilities, and in recent years, interests about AR has grown in accordance with the release of Microsoft's Hololens™, a standalone HMD type device.

The thermal feedback providing system 1000 may provide a thermal sensation that works in conjunction with such an augmented reality application to assist in an existing visual/auditory user experience.

For example, the thermal feedback providing system 1000 may provide useful information to a user by outputting a hot feedback as one of the enhancement elements when a hot object enters the user's field of view.

3.2.3. Game Content

The thermal feedback providing system 1000 may be utilized for game content.

The game content is basically interactive content based on the interaction between the game situation and the users.

The implementation of the game content may be realized through the above-described virtual reality or augmented reality techniques as well as the conventional technique reflecting the user's operation on the game screen outputted through the conventional TV or monitor. The thermal feedback providing system 1000 may add thermal feedback as part of improving a user's immersion in a game environment implemented through the techniques described above. For example, the thermal feedback providing system 1000 may output thermal feedback when a user's avatar is shot by a gun or the like in a first-person shooter-type game.

3.2.4. Video Content

Also, the thermal feedback providing system 1000 may be utilized for video content and the like. The video content may be based on an audiovisual presentation, and the thermal feedback providing system 1000 may allow the multimedia content to provide thermal feedback to a user by outputting thermal feedback corresponding to a specific scene represented by the audiovisual presentation. For example, the thermal feedback providing system 1000 may output the hot feedback in an explosion scene and output the cold feedback in a scene showing a winter sea.

Although the various application fields of the thermal feedback providing system 1000 have been described above, the application fields of the thermal feedback providing system 1000 are not limited to the above examples. In addition to the above-described technical fields, the thermal feedback providing system 1000 may be utilized for various multimedia content including education or learning content or medical applications.

Accordingly, in the present disclosure, the thermal feedback providing system 1000 should be construed as being applicable to any field in which thermal feedback may be provided to improve the user experience.

4. Implementation of Methods for Providing Thermal Feedback

In the above, the thermal feedback providing method may be used to improve the user experience in various technical fields. An appropriate thermal feedback may be output as the multimedia content is reproduced so as to provide a better thermal experience for the user.

Hereinafter, various embodiments of a method for providing a thermal feedback capable of improving a user experience for each technology field will be described.

4.1. First Implementation

A first implementation of the thermal feedback providing method according to an embodiment of the present disclosure is a method of providing a thermal feedback to a user by outputting thermal feedback during reproduction of audio and/or video content.

When associating the thermal feedback with the video or audio during reproduction of the video content, a timing of the thermal feedback may be synchronized with a specific image (specific video scene) or a specific sound (specific audio scene). For example, in the case of the explosion scene, the sensation of the hot feedback may coincide with the video of the explosion.

However, if the feedback controller 1645 applies the power for the thermal feedback output at the time of the specific scene, a time difference may occur between the output timing of the specific scene and the thermal feedback. This is because even if power is applied to the thermoelectric couple array 1643, it takes some time to reach the temperature at which the contact surface 1641 can provide the thermal feedback to the user. That is, there may be a delay between a first time point of the power application and a second time point when the user can feel the thermal feedback. Accordingly, if the power application time point is set to be the same as the output of the specific scene, the user may experience the thermal feedback after the specific scene has passed. Hereinafter, the time duration from an initiation time of thermoelectric operation to a sensation time when the user can sense the thermal feedback will be referred to as the "delay time."

In this embodiment, the synchronization between the video output (or audio output) and the thermal feedback output can be established to improve the user experience.

Hereinafter, the specific scene which is associated with the thermal feedback for enhancing the user experience will be referred to as a thermal event scene. Thermal event scenes typically may include events which involves a heat absorbing or a heat generating in the real world such as an explosion. The thermal event scenes according to the present disclosure are not limited to the above, and the thermal event scenes may include any scenes that can be associated with the thermal feedback to improve user's immersion into the video content. Likewise, a specific audio which is associated with the thermal feedback for improving the user experience will be referred to as a thermal event audio or thermal event audio scene.

FIG. 45 is a flowchart of a first implementation of a thermal feedback providing method according to an embodiment of the present disclosure.

Referring to FIG. 45, a first implementation of the thermal feedback providing method includes loading video content including a thermal event scene and a thermal feedback data related to a thermal feedback associated with the thermal event scene (S110), outputting a video according to the video data (S120), obtaining a sensation time at which the thermal feedback is to be sensed (S130), calculating an initiation time of thermoelectric operation for a thermal feedback based on the sensation time and a correction time (S140), transmitting a thermal feedback start signal at the initiation time (S150), and starting a thermoelectric operation for outputting thermal feedback in accordance with the thermal feedback start signal (S160).

Hereinafter, each step of the above-described embodiment will be described in more detail.

The content reproduction device 1200 may load video data including the thermal event scene and the thermal feedback data related to a thermal feedback associated with the thermal event scene (S110). Specifically, the controller 1260 may load the video content stored in the memory 1240 or receive the video content through the communication module 1220 in a downloading method or a streaming method.

The video content may include the video data and the thermal feedback data. The video content may be provided as one file including the video data and the thermal feedback data, but the video content which is associated with the thermal feedback may alternatively be provided separately in a video file including the video data and a thermal feedback file including the thermal feedback data.

FIG. 46 is a diagram illustrating an example of thermal feedback data used in the first implementation of the thermal feedback providing method according to an embodiment of the present disclosure.

According to one embodiment, the thermal feedback data may be provided in a form similar to the subtitle file used to overlay the subtitles at the time of video output, loaded with the video file, similar to that shown in FIG. 46.

Here, a correction time may be defined in the section "<HEADER>". The correction time may be defined for each type of the thermal feedback to be output. In addition, the correction time may be defined for each intensity of the thermal feedback to be output. The correction time may correspond to the delay time. For example, in the case of FIG. 46, five correction times from the first level to the fifth level are set for the hot feedback and the cold feedback in the header portion.

Here, a time information (thermal feedback providing time), a type, an intensity, a thermal feedback target and/or the thermoelectric couple array for the thermal feedback may be provided in the "<BODY>" section. As described above, the time information may include the start time and the end time for the thermal feedback, and the start time may be defined as a time that may be the same as the output timing of the thermal event scene associated with the thermal feedback.

The video data includes information about scenes to be output at the time of reproducing the video content. Also, the thermal event scene may be included in the scenes to be output.

The content reproduction device 1200 may output a video and/or audio according to the video data (S120). For example, the controller 1260 may decode video data using a video codec and output the video. The video output may be performed through an external or internal display.

The content reproduction device 1200 may obtain a time point at which the thermal feedback is to be sensed (S130). Specifically, the controller 1260 may obtain the time point at which the user should experience thermal feedback from the thermal feedback data. The time point of the thermal feedback may be the same as the output time of the specific scene to be associated with the thermal feedback.

The content reproduction device 1200 may calculate the start time of the thermoelectric operation for the thermal feedback based on the obtained time point (sensation time) of the thermal feedback and the correction time (S140). Specifically, the controller 1260 may calculate the start time of the thermoelectric operation for the thermal feedback by subtracting the correction time from the sensation time (the obtained time at S130) of the thermal feedback.

The correction time may be a time interval from the power application time point when the power is applied to the thermoelectric couple array 1643 until the temperature at which the contact surface 1641 becomes a temperature at which the user can experience thermal feedback.

The controller 1260 may determine the correction time with reference to a correction time table stored in the memory 1240. Alternatively, when the video data includes information on the correction time, the controller 1260 may determine the correction time with reference to the information included in the video data.

The correction time may be a predetermined value irrespective of the type and intensity of the thermal feedback. Otherwise, as described above, the correction time may vary depending on the type and/or the intensity of the thermal feedback.

In this case, the controller 1260 may determine the correction time based on at least one of the type of the thermal feedback and the intensity of the thermal feedback.

For example, since the delay time for the hot feedback and the delay time for the cold feedback may be different from each other, the correction time may depend on whether the thermal feedback is the hot feedback or the cold feedback. Specifically, in the case of the hot feedback and the cold feedback of the same intensity, the time for the contact surface to reach the saturation temperature by the heat generating operation for the hot feedback may be faster than the time for the contact surface to reach the saturation temperature by the heat absorbing operation for the cold feedback. That is, the delay time for the hot feedback may be shorter than the delay time for the cold feedback.

In some embodiments, the intensity of the thermal feedback may be classified into a plurality of grades. In such embodiments, the delay times for thermal feedback may dependent on the intensity of the thermal feedback. For example, the delay time of a stronger intensity may be different than the delay times for thermal feedback of a weaker intensity. A stronger intensity may be require a high saturation temperature while a weaker intensity may only require a low saturation temperature. Such difference in saturation temperatures may result in different temperature change rates, temperature gradients, and/or temperature change velocities, impacting the delay times. Accordingly, the controller 1260 may determine the correction time based on the intensity of the thermal feedback.

In some embodiments, controller 1260 may determine that the correction time for a stronger intensity may be set shorter than the correction time for a weaker intensity to take into account differences in temperature change velocities. For example, because a stronger intensity requires a high saturation temperature and the temperature changes quickly, a short correction time is required to synchronize when contact surface 1641 reaches a temperature at which the user can experience thermal feedback. However, the weaker intensity, with a lower saturation temperature and the slower temperature change rate, may require longer correction times. In other embodiments, the correction time for the stronger intensity may be set larger than the correction time for the weaker intensity. For example, when thermoelectric couple array 1643 is configured to have uniform temperature gradients or changes, or when thermoelectric couple array 1643 includes thresholds temperature changes, controller 1260 may set longer correction times for the stronger intensity based on an expected temperature change velocity.

Alternatively, since the delay time for the thermal feedback may be an inherent characteristic of the feedback device 1600 outputting the thermal feedback, the controller 1260 may determine the delay time in consideration of the identification information of the feedback device 1600. For this, the controller 1260 may receive and obtain the identification information of the feedback device 1600 through the communication module 1220. Alternatively, the feedback device 1600 itself may store information regarding the delay time and/or the correction time, and the controller 1260 may set the correction time based on the delay time and/or the correction time information received from the feedback device 1600.

The content reproduction device 1200 may transmit a thermal feedback start signal at the start time of the thermoelectric operation for the thermal feedback (S150). When the start time of the thermoelectric operation is determined, the controller 1260 controls the communication module 1220 to transmit the thermal feedback start signal to the feedback device 1600 at the determined start time. The start time may be a relative value with respect to a playback time of the video content. The start time may be determined based on a playback duration (playback timeline) of the video content.

The feedback device 1600 may initiate a thermal feedback output operation in accordance with the start signal of the thermal feedback (S160).

Figure 47:
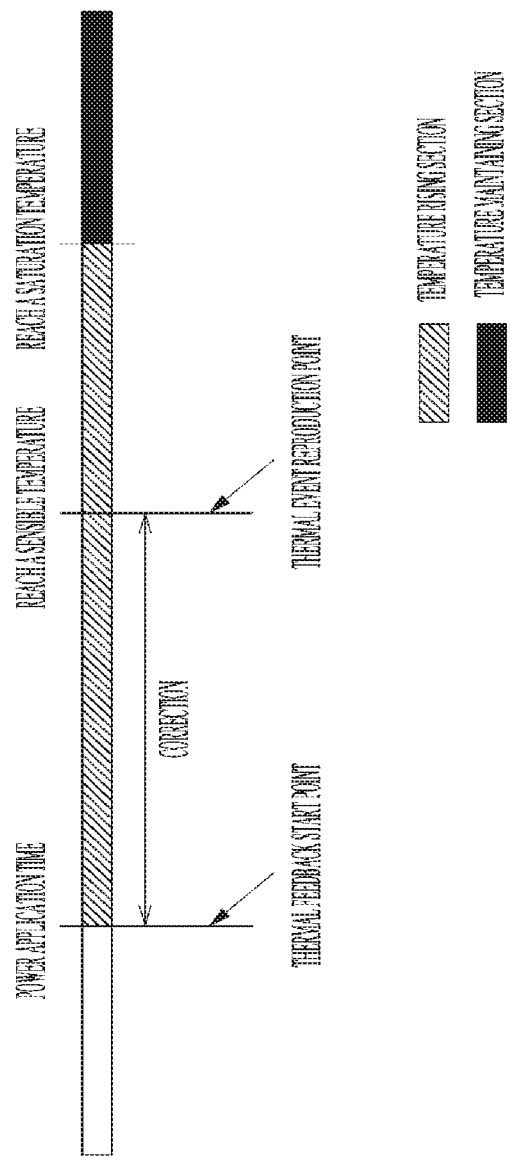
FIG. 47 is a diagram of a thermal feedback output operation of a first implementation of a thermal feedback providing method according to an embodiment of the present disclosure.

FIG. 47 is a diagram of a thermal feedback output operation of a first implementation of a thermal feedback providing method according to an embodiment of the present disclosure.

Specifically, the feedback controller 1645 applies power to the thermoelectric couple array 1643 in response to the receipt of the start signal (which is substantially the same as the start time of the thermoelectric operation). The thermoelectric couple array 1643 may perform the heat generating operation or the heat absorbing operation from the power application time. When the correction time elapses from the power application time, the temperature of the contact surface 1641 may reach a temperature at which the user can feel the thermal feedback.

Accordingly, the user can feel the thermal feedback at the output timing of the thermal event scene at the playback time of the video content. Under the control of the content reproduction device 1200, the feedback device 1600 may apply power to the thermoelectric element at the start time of the thermoelectric operation, which may be set at a time point earlier than the output time point of the specific scene to be associated with the thermal feedback so that the user may experience the thermal feedback at the output time of the thermal event scene.

In the above description, the synchronization between the video and the thermal feedback has been described with reference to this embodiment. However, the audio and the thermal feedback may be synchronized by replacing the video with the audio. This can be similarly applied to other embodiments of the thermal feedback providing method to be described later.

According to the above-described embodiment, the audio-visual experience according to the video or audio and the thermal experience according to the thermal feedback may be provided in harmony, so that the user experience can be improved.

4.2. Second Implementation

In some games or 4D movies, etc., in conventional multimedia content, a vibration feedback is associated to video or audio output to improve user immersion.

The second implementation of the thermal feedback providing method according to an embodiment of the present disclosure is a method of providing a thermal feedback to a user by outputting the vibration feedback associated with the thermal feedback.

Figure 48:
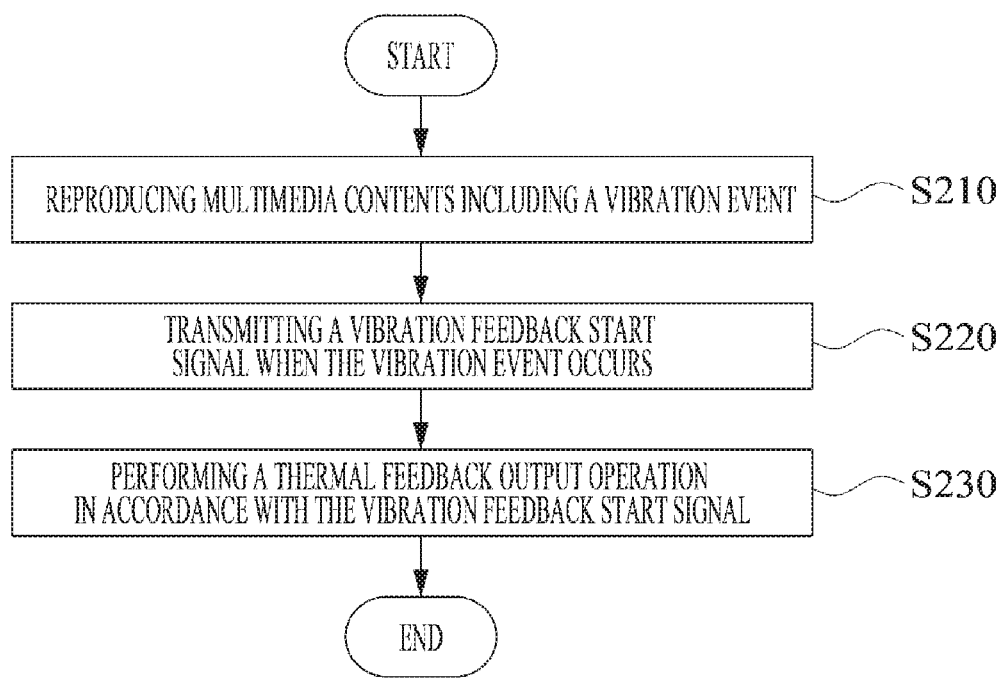
FIG. 48 is a flowchart of the second embodiment of the thermal feedback providing method according to an embodiment of the present disclosure.

FIG. 48 is a flowchart of the second embodiment of the thermal feedback providing method according to an embodiment of the present disclosure.

Referring to FIG. 48, the second implementation of the thermal feedback providing method may include reproducing multimedia content including a vibration event (S210), transmitting a vibration feedback start signal when the vibration event occurs (S220), and performing a thermal feedback output operation in accordance with the vibration feedback start signal (S230).

Hereinafter, each step of the above-described embodiment will be described in more detail.

The content reproduction device 1200 may reproduce the multimedia content including the vibration event (S210). Specifically, the controller 1260 may load the multimedia content from the memory 1240 or through the communication module 1220. For example, the content reproduction device 1200 may reproduce a video content or execute a game application, a virtual reality application or an augmented reality application.

The multimedia content may include a vibration feedback data in addition to video data and audio data. The content reproduction device 1200 may determine whether the vibration event has occurred or not according to the reproduction of the multimedia content based on the vibration feedback data. A vibration event is an event that requires the vibration feedback output during the reproduction of the multimedia content. For example, in the case of video content, the vibration feedback data may be set as a vibration event requiring a vibration feedback output for a reproduction time point such as a car crash scene point or a gun-shot scene point in video data. In another example, the vibration event may include a character being hit, e.g., by a punch, or a character using a certain skill, e.g., jumping a far distance.

When a vibration event occurs, the content reproduction device 1200 may transmit a vibration feedback start signal to the feedback device 1600 (S220), and the feedback device 1600 may perform a thermal feedback output operation in accordance with the vibration feedback start signal (S230).

The controller 1260 may transmit a vibration feedback start signal to the feedback device 1600 via the communication module 1220 when it is determined that the vibration event has occurred. In addition, the feedback controller 1645 may receive the vibration feedback start signal through the communication module 1620, and may apply a power to the thermoelectric couple array 1643 to perform a thermal feedback output operation.

Alternatively, if the feedback device 1600 includes the vibration module 1670, the feedback device 1600 may output the vibration feedback along with the output of the thermal feedback through the vibration module 1670.

The present implementation described above is a method for implementing a thermal feedback in multimedia content in which thermal feedback data is absent, but vibration feedback data is present. Other data included in the multimedia content may be used to output the thermal feedback instead of the vibration feedback data.

As an example, the present implementation may be modified to output thermal feedback in response to a screen shaking event instead of a vibration event. Some games, including FPS, use a screen shaking technique to shake a virtual camera in the game engine so as to shake the video presentation when, e.g., a collision occurs. Accordingly, the controller 1260 may reproduce the multimedia content including the screen shaking event instead of the vibration event. In this case, the controller 1260 may transmit a thermal feedback start signal to the feedback device 1600 through the communication module 1220 when a screen shaking event occurs during the reproduction, so that the feedback controller 1645 may perform a thermal feedback output operation in accordance with the thermal feedback start signal.

As another example, the present implementation may be modified to output thermal feedback according to a specific audio instead of a vibration event. More specifically, when the controller 1260 reproduces multimedia content and a specific audio is output during the reproduction, the controller 1260 may transmit a thermal feedback start signal to the feedback device 1600 via the communication module 1220, and the feedback controller 1645 may perform a thermal feedback output operation according to the feedback start signal. The specific audio may be, for example, an audio generated in a collision, an audio generated in an explosion, a scream, or the like. When the audio output is equal to or higher than a predetermined volume, or falls within a predetermined frequency band, the controller 1260 may determine it to trigger a thermal feedback.

According to the present implementation, a thermal feedback may be provided even when there's no thermal feedback data provided with the multimedia content by using other data associated with the audio or video content instead of the thermal feedback data.

4.3. Third Implementation

A third implementation of the thermal feedback providing method according to an embodiment of the present disclosure is a method of providing a thermal feedback to a user by outputting a thermal feedback associated with an element attribute of a skill at the time of actuating the skill or being hit during a game.

Here, an element attribute is the attribute given to a skill in the game. The element attributes of a skill may be defined according to the skill attribute design of the game developer. For example, an element attribute of the skill may include a fire attribute (or a flame attribute), an ice attribute (or a freeze attribute), a wind attribute, a lightning attribute (or an electric attribute), and the like.

In the present implementation, the game should be understood as a comprehensive concept including stereoscopic 3D games, games using virtual reality technique or augmented reality techniques, as well as conventional 2D games. The same is also true of other embodiments of the thermal feedback providing method according to embodiments of the present disclosure to be described later.

Figure 49:
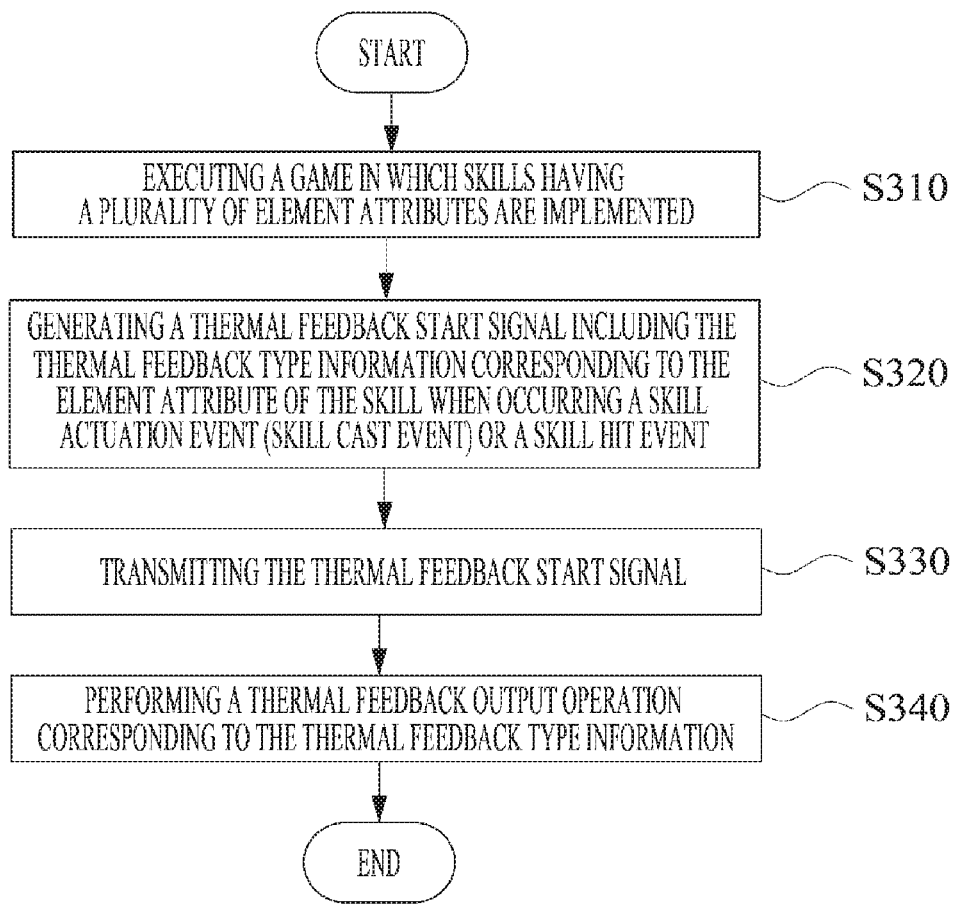
FIG. 49 is a flowchart of a third embodiment of a method for providing a thermal feedback according to an embodiment of the present disclosure.

FIG. 49 is a flowchart of a third embodiment of a method for providing a thermal feedback according to an embodiment of the present disclosure.

Referring to FIG. 49, the third implementation of the thermal feedback providing method may include executing a game in which skills having a plurality of element attributes are implemented (S310), generating a thermal feedback start signal including the thermal feedback type information corresponding to the element attribute of the skill when occurring a skill actuation event (skill cast event) or a skill hit event (S320), transmitting the thermal feedback start signal (S330), and performing a thermal feedback output operation according to the thermal feedback start signal, wherein the thermal feedback may include outputting a thermal feedback corresponding to the thermal feedback type information (S340).

Hereinafter, each step of the above-described embodiment will be described in more detail.

The content reproduction device 1200 may execute a game in which the skills having a plurality of element attributes are implemented (S310). The controller 1260 may load and execute such a game.

The skill may correspond to an operation such as a spell used by a virtual character in a game and/or a shooting action of a projectile, and the like. Another representative example of the skill may include firewalls, ice bolts, and lightning chains, etc. As some other examples, there may be an action for wielding a weapon, an action for launching a projectile, etc. In this case, the attribute given to the weapon or the projectile may be treated as an attribute of the skill. The virtual character may include a player character controlled by the player or an enemy character attacking the player character. In the case of a first person game including VR/AR, a field of view of the player character controlled by the player may be displayed and/or shown instead of displaying the player character on the screen in the virtual reality environment or the augmented reality environment. Here, the term "player" is a generic term encompassing a virtual character (playable character) controlled by the player (a user) or an avatar thereof in the virtual space or augmented space.

Skills in the game may have element attributes. For example, there may be given a fire attribute (flame attribute) in the case of a fire ball, an ice attribute (freeze attribute) in the case of an ice bolt, and, and an electric attribute in the case of a lightning chain.

In addition, each skill may be given a skill level. In an example, a skill in a game may be implemented in such a way that a power of the skill increases as the player rises in skill level. For example, a fireball skill is given a level, and the fireball of level 1 may be upgraded to a fireball of level 2, in which case an effect of the fireball skill is enhanced.

For skills having a same element attribute, one skill may be superior to another skill. That is, a skill may be given a skill tier. For example, when skills of the flame attribute include fire bolts, fireballs, and firestorms in the game, level 1 may be assigned to the fire bolts, level 2 may be assigned to the fireballs, and level 3 may be assigned to the firestorms.

Or, each skill may have a damage value. For example, a fire bolt's damage may be given as a value between 100 to 200 damage points, a fireball's damage may be given as a value between 200 to 300 damage points, and a firestorm's damage may be given as a value between 300 to 400 damage points.

The content reproduction device 1200 may generate a thermal feedback start signal including thermal feedback type information corresponding to an element attribute of the skill in the case where a skill actuation event or a shooting event occurs during the game (S320).

When a user input instructing an actuation of a skill in the game is detected, the controller 1260 may regard the user input as a skill actuation event (skill cast event). Alternatively, when the skill invoked by another character hits the player character in the game, the controller 1260 may determine the hit action as a skill hit event.

When the controller 1260 detects the skill actuation event or the skill hit event, the controller 1260 may determine a type of thermal feedback based on an element attribute corresponding to a skill activated by a user player or a skill hitting the user player. For example, the type of the thermal feedback may be determined as the hot feedback for a skill having a flame attribute, and the type of the thermal feedback may be determined as the cold feedback for a skill having an ice attribute. In addition, the type of the thermal feedback may be set as the thermal grill feedback for a skill having an electric attribute.

The controller 1260 may determine an intensity of the thermal feedback based on at least one of a skill type, a skill grade (skill level), a skill damage (damage of the skill activated by the user player), and the hit damage (damage of the skill hitting on the user player). For example, if fire bolts, fireballs and firestorms are implemented in the game, the intensity for the thermal feedback may be determined as a weak intensity for the fire bolts, as an intermediate intensity for the fireballs, and as a strong intensity for the firestorms. For another example, the intensity of the thermal feedback may be determined as a weak intensity for a fireball of a first level, as an intermediate intensity for a fire ball of a second level, and as a strong intensity for a fireball of a third level. For another example, the stronger intensity may be determined based on the damage value of the skill. For another example, when the skill hit event occurs, the intensity of the thermal feedback may be set to be stronger as the damage on the player increases.

The controller 1260 may also determine a duration time for the thermal feedback. For example, the user player (a virtual character) hit by a skill of the flame attribute may suffer a flaming effect for a predetermined time period, and the virtual character hit by a skill of the ice attribute may suffer a stop effect or slow effect for a predetermined time period. Also, the character shot by a skill of lightning attribute may suffer a paralyzing effect or the like for a predetermined time period. The controller 1260 may determine a duration time for providing the thermal feedback according to the duration (the predetermined time period) of the special effects caused by the skills for the character.

These special effects may be a buff effect which is beneficial on the target of the skill or a debuff effect which is detrimental on the target of the skill. For example, if a debuff effect is generated for the player according to the skill hit event, the thermal feedback may be output during a duration time of the debuff effect. Also, the thermal feedback may be output during a duration time of the buff effect induced on a player according to the skill actuation event.

Also, the controller 1260 may gradually decrease the intensity of the thermal feedback during the duration time of the thermal feedback, so that the user can sense the end points of the buff effect or debuff effect.

The controller 1260 may generate a thermal feedback start signal including information on the type of the thermal feedback. The thermal feedback start signal may also include information on the intensity of the thermal feedback. Also, the thermal feedback start signal may also include information on the duration time of the thermal feedback.

Alternatively, when the controller 1260 determines the type and the intensity of the thermal feedback, the controller 1260 may refer to a skill-thermal feedback table stored in game content or the memory 1240, as shown in FIG. 50.

FIG. 50 is a diagram of a skill-thermal feedback table used in the third implementation of the thermal feedback providing method according to an embodiment of the present disclosure.

Referring to FIG. 50, the table may include information regarding an identifier of the skill, an element attribute of the skill, a type of the thermal feedback for the skill according to the element attribute, a tier of the skill, a level of skill, an intensity of the thermal feedback for the skill, and a time duration for providing the thermal feedback for the skill.

The content reproduction device 1200 may transmit the thermal feedback start signal (S330). The controller 1260 may transmit the generated thermal feedback start signal to the feedback device 1600 through the communication module 1220.

The feedback device 1600 may perform a thermal feedback output operation according to the thermal feedback start signal, wherein the thermal feedback output operation may reflect the thermal feedback type information (S340).

When the thermal feedback start signal is received, the feedback controller 1645 may apply a power to the thermoelectric couple array 1643 to perform the thermal feedback output operation. The feedback controller 1645 may generate a power supplying signal according to the information included in the thermal feedback start signal. For example, the controller 1260 may determine whether to perform a heat generating operation, a heat absorbing operation, or a thermal grill operation by referring to the type of the thermal feedback, and generate a power supply signal corresponding thereto. Also, the controller 1260 may determine the voltage level by referring to the intensity of the thermal feedback.

The controller 1260 may also determine a length of time to apply a power supplying signal based on the providing time or the duration time of the thermal feedback. The controller 1260 may output a thermal feedback of a predetermined constant intensity during the duration time. Alternatively, the thermal feedback may be output with an intensity that gradually decreases over the time duration. For example, if a virtual character is hit by a skill for the first time, it may output a strong-intensity thermal feedback, and after a predetermined time period, a weaker intensity of the thermal feedback may be output during the duration time of a special effect induced by the skill hit event of the skill actuation event (for example, paralysis or slowness). According to this, the user can sense whether or not the virtual character was hit by the strong thermal feedback at the hitting time. The user can also sense whether the virtual character is under the special effects via the weak thermal feedback. In addition, the user can also sense whether the special effects have terminated by the termination of the thermal feedback. This may improve the intuitiveness of the game and the immersion of the user in the game environment.

According to the above-described method, the feedback device 1600 may apply a constant voltage to the thermoelectric element at the time of actuating or being hit by the flame attribute skill, and apply a reverse voltage to the thermoelectric element for the cold attribute skill. The feedback device 1600 may also control the content reproduction device 1200 to apply the constant voltage and the reverse voltage in combination for the lightening attribute skill.

The following description will be made on the basis that the element attribute of the skill includes fire, ice, or lightning. It should be noted, however, that this is just for convenience of explanation, and that the elemental attributes of the skill may be defined differently.

In the above description, the hot/cold/thermal grill feedback corresponds to the element attribute, but the matching relationship between the type of the thermal feedback and the type of the element attribute may be freely changed according to the designer's choice. In the thermal grill feedback, a neutral thermal grill feedback/hot thermal grill feedback/cold thermal grill feedback may be used. For example, the hot thermal grill feedback may be matched to the flame attribute, the cold thermal grill feedback to the ice attribute, and the neutral thermal grill feedback to the lightning attribute.

Although the above explanation is mainly focused on the actuation of a skill and hits by a skill, a similar thermal feedback may be provided for other attack actions. For example, the attack action may include a weapon attack in addition to a skill attack. The weapon attacks may include, e.g., melee weapon attacks and ranged weapon attacks.

The element attribute of the attack action may be determined according to an element attribute of a weapon used for the weapon attacks instead of the element attribute of the skill attack. In addition, if the ranged weapon is used for the weapon attack, the element attribute for the weapon attack may be determined according to an element attribute given to a projectile of the ranged weapon. If the element attributes are given to both the ranged weapon and the projectile, one of the two elemental attributes may be prioritized to determine as the element attribute of the weapon attack.

If the attack action is a skill attack, the intensity of the thermal feedback may be determined based on at least one of the skill level, the damage amount of the skill and the skill's tier on a skill tree including the plurality of skills having the same element attribute. If the attack action is a weapon attack, the intensity of the thermal feedback may be determined based on at least one of a class (grade) of the weapon, an attack power of the weapon, a class of a projectile of the weapon (in case of the ranged weapon) and the attack power of the projectile.

In addition, the intensity of the thermal feedback may be determined based on at least one of an attack power of the attack action, a damage amount of the player according to the skill hit event, a ratio of damage to the total health points of the player, and the remaining health points of the player.

In some embodiments, a type of the thermal feedback may be selected according to a type of the weapon. For example, if the weapon used for the skill actuation event or the skill hit event is an ice attribute weapon, a cold thermal grill feedback may be matched thereto and if the weapon is a flame attribute weapon, the hot thermal grill feedback may be matched thereto.

According to the above-described implementation, the user's enjoyment and immersion for the game may be improved by outputting the thermal feedback corresponding to the element attribute of the skill in response to the actuation of the skill or the hit by the skill in the game.

4.4. Fourth Implementation

The fourth implementation of the thermal feedback providing method according to an embodiment of the present disclosure is a method of providing a thermal feedback to a user by outputting the thermal feedback associated with an emotional expression or a text selection for a character and/or player.

The emotional expression of the character may include pleasure, anger, fear, and the like. In some cases, an emotional state of the character may be defined as a kind of character attribute in a game. In other cases, the character may directly express his emotional state by performing a certain action or making a certain facial expression. In the present implementation, the emotional expression should be interpreted to include specific actions or facial expression with which a character expresses his emotions, as well as the attribute directly indicating the emotion.

Here, a text selection means selecting one among plural selectable texts provided to the user during the progress of the game. For example, the selectable texts may be presented in the game conversation situation between a playable character (PC) operated by a user and a non-playable character (NPC) or in a situation in which a user must make a decision, which the user may effect by selecting one of the texts.

Figure 51:
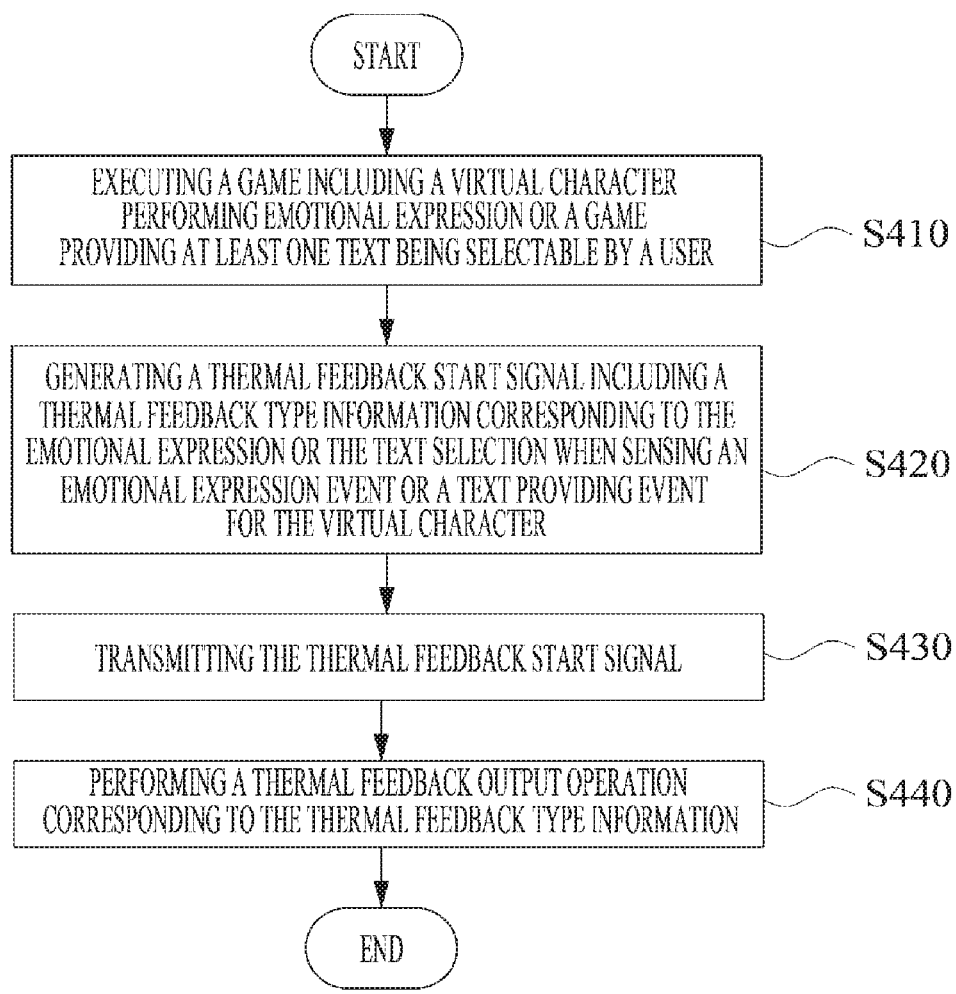
FIG. 51 is a flowchart of the fourth implementation of the thermal feedback providing method according to an embodiment of the present disclosure.

FIG. 51 is a flowchart of the fourth implementation of the thermal feedback providing method according to an embodiment of the present disclosure.

Referring to FIG. 51, the fourth implementation of the thermal feedback providing method may include executing a game including a virtual character performing emotional expression or a game providing at least one text being selectable by a user (S410), generating a thermal feedback start signal including a thermal feedback type information corresponding to the emotional expression or the text selection when sensing an emotional expression event or a text providing event for the virtual character (S420), transmitting the thermal feedback start signal (S430), and performing a thermal feedback output operation according to the thermal feedback start signal, which may include outputting a thermal feedback corresponding to the thermal feedback type information (S440).

Hereinafter, each step of the above-described embodiment will be described in more detail.

The content reproduction device 1200 may execute a game that includes the virtual character performing emotional expression or that provides at least one text being selectable by the user (S410). The controller 1260 may execute the game.

When it is detected that the emotional expression event or the text providing event has occurred, the content reproduction device 1200 may generate the thermal feedback start signal including the thermal feedback type information corresponding to the emotional expression or the text selection (S420). The controller 1260 may detect the emotional expression event of the virtual character during the game progress. For example, the virtual character's emotional expression event may occur by performing a specific action or making a specific facial expression. The emotional expression event may occur according to the user's input. The emotional expression event of the virtual character may also occur in a specific situation during the characters' conversation. The text providing event may correspond to a dialog action between the playable character and the non-playable character or by the story progress during the game.

When the emotional expression event or the text providing event occurs, the controller 1260 may determine a type of the emotion expressed by the character or a type of the text selected in response to the text providing event. The controller 1260 may determine a type of the thermal feedback according to the type of the determined emotion or the type of the selected text. The controller 1260 may determine the type of the thermal feedback by referring to the table for the emotion/text that is stored in the memory 1240 or stored in the game program. The table for emotion/text may define the type of thermal feedback depending on the emotion state and/or the text type.

Figure 52:
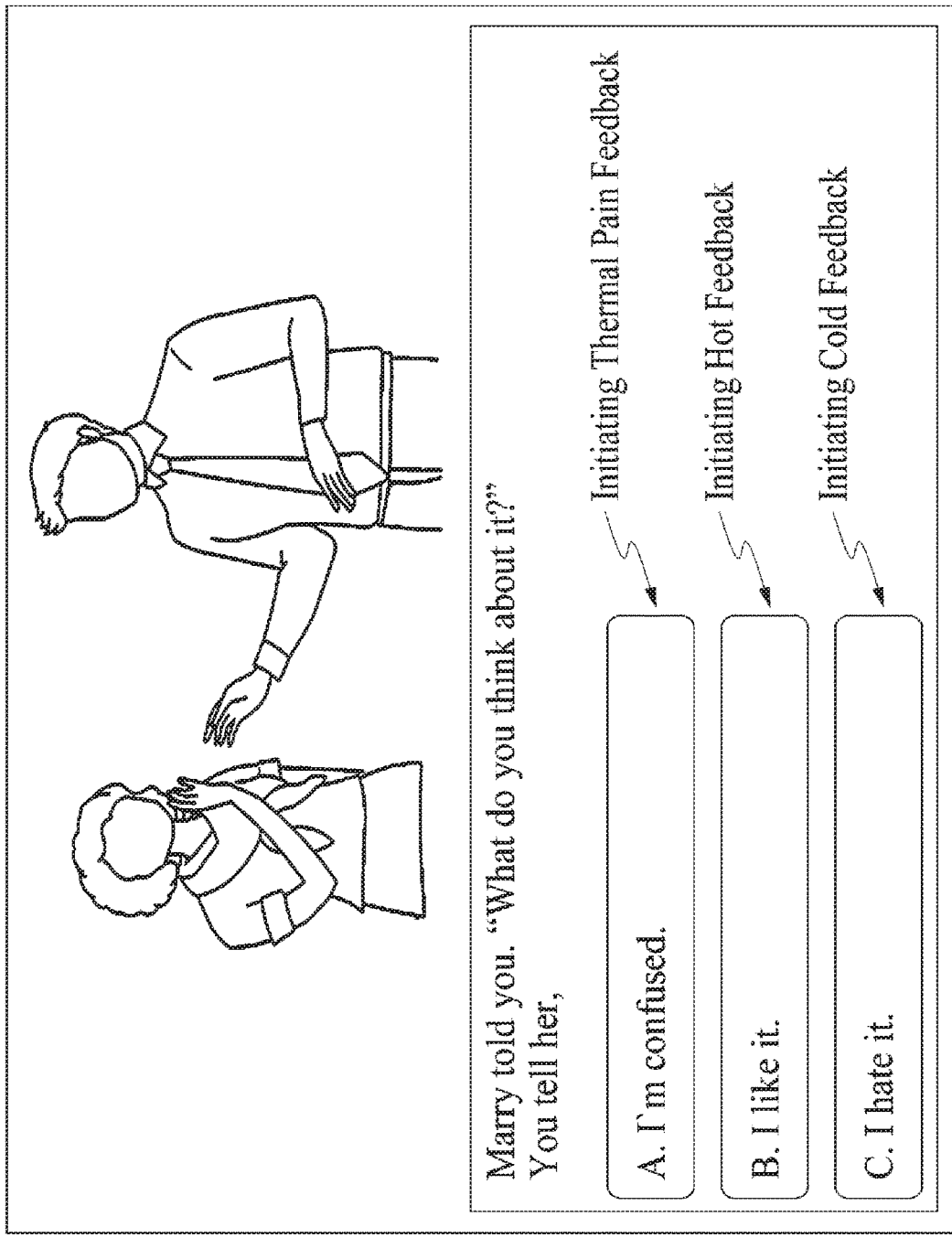
FIG. 52 is a diagram related to the text presentation event provided in the fourth implementation of the thermal feedback providing method according to an embodiment of the present disclosure.

FIG. 52 is a diagram related to the text presentation event provided in the fourth implementation of the thermal feedback providing method according to an embodiment of the present disclosure.

Referring to FIG. 52, during a conversation between the player's character and the non-player character, the texts are presented for user's selection. The controller 1260 may receive a user input from the input device via the communication module 1220 to select a particular text, and thus may determine the type of the thermal feedback.

The content reproduction device 1200 may transmit the thermal feedback start signal (S430). The controller 1260 may transmit the thermal feedback start signal including the thermal feedback type information to the feedback device 1600 through the communication module 1220.

The feedback device 1600 may perform the thermal feedback output operation in accordance with the thermal feedback start signal, and may output the thermal feedback corresponding to the thermal feedback type information (S440).

When the thermal feedback start signal is received, the feedback controller 1645 may apply a power to the thermoelectric couple array 1643 to perform the thermal feedback output operation. The feedback controller 1645 may generate a power supplying signal according to the information included in the thermal feedback start signal. For example, the controller 1260 may determine whether to perform a heat generating operation, a heat absorbing operation, or a thermal grill operation by referring to the type of the thermal feedback.

According to the above-described embodiment, the user's game immersion level may be improved by providing a thermal feedback suitable for the emotion of the virtual character, such as outputting a hot feedback when the virtual character is angry and outputting a cold feedback when it is scared. Similarly, when the virtual character selects a text, a suitable thermal feedback may be provided for each text selection in the game such as outputting a hot feedback for making a good decision and outputting a cold feedback for making an evil decision, thereby improving a user's game immersion.

4.5 Fifth Implementation

The fifth implementation of the thermal feedback providing method according to an embodiment of the present disclosure is a method of providing a thermal feedback to a user by outputting thermal feedback associated with a moving speed in a game during a game. Here, a moving speed may mean the moving speed of the playable character in a virtual space provided in the game.

Figure 53:
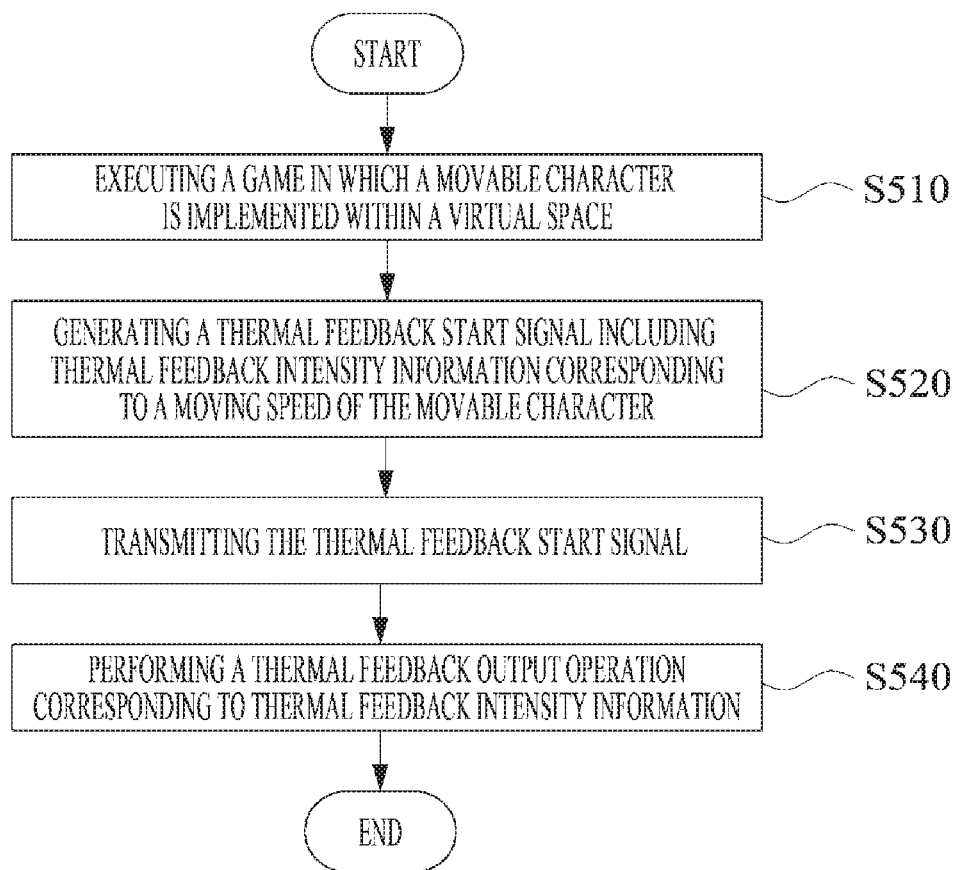
FIG. 53 is a flowchart of the fifth implementation of the thermal feedback providing method according to an embodiment of the present disclosure.

FIG. 53 is a flowchart of the fifth implementation of the thermal feedback providing method according to an embodiment of the present disclosure.

Referring to FIG. 53, the fifth implementation of the thermal feedback providing method may include executing a game in which a movable character is implemented within a virtual space (S510), generating a thermal feedback start signal including intensity information corresponding to a moving speed of the movable character (S520), transmitting the thermal feedback start signal (S530), and performing a thermal feedback output operation in accordance with the thermal feedback start signal, which may include outputting thermal feedback corresponding to thermal feedback information (S540).

The content reproduction device 1200 may execute the game that implements the virtual space and the movable character therein (S510). The controller 1260 may execute the game including the virtual space and the movable character therein. The character may be a virtual character controlled by the user of the game content in the virtual space of the game. Although the virtual character is displayed (output) on the screen in the third person game, only a part of the virtual characters may or may not be displayed on the screen in the first person game. Alternatively, in a game using a virtual reality technique, a body of a user or an input device may be regarded as the character.

The content reproduction device 1200 may generate the thermal feedback start signal including the intensity information of the thermal feedback corresponding to the moving speed of the character during the movement (S520). The controller 1260 may detect the movement of the character in the virtual space of the game. For example, the movement of the character may be made according to a user input instructing a movement of the character. The controller 1260 may obtain the user input for instructing the character movement from the input device via the communication module (1220), thereby moving the character or manipulating the movement of the character accordingly. In addition, the character may move on a ride provided in the virtual space of the game. For example, in a game such as a racing game or a flight simulation, the character may be represented by an airplane or an automobile that moves according to a user's manipulation. The controller 1260 may determine the intensity of the thermal feedback according to the moving speed of the character in the virtual space. For example, the controller 1260 may increase the intensity of the thermal feedback as the moving speed of the character becomes faster in the virtual space. When the intensity is determined, the controller 1260 may generate the thermal feedback start signal including the intensity information of the thermal feedback.

The content reproduction device 1200 may transmit the thermal feedback start signal (S530). The controller 1260 may transmit the thermal feedback start signal including the intensity information of the thermal feedback to the feedback device 1600 via the communication module 1220.

The feedback device 1600 may perform the thermal feedback output operation in accordance with the thermal feedback start signal, and may output the thermal feedback corresponding to the intensity information of the thermal feedback (S540).

When the thermal feedback start signal is received, the feedback controller 1645 may apply a power to the thermoelectric couple array 1643 to perform the thermal feedback output operation. The feedback controller 1645 may generate a power supplying signal according to the information included in the thermal feedback start signal. For example, the controller 1260 may control the intensity of the thermal feedback by adjusting the voltage value of the power supply referring to the intensity information of the thermal feedback.

In this implementation, the cold feedback may be mainly used as the thermal feedback. In some embodiments, a hot feedback may be temporarily output when the movement of the character is stopped. The controller 1260 may determine whether the movement of the character is terminated or not, and generate a thermal feedback start signal including a thermal feedback information for instructing a hot feedback and transmit the thermal feedback start signal to the feedback device 1600 through the communication module 1220.

4.6 Sixth Implementation

The sixth implementation of a thermal feedback providing method according to an embodiment of the present disclosure is a method of providing a thermal feedback to a user by outputting thermal feedback associated with a health points of a character during a game.

Figure 54:
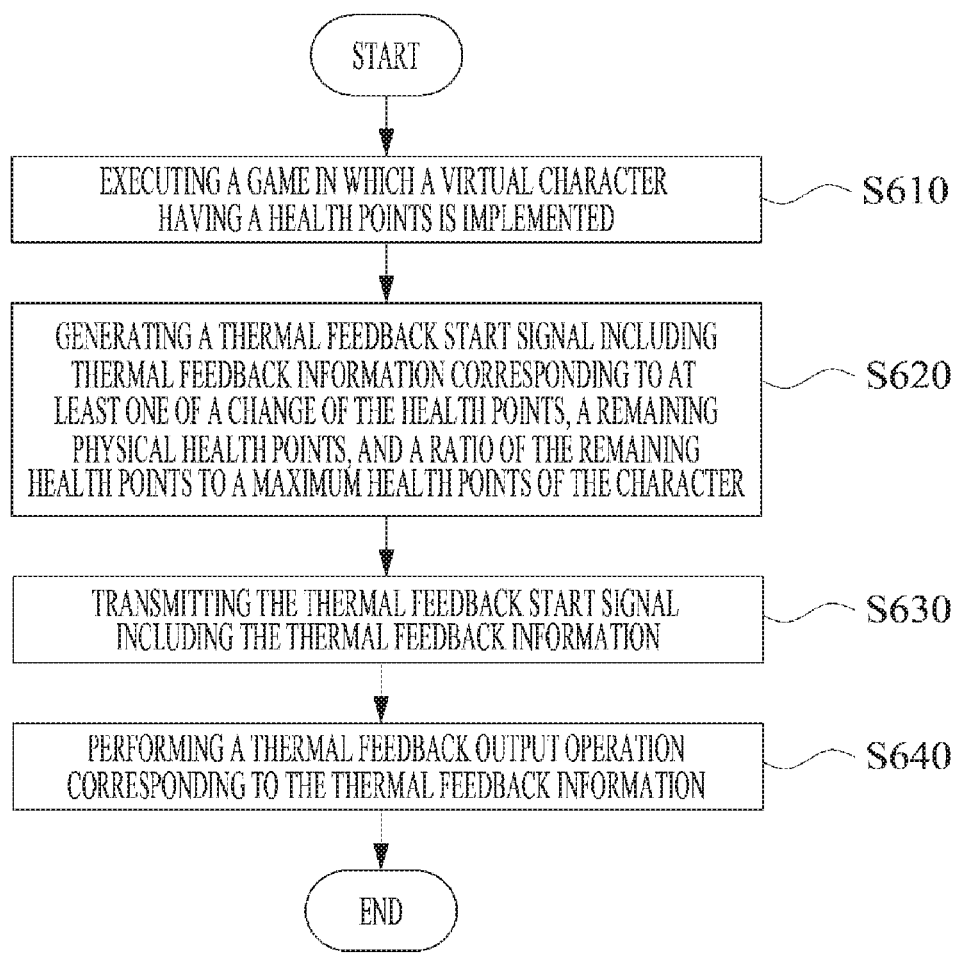
FIG. 54 is a flowchart of the sixth implementation of the thermal feedback providing method according to an embodiment of the present disclosure.

FIG. 54 is a flowchart of the sixth implementation of the thermal feedback providing method according to an embodiment of the present disclosure.

Referring to FIG. 54, the sixth implementation of the method for providing a thermal feedback may include executing a game in which a virtual character having health points is implemented (S610), generating a thermal feedback start signal including thermal feedback information corresponding to at least one of a change of the health points, a remaining physical health points, and a ratio of the remaining health points to a maximum health points of the character (S620), transmitting the thermal feedback start signal including the thermal feedback information (S630), and performing a thermal feedback output operation according to the thermal feedback start signal, and which may include outputting the thermal feedback corresponding to the thermal feedback information (S640).

Hereinafter, each step of the above-described implementation will be described in more detail.

The content reproduction device 1200 may execute a game in which a character having a health points appears (S610). The controller 1260 may execute the game including the character operated by the user. Health points may be assigned to the character. The health points may be information indicating a life force (vitality) of the character in the game. For example, if character's health points are exhausted, the character may die in the game. The health points may be increased or decreased depending on events in the game. For example, the health points may be decreased if the character is hit, and the health points may be increased if the character uses a healing skill or a recovery item such as health portion.

The content reproduction device 1200 may generate the thermal feedback start signal including the thermal feedback information corresponding to at least one of a change of the health points, a remaining physical health points, and a ratio of the remaining health points to a maximum health points of the character (S620).

When the health points is changed during the game progress, the controller 1260 may generate the thermal feedback information according to the change of the health points.

In one example, the controller 1260 may determine a type of the thermal feedback depending on whether the health points is decreased or increased. For example, the controller 1260 may determine the type of thermal feedback as a cold feedback when the health points are decreased. For another example, the controller 1260 may determine the type of the thermal feedback as a hot feedback when the health points is increased.

In another example, the controller 1260 may determine an intensity of the thermal feedback according to a change amount of the health points. The larger the change amount of the health points, for example, the stronger the intensity of the thermal feedback.

In another example, the controller 1260 may determine the intensity of the thermal feedback according to the ratio of the change amount of the health points to the maximum health points. The larger the ratio of the change amount of the health points to the maximum health points, for example, the stronger the intensity of the thermal feedback.

Further, the controller 1260 may determine the thermal feedback information according to the remaining health points. The smaller the remaining health points, for example, the stronger the intensity of the thermal feedback health points. As another example, the controller 1260 may determine a type of the thermal feedback based on a value of remaining health points. For example, as the thermal feedback type, the cold feedback may be determined when the value of the remaining health points is within a first range, and a hot feedback may be determined when the value is within a second range.

The controller 1260 may determine the thermal feedback information according to the ratio of the remaining health points to the maximum health points. The lower the ratio, for example, the stronger the intensity of the thermal feedback. As another example, the controller 1260 may determine the type of the thermal feedback according to the health ratio. For example, as the thermal feedback type, the cold feedback may be determined when the health ratio is within a first range, and the hot feedback may be determined when the health ratio is within a second range.

As described above, once the thermal feedback information is determined, the controller 1260 may generate the thermal feedback start signal including the determined thermal feedback information.

The content reproduction device 1200 may transmit the thermal feedback start signal including the thermal feedback information (S630). The controller 1260 may transmit the thermal feedback start signal including the thermal feedback information to the feedback device 1600 via the communication module 1220.

The feedback device 1600 may perform the thermal feedback output operation in accordance with the thermal feedback start signal, and may output thermal feedback corresponding to the thermal feedback information (S640).

When the thermal feedback start signal is received, the feedback controller 1645 may apply a power to the thermoelectric couple array 1643 to perform the thermal feedback output operation. The feedback controller 1645 may generate a power supplying signal according to the information included in the thermal feedback start signal.

Accordingly, when the change in the health points occurs, the feedback device 1600 may output a different thermal feedback depending on the change amount of the health points, the ratio of the change amount to the maximum health points, the remaining health points and/or the ratio of the remaining health points to the maximum health points.

In the above description, the thermal feedback information may be determined to correspond to the health points. Alternatively, the thermal feedback information may correspond to the other points used in the game. For example, in the case of a racing game, the thermal feedback may be associated with fuel amount points instead of the health points. As another example, the thermal feedback may be associated with mana (magic) points. That is, this implementation is comprehensively applicable to a variable resource points in relation to the character in the game.

When a plurality of resources in association with the character are provided, a different type of the thermal feedback may be assigned to each resource. For example, the controller 1260 may execute a game for operating the character having the resource points in the game including a health points and a mana points. The controller 1260 may also generate a thermal feedback information corresponding to at least one of change amount of the resource points, increase and decrease thereof, the remaining amount thereof, and the ratio of the remaining points to the maximum points.

The controller 1260 may also transmit a thermal feedback start signal including the generated information to the feedback device 1600 via the communication module 1220. The controller 1645 then may output a thermal feedback operation in accordance with the thermal feedback information. The controller 1260 may determine a type of the thermal feedback to correspond to a type of the changed resource points. For example, as the thermal feedback, a hot feedback may be determined for health points, and a cold feedback may be determined for mana points.

According to the above-described implementation, the information about a vital condition (health points) of the character in the game is provided to a user through the thermal feedback, thereby helping a user's intuitive understanding for the game and improving the immersion in the game.

4.7 Seventh Implementation

The seventh implementation of the thermal feedback providing method according to an embodiment of the present disclosure is a method of providing a thermal feedback to a user based on a user input timing associated with a timing action during a game.

Figure 55:
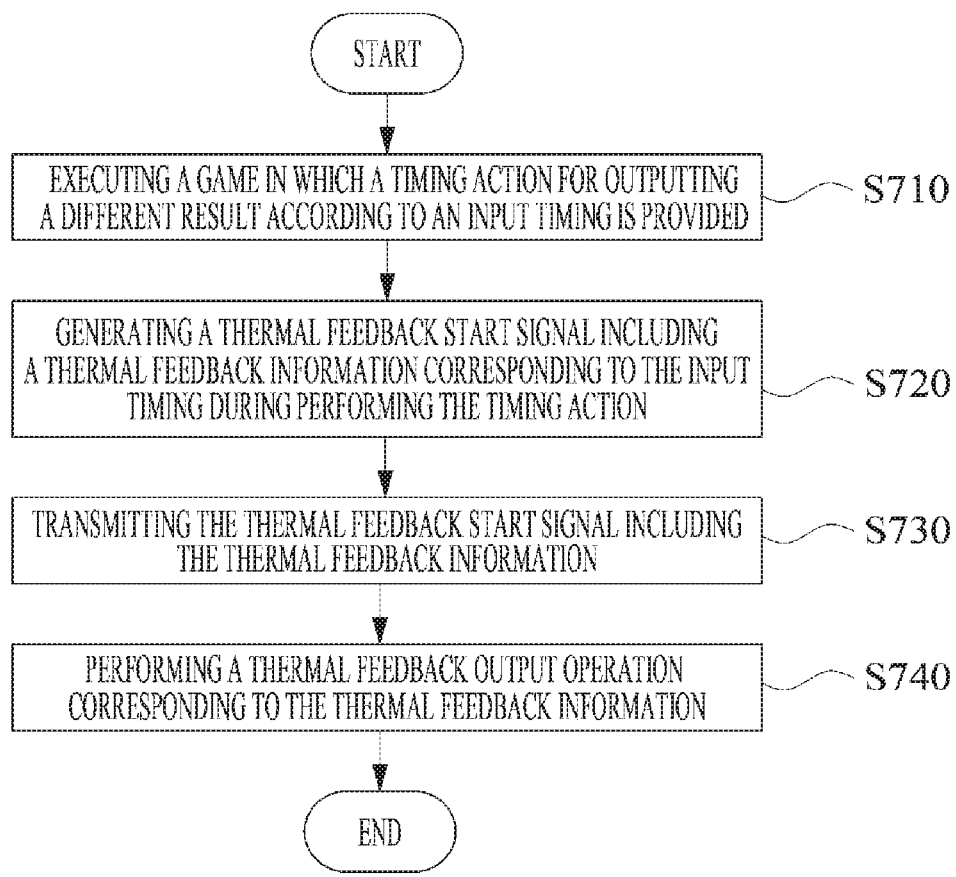
FIG. 55 is a flowchart of the seventh implementation of a method for providing a thermal feedback according to an embodiment of the present disclosure.

FIG. 55 is a flowchart of the seventh implementation of a method for providing a thermal feedback according to an embodiment of the present disclosure.

Referring to FIG. 55, the seventh implementation of the thermal feedback providing method may include executing a game in which a timing action is provided (S710), generating a thermal feedback start signal including a thermal feedback information corresponding to the user input timing input during performing of the timing action (S720), transmitting the thermal feedback start signal including the thermal feedback information (S730), and performing a thermal feedback output operation in response to the thermal feedback start signal, which may include outputting a thermal feedback corresponding to the thermal feedback information (S740).

Hereinafter, each step of the above-described implementation will be described in more detail.

The content reproduction device 1200 may execute the game in which the timing action is provided, in which the result is based on the user input timing (S710).

The controller 1260 may execute the game. The game executed in this implementation may include the timing action, the results of which are based on a user input timing.

Figure 56:
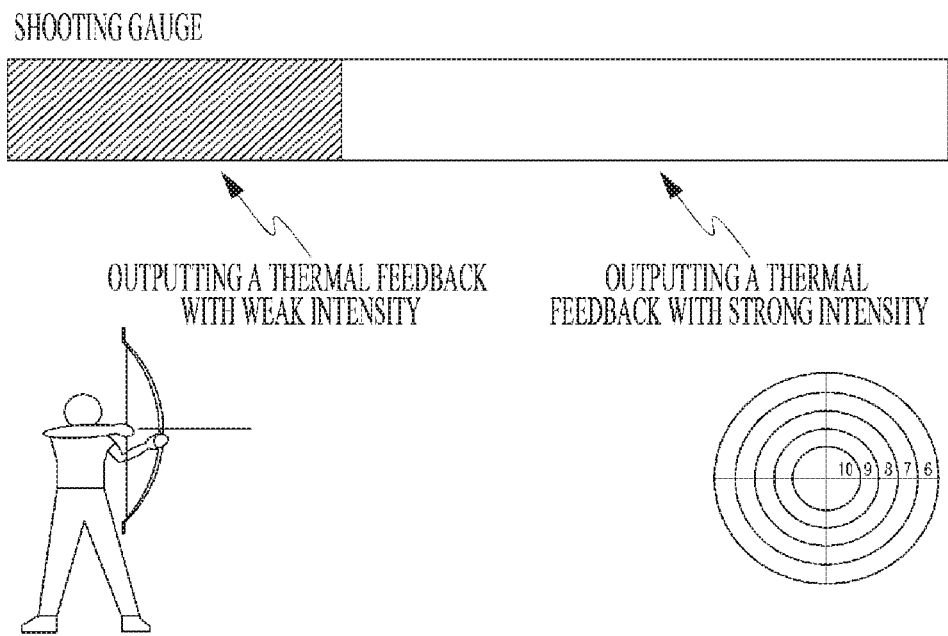
FIG. 56 is a diagram of a game providing a timing action according to the seventh implementation of a method for providing a thermal feedback according to an embodiment of the present disclosure.

FIG. 56 is a diagram of a game providing a timing action according to the seventh implementation of a method for providing a thermal feedback according to an embodiment of the present disclosure.

FIG. 56 is a screen of a game in which an arrow can be shot in a virtual space, based on a timing action. In the game according to FIG. 56, the distance that the arrow flies may be increased in proportion to the time that the user pulls back on the bow. When the user presses the button to which the shooting action is assigned, the action of pulling the bow starts. When the button is continuously pressed, the string of the bow is continuously and gradually pulled back. The arrow is shot from the bow at the moment of releasing the button. In FIG. 56, a gauge (which reflects the extent to which the string of the bow is pulled back) is provided so that the user can visually check the duration of the timing action. Another examples of a timing action may include a ball shooting action that continuously increases an intensity and/or accuracy of a shot during a soccer game. Another examples of a timing action may include the playing of a virtual piano with a correct rhythm.

The content reproduction device 1200 may generate the thermal feedback start signal including the thermal feedback information corresponding to the input timing at the time of performing the timing action (S720).

As an example, the controller 1260 may count the elapsed time from the time point when a timing action begins during game progress, and determine the intensity of the thermal feedback according to the elapsed time. The larger the elapsed time, for example, the larger the thermal feedback intensity.

As another example, the controller 1260 may determine the thermal feedback intensity according to a difference between a predetermined reference value and an elapsed time. The smaller the difference, for example, the greater the intensity of the thermal feedback.

As another example, the controller 1260 may determine the thermal feedback intensity according to whether a length of the elapsed time is over a predetermined reference length. The larger the elapsed time, for example, the greater the thermal feedback intensity is output until the length is over the predetermined reference length, at which point the thermal feedback would no longer be output.

As another example, the controller 1260 may determine a type of the thermal feedback depending on whether the elapsed time has exceeded a predetermined reference value. For example, a hot feedback may be output before the elapsed time exceeds the predetermined reference value, and a cold feedback may be output after the elapsed time exceeds the predetermined reference value.

After the thermal feedback information is determined, the controller 1260 may generate the thermal feedback start signal including the thermal feedback information.

The content reproduction device 1200 may transmit the thermal feedback start signal including the thermal feedback information (S730). The controller 1260 may transmit the thermal feedback start signal including the thermal feedback information to the feedback device 1600 via the communication module (1220).

The feedback device 1600 may perform the thermal feedback output operation according to the thermal feedback start signal, and may output the thermal feedback corresponding to the thermal feedback information (S740). When the thermal feedback start signal is received, the feedback controller 1645 may apply a power to the thermoelectric couple array 1643 to perform the thermal feedback output operation. The feedback controller 1645 may generate a power-supplying signal according to the thermal feedback information included in the thermal feedback start signal.

According to the above-described implementation, the input timing may be sensed by a user through the thermal feedback, thereby increasing the intuitiveness of the game.

4.8. Eighth Implementation

The eighth implementation of the thermal feedback providing method according to an embodiment of the present disclosure is a method of providing a thermal feedback to a user by outputting a thermal feedback according to attributes of a virtual space in a game.

Figure 57:
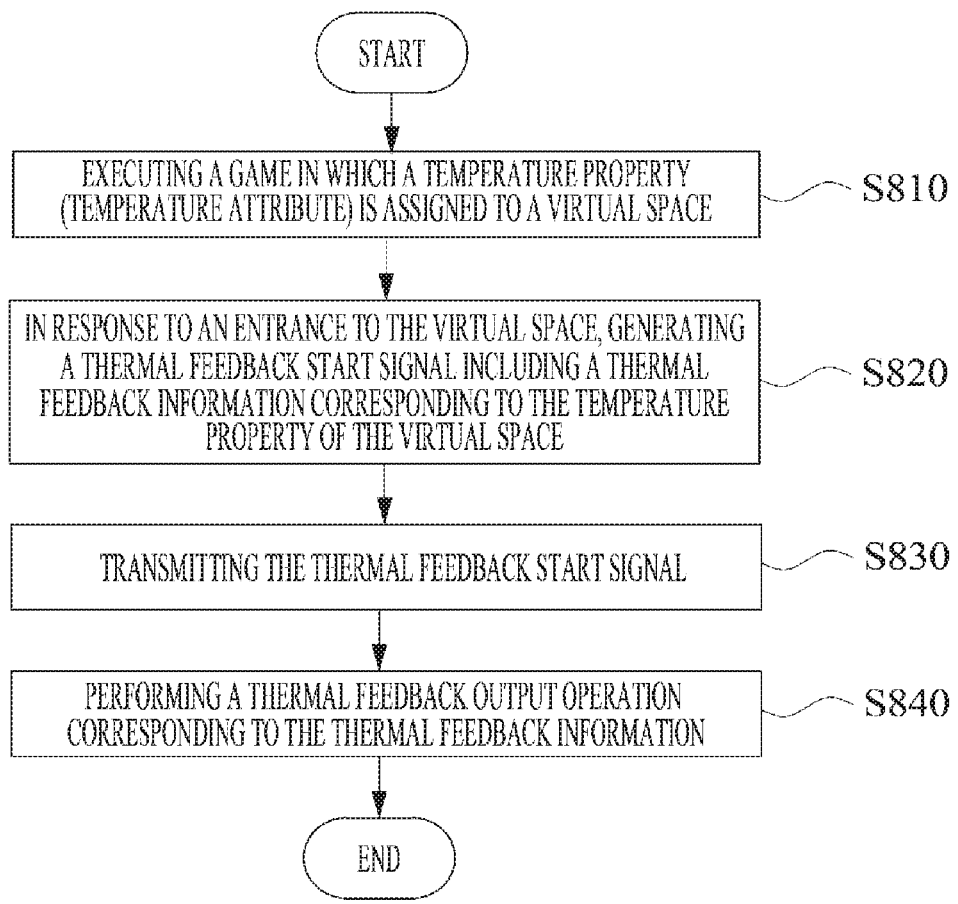
FIG. 57 is a flowchart of the eighth implementation of the thermal feedback providing method according to an embodiment of the present disclosure.

FIG. 57 is a flowchart of the eighth implementation of the thermal feedback providing method according to an embodiment of the present disclosure.

Referring to FIG. 57, the eighth implementation of the thermal feedback providing method may include executing a game in which a temperature property (temperature attribute) is assigned to a virtual space (S810), in response to an entrance to the virtual space, generating a thermal feedback start signal including a thermal feedback information corresponding to the temperature property of the virtual space (S820), transmitting the thermal feedback start signal (S830), and performing a thermal feedback output operation in accordance with the thermal feedback start signal, which may include outputting a thermal feedback corresponding to the thermal feedback information (S840).

Hereinafter, each step of the above-described implementation will be described in more detail.

The content reproduction device 1200 may execute a game in which a temperature property is assigned to a virtual space (S810). The controller 1260 may execute the game. The virtual space in the game may be given a temperature property. For example, an area-temperature property table may be stored in the memory (1240) or a game program. In the area-temperature property table, a first temperature property may be matched to a first area of the virtual space and a second temperature property may be matched to a second area of the virtual space.

Figure 58:
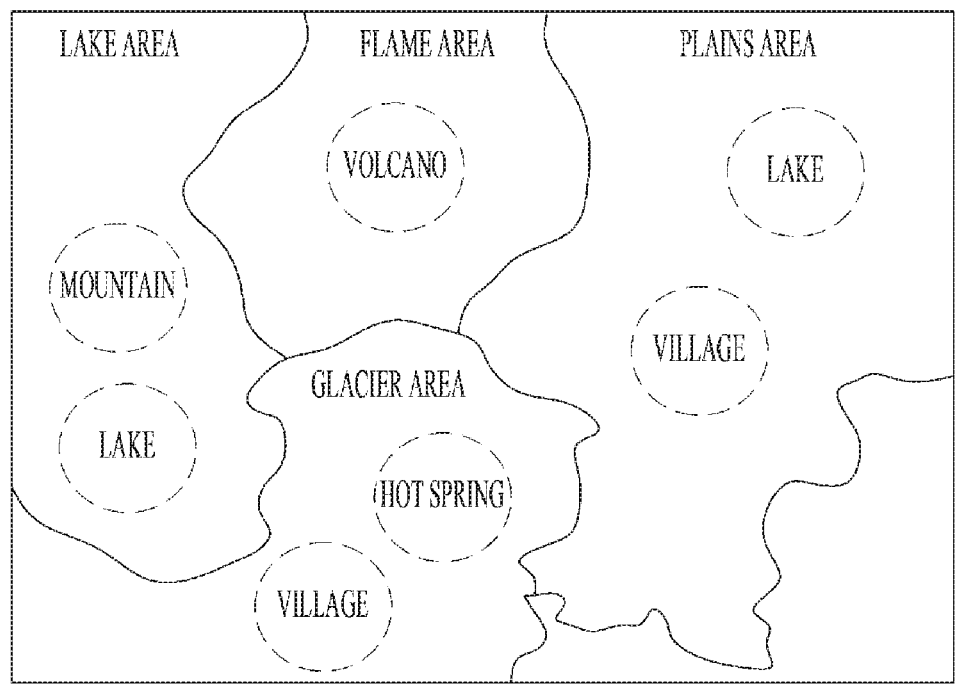
FIG. 58 is a view showing a virtual space in a game in the eighth implementation of the thermal feedback providing method according to an embodiment of the present disclosure.

FIG. 58 is a view showing a virtual space in a game in the eighth implementation of the thermal feedback providing method according to an embodiment of the present disclosure.

Referring to FIG. 58, the virtual space in the game may include a flame area, a glacier area, a plains area, a lake area, and the like as a global area. The flame area may be given a hot-temperature property as the temperature property, and the glacier area may be given a cold-temperature property.

The content reproduction device 1200 may generate the thermal feedback start signal including a thermal feedback information corresponding to a temperature property of the virtual space (S820). The thermal feedback start signal may be generated in response to a player character entering to the virtual space.

The controller 1260 may determine a current area where a player character is currently located by checking a location of the character in the virtual space in virtual reality game. The controller 1260 may determine a current area where a user is currently located by checking a location of the user in an augmented virtual space in an augmented reality game. The determination may be made in real time. Alternatively, the controller 1260 may determine an entry area when a playable character or a user enters a specific area in the virtual space. If the current area or the entry area is determined, the controller 1260 may determine the thermal feedback information according to the temperature property assigned to the corresponding area (the current area or the entry area) with reference to the area-temperature property table.

As an example, a type of thermal feedback may be determined according to the temperature property. For example, the type of the thermal feedback may be determined as a hot feedback in the case of that a hot temperature property is assigned to the corresponding area and be determined as a cold feedback in the case of that a cold temperature property is assigned to the corresponding area.

As another example, an intensity of the thermal feedback may be determined according to the temperature property. For example, the temperature property may include a value corresponding to the temperature value given to the corresponding area, and the controller 1260 may determine the intensity of the thermal feedback according to the value.

Once the intensity of the thermal feedback is determined, the controller 1260 may generate a thermal feedback start signal including thermal feedback intensity information.

The content reproduction device 1200 may transmit the thermal feedback start signal including the thermal feedback information (S830), and the feedback device 1600 may perform a thermal feedback output operation in accordance with the thermal feedback start signal, and may output a thermal feedback corresponding to the thermal feedback information (S840).

The controller 1260 may transmit the thermal feedback start signal including the thermal feedback information to the feedback device 1600 via the communication module 1220. When the thermal feedback start signal is received, the feedback controller 1645 may apply a power to the thermoelectric couple array 1643 to perform a thermal feedback output operation. The feedback controller 1645 may generate a power supplying signal according to the information included in the thermal feedback start signal.

Furthermore, the virtual space may be classified in a hierarchical structure. An upper class area may include a lower class area. For example, the virtual space may be a global area which is the largest area class, a local area included in the global area as a sub-area of the global area, a sub-local area included in the local area as a sub-area of the local area, and the like. Referring to FIG. 58, a flame area (global area) may include a volcanic sub area (local area), a lake area (global area) may include a mountain area (local area) and a lake area (local area), a plains area (global area) may include a lake area (local area) and a village area (local area), and a glacier area (global area) may include a hot spring area (local area) and a village area (local area). If the flame area, the plains area, the lake area, and the ice area are defined as the local area, the above sub-areas may be defined as the sub-local area.

Here, when the player (the character of the user) is in the glacier area, a cold feedback may be output as the thermal feedback, but when the player is in the hot spring area which is the sub-area of the glacier area, a hot thermal feedback may be output as the thermal feedback. That is, the temperature property assigned to the sub area (lower class area) may be prioritized to the temperature property assigned to the upper class area. If the player exits from the hot spring area, a cold feedback may be output as the thermal feedback. In case of that the same temperature property is assigned to the upper class area and the lower class area (for example, the flame area and the volcanic sub area), a weaker feedback may be output to the user for the upper class area and a stronger feedback may be output for the lower class area. For example, a weak hot feedback may be assigned to the flame area, and a strong hot feedback may be assigned to the volcanic sub area.

According to the above-described implementation, when a playable character enters the virtual space in the virtual reality or when the user enters the virtual space in the virtual reality or the augmented reality, a thermal feedback suitable for a virtual environment of the area may be output to provide a realistic thermal feedback to the user.

4.9. Ninth Implementation

The ninth implementation of a thermal feedback providing method according to an embodiment of the present disclosure is a method of providing a thermal feedback to a user by outputting thermal feedback according to a shooting event in the game.

Figure 59:
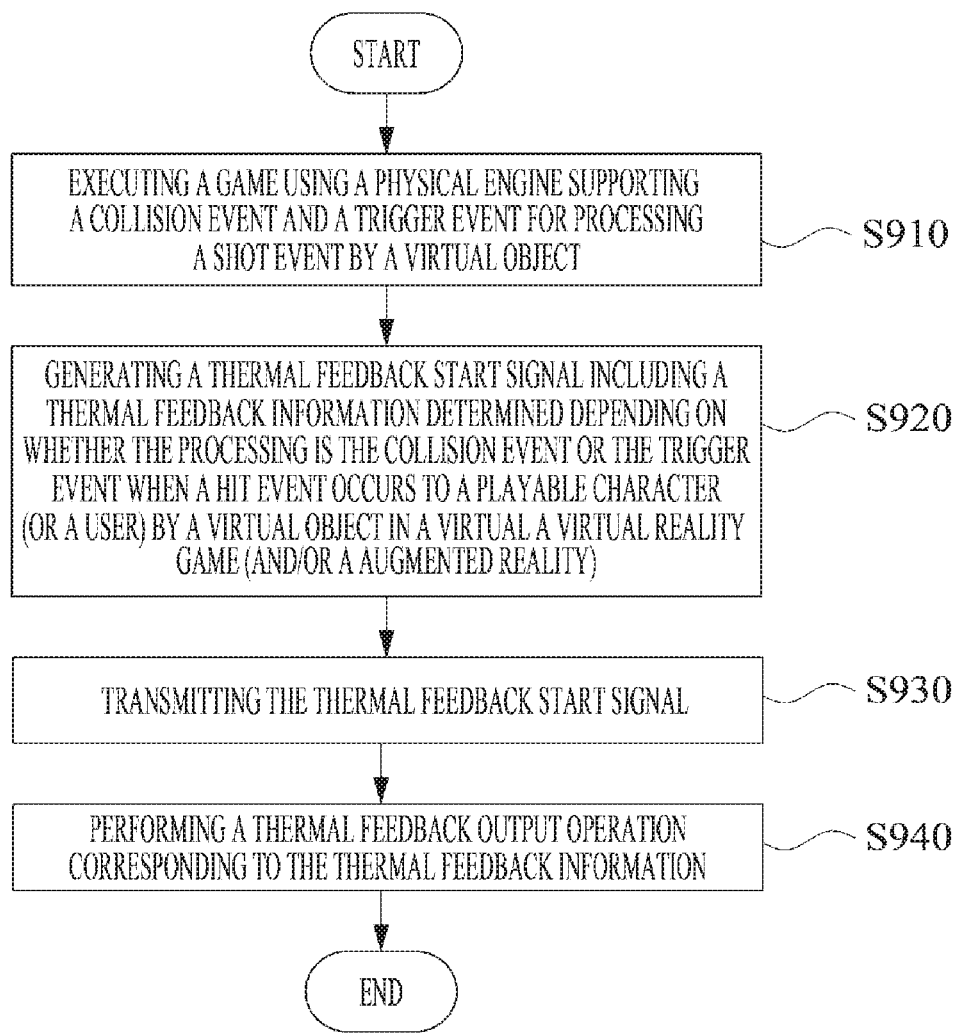
FIG. 59 is a flowchart of the ninth implementation of a thermal feedback providing method according to an embodiment of the present disclosure.

FIG. 59 is a flowchart of the ninth implementation of a thermal feedback providing method according to an embodiment of the present disclosure.

Referring to FIG. 59, the ninth implementation of the thermal feedback providing method may include executing a game using a physics engine supporting a collision event and a trigger event for processing a shooting event (S910), generating a thermal feedback start signal including thermal feedback information determined based on whether the processing is the collision event or the trigger event when a hit event occurs to a playable character (or a user) (S920), transmitting the thermal feedback start signal (S930), and performing a thermal feedback output operation in accordance with the thermal feedback start signal, which may include outputting a thermal feedback corresponding to the thermal feedback information (S940).

Hereinafter, each step of the above-described implementation will be described in more detail.

The content reproduction device 1200 may execute a game using a physics engine supporting a collision event and a trigger event for processing a hit event by a virtual object (S910).

The controller 1260 may execute the game. The game executed in the present implementation may be a game for processing a hit event using a physics engine.

The physics engine is software used to simulate physical phenomena in the fields of computer graphics, video games, movies, and the like. The physics engine is mainly used in the above-mentioned fields for realizing image processing more realistically. The physics engine may also be provided as a middleware for computing physical phenomena in real time on the game field. Representative functions of the physics engine may include the processing of collisions between virtual objects.

A hit event occurs when a playable character operated by a user or a user in a virtual reality and/or augmented reality gets hit by a virtual object. In this implementation, the game may process the hit event as a collision event or a trigger event using the physics engine.

Specifically, the physics engine may assign the collision determination attribute to the virtual object. The collision determination attribute may include a collision attribute and a trigger attribute. In a virtual space implemented by a physics engine, a virtual object assigned by the collision attribute is processed so as to be able to collide with another virtual object. In contrast, the virtual object assigned by the trigger attribute is processed so as not to collide with another virtual object.

Thus, when two virtual objects are located at the same coordinates in the virtual space, if the attributes of both virtual objects are the collision attributes, the physics engine may treat them as a collision event. Alternatively, if at least one of the two virtual objects has the trigger attribute, the physics engine may treat it as a trigger event. Here, in case of the collision event, the bodies of two virtual objects are not overlapped with each other and react as if they collide with each other as in the real world. In contrast, according to the trigger event, the spaces occupied by the two virtual objects overlap each other, so that one object can pass through another object.

A playable character or the user of the virtual reality typically has the collision attribute. If a virtual object having the collision attribute hits the player's character, the physics engine may generate the collision event. On the other hand, the physics engine may generate a trigger event if the object hitting the playable character has the trigger attribute.

For example, when a playable character falls onto a ground from a high place in the virtual reality and/or augmented reality, the collision event may occur because the ground is given the collision attribute. Similarly, since other characters or virtual vehicles in the game also have the collision attribute, they can cause collision events when they hit the user's playable character. In another example, in a shooting game, a bullet is typically given the trigger attribute, so a trigger event occurs when the character or other virtual object is hit by the bullet.

The content reproduction device 1200 may generate a thermal feedback start signal including a thermal feedback information determined depending on whether the processing is the collision event or the trigger event when a hit event occurs to a playable character (or a user) by a virtual object in a virtual a virtual reality game (and/or a augmented reality) (S920).

When a hit event occurs in the game, the controller 1260 may determine whether the hit event is a collision event or a trigger event. This can be determined according to the collision determination attribute of the hit object. The controller 1260 may determine an intensity of the thermal feedback in a different manner for the collision event and the trigger event.

In one example, the controller 1260 may determine the intensity of the thermal feedback based on an amount of impulse calculated in the physics engine if the hit event is determined to be a collision event. For example, the larger the impulse amount, the stronger the intensity of the thermal feedback. The amount of the impulse in the physics engine can be calculated based on the relative speed between the virtual objects and the mass value given to the virtual objects. That is, as the mass of the impulse object is large and the relative speed is high, the intensity of the thermal feedback may be determined to be strong.

As another example, when the hit event is determined as the trigger event, the controller 1260 may determine the intensity of the thermal feedback based on a type of a virtual object or a projectile, or the speed of a virtual object, since the physics engine does not calculate the amount of impulse at the time of the trigger event. For example, if hit by a bullet having a trigger attribute, the controller 1260 may determine that the higher the absolute velocity of the bullet, the stronger the intensity of the thermal feedback. For another example, if hit by a bullet with the trigger attribute, the controller 1260 may determine the intensity of the thermal feedback according to a type of bullet. For another example, if hit by a bullet with a trigger attribute, the controller 1260 can determine the intensity of the thermal feedback according to a type of weapon that fired the bullet. The controller 1260 may refer to a table in which the thermal feedback intensity is set for each type of the weapon. For example, the stronger the weapon is, the stronger the intensity of thermal feedback is. To set the intensity of the thermal feedback depending on the type of the projectile or the weapon, the controller 1260 can refer to the table in which the thermal feedback intensity is set for each type of projectile or weapon.

The content reproduction device 1200 may transmit the thermal feedback start signal including the thermal feedback information (S930), and the feedback device 1600 may perform a thermal feedback output operation in accordance with the thermal feedback start signal, which may be outputting a thermal feedback corresponding to the thermal feedback information (S940).

The controller 1260 may transmit the thermal feedback start signal including the thermal feedback information to the feedback device 1600 via the communication module 1220. When the thermal feedback start signal is received, the feedback controller 1645 may apply a power to the thermoelectric couple array 1643 to perform the thermal feedback output operation. The feedback controller 1645 may generate the power supplying signal according to the information included in the thermal feedback start signal.

According to the above-described implementation, a realistic thermal feedback may be output based on a hit event occurring in a virtual space. In the case of being hit by the virtual object having a collision attribute, the intensity of the thermal feedback could be adjusted using the amount of impulse calculated by the physics engine, thereby providing a thermal feedback corresponding to the actual reality. In addition, in cases where the amount of impulse is difficult to calculate, other appropriate parameters may be used instead of the amount of impulse to realistically provide the thermal feedback corresponding to the hit event.

4.10. Tenth Implementation

The tenth implementation of the thermal feedback providing method according to an embodiment of the present disclosure is a method of providing a thermal feedback to a user by outputting a thermal feedback associated with a heat transfer attribute of a virtual object in a game.

Figure 60:
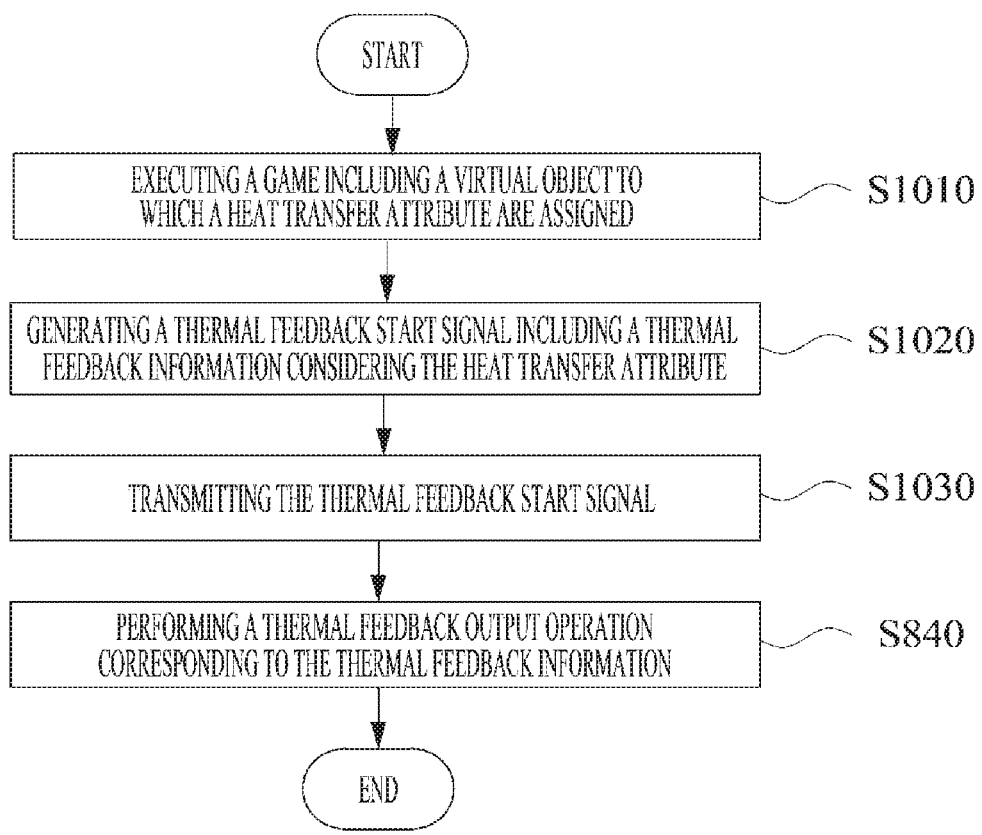
FIG. 60 is a flowchart of the tenth implementation of the thermal feedback providing method according to an embodiment of the present disclosure.

FIG. 60 is a flowchart of the tenth implementation of the thermal feedback providing method according to an embodiment of the present disclosure.

Referring to FIG. 60, the tenth implementation of a thermal feedback providing method may include executing a game including a virtual object to which a heat transfer attribute are assigned (S1010), generating a thermal feedback start signal including a thermal feedback information considering the heat transfer attribute (S1020), transmitting the thermal feedback start signal (S1030), and performing a thermal feedback output operation in accordance with the thermal feedback start signal, which may include outputting a thermal feedback corresponding to the thermal feedback information (S1040).

Hereinafter, each step of the above-described implementation will be described in more detail.

The content reproduction device 1200 may execute a game including a virtual object to which heat transfer attributes are assigned (S1010).

The controller 1260 may execute the game. In this implementation, the game includes the virtual object, and the virtual object may be given a heat transfer attribute. The heat transfer attribute may indicate how the virtual object delivers heat to a player (character) and/or a user.

The virtual object with the heat transfer attribute may be treated as a heat source in the game. The heat source may include a conduction heat source and a radiant heat source. The conductive heat source can transfer a heat only when substantially contacted with the user (or playable character) in the game. The radiant heat source can transfer a heat even when away from the user (or player's character) in the game.

The content reproduction device (1200) may generate a thermal feedback start signal including a thermal feedback information in consideration of the heat transfer attribute of the virtual object (S1020).

The controller 1260 may generate the thermal feedback start signal including the thermal feedback information in consideration of the thermal transfer attribute of the virtual object.

For example, if the heat transfer attribute of the virtual object is the conductive heat source, the controller 1260 may determine whether a user (or a playable character) and a virtual object are substantially in contact with each other. The controller 1260 may generate the thermal feedback start signal when the conductive heat source contacts with the user (or playable character). The controller 1260 may determine a type and an intensity of the thermal feedback based on the temperature attribute assigned to the conductive heat source. Conversely, the controller 1260 may not generate a thermal feedback start signal if the user (or player's character) is apart from the conductive heat source.

In another example, if the heat transfer attribute of the virtual object is a radiant heat source, the controller 1260 may generate a thermal feedback start signal even when the user (or the playable character) is spaced apart from the virtual object. The controller 1260 may determine a type of the thermal feedback based on the temperature attribute assigned to the radiant heat source (the virtual object). The controller 1260 may also determine an intensity of the thermal feedback according to the temperature attribute assigned to the radiant heat source (the virtual object).

Alternatively, when determining the thermal feedback information for the radiant heat source, the controller 1260 may further consider a type of radiant heat source and a distance between the user (or player's character) and the radiant heat source.

A radiant heat sources may be divided into several types depending on a relationship between a distance (between the radiant heat source and the playable character (a user) and an amount of the heat transferred therewith. For example, the radiant heat source may include an emissive heat source, a directional heat source, and an areal heat source. The emissive heat source is a heat source that the transmitted heat amount becomes smaller as the distance from the heat source increases. The directional heat source is a heat source that transfers a constant heat regardless of the distance from the heat source. The areal heat source is a heat source that transfers heat only to a region within a predetermined distance from a heat source and does not transfer heat to a region beyond the predetermined distance. Also, the areal heat source may be set to transfer a constant heat, or to transfer a smaller heat as the distance increases from the center of the area.

Accordingly, in the case where the radiant heat source is the emissive heat source, the controller 1260 may set the thermal feedback intensity to be stronger as the distance to the user (or the player's character) becomes closer. When the radiant heat source is the directional heat source, the controller 1260 may set the thermal feedback intensity only considering the temperature of the heat source regardless of the distance from the user (or the player's character). When the radiant heat source is an areal heat source, the controller 1260 may determine the thermal feedback intensity according to the temperature of the heat source when the user (or the player character) is within a predetermined region from the heat source. The thermal feedback intensity may also be determined in consideration of the distance of the heat source to the user (or the player's character) and the temperature of the heat source as described above. Moreover, the thermal feedback start signal may be not generated when the user (or the player's character) is outside the predetermined region.

To calculate the heat transferred by the heat source in the game, the game of this implementation may use the physics engine described above.

When the thermal feedback information is determined, the controller 1260 may generate the thermal feedback start signal including the thermal feedback information.

The content reproduction device 1200 may transmit the thermal feedback start signal including the thermal feedback information (S1030), and the feedback device 1600 may perform a thermal feedback output operation in accordance with the thermal feedback start signal, and may output a thermal feedback corresponding to the thermal feedback information (S1040).

The controller 1260 may transmit the thermal feedback start signal including the thermal feedback information to the feedback device (1600) via the communication module 1220. When the thermal feedback start signal is received, the feedback controller 1645 may apply a power to the thermoelectric couple array 1643 to perform a thermal feedback output operation. The feedback controller 1645 may generate a power supplying signal according to the information included in the thermal feedback start signal.

According to the above-described implementation, the heat transferred to the user or the playable character may be calculated according to the distance and other information related to the heat source on the virtual space, and the corresponding thermal feedback may be output to give a realistic thermal experience to the user.

4.11. Eleventh Implementation

The eleventh implementation of the thermal feedback providing method according to an embodiment of the present disclosure is a method of providing a thermal feedback to a user by associating and outputting thermal feedback associated with a thermal conductivity of a virtual object in a game.

Figure 61:
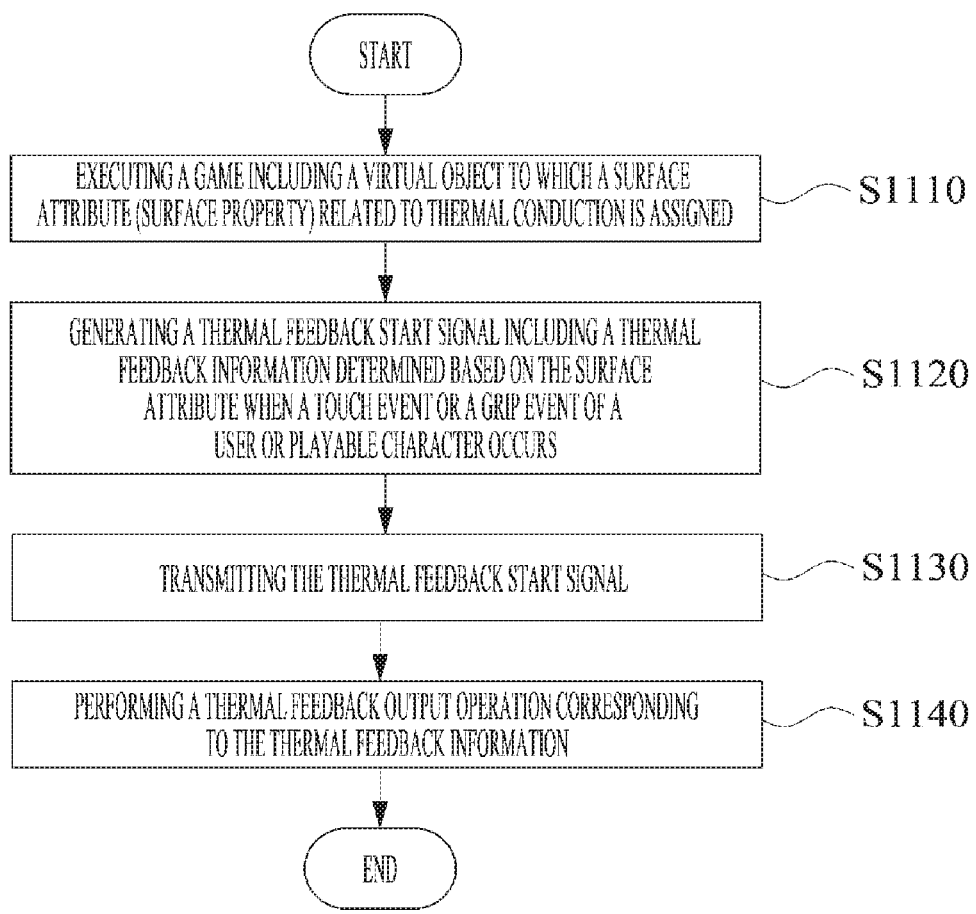
FIG. 61 is a flowchart of the eleventh implementation of the thermal feedback providing method according to an embodiment of the present disclosure.

FIG. 61 is a flowchart of the eleventh implementation of the thermal feedback providing method according to an embodiment of the present disclosure.

Referring to FIG. 61, the eleventh implementation of a thermal feedback providing method may include executing a game including a virtual object to which a surface attribute (surface property) related to thermal conduction is assigned (S1110), generating a thermal feedback start signal including a thermal feedback information determined based on the surface attribute when a touch event or a grip event occurs (e.g., when the user or playable character touches or grabs the object) (S1120), transmitting the thermal feedback start signal (S1130), and performing a thermal feedback output operation in accordance with the thermal feedback start signal, which may include outputting a thermal feedback corresponding to the thermal feedback information (S1140).

Hereinafter, each step of the above-described implementation will be described in more detail.

The content reproduction device 1200 may play a game including a virtual object to which a surface attribute related to thermal conduction is assigned, in the eleventh implementation of the thermal feedback providing method (S1110).

The content reproduction device 1200 may present a game including the virtual object to which the surface attribute related to thermal conduction is assigned, in the eleventh implementation of the thermal feedback providing method (S1110).

The content reproduction device 1200 may generate a thermal feedback start signal including a thermal feedback information. The thermal feedback information is determined in association with the surface attribute of the virtual object upon a touch event or a grip event involving the virtual object (S1120).

The controller 1260 may generate the thermal feedback start signal when the touch event or the grip event occurs. The controller 1260 may determine the thermal feedback information to be included in the thermal feedback start signal.

As an example, a type of thermal feedback may be determined based on the temperature (temperature attribute) assigned to the virtual object. For example, the type of the thermal feedback may be selected among a hot feedback, a cold feedback and a thermal grill feedback based on the temperature assigned to the virtual object. The controller 1260 may also determine an intensity of the thermal feedback based on the temperature of the heat source (virtual object).

When the thermal feedback information is determined, the controller 1260 may generate the thermal feedback start signal including the thermal feedback information.

The content reproduction device 1200 may transmit the thermal feedback start signal including the thermal feedback information (S1030), and the feedback device 1600 may perform a thermal feedback output operation in accordance with the thermal feedback start signal, and output the thermal feedback corresponding to the thermal feedback information (S1040).

The controller 1260 may transmit the thermal feedback start signal including the thermal feedback information to the feedback device 1600 via the communication module 1220. When the thermal feedback start signal is received, the feedback controller 1645 may apply a power to the thermoelectric couple array 1643 to perform the thermal feedback output operation. The feedback controller 1645 may generate a power supplying signal according to the information included in the thermal feedback start signal.

The content reproduction device 1200 may transmit the thermal feedback start signal including a thermal feedback information (S1130), and the feedback device 1600 may perform a thermal feedback output operation in accordance with the thermal feedback start signal, and output the thermal feedback corresponding to the thermal feedback information (S1140).

The controller 1260 may transmit the thermal feedback start signal including the thermal feedback information to the feedback device 1600 via the communication module 1220. When the thermal feedback start signal is received, the feedback controller 1645 may apply a power to the thermoelectric couple array 1643 to perform the thermal feedback output operation. The feedback controller 1645 may generate a power supplying signal according to the information included in the thermal feedback start signal.

4.12. Twelfth Implementation

The twelfth implementation of the thermal feedback providing method according to an embodiment of the present disclosure is a method of providing a thermal feedback to a user by outputting a thermal feedback based on the priority of a thermal event that occurs in a game.

In a multimedia environment including games, the thermal events (for example, the hit event, the touch event, the grip event or entry into a specific area) may occur at the same time.

The thermal event means an event that induces an output of thermal feedback. Examples of the thermal event may include a change in the health points (sixth embodiment), entering into a thermal attribute assigned area (eighth embodiment), and getting hit or shot (ninth embodiment), or the like For example, a hit event (a shooting event) inducing a hot feedback may occur in a state in which a playable character (or a user) enters a specific area inducing a cold feedback.

The content reproduction device 1200 may determine the priority between the thermal events, and output a thermal feedback for one thermal event which has a higher priority than the other thermal event.

For example, when a bullet inducing a hot feedback is hit on the character or a user in a lake area inducing a cold feedback, the priority on the thermal events may be determined. In the case where a priority for the hit event by the bullet is determined as being higher than a priority for the lake-entering event, the hot feedback included by the hit event will be output first.

Specifically, when the hit event inducing the hot feedback occurs in the state where a character or a user enters a specific region for inducing the cold feedback, the controller 1260 may generate a thermal feedback start signal including a thermal feedback information, wherein the thermal feedback information may be configured to output the thermal feedback for the concurrently-occurred thermal events with priority given to outputting the hot feedback due to the hit event rather than the cold feedback due to entry into the specific region, until the effect of the hit event is terminated. Then, the controller 1260 may transmit the thermal feedback start signal to the feedback device 1600 through the communication module 1220 so that the feedback controller 1645 performs a feedback output operation according to the thermal feedback information. In addition, in the above case, after the effect for the thermal event having a higher priority (for example, the hit event) is terminated, the other thermal feedback induced by the other thermal event (for example, the entry into the specific region) may be provided or resumed. For example, when thermal feedback based on an area event is output, and an object event occurs in this state, thermal feedback based on the object event is output. When the object event comes to an end, the thermal event based on the area event may be resumed.

4.13. Thirteenth Implementation

The twelfth implementation of the thermal feedback providing method according to an embodiment of the present disclosure described above relates to which thermal event should be prioritized when thermal events occur at the same time.

However, the thermal feedback associated with two concurrent thermal events may be combined.

For example, if a hot feedback and a cold feedback are output simultaneously, a thermal grill feedback can be output. If the intensity of the hot feedback is stronger than the intensity determined based on the neutral ratio, the content reproduction device 1200 may output a hot grill feedback, and in the opposite case, the content reproduction device 1200 may output a cold grill feedback.

That is, the controller 1260 may generate a thermal feedback start signal such that a hot feedback induced by one thermal event and a cold feedback induced by the other thermal event are simultaneously provided to the user, thereby outputting the thermal grill feedback (cold thermal grill feedback or hot thermal grill feedback). Further, the controller 1260 may determine a type of the thermal grill feedback by comparing the intensity of the hot feedback induced by the one thermal event with the intensity of the cold feedback induced by the other thermal event. For example, when the intensity of the hot feedback is stronger, the type of thermal grill feedback may be determined as a hot thermal grill feedback. When the intensity of the cold feedback is stronger, the type of the thermal feedback may be determined as a cold thermal grill feedback.

The controller 1260 then may transmit the thermal feedback start signal generated through the communication module 1220 to the feedback device 1600. The feedback device 1600 may refer to the thermal feedback information included in the thermal feedback start signal, and perform an output operation.

4.14. Fourteenth Implementation

The fourteenth implementation of the thermal feedback providing method according to an embodiment of the present disclosure is a method of providing a thermal feedback to a user by outputting a thermal feedback associated with consideration of a thermal resistance of a character when a thermal event occurs in a game.

Figure 62:
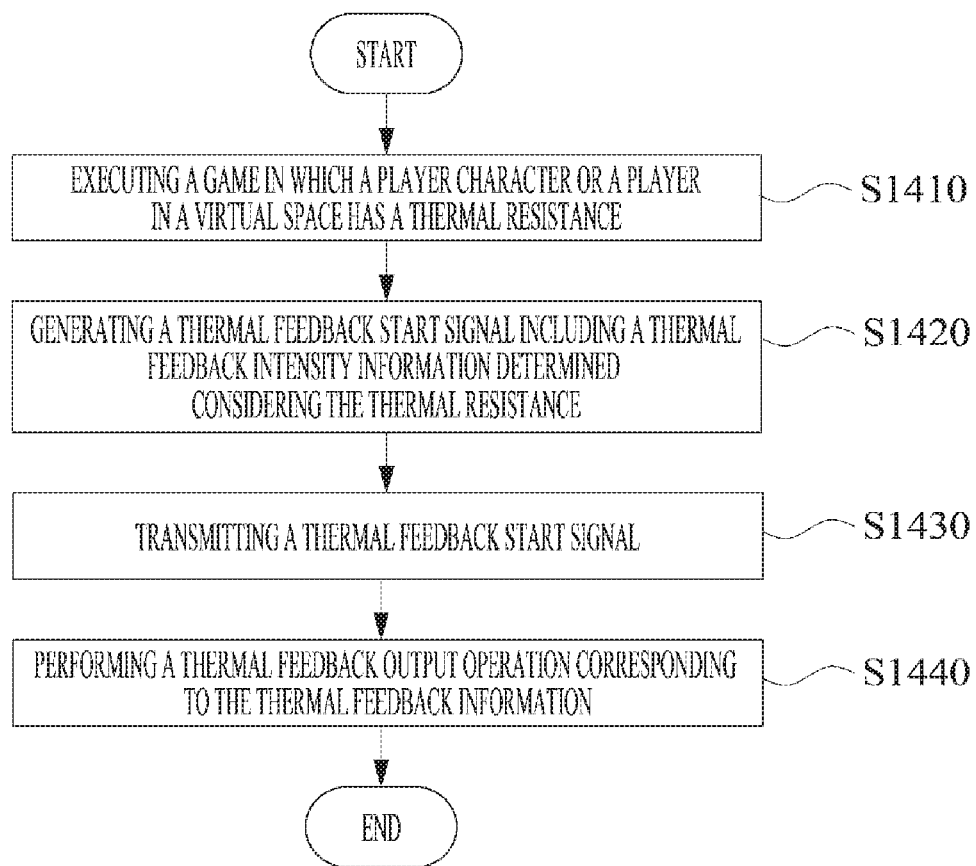
FIG. 62 is a flow chart of the fourteenth implementation of a thermal feedback providing method according to an embodiment of the present disclosure.

FIG. 62 is a flow chart of the fourteenth implementation of a thermal feedback providing method according to an embodiment of the present disclosure.

Referring to FIG. 62, the fourteenth implementation of a thermal feedback providing method may include executing a game in which a player character or a player in a virtual space has a thermal resistance (S1410), generating a thermal feedback start signal including a thermal feedback intensity information determined considering the thermal resistance (S1420), transmitting a thermal feedback start signal (S1430), and performing a thermal feedback output operation in accordance with the thermal feedback start signal, which may include outputting a thermal feedback corresponding to the thermal feedback information (S1440).

Hereinafter, each step of the above-described implementation will be described in more detail.

The content reproduction device 1200 may execute a game in which a player character or a player in the virtual space has a thermal resistance (S1410).

The controller 1260 may execute the game. Here, in the game executed in this implementation, the thermal resistance may be given to the player character or the user avatar in the virtual reality. The thermal resistance may be assigned to the character or avatar in the form of a capacity or ability. In addition, if the character or avatar is equipped with equipment such as weapon or armor, a total thermal resistance of the character may be determined by adding the capacity of the thermal resistance of the equipment to the thermal resistance of the character or avatar.

The content reproduction device 1200 may generate a thermal feedback start signal including thermal feedback intensity information determined in consideration of the thermal resistance (total thermal resistance) at the time of occurrence of a thermal event (S1420).

The controller 1260 may process the thermal feedback information according to the thermal event when the thermal event occurs. If the character is given the thermal resistance, the controller 1260 may adjust the intensity of the thermal feedback considering the thermal resistance of the character. For example, the higher the thermal resistance, the lower the intensity of the thermal feedback.

Alternatively, the thermal resistance may be classified into a hot resistance/a cold resistance/a pain resistance. In this case, the controller 1260 may determine a type of the thermal feedback induced by the thermal event occurrence, select a type of thermal resistance to be considered according to the type of thermal feedback, and adjust the intensity of the thermal feedback according to the selected thermal resistance.

The content reproduction device 1200 may transmit the thermal feedback start signal including thermal feedback information (S1430), and the feedback device 1600 may perform a thermal feedback output operation in accordance with the thermal feedback start signal and output a thermal feedback corresponding to the thermal feedback information (S1440).

The controller 1260 may transmit the thermal feedback start signal including thermal feedback information to the feedback device 1600 via the communication module 1220. When the thermal feedback start signal is received, the feedback controller 1645 may apply a power to the thermocouple array 1643 to perform the thermal feedback output operation. The feedback controller 1645 may generate the power supplying signal according to the information included in the thermal feedback start signal.

According to the above-described implementation, since the intensity of the thermal feedback is adjusted according to the thermal resistance in the virtual space, a thermal feedback may be provided that reflects the degree of equipment and growth of characters in a role playing game (RPG).

4.15. Fifteenth Implementation

The fifteenth implementation of the thermal feedback providing method according to an embodiment of the present disclosure is a method of providing a thermal feedback to a user by outputting a thermal feedback associated with consideration of the size of an image related to a thermal event displayed in a field of view (FOV) when the thermal event occurs in a game.

Figure 63:
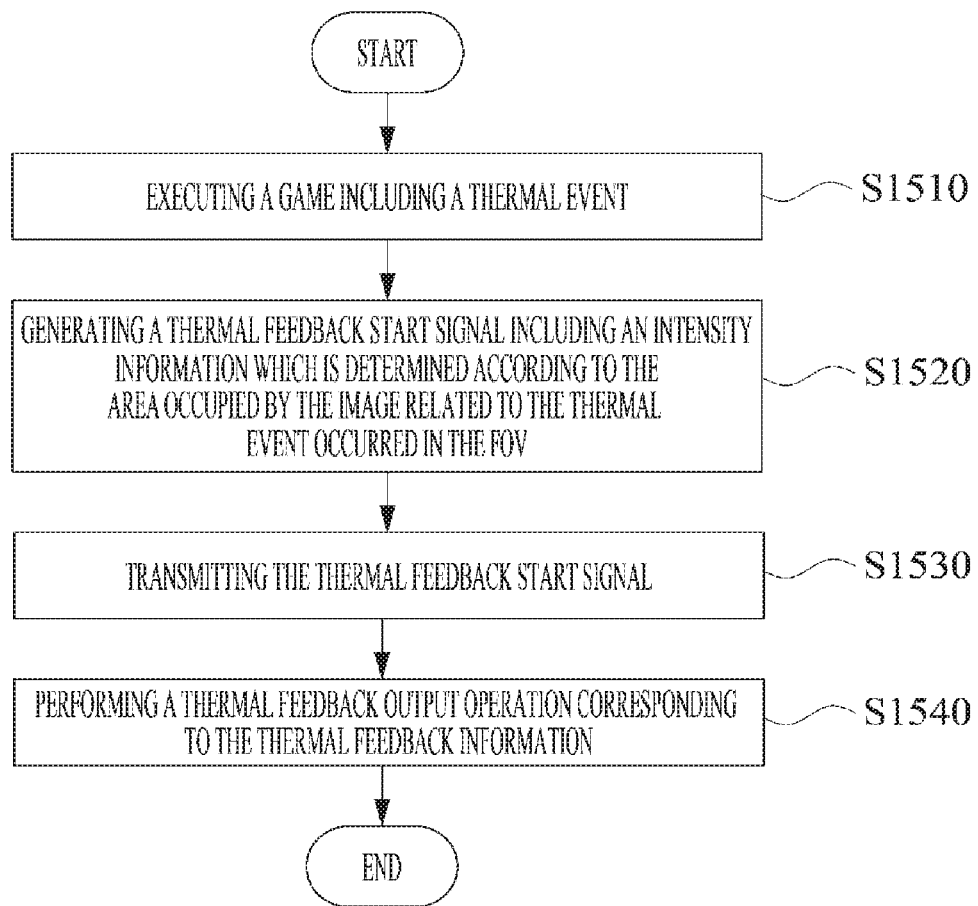
FIG. 63 is a flowchart of the fifteenth implementation of a method for providing a thermal feedback according to an embodiment of the present disclosure.

FIG. 63 is a flowchart of the fifteenth implementation of a method for providing a thermal feedback according to an embodiment of the present disclosure.

Referring to FIG. 63, the fifteenth implementation of a method for providing a thermal feedback may include executing a game including a thermal event (S1510), generating a thermal feedback start signal including an intensity information which is determined according to the area occupied by the image related to the thermal event occurred in the FOV (S1520), transmitting the thermal feedback start signal (S1530), and performing a thermal feedback output operation in accordance with the thermal feedback start signal, which may include outputting a thermal feedback corresponding to the thermal feedback information (S1540).

Hereinafter, each step of the above-described implementation will be described in more detail.

The content reproduction device 1200 may execute a game including a thermal event (S1510), which may be performed by the controller 1260. Also, the controller 1260 may output a video signal during the game, which may be a video signal according to the FOV of the virtual camera 1480 in the virtual space.

The content reproduction device 1200 may generate a thermal feedback start signal including thermal feedback intensity information determined according to an area occupied by an image related to a thermal event when the thermal event occurs in the FOV (S1520).

The controller 1260 may calculate the area occupied by the image related to the thermal event occurs in the FOV. The controller 1260 may then determine the thermal feedback intensity information according to the occupied area and include it to generate a thermal feedback start signal. For example, as the number of pixels occupied by an image associated with the thermal event increases, the intensity of the thermal feedback may be increased.

The content reproduction device 1200 may transmit the thermal feedback start signal including the thermal feedback information (S1530), and the feedback device 1600 may perform a thermal feedback output operation in accordance with the thermal feedback start signal and may output a thermal feedback corresponding to the thermal feedback information (S1540).

The controller 1260 may transmit a thermal feedback start signal including thermal feedback information to the feedback device 1600 via the communication module 1220. When the thermal feedback start signal is received, the feedback controller 1645 may apply a power to the thermocouple array 1643 to perform a thermal feedback output operation. The feedback controller 1645 may generate the power supplying-signal according to the information included in the thermal feedback start signal.

According to the above-described embodiment, even though the same thermal event is generated, a strong thermal feedback may be output when the user zooms-in on the visual field in the thermal event direction, and weak thermal feedback can be output when the user zooms-out. Similarly, the thermal feedback may be weakened by turning the FOV such that the user moves the thermal event out of the FOV and may be enhanced by turning the FOV such that the thermal event enters into the FOV. Accordingly, the user's thermal feedback can be further improved.

4.16. Sixteenth Implementation

The sixteenth implementation of the thermal feedback providing method according to an embodiment of the present disclosure is a method of providing a thermal feedback to a user by outputting a thermal feedback associated with the augmented reality in a game.

Figure 64:
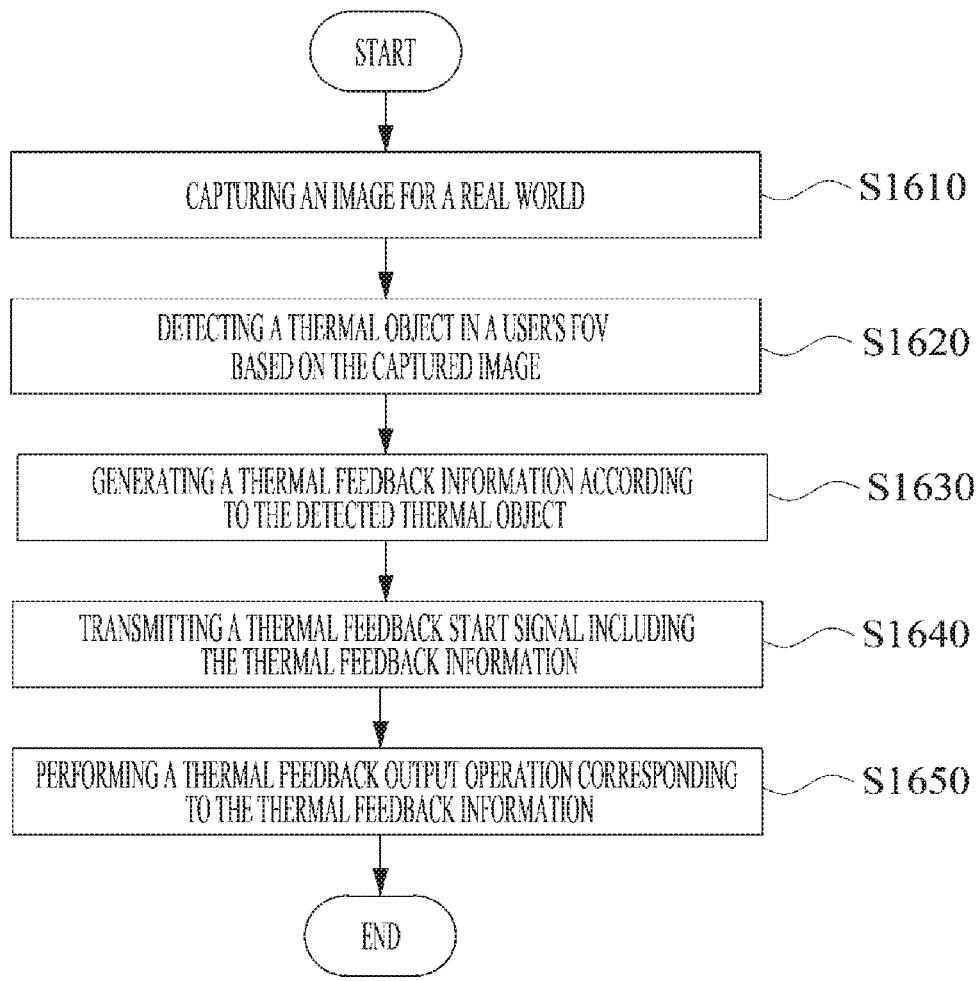
FIG. 64 is a flow chart of the sixteenth implementation of a thermal feedback providing method according to an embodiment of the present disclosure.

FIG. 64 is a flow chart of the sixteenth implementation of a thermal feedback providing method according to an embodiment of the present disclosure.

Referring to FIG. 64, the sixteenth implementation of a thermal feedback providing method may include capturing an image for a real world (S1610), detecting a thermal object in a user's FOV based on the captured image (S1620), generating a thermal feedback information according to the detected thermal object (S1630), transmitting a thermal feedback start signal including the thermal feedback information (S1650), and performing a thermal feedback output operation in accordance with the thermal feedback start signal, which may be outputting a thermal feedback corresponding to the thermal feedback information (S1650).

Hereinafter, each step of the above-described implementation will be described in more detail.

The content reproduction device 1200 may capture an image of the real world through a camera 1480 (S1610). The content reproduction device 1200 may be provided in the form of an HMD including a camera 1480. Alternatively, the content reproduction device 1200 may be provided as a console device being associated with an HMD. In this case, content reproduction device may obtain (receive) the image (video) of the real world obtained by a camera of the HMD through a communication module 1220.

The content reproduction device 1200 may detect a thermal object in the FOV of the user based on the image (S1620). The controller 1260 may identify the thermal object included in the image through an image recognition algorithm. The thermal object may be a real object or a virtual object inserted into the real world by the augmented reality application.

The content reproduction device 1200 may generate a thermal feedback information according to the detected thermal object (S1630). The controller 1260 may obtain a temperature attribute (temperature property) assigned to the thermal object using the identification result of the thermal object. Further, the controller 1260 may determine a type of thermal feedback according to the temperature attribute.

The content reproduction device 1200 may transmit the thermal feedback start signal including the thermal feedback information (S1640), and the feedback device 1600 may perform a thermal feedback output operation in accordance with the thermal feedback start signal, which may be outputting a thermal feedback corresponding to the thermal feedback information (S1650).

The controller 1260 may transmit the thermal feedback start signal including thermal feedback information to the feedback device 1600 via the communication module 1220. When the thermal feedback start signal is received, the feedback controller 1645 may apply a power to the thermocouple array 1643 to perform a thermal feedback output operation. The feedback controller 1645 may generate a power-supplying signal according to the information included in the thermal feedback start signal.

4.17. Seventeenth Implementation

The seventeenth implementation of the thermal feedback providing method according to an embodiment of the present disclosure is a method for providing a thermal feedback to a user by outputting a thermal feedback associated with considering a field of view (FOV) or a character position where a thermal event occurs, and a position of the thermal event in the screen.

The present implementation will be described based on the case where a user uses a feedback devices 1600 in both hands.

Figure 65:
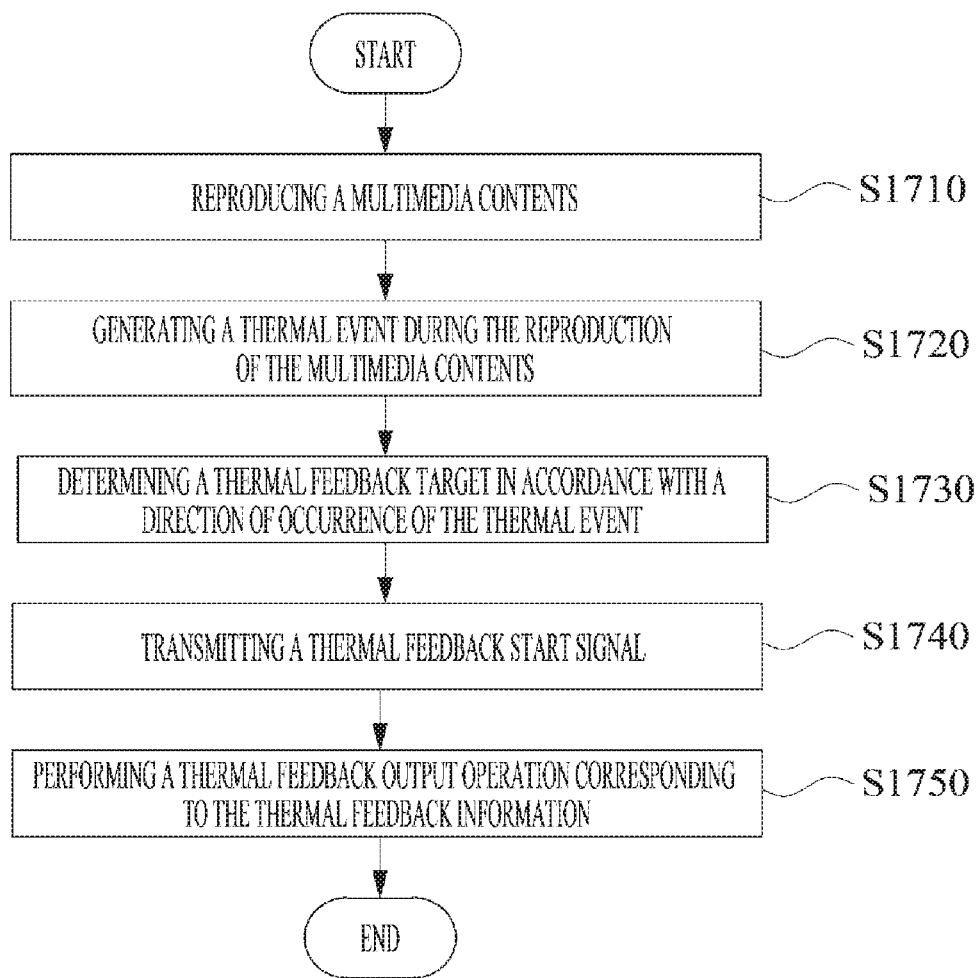
FIG. 65 is a flowchart of the seventeenth implementation of a method for providing thermal feedback according to an embodiment of the present disclosure.

FIG. 65 is a flowchart of the seventeenth implementation of a method for providing thermal feedback according to an embodiment of the present disclosure.

Referring to FIG. 65, the seventeenth implementation of the thermal feedback providing method may include reproducing a multimedia content (S1710), generating a thermal event during the reproduction of the multimedia content (S1720), determining a thermal feedback target in accordance with a direction of occurrence of the thermal event (S1730), transmitting a thermal feedback start signal in accordance with the determination of the thermal feedback target (S1740), and performing a thermal feedback output operation in response to the reception of the thermal feedback start signal, which may be outputting a thermal feedback corresponding to the thermal feedback information (S1750).

Hereinafter, each step of the above-described implementation will be described in more detail.

The content reproduction device 1200 may reproduce the multimedia content (S1710). The multimedia content may include at least one thermal event. The content reproduction device 1200 may also communicate with a first feedback device 1600 which is gripped by a right hand of a user and a second feedback device 1600 which is gripped by a left hand of the user.

The content reproduction device 1200 may generate a thermal event according to the multimedia content reproduction (S1720). The thermal event may include any of the thermal events described in the above thermal feedback providing methods.

When a thermal event occurs during the reproduction of the multimedia content, the content reproduction device 1200 may determine a thermal feedback target according to a direction of the thermal event (S1730).

The controller 1260 may determine the direction of occurrence of a thermal event. Specifically, in the case of the first-person view multimedia content including the virtual reality application or the augmented reality application, the direction of the occurrence of the thermal event may be determined based on a relationship between a position of the thermal event and the FOV. In the case of third-person view content, the direction of the thermal event may be determined based on the position of the player character in the game.

When the direction of the occurrence of the thermal event is determined, the controller 1260 may determine the thermal feedback target according to the generation direction.

Figure 66:
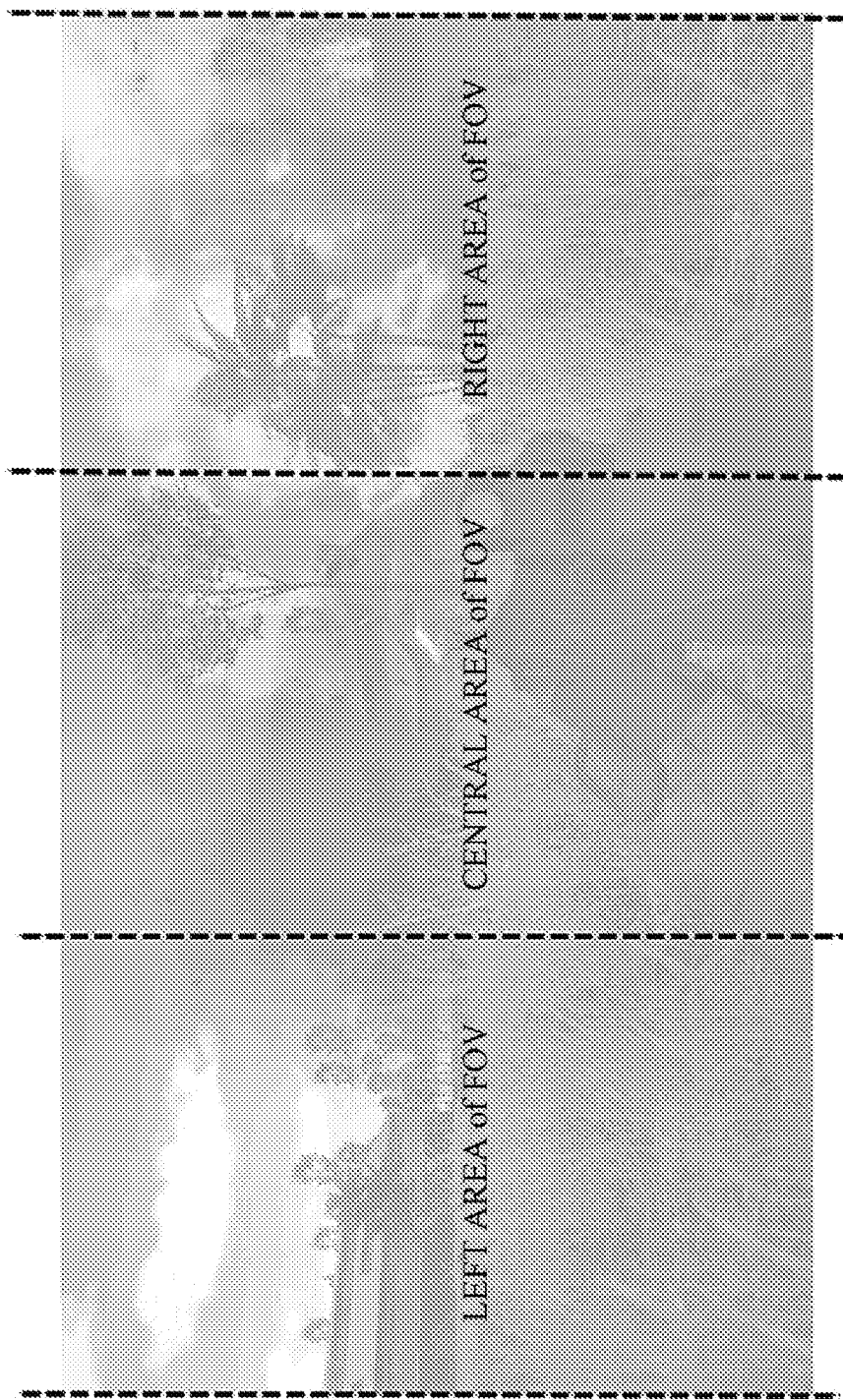
FIG. 66 is a view showing a thermal feedback target object according to an occurrence point of a thermal event in a first-person game according to the seventeenth implementation of the thermal feedback providing method according to an embodiment of the present disclosure.

FIG. 66 is a view showing a thermal feedback target object according to an occurrence point of a thermal event in a first-person game according to the seventeenth implementation of the thermal feedback providing method.

For example, referring to FIG. 66, when a thermal event occurs in the central part of the FOV in the first-person-view application, the controller 1260 may determine a thermal feedback target to be both the first feedback device 1600 and the second feedback device 1600. Also, when a thermal event occurs on the right side based on the FOV, the controller 1260 may determine the thermal feedback target to be the first feedback device 1600. Alternatively, when a thermal event occurs on the left side based on the FOV, the controller 1260 may determine the thermal feedback target to be the second feedback device 1600.

The content reproduction device 1200 may transmit a thermal feedback start signal in accordance with the determination of the thermal feedback target (S1740).

Once the thermal feedback target is determined, the controller 1260 may transmit a thermal feedback start signal via the communication module 1220 to the feedback device 1600 which is the determined thermal feedback target.

When the thermal feedback start signal is received, the feedback device 1600 may perform a thermal feedback output operation in response to the reception of the thermal feedback start signal. The thermal feedback output may be output based on the thermal feedback information (S1750).

Alternatively, in this implementation, as the point of occurrence of the thermal event moves, the feedback device 1600 outputting the thermal feedback may be changed. For example, if a user turns the FOV while a thermal event occurs on the right side of the FOV, the point where the thermal event occurs can move through the center to the left side. The thermal feedback target move from the right feedback device 1600, to both feedback devices 1600, to the left feedback device 1600.

Although the present embodiment has been described above as being performed in an environment using a plurality of feedback devices 1600, it is not necessarily so. For example, this implementation may be applied when a single feedback device 1600 is used. For example, if there is a plurality of thermal output modules 1640 arranged in one gaming controller gripped by both hands, the feedback controller 1645 of the feedback device 1600 may determine which of the first thermal output module 1640 and the second thermal output module 1640 included in the gaming controller may be selected as the target, and the thermal output module 1640 may output the thermal feedback accordingly. As another example, the present implementation may be applied even in the case of the feedback device 1600 having only one thermal output module 1640. For example, the only one module may include a thermocouple array 1643 constituted by a plurality of thermocouple groups 1644 (that is, the one thermal module may be configured to be controllable by region), the feedback controller 1645 of the feedback device 1600 may determine which region (the center/right/left/whole) of the module will be designated as the target of the thermal feedback and the thermal output module 1640 may output the thermal feedback accordingly.

The methods of providing thermal feedback according to embodiments of the present disclosure described above can be used alone or in combination with each other. In addition, since each of the steps described in each thermal feedback providing method is not essential, the method of providing thermal feedback can be performed by including all or part of the steps. Also, since the order in which the steps are described is merely for convenience of explanation, the steps in the method of providing thermal feedback are not necessarily performed in the order described.

Also, in the method of providing thermal feedback according to an embodiment of the present disclosure described above, any steps not described as being executed by a specific controller may be performed by one or both of the application controller and the feedback controller 1645 of the feedback device 1600. In addition, in the above description, the steps described as being performed by the application controller may be performed by the feedback controller 1645, and vice versa. In addition, steps described above as being performed by one of the application controller or the feedback controller 1645 maybe performed by the collaborative operation of both controllers. As already mentioned, the application controller and feedback controller 1645 may be implemented as a single controller 1260.

5. A Method for Generating Multimedia Content

Hereinafter, a method of generating multimedia content used in the thermal feedback providing method will be described. The method of generating multimedia content according to an embodiment of the present disclosure may include a method of generating video content and a method of generating a game or a sensory application.

5.1. An Electronic Device

The method for generating multimedia content according to an embodiment of the present disclosure may be performed by the electronic device 2000. For example, the electronic device 2000 may include a PC, a workstation, a laptop, notebook, tablet PC, smart phone, and the like.

Figure 67:
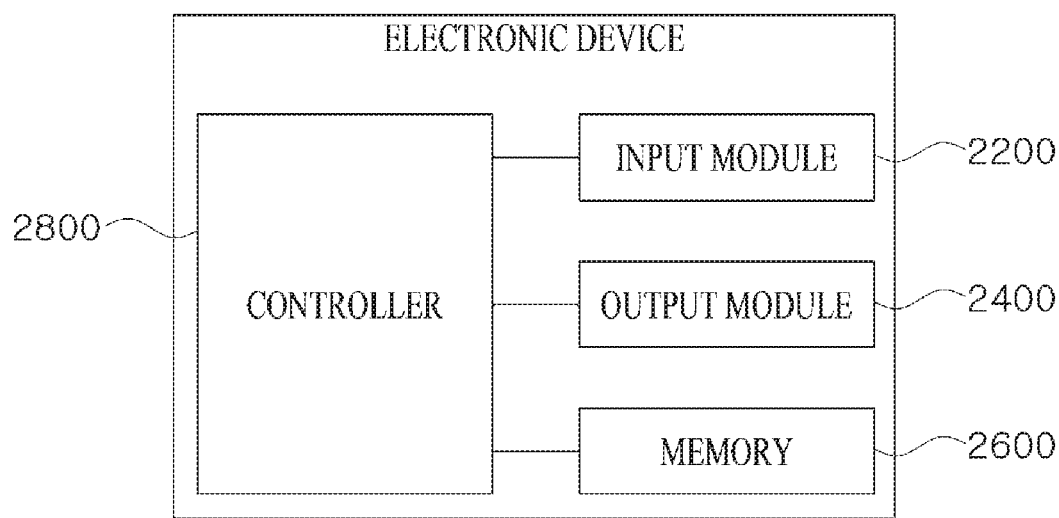
FIG. 67 is a block diagram of an electronic device 2000 according to an embodiment of the present disclosure.

FIG. 67 is a block diagram of an electronic device 2000 according to an embodiment of the present disclosure.

Referring to FIG. 67, the electronic device 2000 may include an input module 2200, an output module 2400, a memory 2600, and a controller 2800.

The input module 2200 may receive user input from a user. The user input may be in various forms including keyboard input, touch input, and phonetic input, and the like. Examples of the input module 2200 may include a conventional type of a keypad, a keyboard, and a mouse, a touch sensor for sensing a user's touch, and other various known types of input devices. Also, the input module 2200 may be implemented in the form of an input interface (USB port, PS/2 port, etc.) that connects an external input device receiving the user input with the electronic device, instead of a device sensing the user input in itself.

The output module 2400 may output various information and provide it to a user. The output module 2400 may include, e.g., a display for outputting video, a speaker for outputting sounds, a haptic device for generating vibration, and other various known types of output devices. In addition, the output module 2400 may be implemented in the form of a port-type output interface that connects the above-described individual output devices to the electronic device 2000.

The memory 2600 may store various kinds of information. The memory may store data temporarily or semi-permanently. Examples of the memory include a HDD, a SSD, a flash memory, a ROM, and a RAM. The memory 2600 may be provided in a form embedded in the electronic device 2000 or in a detachable form. The memory (2600) may store various data needed or used for driving the electronic device 2000, including the OS data for driving the electronic device 2000.

The controller 2800 controls an overall operation of the electronic device (2000). That is, the controller 2800 may perform calculations and processes of various information and control the operation of other components of the electronic device. The controller may be implemented in a computer or similar device depending on the hardware, software or a combination thereof. In hardware, a controller may be provided in the form of an electronic circuit, such as a microprocessor, that performs a control function with an electrical signal processing. In software, the controller may be provided in a form of a program that drives a hardware controller. The operation of the electronic device 2000 may be interpreted as being performed by the controller 2800, unless otherwise noted in implementations of the method of generating multimedia content providing the thermal feedback described below.

5.2. First Implementation

Hereinafter, the first implementation of a method for generating multimedia content according to an embodiment of the present disclosure will be described. This embodiment relates to a method of generating video content among multimedia content.

In the first implementation of the thermal feedback providing method described above, in the case of reproducing the video content set so that the thermal event scene reproduction time point coincides with one of the thermal feedback reproduction, the thermal feedback starting time point in the content reproduction device being earlier than the thermal feedback reproduction time point so that the user can feel the thermal feedback at the time point of reproducing the video corresponding to the thermal event.

Alternatively, the reproduction time point of the thermal feedback may be set in advance considering the time difference between the power applying-time point and the user feeling the thermal feedback. The method for generating multimedia content providing a thermal feedback according to an embodiment of the present disclosure relates to a method for generating thermal feedback data of video content to be linked to video or audio, even if the thermal feedback providing system 1000 performs the thermal feedback output operation at the reproduction time of the thermal feedback according to the thermal feedback data of the video content.

Figure 68:
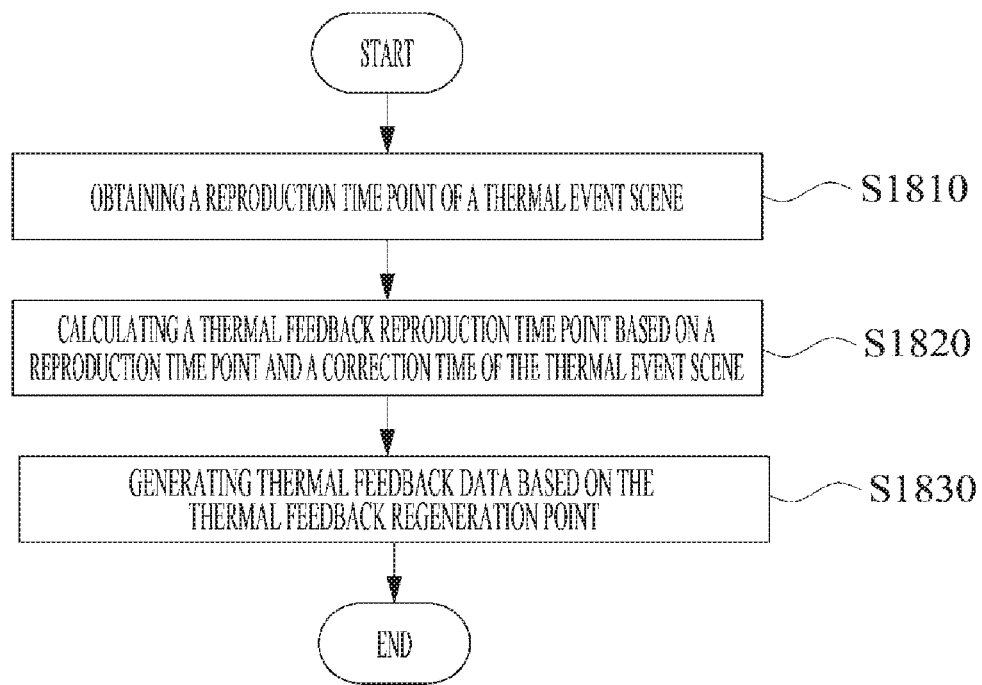
FIG. 68 is a flowchart of the first implementation of the method for generating multimedia content according to an embodiment of the present disclosure.

FIG. 68 is a flowchart of the first implementation of the method for generating multimedia content according to an embodiment of the present disclosure.

In FIG. 68, the first implementation of the method for generating multimedia content may include obtaining a reproduction time point of a thermal event scene (S1810), calculating a thermal feedback reproduction time point based on a reproduction time point and a correction time of the thermal event scene (S1820) and generating thermal feedback data based on the thermal feedback regeneration point (S1830).

Hereinafter, each step of the above-described implementation will be described in more detail.

The electronic device 2000 may obtain the output time point of the thermal event scene (S310). The controller 2800 may receive a user input relating to a reproduction timing of a thermal event scene to be linked to thermal feedback through the input module 2200.

The electronic device 2000 may provide a UI screen that allows a user to be able to easily input a reproduction time point of a thermal event scene through an output module 2400 such as a display. The UI screen may be provided somewhat similar to the screen provided by the conventional image editing program.

The UI screen may include a progressive bar reflecting the reproduction time point of the video content, an indicator disposed on the progressive bar, and a video window for outputting a scene corresponding to the time point indicated by the indicator. The UI screen may also include a control panel for controlling a reproduction of the video content. The user can move the indicator on the progressive bar or reproduce the video content using the control panel, and in doing so, the user can see the scene output through the video window during this process. When a scene desired to be a thermal event scene is displayed at the video window, the user can select a time point as the reproduction time point of the thermal event scene, at which the indicator on the progressive bar is located corresponding to the scene. The UI screen may be provided along with a menu for further selecting the object, type, strength and duration of the thermal feedback.

Via the UI screen, the user can search a scene to be linked with thermal feedback through the video window and select a time point of outputting a desired scene in the video window. The controller 2800 may obtain the output time point of the specific scene by receiving the user input through the input module 2200.

The electronic device 2000 may calculate the power applying-time point for the thermal feedback based on the output time point and the correction time of the thermal event scene (S1820).

The controller 2800 may determine the correction time as described above. The controller 2800 may further calculate a time point to apply the power by subtracting the correction time from the obtained output time point.

When the power applying-time point is calculated, the electronic device 2000 may generate thermal feedback data based on this time point (S1830). The thermal feedback data may include information on the type and intensity of thermal feedback, and information on the power applying-time point for starting the output of the thermal feedback. The thermal feedback data may further include information about a target feedback device to which the thermal feedback is to be output as described above.

The thermal feedback data generated in this way can be used to output thermal feedback linked to the video output, which is referred to when reproducing the video content. For this, the thermal feedback data may be provided as a separate file from a video file, such as a subtitle file providing subtitles during the video output. Alternatively, it may be provided as a single file in which thermal feedback data and video data are integrated.

As in this embodiment, when the thermal feedback data is generated in consideration of the delay time, the content reproduction device 1200 does not need to correct the output time point of the thermal feedback to account for the delay time, which advantageously reduces the computations needed to reproduce the multimedia content.

Alternatively, since the delay time may be slightly different depending on the manufacturer of the feedback device 1600, the correction time can be adaptively processed for each situation in consideration of the type of the feedback device 1600.

In the above description of the implementation, the video content among the multimedia content is explained, but the embodiment can be applied to other types of multimedia content such as a game or a sensory application. Typically, the embodiment may be used for a scene in which a video cut scene appears in the course of a game, and may be the same as the first implementation of the thermal feedback providing method.

In this embodiment and the first embodiment of the thermal feedback providing method, the effect described above may be somewhat small when the response time of the thermoelectric element is fast. However, in case of treating the contact surface 1641 with a material such as rubber to improve the grip feeling of the user in the gaming controller, the time required for heat transfer from the thermoelectric element to the contact surface 1641 may become longer, and in such a case, the advantage is expected to be further exerted.

5.3. Second Implementation

Hereinafter, the second implementation of a method for generating multimedia content according to an embodiment of the present disclosure will be described. This embodiment relates to a method of generating multimedia content provided in the form of a game or a sensory application of multimedia content.

The second implementation of the thermal feedback providing method described above may include generating a virtual object and assigning thermal characteristics to the generated virtual object.

The virtual object refers to an object capable of interacting with a player inside a game, a sensory game application, or the like.

When a virtual object is generated, the generated virtual object can be given a thermal characteristic. Thermal characteristics (attributes, properties) are directly or indirectly related to the type and intensity of thermal feedback.

In addition, various thermal properties (attributes) may be defined. Some examples are temperature values, material values, resistance values, and the like. In concrete examples, all the information used in the determination of the intensity/type/target device of the thermal feedback may be the thermal characteristics of the object in the thermal feedback providing method.

In an example, the virtual object is given an element property so that the type of thermal feedback can be determined accordingly. This is explained in detail in the third implementation of the thermal feedback providing method.

In another example, a heat transfer method may be determined corresponding to the thermal property (attribute) assigned to the object, which is illustrated in the tenth embodiment of a thermal feedback providing method.

Also, this implementation may be utilized on a game production engine. For example, an existing game production engine may include a physics engine that processes object collision and light paths, and a thermal processing functionality may be added to such physics engine.

Figure 69:
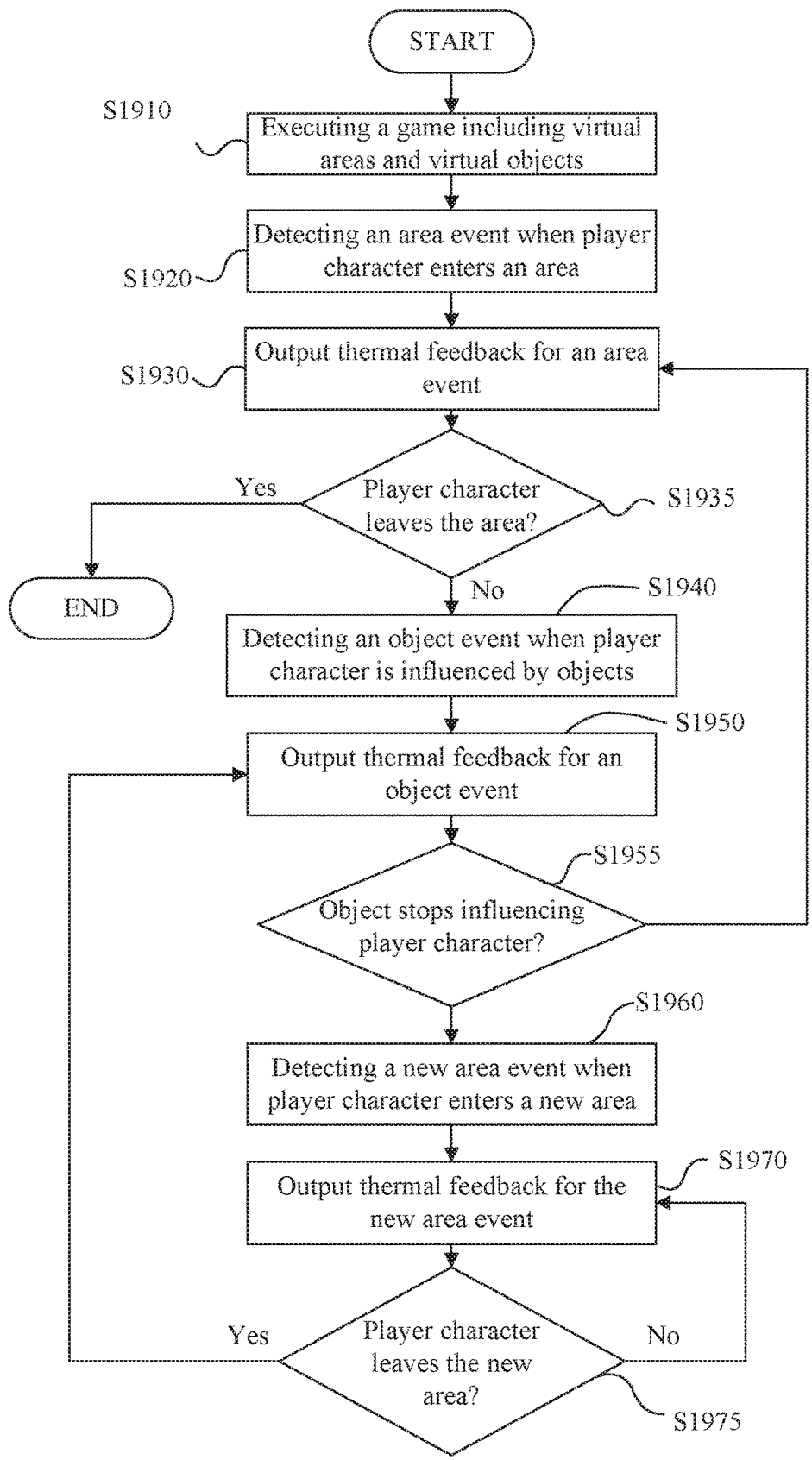
FIG. 69 is a flowchart of the thermal feedback providing method according to an embodiment of the present disclosure.

FIG. 69 is a flowchart of the thermal feedback providing method according to an embodiment of the present disclosure.

In step S1910 the reproduction content device 1200 may execute a game. For example, the controller 1260 may execute the game. The game may include virtual areas and virtual objects.

In step 1920, controller 1260 may detect an area event. An area event may reflect that a player character, which is controlled by a user, enters an area. In some embodiments, the is a local area. In other embodiments, the area is a global area.

In step 1930, controller 1260 may send a signal to feedback device 1600 to output a thermal feedback corresponding the area in which the player character enters.

In step 1935, controller 1260 may determine whether the player character left the area. If the player character leaves the area (step S1935: Yes), controller 1260 may finalize the process. However, if the player character does not leave the area (step S1935: No), controller 1260 may continue to step 1940.

In step 1940, controller 1260 may detect an object event. In some embodiments, an object event may represent that a virtual object is influencing the player's character. In other embodiments, the object event may represent a collision between player's character and a virtual object.

In step 1950, controller 1260 may send a signal to feedback device 1600 to output a thermal feedback corresponding the object event. In some embodiments, the thermal feedback corresponding the object event may be based on the area event. For example, if player character is in a hot area, such as the flame area, and the object is a fire bolt, the thermal feedback corresponding the object event may have a low intensity. However, if the player character is in a hot area and the object is an ice bolt, the thermal feedback corresponding the object event may have a high intensity.

In step 1955, controller 1260 may determine whether the virtual object stops influencing the player's character. If the virtual object stops influencing player's character, controller 1260 may return to step 1930. However, if the virtual object continues influencing player's character, controller 1260 may continue to step 1960.

In step 1960, controller 1260 may detect a new area event. The new area event may reflect that the player's character enters a new area. In some embodiments, the new area may be different from the area of step 1920. In other embodiments, the new area may be within the area of step 1920.

In step 1970, controller 1260 may send a signal to feedback device 1600 to output a thermal feedback corresponding the new area in which the player character enters. The thermal feedback corresponding the new area may be determined based on the object event. For example, if the new area is a lake and the object event is a fire bolt, the thermal feedback corresponding the new area may be low intensity cold. However, if the new area is a volcano and the object is a fire bolt, the thermal feedback corresponding the new area may be high intensity hot.

In step 1975, controller 1260 may determine whether the player leaves the new area. If the player leaves the new area controller 1260 may return to step 1950. However, if the player does not leave the new area, controller 1260 may return to step 1970.

The multimedia content generation methods providing the thermal feedback according to an embodiments of the present disclosure described above can be used alone or in combination with each other. In addition, since each of the steps described in each multimedia content generation method is not essential, the multimedia content generation method can be performed by including all or part of the steps. Also, since the order in which the steps are described is merely to facilitate explanations, the steps in the method of providing thermal feedback are not necessarily performed in the order described. Non-dependent steps may be performed in any order or in parallel.

The foregoing description is merely illustrative of the technical idea of the present disclosure and various changes and modifications may be made without departing from the essential characteristics of the present disclosure by those skilled in the art. Therefore, the embodiments of the present disclosure described above may be implemented separately or in combination.

Therefore, the embodiments disclosed in the present disclosure are intended to illustrate rather than limit the scope of the present disclosure, and the scope of the technical idea of the present disclosure is not limited by these embodiments. The scope of protection of the present disclosure should be construed according to the following claims, and all technical ideas within the scope of equivalents thereof should be construed as being included in the scope of the present disclosure.

The invention claimed is:

1. A content reproduction device, wherein the content reproduction device reproduces a multimedia content and cooperates with a plurality of feedback devices performing thermoelectric operation, the content reproduction device comprising:
a memory configured to store data;
a communication module configured to communicate with the plurality of feedback devices; and
a controller configured to:
execute a virtual reality application providing a virtual character moving in a virtual space,
obtain a facing direction of the virtual character in the virtual space,
when a thermal event occurs in the virtual space, determine at least one target feedback device among the plurality of feedback devices based on a relative orientation of a position where the thermal event occurs in the virtual space with respect to the facing direction of the virtual character, and
transmit, to the target feedback device, a signal instructing to perform thermoelectric operation according to the thermal event.

2. The content reproduction device of claim 1, wherein:
the plurality of feedback devices includes a first feedback device configured to be held with a user's left hand and a second feedback device configured to be held with a user's right hand, and
the controller is configured to when the relative orientation is within a predetermined range, determine both the first feedback device and the second feedback device as the target feedback device.

3. The content reproduction device of claim 2, wherein the controller is configured to control the first feedback device and the second feedback device to perform the thermoelectric operation according to the thermal event with the same intensity.

4. The content reproduction device of claim 2, wherein the controller is configured to when the relative orientation is out of the predetermined range, determine one of the first feedback device and the second feedback device as the target feedback device.

5. The content reproduction device of claim 2, wherein the controller is configured to, when the relative orientation is out of the predetermined range, determine both the first feedback device and the second feedback device as the target feedback device and control the first feedback device and the second feedback device to perform the thermoelectric operation according to the thermal event with different intensities.

6. A content reproduction device, wherein the content reproduction device reproduces a multimedia content and cooperates with a plurality of feedback devices performing thermoelectric operation, the content reproduction device comprising:
a memory configured to store data;
a communication module configured to communicate with the plurality of feedback devices; and
a controller configured to:
execute a virtual reality application providing a virtual space,
obtain a FOV (field of view) being displayed to a user, wherein the FOV is determined according to a facing direction of a user's head,
when a thermal event occurs in the virtual space, determine at least one target feedback device among the plurality of feedback devices based on a position where the thermal event occurs with respect to the FOV, and
transmit, to the target feedback device, a signal instructing to perform thermoelectric operation according to the thermal event.

7. The content reproduction device of claim 6, wherein:
the plurality of feedback devices includes a first feedback device configured to be held with a user's left hand and a second feedback device configured to be held with a user's right hand, and the controller is configured to when the thermal event occurs in a central area of the FOV, determine both the first feedback device and the second feedback device as the target feedback device.

8. The content reproduction device of claim 7, wherein the controller is configured to control the first feedback device and the second feedback device to perform the thermoelectric operation according to the thermal event with the same intensity.

9. The content reproduction device of claim 7, wherein the controller is configured to:
when the thermal event occurs in a left area of the FOV, determine the first feedback device as the target feedback device, and
when the thermal event occurs in a right area of the FOV, determine the second feedback device as the target feedback device.

10. The content reproduction device of claim 7, wherein the controller is configured to, when the thermal event occurs in one of a left area and a right area of the FOV, determine both the first feedback device and the second feedback device as the target feedback device and control the first feedback device and the second feedback device to perform the thermoelectric operation according to the thermal event with different intensities.

11. A method for providing thermal feedback by using a plurality of feedback devices performing thermoelectric operation, the method comprising:
executing a virtual reality application providing a virtual character moving in a virtual space;
obtaining a facing direction of the virtual character in the virtual space;
when a thermal event occurs in the virtual space, determining at least one target feedback device among the plurality of feedback devices based on a relative orientation of a position where the thermal event occurs in the virtual space with respect to the facing direction of the virtual character; and
transmitting, to the target feedback device, a signal instructing to perform thermoelectric operation according to the thermal event.

12. The method of claim 11, wherein:
the plurality of feedback devices includes a first feedback device configured to be held with a user's left hand and a second feedback device configured to be held with a user's right hand, and
the determining the at least one target feedback device comprises when the relative orientation is within a predetermined range, determining both the first feedback device and the second feedback device as the target feedback device.

13. The method of claim 12, further comprising:
controlling the first feedback device and the second feedback device to perform the thermoelectric operation according to the thermal event with the same intensity.

14. The method of claim 12, wherein determining the at least one target feedback device comprises, when the relative orientation is out of the predetermined range, determining one of the first feedback device and the second feedback device as the target feedback device.

15. The method of claim 12, wherein determining the at least one target feedback device comprises, when the relative orientation is out of the predetermined range, determining both the first feedback device and the second feedback device as the target feedback device and controlling the first feedback device and the second feedback device to perform the thermoelectric operation according to the thermal event with different intensities.

* * * * *